US007173129B2

(12) United States Patent
Worsencroft et al.

(10) Patent No.: US 7,173,129 B2
(45) Date of Patent: Feb. 6, 2007

(54) SULFONAMIDE-SUBSTITUTED CHALCONE DERIVATIVES AND THEIR USE TO TREAT DISEASES

(75) Inventors: Kimberly J. Worsencroft, Alpharetta, GA (US); Liming Ni, Duluth, GA (US); Zhihong Ye, Lilburn, GA (US); Charles Q. Meng, Alpharetta, GA (US); M. David Weingarten, Cumming, GA (US); Jacob E. Simpson, Lawrenceville, GA (US); James A. Sikorski, Atlanta, GA (US)

(73) Assignee: Athero Genics, Inc., Alpharetta, GA (US)

( * ) Notice: Subject to any disclaimer, the term of this patent is extended or adjusted under 35 U.S.C. 154(b) by 360 days.

(21) Appl. No.: 10/863,115

(22) Filed: Jun. 7, 2004

(65) Prior Publication Data

US 2005/0049236 A1 Mar. 3, 2005

Related U.S. Application Data

(60) Provisional application No. 60/476,708, filed on Jun. 6, 2003.

(51) Int. Cl.

| | |
|---|---|
| ***C07D 413/00*** | (2006.01) |
| ***C07D 419/00*** | (2006.01) |
| ***C07D 239/02*** | (2006.01) |
| ***C07D 403/00*** | (2006.01) |
| ***C07D 405/00*** | (2006.01) |
| ***C07D 409/00*** | (2006.01) |
| ***C07D 411/00*** | (2006.01) |

(52) U.S. Cl. ...................... 544/137; 544/143; 544/297; 544/372; 544/374; 546/213; 546/276.4; 546/280.4; 546/281.4; 548/194; 548/246; 548/247; 548/253; 548/314.7; 548/315.1; 548/365.7; 548/406; 548/509; 548/510; 548/511; 548/571

(58) Field of Classification Search ..................... None
See application file for complete search history.

(56) References Cited

U.S. PATENT DOCUMENTS

| | | | | |
|---|---|---|---|---|
| 3,595,656 | A * | 7/1971 | Ruckert et al. | ............. 430/196 |
| 4,085,135 | A | 4/1978 | Kyogoku et al. | |
| 4,855,438 | A | 8/1989 | Kaulen et al. | |
| 5,155,250 | A | 10/1992 | Parker et al. | |
| 5,217,999 | A | 6/1993 | Levitzki et al. | |
| 5,380,747 | A | 1/1995 | Medford et al. | |
| 5,608,095 | A | 3/1997 | Parker et al. | |
| 5,744,614 | A | 4/1998 | Merkle et al. | |
| 5,750,351 | A | 5/1998 | Medford et al. | |
| 5,773,209 | A | 6/1998 | Medford et al. | |
| 5,773,231 | A | 6/1998 | Medford et al. | |
| 5,783,596 | A | 7/1998 | Medford et al. | |
| 5,792,787 | A | 8/1998 | Medford et al. | |
| 5,807,884 | A | 9/1998 | Medford et al. | |
| 5,811,449 | A | 9/1998 | Medford et al. | |
| 5,821,260 | A | 10/1998 | Medford et al. | |
| 5,846,959 | A | 12/1998 | Medford et al. | |
| 5,877,203 | A | 3/1999 | Medford et al. | |
| 5,951,841 | A | 9/1999 | Wehlage et al. | |
| 6,046,212 | A | 4/2000 | Zwaagstra et al. | |
| 6,423,740 | B1 | 7/2002 | Bombardelli et al. | |
| 6,462,075 | B1 | 10/2002 | Bowen et al. | |
| 6,608,101 | B1 | 8/2003 | Ni et al. | |
| 2003/0232877 | A1 | 12/2003 | Sikorski et al. | |
| 2003/0236298 | A1 | 12/2003 | Meng et al. | |
| 2004/0048858 | A1 | 3/2004 | Sikorski et al. | |

FOREIGN PATENT DOCUMENTS

| | | |
|---|---|---|
| EP | 307762 | 3/1989 |
| EP | 0 271 307 | 1/1992 |
| JP | 63010720 | 7/1986 |
| JP | 04217621 | 10/1990 |
| JP | 06092950 | 9/1992 |
| JP | 06116206 | 10/1992 |
| JP | 07330814 | 6/1994 |
| WO | WO 95/15760 | 6/1995 |

(Continued)

OTHER PUBLICATIONS

Liu et al., "Antimalarial Alkoxylated and Hydroxylated Chalones: Structures-Activity Relationship Analysis", *J.Med. Chem.* 2001, 44, 4443-4452.

Herencia, et al, "Novel Anti-inflammatory Chalcone Derivatives Inhibit the Induction of Nitric Oxide Synthase and Cyclooxygenase-2 in Mouse Peritoneal Macrophages", *FEBS Letters*, 1999, 453, 129-134.

Herencia, et al., "Synthesis and Anti-inflammatory Activity of Chalcone Derivatives", *Bioorganic & Medicinal Chemistry Letters* 8 (1998) 1169-1174.

(Continued)

*Primary Examiner*—Brian Davis
(74) *Attorney, Agent, or Firm*—Alan Scrivner, Esq.; King & Spalding LLP

(57) ABSTRACT

The invention relates to compounds, pharmaceutical compositions and methods of using compounds of the general formula

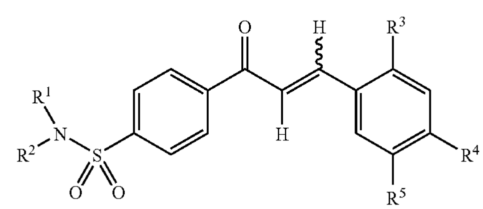

or its pharmaceutically acceptable salt or ester, wherein the substituents are defined in the application.

37 Claims, No Drawings

FOREIGN PATENT DOCUMENTS

| | | |
|---|---|---|
| WO | WO 96/20936 | 7/1996 |
| WO | WO 97/12613 | 4/1997 |
| WO | WO 98/23581 | 6/1998 |
| WO | WO 98/51289 | 11/1998 |
| WO | WO 98/51662 | 11/1998 |
| WO | WO 99/00114 | 1/1999 |
| WO | WO 00/47554 | 8/2000 |

OTHER PUBLICATIONS

Hsieh et al., "Synthesis and Anti-inflammatory Effect of Chalcones and Related Compounds", *Pharmaceutical Research*, 1998, vol. 15, No. 1, 39-46.

Hsieh, et al., "Synthesis and Anti-inflammatory Effect of Chalcones", *J. Pharm. Pharmacol.* 2000, 52; 163-171..

Jones, R.; Bischofberger, N., "Minireview: Nucleotide Prodrugs", *Antiviral Research*, 27 (1995) 1-17.

Yang, Y., et al., 'Synthesis of Some 5-Substituted Indoles' *Heterocycles*, 1992, 34(6), 1169-1175.

Zwaagstra, et al., "Synthesis and Structure-Activity Relationships of Carboxylated Chalcones: A Novel Series of $CysLT_1$ ($LT_4$) Receptor Antagonists", *J. Med. Chem.*, 1997, 40, 1075-1089.

* cited by examiner

SULFONAMIDE-SUBSTITUTED CHALCONE DERIVATIVES AND THEIR USE TO TREAT DISEASES

CROSS REFERENCE TO RELATED APPLICATIONS

This application claims priority to U.S. provisional patent application Ser. No. 60/476,708 filed Jun. 6, 2003.

FIELD OF THE INVENTION

The present invention is in the field of novel chalcone derivatives, pharmaceutical compositions and methods for treating a variety of diseases and disorders, including inflammation and cardiovascular disease.

BACKGROUND OF THE INVENTION

Adhesion of leukocytes to the endothelium represents a fundamental, early event in a wide variety of inflammatory conditions, autoimmune disorders and bacterial and viral infections. Leukocyte recruitment to endothelium is mediated in part by the inducible expression of adhesion molecules on the surface of endothelial cells that interact with counterreceptors on immune cells. Endothelial cells determine which types of leukocytes are recruited by selectively expressing specific adhesion molecules, such as vascular cell adhesion molecule-l (VCAM-1), intercellular adhesion molecule-1 (ICAM-1), and E-selectin. VCAM-1 binds to the integrin VLA-4 expressed on lymphocytes, monocytes, macrophages, eosinophils, and basophils but not neutrophils. This interaction facilitates the firm adhesion of these leukocytes to the endothelium. VCAM-1 is an inducible gene that is not expressed, or expressed at very low levels, in normal tissues. VCAM-1 is upregulated in a number of inflammatory diseases, including arthritis (including rheumatoid arthritis), asthma, dermatitis, psoriasis, cystic fibrosis, post transplantation late and chronic solid organ rejection, multiple sclerosis, systemic lupus erythematosis, inflammatory bowel diseases, autoimmune diabetes, diabetic retinopathy, rhinitis, ischemia-reperfusion injury, post-angioplasty restenosis, chronic obstructive pulmonary disease (COPD), glomerulonephritis, Graves disease, gastrointestinal allergies, conjunctivitis, atherosclerosis, coronary artery disease, angina and small artery disease.

U.S. Pat. Nos. 5,750,351; 5,807,884; 5,811,449; 5,846,959; 5,773,231, and 5,773,209 to Medford, et al., as well as the corresponding WO 95/30415 to Emory University indicate that polyunsaturated fatty acids ("PUFAs") and their hydroperoxides ("ox-PUFAs"), which are important components of oxidatively modified low density lipoprotein (LDL), induce the expression of VCAM-1, but not intracellular adhesion molecule-1 (ICAM-1) or E-selectin in human aortic endothelial cells, through a mechanism that is not mediated by cytokines or other noncytokine signals. This is a fundamental discovery of an important and previously unknown biological pathway in VCAM-1 mediated immune responses. As non-limiting examples, linoleic acid, linolenic acid, arachidonic acid, linoleyl hydroperoxide (13-HPODE) and arachidonic hydroperoxide (15-HPETE) induce cell-surface gene expression of VCAM-1 but not ICAM-1 or E-selectin. Saturated fatty acids (such as stearic acid) and monounsaturated fatty acids (such as oleic acid) do not induce the expression of VCAM-1, ICAM-1 or E-selectin.

Chalcone (1,3-bis-aromatic-prop-2-en-1-ones) compounds are natural products related to flavonoids. WO 99/00114 (PCT/DK98/00283) discloses the use of certain chalcones, 1,3-bis-aromatic-propan-1-ones (dihydrochalcones), and 1,3-bisaromatic-prop-2-yn-1-ones for the preparation of pharmaceutical compositions for the treatment of prophylaxis of a number of serious diseases including i) conditions relating to harmful effects of inflammatory cytokines, ii) conditions involving infection by *Helicobacter* species, iii) conditions involving infections by viruses, iv) neoplastic disorders, and v) conditions caused by microorganisms or parasites.

U.S. Pat. No. 4,085,135 to Kyogoku et al. discloses a process for preparation of 2'-(carboxymethoxy)-chalcones having antigastric and anti duodenal activities with low toxicity and high absorptive ratio in the body.

European Patent No 307762 assigned to Hofmann-La Roche discloses substituted phenyl chalcones.

Herencia, et al., in Synthesis and Anti-inflammatory Activity of Chalcone Derivatives, *Bioorganic & Medicinal Chemistry Letters* 8 (1998) 1169–1174, discloses certain chalcone derivatives with anti-inflammatory activity.

Hsieh, et al., Synthesis and Antiinflammatory Effect of Chalcones, *J. Pharm. Pharmacol.* 2000, 52; 163–171 describes that certain chalcones have potent antiinflammatory activity.

Zwaagstra, et al., Synthesis and Structure-Activity Relationships of Carboxylated Chalcones: A Novel Series of $CysLT_1$ ($LT_4$) Receptor Antagonists; J. Med. Chem., 1997, 40, 1075–1089 discloses that in a series of 2-, 3-, and 4-(2-quinolinylmethoxy)- and 3- and 4-[2-(2-quinolinyl) ethenyl]-substituted, 2', 3', 4', or 5' carboxylated chalcones, certain compounds are $CysLT_1$ receptor antagonists.

JP 63010720 to Nippon Kayaku Co., LTD discloses that chalcone derivatives of the following formula (wherein $R^1$ and $R^2$ are hydrogen or alkyl, and m and n are 0–3) are 5-lipoxygenase inhibitors and can be used in treating allergies.

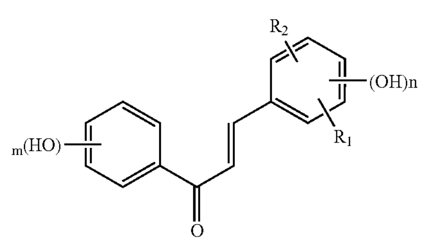

JP 06116206 to Morinaga Milk Industry Co. Ltd, Japan, discloses chalcones of the following structure as 5-lipoxygenase inhibitors, wherein R is acyl and $R^1$–$R^5$ are hydrogen, lower alkyl, lower alkoxy or halo, and specifically that in which R is acyl and $R^1$–$R^5$ are hydrogen.

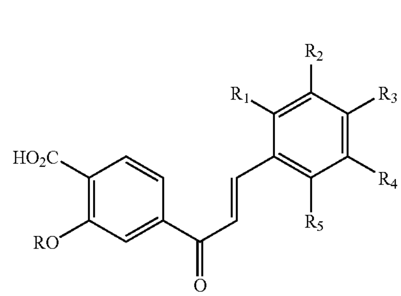

I R = Ac
II R–$R_5$ = H

U.S. Pat. No. 6,046,212 to Kowa Co. Ltd. discloses heterocyclic ring-containing chalcones of the following formula as antiallergic agents.

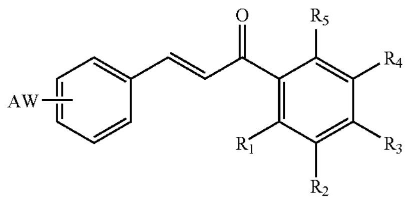

Reported bioactivies of chalcones have been reviewed by Dimmock, et al., in Bioactivities of Chalcones, *Current Medicinal Chemistry* 1999, 6, 1125–1149; Liu, et al., Antimalarial Alkoxylated and Hydroxylated Chalones: Structure-Activity Relationship Analysis, *J. Med. Chem.* 2001, 44, 4443–4452; Herencia et al, Novel Anti-inflammatory Chalcone Derivatives Inhibit the Induction of Nitric Oxide Synthase and Cyclooxygenase-2 in Mouse Peritoneal Macrophages, *FEBS Letters,* 1999, 453, 129–134; and Hsieh et al., Synthesis and Anti-inflammatory Effect of Chalcones and Related Compounds, *Pharmaceutical Research,* 1998, Vol. 15, No. 1, 39–46.

U.S. patent application Ser. No. 09/866,348, filed Jun. 20, 2001 and Ser. No. 10/324,987, filed Dec. 19, 2002 both assigned to AtheroGenics, Inc., and herein incorporated by reference, disclose particular derivatives of chalcones suitable to treat diseases mediated by VCAM-1.

Given that VCAM-1 is a mediator of chronic inflammatory disorders, it is a goal of the present work to identify new compounds, compositions and methods that can inhibit the expression of VCAM-1. A more general goal is to identify selective compounds and methods for suppressing the expression of redox sensitive genes or activating redox sensitive genes that are suppressed. An even more general goal is to identify selective compounds, pharmaceutical compositions and methods of using the compounds for the treatment of inflammatory diseases.

It is therefore an object of the present invention to provide new compounds for the treatment of disorders mediated by VCAM-1.

It is also an object to provide new pharmaceutical compositions for the treatment of diseases and disorders mediated by the expression of VCAM-1.

It is a further object of the invention to provide compounds, compositions, and methods of treating disorders and diseases mediated by VCAM-1, including cardiovascular and inflammatory diseases.

Another object of the invention is to provide compounds, compositions, and method of treating cardiovascular and inflammatory diseases.

It is another object of the invention to provide compounds, compositions and methods to treat arthritis.

Another object of the invention is to provide compounds, compositions and methods to treat rheumatoid arthritis. The inventions compounds, compositions and methods are also suitable as disease modifying anti-rheumatoid arthritis drugs (DMARDs).

It is yet another object of the invention to provide compounds, compositions and methods to treat asthma.

It is another object of the invention to provide compounds, methods and compositions to inhibit the progression of atherosclerosis.

It is still another object of the invention to provide compounds, compositions, and methods to treat or prevent transplant rejection.

It is a further object of the present invention to provide compounds, methods and compositions for the treatment of lupus.

It is a further object of the present invention to provide compounds, methods and compositions for the treatment of inflammatory bowel disease.

It is a further object of the present invention to provide compounds, methods and compositions for the treatment of autoimmune diabetes.

It is a further object of the present invention to provide compounds, methods and compositions for the treatment of multiple sclerosis.

It is a further object of the present invention to provide compounds, methods and compositions for the treatment of diabetic retinopathy.

It is a further object of the present invention to provide compounds, methods and compositions for the treatment of diabetic nephropathy.

It is a further object of the present invention to provide compounds, methods and compositions for the treatment of diabetic vasculopathy.

It is a further object of the present invention to provide compounds, methods and compositions for the treatment of rhinitis.

It is a further object of the present invention to provide compounds, methods and compositions for the treatment of ischemia-reperfusion injury.

It is a further object of the present invention to provide compounds, methods and compositions for the treatment of post-angioplasty restenosis.

It is a further object of the present invention to provide compounds, methods and compositions for the treatment of chronic obstructive pulmonary disease (COPD).

It is a further object of the present invention to provide compounds, methods and compositions for the treatment of glomerulonephritis.

It is a further object of the present invention to provide compounds, methods and compositions for the treatment of Graves disease.

It is a further object of the present invention to provide compounds, methods and compositions for the treatment of gastrointestinal allergies.

It is a further object of the present invention to provide compounds, methods and compositions for the treatment of conjunctivitis.

It is a further object of the present invention to provide compounds, methods and compositions for the treatment of dermatitis.

It is a further object of the present invention to provide compounds, methods and compositions for the treatment of psoriasis.

It is a further object of the present invention to provide compounds, methods and compositions for the treatment of ocular inflammation, including uveitis.

In a broader sense, an object of the present invention is to provide compounds, methods and compositions that can be used as adjunct or combination therapy both simultaneously, and and in series.

SUMMARY OF THE INVENTION

It has been discovered that particular sulfonamide substituted chalcone derivatives inhibit the expression of VCAM-1, and thus can be used to treat a patient with a disorder mediated by VCAM-1. Examples of inflammatory disorders that are mediated by VCAM-1 include, but are not limited to arthritis, asthma, dermatitis, cystic fibrosis, post transplantation late and chronic solid organ rejection, multiple sclerosis, systemic lupus erythematosis, inflammatory bowel diseases, autoimmune diabetes, diabetic retinopathy, diabetic nephropathy, diabetic vasculopathy, rhinitis, ocular inflammation, uveitis, ischemia-reperfusion injury, post-angioplasty restenosis, chronic obstructive pulmonary disease (COPD), glomerulonephritis, Graves disease, gastrointestinal allergies, conjunctivitis, atherosclerosis, coronary artery disease, angina and small artery disease.

The compounds disclosed herein can also be used in the treatment of inflammatory skin diseases that are mediated by VCAM-1, as well as human endothelial disorders that are mediated by VCAM-1, which include, but are not limited to psoriasis, dermatitis, including eczematous dermatitis, Kaposi's sarcoma, multiple sclerosis, as well as proliferative disorders of smooth muscle cells.

In yet another embodiment, the compounds disclosed herein can be selected to treat anti-inflammatory conditions that are mediated by mononuclear leucocytes.

In one embodiment, the compounds of the present invention are selected for the prevention or treatment of tissue or organ transplant rejection. Treatment and prevention of organ or tissue transplant rejection includes, but is not limited to treatment of recipients of heart, lung, combined heart-lung, liver, kidney, pancreatic, skin, spleen, small bowel, or corneal transplants. The compounds can also be used in the prevention or treatment of graft-versus-host disease, such as sometimes occurs following bone marrow transplantation.

In an alternative embodiment, the compounds described herein are useful in both the primary and adjunctive medical treatment of cardiovascular disease. The compounds are used in primary treatment of, for example, coronary disease states including atherosclerosis, post-angioplasty restenosis, coronary artery diseases and angina. The compounds can be administered to treat small vessel disease that is not treatable by surgery or angioplasty, or other vessel disease in which surgery is not an option. The compounds can also be used to stabilize patients prior to revascularization therapy.

Compounds of the present invention are of the formula

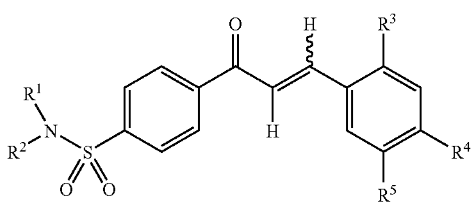

or its pharmaceutically acceptable salt or ester, wherein the substituents are defined herein.

A further embodiment of the invention is to supply intermediates suitable for manufacturing compounds of the invention that may have independent therapeutic value. Such intermediates having the formulas

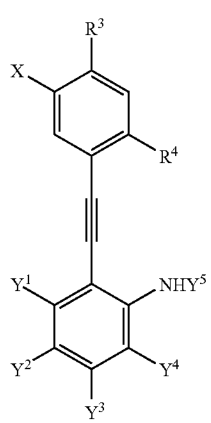

and

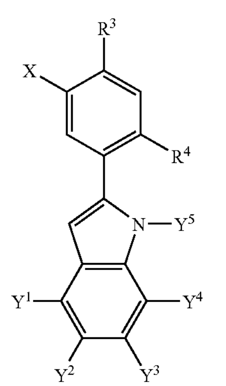

wherein

X is —C(O)H or —$CH_2$OH;

$R^3$ and $R^4$ are independently selected from the group consisting of hydroxy, alkoxy, lower alkoxy, —(O$(CH_2)_2)_{1-3}$—O-lower alkyl, cycloalkyloxy, cycloalkylalkoxy, haloalkoxy, aryloxy, arylalkoxy, heteroaryloxy, heteroarylalkoxy, heteroaryl lower alkoxy, heterocyclicoxy, heterocyclicalkoxy, heterocyclic lower alkoxy, —OC$(R^9)_2$C(O)N$(R^9)_2$, and —OC$(R^9)_2$C(O)N$R^7R^8$, wherein all substituents may be optionally substituted by one or more selected from the group consisting of halo, alkyl, lower alkyl, alkenyl, cycloalkyl, haloalkyl, acyl, hydroxy, hydroxyalkyl, heterocyclic, amino, aminoalkyl, —N$R^7R^8$, alkoxy, oxo, cyano, carboxy, carboxyalkyl, alkoxycarbonyl, —C(O)N$R^7R^8$, and —C(O)N$(R^9)_2$;

$Y^1$, $Y^2$, $Y^3$, and $Y^4$ are independently selected from the group consisting of hydrogen, hydroxyl, halo, alkyl, lower alkyl, alkenyl, cycloalkyl, haloalkyl, acyl, hydroxy, hydroxyalkyl, heterocyclic, amino, aminoalkyl, —N$R^7R^8$, alkoxy, oxo, cyano, carboxy, carboxyalkyl, alkoxycarbonyl, heteroaryl, —C(O)N$R^7R^8$, and —C(O)N$(R^9)_2$, wherein all substituents, when possible may be optionally substituted by one or more selected from the group consisting of hydroxyl, halo, alkyl, lower alkyl, alkenyl, cycloalkyl, haloalkyl, acyl, hydroxy, hydroxyalkyl, heterocyclic, amino, aminoalkyl, —N$R^7R^8$, alkoxy, oxo, cyano, carboxy, carboxyalkyl, alkoxycarbonyl, heteroaryl, —C(O)N$R^7R^8$, and —C(O)N$(R^2)^2$.

$Y^5$ is selected from the group consisting of hydrogen, alkyl, lower alkyl, acyl, and alkoxycarbonyl wherein all substituents, when possible may be optionally substituted by one or more selected from the group consisting of hydroxyl, halo, alkyl, lower alkyl, alkenyl, cycloalkyl, haloalkyl, acyl, hydroxy, hydroxyalkyl, heterocyclic, amino, aminoalkyl, —N$R^7R^8$, alkoxy, oxo, cyano, carboxy, carboxyalkyl, alkoxycarbonyl, heteroaryl, —C(O)N$R^7R^8$, and —C(O)N$(R^9)_2$;

$R^9$ is independently selected from the group consisting of alkyl, lower alkyl, carbocyclic, cycloalkyl, hydroxy, alkoxy, lower alkoxy, trialkylsilyloxy, cycloalkyloxy, cycloalkylalkoxy, heterocyclicoxy, aryl, heteroaryl, heterocyclic, arylalkyl, heteroarylalkyl, acyl, alkoxycarbonyl, and heterocyclicalkyl, wherein all substituents may be optionally substituted by one or more selected from the group consisting of halo, alkyl, lower alkyl, alkenyl, cycloalkyl, haloalkyl, acyl, hydroxy, hydroxyalkyl, heterocyclic, amino, aminoalkyl, —N$R^7R^8$, —NH$R^9$, —N$(R^9)_2$, alkoxy, oxo, cyano, carboxy, carboxyalkyl, alkoxycarbonyl, heteroaryl, —C(O)N$R^7R^8$, —N$R^9R^9$ and —C(O)N$(R^9)_2$;

$R^7$ and $R^8$ are independently selected from the group consisting of alkyl, alkenyl and aryl and linked together forming a 4- to 12-membered monocyclic, bicylic, tricyclic or benzofused ring, which may be optionally substituted by one or more selected from the group consisting of halo, alkyl, lower alkyl, alkenyl, cycloalkyl, haloalkyl, acyl, hydroxy, hydroxyalkyl, heterocyclic, amino, aminoalkyl, —N$R^7R^8$, alkoxy, oxo, cyano, carboxy, carboxyalkyl, alkoxycarbonyl, —C(O)N$R^7R^8$, and —C(O)N$(R^9)_2$.

DETAILED DESCRIPTION OF THE INVENTION

It has been discovered that compounds of the invention inhibit the expression of VCAM-1, and thus can be used to treat a patient with a disorder mediated by VCAM-1. These compounds can be administered to a host as monotherapy, or if desired, in combination with another compound of the invention or another biologically active agent, as described in more detail below.

In a 1st embodiment, the invention is represented by Formula 1

(I)

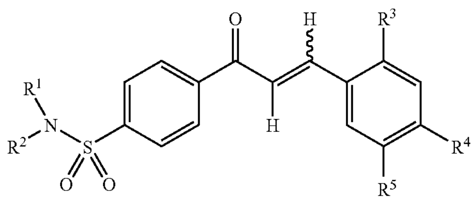

or its pharmaceutically acceptable salt, wherein:

$R^1$ is selected from the group consisting of hydrogen, alkyl, lower alkyl, carbocyclic, cycloalkyl, aryl, heteroaryl, heterocyclic, arylalkyl, heteroarylalkyl, acyl and heterocyclicalkyl, wherein all substituents may be optionally substituted by one or more selected from the group consisting of halo, alkyl, lower alkyl, alkenyl, cycloalkyl, haloalkyl, acyl, hydroxy, hydroxyalkyl, heterocyclic, amino, aminoalkyl, —$NR^7R^8$, alkoxy, oxo, cyano, carboxy, carboxyalkyl, alkoxycarbonyl, heteroaryl, —$C(O)NR^7R^8$, and —$C(O)N(R^2)_2$;

$R^2$ is independently selected from the group consisting of alkyl, lower alkyl, carbocyclic, cycloalkyl, hydroxy, alkoxy, lower alkoxy, trialkylsilyloxy, cycloalkyloxy, cycloalkylalkoxy, heterocyclicoxy, aryl, heteroaryl, heterocyclic, arylalkyl, heteroarylalkyl, acyl, alkoxycarbonyl, and heterocyclicalkyl, wherein all substituents may be optionally substituted by one or more selected from the group consisting of halo, alkyl, lower alkyl, alkenyl, cycloalkyl, haloalkyl, acyl, hydroxy, hydroxyalkyl, heterocyclic, amino, aminoalkyl, —$NR^7R^8$, alkoxy, oxo, cyano, carboxy, carboxyalkyl, alkoxycarbonyl, heteroaryl, —$C(O)NR^7R$ , —$NR^1R^2$ and —$(O)N(R^2)_2$;

$R^1$ and $R^2$ may be taken together to form a 4- to 12-membered saturated or unsaturated heterocyclic ring which can be optionally substituted by one or more selected from the group consisting of halo, alkyl, lower alkyl, alkenyl, cycloalkyl, haloalkyl, acyl, hydroxy, hydroxyalkyl, heterocyclic, amino, aminoalkyl, —$NR^7R^8$, alkoxy, oxo, cyano, carboxy, carboxyalkyl, alkoxycarbonyl, —$C(O)NR^7R^8$, and —$C(O)N(R^2)_2$;

$R^7$ and $R^8$ are independently selected from the group consisting of alkyl, alkenyl and aryl and linked together forming a 4- to 12-membered monocyclic, bicylic, tricyclic or benzofused ring, which may be optionally substituted by one or more selected from the group consisting of halo, alkyl, lower alkyl, alkenyl, cycloalkyl, haloalkyl, acyl, hydroxy, hydroxyalkyl, heterocyclic, amino, aminoalkyl, —$NR^7R^8$, alkoxy, oxo, cyano, carboxy, carboxyalkyl, alkoxycarbonyl, —$C(O)NR^7R^8$, and —$C(O)N(R^2)_2$;

$R^3$ and $R^4$ are independently selected from hydroxy, alkoxy, lower alkoxy, —$(O(CH_2)_2)_{1-3}$—O-lower alkyl, cycloalkyloxy, cycloalkylalkoxy, haloalkoxy, aryloxy, arylalkoxy, heteroaryloxy, heteroarylalkoxy, heteroaryl lower alkoxy, heterocyclicoxy, heterocyclicalkoxy, heterocyclic lower alkoxy, —$OC(R^1)_2C(O)N(R^2)_2$, and —$OC(R^1)_2C(O)NR^7R^8$, wherein all substituents may be optionally substituted by one or more selected from the group consisting of halo, alkyl, lower alkyl, alkenyl, cycloalkyl, haloalkyl, acyl, hydroxy, hydroxyalkyl, heterocyclic, amino, aminoalkyl, —$NR^7R^8$, alkoxy, oxo, cyano, carboxy, carboxyalkyl, alkoxycarbonyl, —$C(O)NR^7R^8$, and —$C(O)N(R^2)_2$;

$R^5$ is selected from the group consisting of a carbon-carbon linked heteroaryl and a carbon-carbon linked heterocyclic, which may be optionally substituted by one or more selected from the group consisting of halo, alkyl, lower alkyl, alkenyl, cycloalkyl, haloalkyl, acyl, hydroxy, hydroxyalkyl, heterocyclic, amino, aminoalkyl, —$NR^7R^8$, alkoxy, oxo, cyano, carboxy, carboxyalkyl, alkoxycarbonyl, —$C(O)NR^7R^8$, and —$C(O)N(R^2)_2$;

with the proviso that when $R^1$ is hydrogen and $R^2$ is 2-methyl propanoyl, then $R^5$ cannot be 5-benzo[b]thien-2-yl.

In a 2nd embodiment, the invention is represented by Formula 1 or its pharmaceutically acceptable salt, wherein:

$R^1$ is selected from the group consisting of hydrogen, alkyl, and lower alkyl, wherein all substituents may be optionally substituted by one or more selected from the group consisting of halo, alkyl, lower alkyl, haloalkyl, heterocyclic, —$NR^7R^8$, alkoxy, carboxy, carboxyalkyl, alkoxycarbonyl and heteroaryl;

$R^2$ is independently selected from the group consisting of alkyl, lower alkyl, alkoxy, lower alkoxy, heteroaryl, heterocyclic, heteroarylalkyl, and heterocyclicalkyl, wherein all substituents may be optionally substituted by one or more selected from the group consisting of halo, alkyl, lower alkyl, haloalkyl, heterocyclic, —$NR^7R^8$, alkoxy, carboxy, carboxyalkyl, alkoxycarbonyl and heteroaryl;

$R^1$ and $R^2$ may be taken together to form a 5- to 7-membered saturated or unsaturated heterocyclic ring which can be optionally substituted by one or more selected from the group consisting of halo, alkyl, lower alkyl, haloalkyl, heterocyclic, —$NR^7R^8$, alkoxy, carboxy, carboxyalkyl and alkoxycarbonyl;

$R^7$ and $R^8$ are independently selected from the group consisting of alkyl, alkenyl and aryl and linked together forming a 5- to 10-membered monocyclic, bicylic or benzofused ring, which may be optionally substituted by one or more selected from the group consisting of halo, alkyl, lower alkyl, haloalkyl, heterocyclic, —$NR^7R^8$, alkoxy, carboxy, carboxyalkyl and alkoxycarbonyl;

$R^3$ and $R^4$ are independently selected from hydroxy, alkoxy, lower alkoxy, —$(O(CH_2)_2)_{1-3}$—O-lower alkyl, haloalkoxy, heteroaryloxy, heteroarylalkoxy, heteroaryl lower alkoxy, heterocyclicoxy, heterocyclicalkoxy, heterocyclic lower alkoxy, —$OC(R^1)_2C(O)N(R^2)_2$, and —$OC(R^1)_2C(O)NR^7R^8$, wherein all substituents may be optionally substituted by one or more selected from the group consisting of halo, alkyl, lower alkyl, hydroxy, hydroxyalkyl, heterocyclic, —$NR^7R^8$, alkoxy, —$C(O)NR^7R^8$, and —$C(O)N(R^2)_2$;

$R^5$ is selected from the group consisting of a carbon-carbon linked heteroaryl and a carbon-carbon linked heterocyclic, which may be optionally substituted by one or more selected from the group consisting of halo, alkyl, lower alkyl, haloalkyl, heterocyclic, —$NR^7R^8$ and alkoxy.

In a 3rd embodiment, the invention is represented by Formula 1 or its pharmaceutically acceptable salt, wherein:

$R^1$ is selected from the group consisting of hydrogen and lower alkyl;

$R^2$ is independently selected from the group consisting of lower alkyl, lower alkoxy, heteroaryl, heterocyclic, heteroarylalkyl, and heterocyclicalkyl, wherein all substituents may be optionally substituted by one or more selected from the group consisting of halo, lower alkyl, haloalkyl, heterocyclic, —$NR^7R^8$ and carboxy;

$R^1$ and $R^2$ may be taken together to form a 5- to 6-membered heterocyclic saturated ring which can be optionally substituted by one or more selected from the group consisting of halo, lower alkyl and carboxy;

$R^7$ and $R^8$ are independently selected from the group consisting of alkyl and alkenyl, and linked together forming a 5- to 7-membered monocyclic ring, which may be optionally substituted by one or more selected from the group consisting of halo, lower alkyl, haloalkyl, heterocyclic and carboxy;

$R^3$ and $R^4$ are independently selected from hydroxy, lower alkoxy, —$(O(CH_2)_2)_{1-3}$—O-lower alkyl, heteroaryl lower alkoxy, heterocyclicoxy, heterocyclicalkoxy, heterocyclic lower alkoxy, —$OC(R^1)_2C(O)N(R^2)_2$, and —$OC(R^1)_2C(O)NR^7R^8$, wherein all substituents may be optionally substituted by one or more selected from the group consisting of hydroxy, hydroxyalkyl, heterocyclic, —$NR^7R^8$, —$C(O)NR^7R^8$, and —$C(O)N(R^2)_2$;

$R^5$ is selected from the group consisting of a carbon-carbon linked heteroaryl and a carbon-carbon linked heterocyclic, which may be optionally substituted by one or more lower alkyl.

In a 4th embodiment, the invention is represented by Formula 1 or its pharmaceutically acceptable salt, wherein:

$R^1$ is hydrogen;

$R^2$ is independently selected from the group consisting of lower alkyl, heteroaryl, heteroarylalkyl, and heterocyclicalkyl, wherein all substituents may be optionally substituted by one or more selected from the group consisting of halo and lower alkyl;

$R^1$ and $R^2$ may be taken together to form a 5- to 6-membered heterocyclic saturated ring;

$R^7$ and $R^8$ are independently alkyl and linked together forming a 5- to 7-membered saturated monocyclic ring;

$R^3$ and $R^4$ are independently selected from hydroxy, lower alkoxy and heterocyclic lower alkoxy;

$R^5$ is selected from the group consisting of a carbon-carbon linked heteroaryl and a carbon-carbon linked heterocyclic, which may be optionally substituted by one or more lower alkyl.

In a 5th embodiment, the invention is represented by Formula 1 or its pharmaceutically acceptable salt, wherein:

$R^1$ is hydrogen;

$R^2$ is independently selected from the group consisting of lower alkyl, heteroaryl, heteroarylalkyl, and heterocyclicalkyl, wherein all substituents may be optionally substituted by one or more selected from the group consisting of halo and lower alkyl;

$R^3$ and $R^4$ are independently selected from lower alkoxy and heterocyclic lower alkoxy;

$R^5$ is a carbon-carbon linked heteroaryl, which may be optionally substituted by one or more lower alkyl.

In a 6th embodiment, the invention is represented by Formula 1 or its pharmaceutically acceptable salt, wherein the compound is selected from 4-[3E-(2,4-Dimethoxy-5-thien-2-yl-phenyl)acryloyl]-N-(5-methylisoxazol-3-yl)benzenesulfonamide;

3E-(2,4-Dimethoxy-5-thien-2-ylphenyl)acryloyl]-N-(5-methylisoxazol-3-yl)benzenesulfonamide sodium salt;

4-[3E-(2,4-Dimethoxy-5-thien-2-ylphenyl)acryloyl]-N-pyrimidin-2-ylbenzenesulfonamide;

4-[3E-(2,4-Dimethoxy-5-thien-2-ylphenyl)acryloyl]-N-(1-H-tetrazol-5-yl)benzenesulfonamide;

4-[3E-(2,4-Dimethoxy-5-thien-2-ylphenyl)acryloyl]-N-pyridin-2-ylbenzenesulfonamide;

4-[3E-(2,4-Dimethoxy-5-thien-2-ylphenyl)acryloyl]-N-(1H-pyrazol-3-yl)benzenesulfonamide;

4-[3E-(2,4-Dimethoxy-5-thien-2-ylphenyl)acryloyl]-N-isoxazol-3-ylbenzenesulfonamide;

4-[3E-(2,4-Dimethoxy-5-thien-2-ylphenyl)acryloyl]-N-thiazol-2-ylbenzenesulfonamide;

4-[3E-(2,4-Dimethoxy-5-thien-2-ylphenyl)acryloyl]-N-(3-methylisoxazol-5-ylbenzenesulfonamide;

N-(5-Chloropyridin-2-yl)-4-[3E-(2,4-dimethoxy-5-thien-2-ylphenyl)acryloyl]benzenesulfonamide;

4-[3E-(2,4-Dimethoxy-5-thien-2-ylphenyl)acryloyl]-N-(5-fluoropyridin-2-yl)benzenesulfonamide;

4-[3E-(2,4-Dimethoxy-5-thien-2-ylphenyl)acryloyl]-N-(5-trifluoromethylpyridin-2-yl)benzenesulfonamide;

4-{3E-[2-(3-Hydroxy-2-hydroxymethylpropoxy)-4-methoxy-5-thien-2-ylphenyl]acryloyl}-N-(5-methylisoxazol-3-yl)benzenesulfonamide;

4-{3E-[4-Methoxy-2-(2-morpholin-4-yl-ethoxy)-5-thien-2-ylphenyl]acryloyl}-N-isoxazol-3-yl)benzenesulfonamide hydrochloride;

4-{3E-[2,4-Dimethoxy-5-(1-methyl-1H-indol-2-yl)phenyl]acryloyl}-N-(5-methylisoxazol-3-yl)benzenesulfonamide;

4-{3E-[2,4-Dimethoxy-5-(1-methyl-1H-indol-2-yl)phenyl]acryloyl}-N-(5-methylisoxazol-3-yl)benzenesulfonamide sodium salt;

4-{3E-[2,4-Dimethoxy-5-(1-methyl-1H-indol-2-yl)phenyl]acryloyl}-N-pyridin-3-ylmethy-benzenesulfonamide;

4-{3E-[2,4-Dimethoxy-5-(1-methyl-1H-indol-2-yl)phenyl]acryloyl}-N-(2-morpholin-4-yl-ethyl)benzenesulfonamide;

4-[3E-(2,4-Dimethoxy-5-thien-2-ylphenyl)acryloyl]-N-pyridin-3-ylmethylbenzenesulfonamide 4-[3E-(2,4-Dimethoxy-5-thien-2-ylphenyl)acryloyl]!-N-(2-morpholin-4-yl-ethyl)benzenesulfonamide;

3E-(2,4-Dimethoxy-5-thien-2-ylphenyl)-1-[4-(4-methylpiperazine-1-sulfonyl)phenyl]propenone;

4-[3E-(2,4-Dimethoxy-5-thien-2-ylphenyl)acryloyl]-N-piperidin-1-ylbenzenesulfonamide;

4-[3E-(2,4-Dimethoxy-5-thien-2-ylphenyl)acryloyl]-N-(3-imidazol-1-ylpropyl)benzenesulfonamide;

4-[3E-(2,4-Dimethoxy-5-thien-2-ylphenyl)acryloyl]-N-(2,2,2-trifluoroethyl)benzenesulfonamide;

4-[3E-(2,4-Dimethoxy-5-thien-2-ylphenyl)acryloyl]-N-(2,2,2-trifluoroethyl)benzenesulfonamide sodium salt;

{4-[3E-(2,4-Dimethoxy-5-thien-2-ylphenyl)acryloyl]benzenesulfonylamino}acetic acid;

2-{4-[3E-(2,4-Dimethoxy-5-thien-2-yl-phenyl)acryloyl]benzenesulfonylamino}-2-methylpropionic acid;

1-{4-[3E-(2,4-Dimethoxy-5-thien-2-ylphenyl)acryloyl]benzenesulfonyl}piperidine-2-carboxylic acid;

4-{3E-[2,4-Dimethoxy-5-(1-methyl-1H-indol-2-yl)phenyl]acryloyl}-N-methyl-benzenesulfonamide;

4-{3E-[2,4-Dimethoxy-5-(1-methyl-1H-indol-2-yl)phenyl]acryloyl}-N-methoxybenzenesulfonamide;

4-{3E-[2,4-Dimethoxy-5-(1-methyl-1H-indol-2-yl)phenyl]acryloyl}-N,N-dimethylbenzenesulfonamide;

4-{3E-[5-(1H-Indol-2-yl)-2,4-dimethoxyphenyl]acryloyl}-N,N-dimethylbenzenesulfonamide;

4-{3E-[2,4-Dimethoxy-5-(1-methyl-1H-indol-2-yl)phenyl]acryloyl}-N-(tert-butyldimethylsiloxy)benzenesulfonamide;

4-{3E-[2,4-Dimethoxy-5-(1-methyl-1H-indol-2-yl)phenyl]-acryloyl}-N-hydroxybenzenesulfonamide;

4-{3E-[2,4-Dimethoxy-5-(1-methyl-1H-pyrrol-2-yl)phenyl]acryloyl}-N-(5-methyl-isoxazol-3-yl)benzenesulfonamide;

4-{3E-[2-(3-Hydroxy-propoxy)-4-methoxy-5-thien-2-ylphenyl]acryloyl}-N-(5-methylisoxazol-3-yl)benzenesulfonamide;

4-{3E-[2,4-Dimethoxy-5-(1-methyl-1H-pyrrol-2-yl)phenyl]acryloyl}-N-(5-methyl-isoxazol-3-yl)benzenesulfonamide;

N-(3-Imidazol-1-yl-propyl)-4-{3E-[5-(1H-indol-2-yl)-2,4-dimethoxy-phenyl]acryloyl}benzenesulfonamide;

(4-{3E-[5-(1H-Indol-2-yl)-2,4-dimethoxyphenyl]acryloyl}benzenesulfonylamino)acetic acid; and 4-{3E-[5-(1H-Indol-2-yl)-2,4-dimethoxyphenyl]acryloyl}-N-pyridin-2-ylbenzenesulfonamide.

In a 7$^{th}$ embodiment, the invention is represented by Formula III (III)

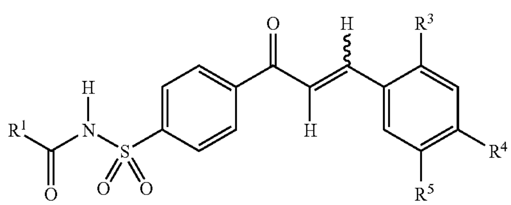

or its pharmaceutically acceptable salt, wherein:

$R^1$ is selected from the group consisting of hydrogen, alkyl, lower alkyl, carbocyclic, cycloalkyl, alkoxy, lower alkoxy, cycloalkyloxy, cycloalkylalkoxy, heterocyclicoxy, aryloxy, heteroaryloxy, aryl, heteroaryl, heterocyclic, arylalkyl, heteroarylalkyl, —$NR^7R^8$, —$NHR^2$, —$N(R^2)_2$, acyl and heterocyclicalkyl, wherein all substituents may be optionally substituted by one or more selected from the group consisting of halo, alkyl, lower alkyl, alkenyl, cycloalkyl, haloalkyl, acyl, hydroxy, hydroxyalkyl, heterocyclic, amino, aminoalkyl, —$NR^7R^8$, —$NHR^2$, —$N(R^2)_2$, alkoxy, oxo, cyano, carboxy, carboxyalkyl, alkoxycarbonyl, heteroaryl, —$C(O)NR^7R^8$, and —$C(O)N(R^2)_2$;

$R^2$ is independently selected from the group consisting of hydrogen, alkyl, lower alkyl, carbocyclic, cycloalkyl, aryl, heteroaryl, heterocyclic, arylalkyl, heteroarylalkyl, acyl, alkoxycarbonyl, and heterocyclicalkyl, wherein all substituents may be optionally substituted by one or more selected from the group consisting of halo, alkyl, lower alkyl, alkenyl, cycloalkyl, haloalkyl, acyl, hydroxy, hydroxyalkyl, heterocyclic, amino, aminoalkyl, —$NR^7R^8$, alkoxy, oxo, cyano, carboxy, carboxyalkyl, alkoxycarbonyl, heteroaryl, —$C(O)NR^7R^8$, —$NR^1R^2$ and—$C(O)N(R^2)_2$;

$R^7$ and $R^8$ are independently selected from the group consisting of alkyl, alkenyl and aryl and linked together forming a 4- to 12-membered monocyclic, bicylic, tricyclic or benzofused ring, which may be optionally substituted by one or more selected from the group consisting of halo, alkyl, lower alkyl, alkenyl, cycloalkyl, haloalkyl, acyl, hydroxy, hydroxyalkyl, heterocyclic, amino, aminoalkyl, —$NR^7R^8$, alkoxy, oxo, cyano, carboxy, carboxyalkyl, alkoxycarbonyl, —$C(O)NR^7R^8$, and —$C(O)N(R^2)_2$;

$R^3$, $R^4$ and $R^5$ are independently selected from hydrogen, hydroxy, alkoxy, lower alkoxy, —$(O(CH_2)_2)_{1-3}$—O-lower alkyl, cycloalkyloxy, cycloalkylalkoxy, haloalkoxy, aryloxy, arylalkoxy, heteroaryloxy, heteroarylalkoxy, heteroaryl lower alkoxy, heterocyclic, heteroaryl, $NR^7R^8$, heterocyclicoxy, heterocyclicalkoxy, heterocyclic lower alkoxy, —$OC(R^1)_2C(O)N(R^2)_2$, and —$OC(R^1)_2C(O)NR^7R^8$, wherein all substituents may be optionally substituted by one or more selected from the group consisting of halo, alkyl, lower alkyl, alkenyl, cycloalkyl, haloalkyl, acyl, hydroxy, hydroxyalkyl, heterocyclic, amino, aminoalkyl, N-linked heteroaryl, —$NR^7R^8$, alkoxy, oxo, cyano, carboxy, carboxyalkyl, alkoxycarbonyl, —$C(O)NR^7R^8$, and —$C(O)N(R^2)_2$;

with the proviso that at least one of $R^3$, $R^4$ or $R^5$ is an N-linked heteroaryl or —$NR^7R^8$.

In an 8$^{th}$ embodiment, the invention is represented by Formula III or its pharmaceutically acceptable salt, wherein:

$R^1$ is selected from the group consisting of hydrogen, alkyl, lower alkyl, alkoxy, lower alkoxy, cycloalkyloxy, cycloalkylalkoxy, heterocyclicoxy, aryloxy, heteroaryloxy, heterocyclic, heteroarylalkyl, acyl and heterocyclicalkyl, wherein all substituents may be optionally substituted by one or more selected from the group consisting of halo, alkyl, lower alkyl, haloalkyl, heterocyclic, amino, aminoalkyl, —$NR^7R^8$, —$NHR^2$, —$N(R^2)_2$, alkoxy, carboxy, carboxyalkyl, alkoxycarbonyl, and heteroaryl;

$R^2$ is independently selected from the group consisting of alkyl, lower alkyl, heteroaryl, heterocyclic, heteroarylalkyl, acyl and heterocyclicalkyl, wherein all substituents may be optionally substituted by one or more selected from the group consisting of halo, alkyl, lower alkyl, haloalkyl, heterocyclic, —$NR^7R^8$, alkoxy, carboxy, carboxyalkyl, alkoxycarbonyl and heteroaryl;

$R^7$ and $R^8$ are independently selected from the group consisting of alkyl, alkenyl and aryl and linked together forming a 5- to 10-membered monocyclic, bicylic or benzofused ring, which may be optionally substituted by one or more selected from the group consisting of halo, alkyl, lower alkyl, haloalkyl, heterocyclic, —$NR^7R^8$, alkoxy, carboxy, carboxyalkyl and alkoxycarbonyl;

$R^3$, $R^4$ and $R^5$ are independently selected from hydrogen, hydroxy, alkoxy, lower alkoxy, —$(O(CH_2)_2)_{1-3}$—O-lower alkyl, haloalkoxy, heteroaryloxy, heteroarylalkoxy, heteroaryl lower alkoxy, heterocyclic, heteroaryl, $NR^7R^8$, heterocyclicoxy, heterocyclicalkoxy, heterocyclic lower alkoxy, —$OC(R^1)_2C(O)N(R^2)_2$, and —$OC(R^1)_2C(O)NR^7R^8$ wherein all substituents may be optionally substituted by one or more selected from the group consisting of halo, alkyl, lower alkyl, hydroxy, hydroxyalkyl, heterocyclic, N-linked heteroaryl, —$NR^7R^8$, alkoxy, —$C(O)NR^7R^8$, and —$C(O)N(R)_2$;

with the proviso that at least one of $R^3$, $R^4$ or $R^5$ is an N-linked heteroaryl or —$NR^7R^8$.

In a 9th embodiment, the invention is represented by Formula III or its pharmaceutically acceptable salt, wherein:

$R^1$ is selected from the group consisting of alkyl, lower alkyl, alkoxy, and lower alkoxy, wherein all substituents may be optionally substituted by one or more selected from the group consisting of halo, alkyl, lower alkyl, amino, —$NR^7R^8$, —$NHR^2$, —$N(R^2)_2$, aminoalkyl, alkoxy, carboxy, carboxyalkyl, alkoxycarbonyl, and heteroaryl;

$R^2$ is independently selected from the group consisting of lower alkyl, heteroarylalkyl, and heterocyclicalkyl, wherein all substituents may be optionally substituted by one or more selected from the group consisting of halo, lower alkyl, haloalkyl, heterocyclic, —$NR^7R^8$ and carboxy;

$R^7$ and $R^8$ are independently selected from the group consisting of alkyl and alkenyl, and linked together forming a 5- to 7-membered monocyclic ring, which may be optionally substituted by one or more selected from the group consisting of halo, lower alkyl, haloalkyl, heterocyclic and carboxy;

$R^3$, $R^4$ and $R^5$ are independently selected from hydrogen, hydroxy, lower alkoxy, —$(O(CH_2)_2)_{1-3}$—O-lower alkyl, heteroaryl lower alkoxy, heterocyclic, heteroaryl, $NR^7R^8$, heterocyclicoxy, heterocyclic lower alkoxy, —$OC(R^1)_2C(O)N(R^2)_2$, and —$OC(R^1)_2C(O)NR^7R^8$, wherein all substituents may be optionally substituted by one or more selected from the group consisting of hydroxy, hydroxyalkyl, heterocyclic, N-linked heteroaryl, —$NR^7R^8$, —$C(O)NR^7R^8$, and —$C(O)N(R^2)_2$;

with the proviso that at least one of $R^3$, $R^4$ or $R^5$ is an N-linked heteroaryl or —$NR^7R^8$.

In a 10th embodiment, the invention is represented by Formula III or its pharmaceutically acceptable salt, wherein:

$R^1$ is selected from the group consisting of lower alkyl, and lower alkoxy, wherein all substituents may be optionally substituted by one or more selected from the group consisting of alkoxy, —$NR^7R^8$, —$NHR^2$, and —$N(R^2)_2$;

$R^2$ is lower alkyl;

$R^7$ and $R^8$ are independently alkyl and linked together forming a 5- to 7-membered saturated monocyclic ring;

$R^3$, $R^4$ and $R^5$ are independently selected from hydrogen, hydroxy, lower alkoxy, heterocyclic, heteroaryl, $NR^7R^8$ and heterocyclic lower alkoxy;

with the proviso that at least one of $R^3$, $R^4$ or $R^5$is an N-linked heteroaryl or —$NR^7R^8$.

In an 11th embodiment, the invention is represented by Formula III or its pharmaceutically acceptable salt, wherein:

$R^1$ is selected from the group consisting of lower alkyl, and lower alkoxy;

$R^7$ and $R^8$ are independently alkyl and linked together forming a 5- to 7-membered saturated monocyclic ring;

$R^3$, $R^4$ and $R^5$ are independently selected from lower alkoxy, $NR^7R^8$ and heterocyclic lower alkoxy;

with the proviso that at least one of $R^3$, $R^4$ or $R^5$ is —$NR^7R^8$.

In the 12th embodiment, the invention is represented by Formula III or its the compound is N-Butyryl-4-[3E-(2,4-dimethoxy-5-pyrrolidin-1-ylphenyl)acryloyl]benzenesulfonamide.

In a 13th embodiment, the invention is represented by Formula III (III)

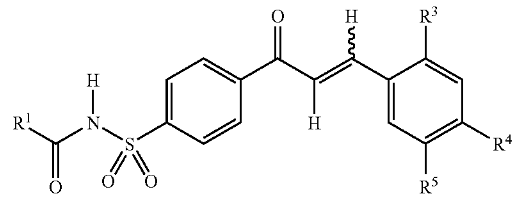

or its pharmaceutically acceptable salt, wherein:

$R^1$ is selected from the group consisting of hydrogen, alkyl, lower alkyl, carbocyclic, cycloalkyl, alkoxy, lower alkoxy, cycloalkyloxy, cycloalkylalkoxy, heterocyclicoxy, aryloxy, heteroaryloxy, aryl, heteroaryl, heterocyclic, arylalkyl, heteroarylalkyl, —$NR^7R^8$, —$NHR^2$, —$N(R^2)_2$, acyl and heterocyclicalkyl, wherein all substituents may be optionally substituted by one or more selected from the group consisting of halo, alkyl, lower alkyl, alkenyl, cycloalkyl, haloalkyl, acyl, hydroxy, hydroxyalkyl, heterocyclic, amino, aminoalkyl, —$NR^7R^8$, —$NHR^2$, —$N(R^2)_2$, alkoxy, oxo, cyano, carboxy, carboxyalkyl, alkoxycarbonyl, heteroaryl, —$C(O)NR^7R^8$, and —$C(O)N(R^2)_2$;

$R^2$ is independently selected from the group consisting of hydrogen, alkyl, lower alkyl, carbocyclic, cycloalkyl, aryl, heteroaryl, heterocyclic, arylalkyl, heteroarylalkyl, acyl, alkoxycarbonyl, and heterocyclicalkyl, wherein all substituents may be optionally substituted by one or more selected from the group consisting of halo, alkyl, lower alkyl, alkenyl, cycloalkyl, haloalkyl, acyl, hydroxy, hydroxyalkyl, heterocyclic, amino, aminoalkyl, —$NR^7R^8$, alkoxy, oxo, cyano, carboxy, carboxyalkyl, alkoxycarbonyl, heteroaryl, —$C(O)NR^7R^8$, —$NR^1R^2$ and —$C(O)N(R^2)_2$;

$R^7$ and $R^8$ are independently selected from the group consisting of alkyl, alkenyl and aryl and linked together forming a 4- to 12-membered monocyclic, bicylic, tricyclic or benzofused ring, which may be optionally substituted by one or more selected from the group consisting of halo, alkyl, lower alkyl, alkenyl, cycloalkyl, haloalkyl, acyl, hydroxy, hydroxyalkyl, heterocyclic, amino, aminoalkyl, —$NR^7R^8$, alkoxy, oxo, cyano, carboxy, carboxyalkyl, alkoxycarbonyl, —$C(O)NR^7R^8$, and —$C(O)N(R^2)_2$;

$R^3$ and $R^4$ are independently selected from hydrogen, hydroxy, alkoxy, lower alkoxy, —$(O(CH_2)_2)_{1-3}$—O-lower alkyl, cycloalkyloxy, cycloalkylalkoxy, haloalkoxy, aryloxy, arylalkoxy, heteroaryloxy, heteroarylalkoxy, heteroaryl lower alkoxy, heterocyclicoxy, heterocyclicalkoxy, heterocyclic lower alkoxy, —$OC(R^1)_2C(O)N(R^2)_2$, and —$OC(R^1)_2C(O)NR^7R^8$, wherein all substituents may be optionally substituted by one or more selected from the group consisting of halo, alkyl, lower alkyl, alkenyl, cycloalkyl, haloalkyl, acyl, hydroxy, hydroxyalkyl, heterocyclic, amino, aminoalkyl, N-linked heteroaryl, —$NR^7R^8$, alkoxy, oxo, cyano, carboxy, carboxyalkyl, alkoxycarbonyl, —$C(O)NR^7R^8$, and —$(O)N(R^2)_2$;

$R^5$ is selected from the group consisting of a carbon-carbon linked heterocyclic and a carbon-carbon linked heteroaryl, which may be optionally substituted by one or more selected from the group consisting of halo, alkyl, lower alkyl, alkenyl, cycloalkyl, haloalkyl, acyl, hydroxy, hydroxyalkyl, heterocyclic, amino, aminoalkyl, —$NR^7R^8$, alkoxy, oxo, cyano, carboxy, carboxyalkyl, alkoxycarbonyl, —$C(O)NR^7R^8$, and —$C(O)N(R^2)_2$;

with the proviso that when $R^1$ is isopropyl, $R^5$ cannot be 5-benzo[b]thien-2-yl.

In a $14^{th}$ embodiment, the invention is represented by Formula III or its pharmaceutically acceptable salt, wherein:

$R^1$ is selected from the group consisting of hydrogen, alkyl, lower alkyl, alkoxy, lower alkoxy, cycloalkyloxy, cycloalkylalkoxy, heterocyclicoxy, aryloxy, heteroaryloxy, heterocyclic, heteroarylalkyl, and heterocyclicalkyl, wherein all substituents may be optionally substituted by one or more selected from the group consisting of halo, alkyl, lower alkyl, haloalkyl, heterocyclic, amino, aminoalkyl, —$NR^7R^8$, —$NHR^2$, —$N(R^2)_2$, alkoxy, carboxy, carboxyalkyl, alkoxycarbonyl, and heteroaryl;

$R^2$ is independently selected from the group consisting of alkyl, lower alkyl, heteroaryl, heterocyclic, heteroarylalkyl, and heterocyclicalkyl, wherein all substituents may be optionally substituted by one or more selected from the group consisting of halo, alkyl, lower alkyl, haloalkyl, heterocyclic, —$NR^7R^8$, alkoxy, carboxy, carboxyalkyl, alkoxycarbonyl and heteroaryl;

$R^7$ and $R^8$ are independently selected from the group consisting of alkyl, alkenyl and aryl and linked together forming a 5- to 10-membered monocyclic, bicylic or benzofused ring, which may be optionally substituted by one or more selected from the group consisting of halo, alkyl, lower alkyl, haloalkyl, heterocyclic, —$NR^7R^8$, alkoxy, carboxy, carboxyalkyl and alkoxycarbonyl;

$R^3$ and $R^4$ are independently selected from hydroxy, alkoxy, lower alkoxy, —$(O(CH_2)_2)_{1-3}$—O-lower alkyl, haloalkoxy, heteroaryloxy, heteroarylalkoxy, heteroaryl lower alkoxy, heterocyclicoxy, heterocyclicalkoxy, heterocyclic lower alkoxy, —$OC(R^1)_2C(O)N(R^2)_2$, and —$OC(R^1)_2C(O)NR^7R^8$, wherein all substituents may be optionally substituted by one or more selected from the group consisting of halo, alkyl, lower alkyl, hydroxy, hydroxyalkyl, heterocyclic, —$NR^7R^8$, alkoxy, —$C(O)NR^7R^8$, and —$C(O)N(R^2)_2$;

$R^5$ is selected from the group consisting of a carbon-carbon linked heteroaryl and a carbon-carbon linked heterocyclic, which may be optionally substituted by one or more selected from the group consisting of halo, alkyl, lower alkyl, haloalkyl, heterocyclic, —$NR^7R^8$ and alkoxy;

with the proviso that when $R^1$ is isopropyl, $R^5$ cannot be 5-benzo[b]thien-2-yl.

In $15^{th}$ embodiment, the invention is represented by Formula III or its pharmaceutically acceptable salt, wherein:

$R^1$is selected from the group consisting of alkyl, lower alkyl, alkoxy, and lower alkoxy, wherein all substituents may be optionally substituted by one or more selected from the group consisting of halo, alkyl, lower alkyl, amino, aminoalkyl, —$NR^7R^8$, —$NHR^2$, —$N(R^2)_2$, alkoxy, carboxy, carboxyalkyl, alkoxycarbonyl, and heteroaryl;

$R^2$ is independently selected from the group consisting of lower alkyl, heteroarylalkyl, and heterocyclicalkyl, wherein all substituents may be optionally substituted by one or more selected from the group consisting of halo, lower alkyl, haloalkyl, heterocyclic, —$NR^7R^8$ and carboxy;

$R^7$ and $R^8$ are independently selected from the group consisting of alkyl and alkenyl, and linked together forming a 5- to 7-membered monocyclic ring, which may be optionally substituted by one or more selected from the group consisting of halo, lower alkyl, haloalkyl, heterocyclic and carboxy;

$R^3$ and $R^4$ are independently selected from hydroxy, lower alkoxy, —$(O(CH_2)_2)_{1-3}$—O-lower alkyl, heteroaryl lower alkoxy, heterocyclicoxy, heterocyclicalkoxy, heterocyclic lower alkoxy, —$OC(R^1)_2C(O)N(R^2)_2$, and —$OC(R^1)_2C(O)NR^7R^8$, wherein all substituents may be optionally substituted by one or more selected from the group consisting of hydroxy, hydroxyalkyl, heterocyclic, —$NR^7R^8$, —$C(O)NR^7R^8$, and —$C(O)N(R^2)_2$;

$R^5$ is selected from the group consisting of a carbon-carbon linked heteroaryl and a carbon-carbon linked heterocyclic, which may be optionally substituted by one or more lower alkyl;

with the proviso that when $R^1$ is isopropyl, $R^5$ cannot be 5-benzo[b]thien-2-yl.

In a $16^{th}$ embodiment, the invention is represented by Formula III or its pharmaceutically acceptable salt, wherein:

$R^1$ is selected from the group consisting of lower alkyl, and lower alkoxy, wherein all substituents may be optionally substituted by one or more selected from the group consisting of alkoxy, —$NR^7R^8$, —$NHR^2$, and —$N(R^2)_2$;

$R^2$ is lower alkyl;

$R^7$ and $R^8$ are independently alkyl and linked together forming a 5- to 7-membered saturated monocyclic ring;

$R^3$ and $R^4$ are independently selected from hydroxy, lower alkoxy and heterocyclic lower alkoxy;

$R^5$ is selected from the group consisting of a carbon-carbon linked heteroaryl and a carbon-carbon linked heterocyclic, which may be optionally substituted by one or more lower alkyl;

with the proviso that when $R^1$ is isopropyl, $R^5$ cannot be 5-benzo[b]thien-2-yl.

In a $17^{th}$ embodiment, the invention is represented by Formula III or its pharmaceutically acceptable salt, wherein:

$R^1$ is selected from the group consisting of lower alkyl, and lower alkoxy;

$R^3$ and $R^4$ are independently selected from lower alkoxy and heterocyclic lower alkoxy;

$R^5$ is a carbon-carbon linked heteroaryl, which may be optionally substituted by one or more lower alkyl;

with the proviso that when $R^1$ is isopropyl, $R^5$ cannot be 5-benzo[b]thien-2-yl.

In a $18^{th}$ embodiment, the invention is represented by Formula III or its pharmaceutically acceptable salt, wherein the compound is selected from the group consisting of 4-{3E-[5-(1H-Indol-2-yl)-2,4-dimethoxyphenyl]acryloyl}-N-isobutyrylbenzenesulfonamide;

4-{3E-[5-(1H-Indol-2-yl)-2,4-dimethoxyphenyl]acryloyl}-N-isobutyrylbenzenesulfonamide sodium salt;

N-Butyryl-4-{3E-[2,4-dimethoxy-5-(1-methyl-1H-indol-2-yl)phenyl]acryloyl}benzenesulfonamide;

N-Ethoxycarbonyl-4-{3E-[5-(1H-indol-2-yl)-2,4-dimethoxyphenyl]acryloyl}benzenesulfonamide potassium salt;

N-Ethoxycarbonyl-4-{3E-[5-(1H-indol-2-yl)-2,4-dimethoxyphenyl]acryloyl}benzenesulfonamide;

N-Acetyl-4-{3E-[5-(1H-indol-2-yl)-2,4-dimethoxyphenyl]acryloyl}benzenesulfonamide;

N-Acetyl-4-{3E-[5-(1H-indol-2-yl)-2,4-dimethoxyphenyl]acryloyl}benzenesulfonamide sodium salt;

4-{3E-[5-(1H-Indol-2-yl)-2,4-dimethoxyphenyl]acryloyl}-N-propionyl-benzenesulfonamide;

4-{3E-[5-(1H-Indol-2-yl)-2,4-dimethoxyphenyl]acryloyl}-N-propionylbenzenesulfonamide sodium salt;

N-Butyryl-4-{3E-[5-(1H-indol-2-yl)-2,4-dimethoxyphenyl]acryloyl}benzenesulfonamide; and N-Butyryl-4-{3E-[5-(1H-indol-2-yl)-2,4-dimethoxyphenyl]acryloyl}benzenesulfonamide sodium salt.

In a $19^{th}$ embodiment, the invention is represented by Formula I (I)

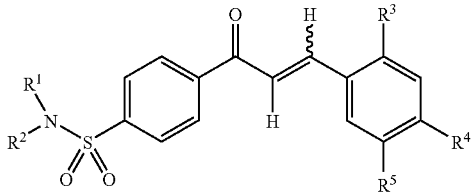

or its pharmaceutically acceptable salt, wherein:

$R^1$ is selected from the group consisting of hydrogen, alkyl, lower alkyl, carbocyclic, cycloalkyl, aryl, heteroaryl, heterocyclic, arylalkyl, heteroarylalkyl, acyl and heterocyclicalkyl, wherein all substituents may be optionally substituted by one or more selected from the group consisting of halo, alkyl, lower alkyl, alkenyl, cycloalkyl, haloalkyl, acyl, hydroxy, hydroxyalkyl, heterocyclic, amino, aminoalkyl, —$NR^7R^8$, alkoxy, oxo, cyano, carboxy, carboxyalkyl, alkoxycarbonyl, heteroaryl, —$C(O)NR^7R^8$, and —$C(O)N(R^2)_2$;

$R^2$ is independently selected from the group consisting of alkyl, lower alkyl, carbocyclic, cycloalkyl, hydroxy, alkoxy, lower alkoxy, trialkylsilyloxy, cycloalkyloxy, cycloalkylalkoxy, heterocyclicoxy, aryl, heteroaryl, heterocyclic, arylalkyl, heteroarylalkyl, acyl, alkoxycarbonyl, and heterocyclicalkyl, wherein all substituents may be optionally substituted by one or more selected from the group consisting of halo, alkyl, lower alkyl, alkenyl, cycloalkyl, haloalkyl, acyl, hydroxy, hydroxyalkyl, heterocyclic, amino, aminoalkyl, —$NR^7R^8$, alkoxy, oxo, cyano, carboxy, carboxyalkyl, alkoxycarbonyl, heteroaryl, —$C(O)NR^7R^8$, —$NR^1R^2$ and —$(O)N(R^2)_2$;

$R^1$ and $R^2$ may be taken together to form a 4- to 12-membered saturated or unsaturated heterocyclic ring which can be optionally substituted by one or more selected from the group consisting of halo, alkyl, lower alkyl, alkenyl, cycloalkyl, haloalkyl, acyl, hydroxy, hydroxyalkyl, heterocyclic, amino, aminoalkyl, —$NR^7R^8$, alkoxy, oxo, cyano, carboxy, carboxyalkyl, alkoxycarbonyl, —$C(O)NR^7R^8$, and —$C(O)N(R^2)_2$;

$R^7$ and $R^8$ are independently selected from the group consisting of alkyl, alkenyl and aryl and linked together forming a 4- to 12-membered monocyclic, bicylic, tricyclic or benzofused ring, which may be optionally substituted by one or more selected from the group consisting of halo, alkyl, lower alkyl, alkenyl, cycloalkyl, haloalkyl, acyl, hydroxy, hydroxyalkyl, heterocyclic, amino, aminoalkyl, —$NR^7R^8$, alkoxy, oxo, cyano, carboxy, carboxyalkyl, alkoxycarbonyl, —$C(O)NR^7R^8$, and —$C(O)N(R^2)_2$;

$R^3$ and $R^4$ are independently selected from hydroxy, alkoxy, lower alkoxy, —$(O(CH_2)_2)_{1-3}$—O-lower alkyl, cycloalkyloxy, cycloalkylalkoxy, haloalkoxy, aryloxy, arylalkoxy, heteroaryloxy, heteroarylalkoxy, heteroaryl lower alkoxy, heterocyclicoxy, heterocyclicalkoxy, heterocyclic lower alkoxy, —$OC(R^1)_2C(O)N(R^2)_2$, and —$OC(R^1)_2C(O)NR^7R^8$, wherein all substituents may be optionally substituted by one or more selected from the group consisting of halo, alkyl, lower alkyl, alkenyl, cycloalkyl, haloalkyl, acyl, hydroxy, hydroxyalkyl, heterocyclic, amino, aminoalkyl, —$NR^7R^8$, alkoxy, oxo, cyano, carboxy, carboxyalkyl, alkoxycarbonyl, —$C(O)NR^7R^8$, and —$C(O)N(R^2)_2$;

$R^5$ is selected from the group consisting of a carbon-nitrogen linked heteroaryl and a carbon-nitrogen linked heterocyclic, which may be optionally substituted by one or more selected from the group consisting of halo, alkyl, lower alkyl, alkenyl, cycloalkyl, haloalkyl, acyl, hydroxy, hydroxyalkyl, heterocyclic, amino, aminoalkyl, —$NR^7R^8$, alkoxy, oxo, cyano, carboxy, carboxyalkyl, alkoxycarbonyl, —$C(O)NR^7R^8$, and —$C(O)N(R^2)_2$.

In a $20^{th}$ embodiment, the invention is represented by Formula I or its pharmaceutically acceptable salt, wherein:

$R^1$ is selected from the group consisting of hydrogen, alkyl, and lower alkyl, wherein all substituents may be optionally substituted by one or more selected from the group consisting of halo, alkyl, lower alkyl, haloalkyl, heterocyclic, —$NR^7R^8$, alkoxy, carboxy, carboxyalkyl, alkoxycarbonyl and heteroaryl;

$R^2$ is independently selected from the group consisting of alkyl, lower alkyl, alkoxy, lower alkoxy, heteroaryl, heterocyclic, heteroarylalkyl, and heterocyclicalkyl, wherein all substituents may be optionally substituted by one or more selected from the group consisting of halo, alkyl, lower alkyl, haloalkyl, heterocyclic, —$NR^7R^8$, alkoxy, carboxy, carboxyalkyl, alkoxycarbonyl and heteroaryl;

$R^1$ and $R^2$ may be taken together to form a 5- to 7-membered saturated or unsaturated heterocyclic ring which can be optionally substituted by one or more selected from the group consisting of halo, alkyl, lower alkyl, haloalkyl, heterocyclic, —$NR^7R^8$, alkoxy, carboxy, carboxyalkyl and alkoxycarbonyl;

$R^7$ and $R^8$ are independently selected from the group consisting of alkyl, alkenyl and aryl and linked together forming a 5- to 10-membered monocyclic, bicylic or benzofused ring, which may be optionally substituted by one or more selected from the group consisting of halo, alkyl, lower alkyl, haloalkyl, heterocyclic, —$NR^7R^8$, alkoxy, carboxy, carboxyalkyl and alkoxycarbonyl;

$R^3$ and $R^4$ are independently selected from hydroxy, alkoxy, lower alkoxy, —$(O(CH_2)_2)_{1-3}$—O-lower alkyl, haloalkoxy, heteroaryloxy, heteroarylalkoxy, heteroaryl lower alkoxy, heterocyclicoxy, heterocyclicalkoxy, heterocyclic lower alkoxy, —$OC(R^1)_2C(O)N(R^2)_2$, and —$OC(R^1)_2C(O)NR^7R^8$, wherein all substituents may be optionally substituted by one or more selected from the group consisting of halo, alkyl, lower alkyl, hydroxy, hydroxyalkyl, heterocyclic, —$NR^7R^8$, alkoxy, —$C(O)NR^7R^8$, and —$C(O)N(R^2)_2$;

$R^5$ is selected from the group consisting of a carbon-nitrogen linked heteroaryl and a carbon-nitrogen linked heterocyclic, which may be optionally substituted by one or more selected from the group consisting of halo, alkyl, lower alkyl, haloalkyl, heterocyclic, —$NR^7R^8$ and alkoxy.

In a $21^{st}$ embodiment, the invention is represented by Formula I or its pharmaceutically acceptable salt, wherein:

$R^1$ is selected from the group consisting of hydrogen and lower alkyl;

$R^2$ is independently selected from the group consisting of lower alkyl, lower alkoxy, heteroaryl, heterocyclic, heteroarylalkyl, and heterocyclicalkyl, wherein all substituents may be optionally substituted by one or more selected from the group consisting of halo, lower alkyl, haloalkyl, heterocyclic, heteroaryl, —$NR^7R^8$ and carboxy;

$R^1$ and $R^2$ may be taken together to form a 5- to 6-membered heterocyclic saturated ring which can be optionally substituted by one or more selected from the group consisting of halo, lower alkyl and carboxy;

$R^7$ and $R^8$ are independently selected from the group consisting of alkyl and alkenyl, and linked together forming a 5- to 7-membered monocyclic ring, which may be optionally substituted by one or more selected from the group consisting of halo, lower alkyl, haloalkyl, heterocyclic and carboxy;

$R^3$ and $R^4$ are independently selected from hydroxy, lower alkoxy, —$(O(CH_2)_2)_{1-3}$-O-lower alkyl, heteroaryl lower alkoxy, heterocyclicoxy, heterocyclicalkoxy, heterocyclic lower alkoxy, —$OC(R^1)_2C(O)N(R^2)_2$, and —$OC(R^1)_2C(O)NR^7R^8$, wherein all substituents may be optionally substituted by one or more selected from the group consisting of hydroxy, hydroxyalkyl, heterocyclic, —$NR^7R^8$, —$C(O)NR^7R^8$, and —$C(O)N(R^2)_2$;

$R^5$ is selected from the group consisting of a carbon-nitrogen linked heteroaryl and a carbon-nitrogen linked heterocyclic, which may be optionally substituted by one or more lower alkyl.

In a 22$^{nd}$ embodiment, the invention is represented by Formula I or its pharmaceutically acceptable salt, wherein:

$R^1$ is hydrogen;

$R^2$ is independently selected from the group consisting of lower alkyl, heteroaryl, heteroarylalkyl, and heterocyclicalkyl, wherein all substituents may be optionally substituted by one or more selected from the group consisting of halo, heterocyclic, heteroaryl, and lower alkyl;

$R^1$ and $R^2$ may be taken together to form a 5- to 6-membered heterocyclic saturated ring;

$R^7$ and $R^8$ are independently alkyl and linked together forming a 5- to 7-membered saturated monocyclic ring;

$R^3$ and $R^4$ are independently selected from hydroxy, lower alkoxy and heterocyclic lower alkoxy;

$R^5$ is selected from the group consisting of a carbon-nitrogen linked heterocyclic, which may be optionally substituted by one or more lower alkyl.

In a 23$^{rd}$ embodiment, the invention is represented by Formula I or its pharmaceutically acceptable salt, wherein:

$R^1$ is hydrogen;

$R^2$ is independently selected from the group consisting of lower alkyl, heteroaryl, heteroarylalkyl, and heterocyclicalkyl, wherein all substituents may be optionally substituted by one or more selected from the group consisting of halo, heterocyclic, heteroaryl, and lower alkyl;

$R^3$ and $R^4$ are independently selected from lower alkoxy and heterocyclic lower alkoxy;

$R^5$ is a carbon-nitrogen linked heterocyclic.

In a 24$^{th}$ embodiment, the invention is represented by Formula I, wherein the compound is selected from the group consisting of:

4-[3E-(2,4-Dimethoxy-5-pyrrolidin-1-yl-phenyl)-acryloyl]-N-pyridin-2-yl-benzenesulfonamide;

4-[3E-(2,4-Dimethoxy-5-pyrrolidin-1-ylphenyl)acryloyl]-N-pyridin-2-ylmethylbenzenesulfonamide;

4-[3E-(2,4-Dimethoxy-5-pyrrolidin-1-ylphenyl)acryloyl]-N-(3-imidazol-1-ylpropyl)benzenesulfonamide;

4-[3E-(2,4-Dimethoxy-5-pyrrolidin-1-ylphenyl)acryloyl]-N-[3-(4-methyl-piperazin-1-yl)propyl]benzenesulfonamide; and {4-[3E-(2,4-Dimethoxy-5-pyrrolidin-1-ylphenyl)acryloyl] benzenesulfonylamino}acetic acid.

In a 25$^{th}$ embodiment, the invention is a pharmaceutical composition comprising a therapeutically effective amount of a compound of embodiment 1, 2, 3, 4, 5, 6, 7, 8, 9, 10, 11, 12, 13, 14, 15, 16, 17, 18, 19, 20, 21, 22, 23 or 24, together with one or more pharmaceutically acceptable carrier.

In a 26$^{th}$ embodiment, the invention is represented by a method for the treatment or prophylaxis of an inflammatory disorder, comprising administering an effective amount of a compound of embodiment 1, 2, 3, 4, 5, 6, 7, 8, 9, 10, 11, 12, 13, 14, 15, 16, 17, 18, 19, 20, 21, 22, 23 or 24.

In a 27$^{th}$ embodiment, the invention is represented by embodiment 26, wherein the disorder is arthritis.

In a 28$^{th}$ embodiment, the invention is represented by embodiment 26, wherein the disorder is rheumatoid arthritis.

In a 29$^{th}$ embodiment, the invention is represented by embodiment 26, wherein the disorder is asthma.

In a 30$^{th}$ embodiment, the invention is represented by embodiment 26, wherein the treatment is disease modifying for the treatment of rheumatoid arthritis.

In a 31$^{st}$ embodiment, the invention is represented by embodiment 26, wherein the disorder is allergic rhinitis.

In a 32$^{nd}$ embodiment, the invention is represented by embodiment 26, wherein the disorder is chronic obstructive pulmonary disease.

In a 33$^{rd}$ embodiment, the invention is represented by embodiment 26, wherein the disorder is atherosclerosis.

In a 34$^{th}$ embodiment, the invention is represented by embodiment 26, wherein the disorder is restinosis.

In a 35$^{th}$ embodiment, the invention is represented by embodiment, the invention is represented by a method for inhibiting the expression of VCAM-1, comprising administering an effective amount of a compound of embodiment 1, 2, 3, 4, 5, 6, 7, 8, 9, 10, 11, 12, 13, 14, 15, 16, 17, 18, 19, 20, 21, 22, 23 or 24.

In further embodiments, the invention is represented by intermediates used to make the final compounds of the invention. Said intermediates are useful as starting materials for making the compounds of the invention as well as having pharmaceutical activity alone. Particular intermediates include the ones represented by embodiment 36, represented by the formulas

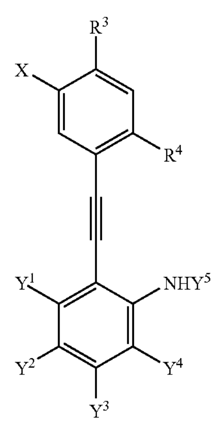

and

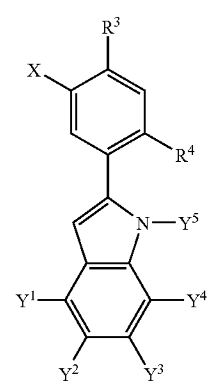

wherein

X is —C(O)H or —$CH_2OH$;

$R^3$ and $R^4$ are independently selected from the group consisting of hydroxy, alkoxy, lower alkoxy, —$(O(CH_2)_2)_{1-3}$—O-lower alkyl, cycloalkyloxy, cycloalkylalkoxy, haloalkoxy, aryloxy, arylalkoxy, heteroaryloxy, heteroarylalkoxy, heteroaryl lower alkoxy, heterocyclicoxy, heterocyclicalkoxy, heterocyclic lower alkoxy, —$OC(R^9)_2C(O)N(R^9)_2$, and —$OC(R^9)_2C(O)NR^7R^8$, wherein all substituents may be optionally substituted by one or more selected from the group consisting of halo, alkyl, lower alkyl, alkenyl, cycloalkyl, haloalkyl, acyl, hydroxy, hydroxyalkyl, heterocyclic, amino, aminoalkyl, —$NR^7R^8$, alkoxy, oxo, cyano, carboxy, carboxyalkyl, alkoxycarbonyl, —$C(O)NR^7R^8$, and —$C(O)N(R^9)_2$;

$Y^1$, $Y^2$, $Y^3$, and $Y^4$ are independently selected from the group consisting of hydrogen, hydroxyl, halo, alkyl, lower alkyl, alkenyl, cycloalkyl, haloalkyl, acyl, hydroxy, hydroxyalkyl, heterocyclic, amino, aminoalkyl, —$NR^7R^8$, alkoxy, oxo, cyano, carboxy, carboxyalkyl, alkoxycarbonyl, heteroaryl, —$C(O)NR^7R^8$, and —$C(O)N(R^9)_2$, wherein all substituents, when possible may be optionally substituted by one or more selected from the group consisting of hydroxyl, halo, alkyl, lower alkyl, alkenyl, cycloalkyl, haloalkyl, acyl, hydroxy, hydroxyalkyl, heterocyclic, amino, aminoalkyl, —$NR^7R^8$, alkoxy, oxo, cyano, carboxy, carboxyalkyl, alkoxycarbonyl, heteroaryl, —$C(O)NR^7R^8$, and —$C(O)N(R^2)_2$.

$Y^5$ is selected from the group consisting of hydrogen, alkyl, lower alkyl, acyl, and alkoxycarbonyl wherein all substituents, when possible may be optionally substituted by one or more selected from the group consisting of hydroxyl, halo, alkyl, lower alkyl, alkenyl, cycloalkyl, haloalkyl, acyl, hydroxy, hydroxyalkyl, heterocyclic, amino, aminoalkyl, —$NR^7R^8$, alkoxy, oxo, cyano, carboxy, carboxyalkyl, alkoxycarbonyl, heteroaryl, —$C(O)NR^7R^8$, and —$C(O)N(R^9)_2$;

$R^9$ is independently selected from the group consisting of alkyl, lower alkyl, carbocyclic, cycloalkyl, hydroxy, alkoxy, lower alkoxy, trialkylsilyloxy, cycloalkyloxy, cycloalkylalkoxy, heterocyclicoxy, aryl, heteroaryl, heterocyclic, arylalkyl, heteroarylalkyl, acyl, alkoxycarbonyl, and heterocyclicalkyl, wherein all substituents may be optionally substituted by one or more selected from the group consisting of halo, alkyl, lower alkyl, alkenyl, cycloalkyl, haloalkyl, acyl, hydroxy, hydroxyalkyl, heterocyclic, amino, aminoalkyl, —$NR^7R^8$, —$NHR^9$, —$N(R^9)_2$, alkoxy, oxo, cyano, carboxy, carboxyalkyl, alkoxycarbonyl, heteroaryl, —$C(O)NR^7R^8$, —$NR^9R^9$ and —$C(O)N(R^9)_2$;

$R^7$ and $R^8$ are independently selected from the group consisting of alkyl, alkenyl and aryl and linked together forming a 4- to 12-membered monocyclic, bicylic, tricyclic or benzofused ring, which may be optionally substituted by one or more selected from the group consisting of halo, alkyl, lower alkyl, alkenyl, cycloalkyl, haloalkyl, acyl, hydroxy, hydroxyalkyl, heterocyclic, amino, aminoalkyl, —$NR^7R^8$, alkoxy, oxo, cyano, carboxy, carboxyalkyl, alkoxycarbonyl, —$C(O)NR^7R^8$, and —$C(O)N(R^9)_2$.

In a $37^{th}$ embodiment, the invention is represented by embodiment 36 wherein the compound is selected from

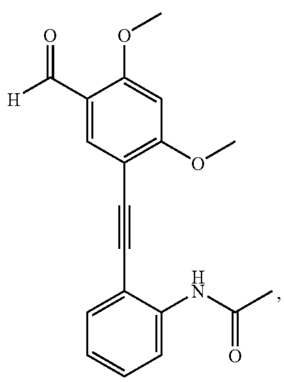
,
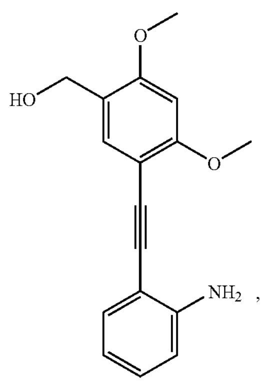
,
or

-continued

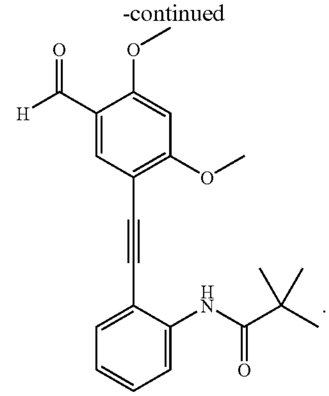
.

Another embodiment of the invention includes the process for making both the intermediates as well as the final compounds.

Definitions

A wavy line used as a bond "∿∿", denotes a bond which can be either the E- or Z-geometric isomer.

When not used as a bond, the wavy line indicates the point of attachment of the particular substituent.

The terms "alkyl" or "alk", alone or in combination, unless otherwise specified, refers to a saturated straight or branched primary, secondary, or tertiary hydrocarbon from 1 to 10 carbon atoms, including, but not limited to methyl, ethyl, propyl, isopropyl, butyl, isobutyl, t-butyl, and sec-butyl. The term "lower alkyl" alone or in combination refers to an alkyl having from 1 to 4 carbon atoms. The alkyl group may be optionally substituted with any moiety that does not otherwise interfere with the reaction or that provides an improvement in the process, including but not limited to but limited to halo, haloalkyl, hydroxyl, carboxyl, acyl, aryl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphonate, either unprotected, or protected as necessary, as known to those skilled in the art, for example, as taught in Greene et al., *Protective Groups in Organic Synthesis,* John Wiley & Sons, Second Edition, 1991, hereby incorporated by reference. Specifically included are $CF_3$ and $CH_2CF_3$.

The term "alkenyl", alone or in combination, means a non-cyclic alkyl of 2 to 10 carbon atoms having one or more unsaturated carbon-carbon bonds. The alkenyl group may be optionally substituted with any moiety that does not otherwise interfere with the reaction or that provides an improvement in the process, including but not limited to but limited to halo, haloalkyl, hydroxyl, carboxyl, acyl, aryl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphonate, either unprotected, or protected as necessary, as known to those skilled in the art, for example, as taught in Greene et al., *Protective Groups in Organic Synthesis,* John Wiley & Sons, Second Edition, 1991, hereby incorporated by reference. Specifically included are $CF_3$ and $CH_2CF_3$.

The term "alkynyl", alone or in combination, means a non-cyclic alkyl of 2 to 10 carbon atoms having one or more triple carbon-carbon bonds, including but not limited to ethynyl and propynyl. The alkynyl group may be optionally substituted with any moiety that does not otherwise interfere with the reaction or that provides an improvement in the process, including but not limited to but limited to halo, haloalkyl, hydroxyl, carboxyl, acyl, aryl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphonate, either unprotected, or protected as necessary, as known to those skilled in the art, for example, as taught in Greene et al., *Protective Groups in Organic Synthesis,* John Wiley & Sons, Second Edition, 1991, hereby incorporated by reference. Specifically included are $CF_3$ and $CH_2CF_3$.

The terms "carboxy", "COOH" and "C(O)OH" are used interchangeably.

The terms "alkoxycarbonyl" and "carboalkoxy" are used interchangeably. Used alone or in combination, the terms mean refer to the radical —C(O)OR, wherein R is alkyl that can be optionally substituted as defined herein.

The term "thio", alone or in combination, means the radical —S—.

The term "thiol", alone or in combination, means the radical —SH.

The term "hydroxy", alone or in combination means the radical —OH.

The term "sulfonyl", alone or in combination means the radical $—S(O)_2—$.

The term "oxo" refers to an oxygen attached by a double bond (═O).

The terms "carbocycle" and "carbocyclic", alone or in combination, means any stable 3- to 7-membered monocyclic or bicyclic or 7- to 14-membered bicyclic or tricyclic or an up to 26-membered polycyclic carbon ring, any of which may be saturated, partially unsaturated, or aromatic. Examples of such carbocyles include, but are not limited to, cyclopropyl, cyclopentyl, cyclohexyl, phenyl, biphenyl, naphthyl, indanyl, adamantyl, or tetrahydronaphthyl (tetralin).

The term "cycloalkyl", alone or in combination, means a saturated or partially unsaturated cyclic alkyl, having from 1 to 10 carbon atoms, including but not limited to mono- or bi-cyclic ring systems such as cyclopropyl, cyclobutyl, cyclopentyl, cyclohexenyl, and cyclohexyl.

The term "aryl", alone or in combination, means a carbocyclic aromatic system containing one, two or three rings wherein such rings may be attached together in a pendent manner or may be fused. The "aryl" group can be optionally substituted with one or more of the moieties selected from the group consisting of alkyl, alkenyl, alkynyl, heteroaryl, heterocyclic, carbocycle, alkoxy, oxo, aryloxy, arylalkoxy, cycloalkyl, tetrazolyl, heteroaryloxy; heteroarylalkoxy, carbohydrate, amino acid, amino acid esters, amino acid amides, alditol, halogen, haloalkylthi, haloalkoxy, haloalkyl, hydroxyl, carboxyl, acyl, acyloxy, amino, aminoalkyl, aminoacyl, amido, alkylamino, dialkylamino, arylamino, nitro, cyano, thiol, imide, sulfonic acid, sulfate, sulfonate, sulfonyl, alkylsulfonyl, aminosulfonyl, alkylsulfonylamino, haloalkylsulfonyl, sulfanyl, sulfinyl, sulfamoyl, carboxylic ester, carboxylic acid, amide, phosphonyl, phosphinyl, phosphoryl, thioester, thioether, oxime, hydrazine, carbamate, phosphonic acid, phosphate, phosphonate, phosphinate, sulfonamido, carboxamido, hydroxamic acid, sulfonylimide or any other desired functional group that does not inhibit the pharmacological activity of this compound, either unprotected, or protected as necessary, as known to those skilled in the art, for example, as taught in Greene, et al., "Protective Groups in Organic Synthesis," John Wiley and Sons, Second Edition, 1999. In addition, adjacent groups on an "aryl" ring may combine to form a 5- to 7-membered saturated or partially unsaturated carbocyclic, aryl, heteroaryl or heterocyclic ring, which in turn may be substituted as above.

The term "heterocyclic", alone or in combination, refers to a nonaromatic cyclic group that may be partially (containing at least one double bond) or fully saturated and wherein the ring contains at least one heteroatom selected from oxygen, sulfur, nitrogen, or phosphorus. The terms "heteroaryl" or "heteroaromatic", alone or in combination, refer to an aromatic ring containing at least one heteroatom selected from sulfur, oxygen, nitrogen or phosphorus. The heteroaryl or heterocyclic ring may optionally be substituted by one or more substituent listed as optional substituents for aryl. In addition, adjacent groups on the heteroaryl or heterocyclic ring may combine to form a 5- to 7-membered carbocyclic, aryl, heteroaryl or heterocyclic ring, which in turn may be substituted as above. Nonlimiting examples of heterocylics and heteroaromatics are pyrrolidinyl, tetrahydrofuryl, tetrahydrofuranyl, pyranyl, purinyl, tetrahydropyranyl, piperazinyl, piperidinyl, morpholino, thiomorpholino, tetrahydropyranyl, imidazolyl, pyrolinyl, pyrazolinyl, indolinyl, dioxolanyl, or 1,4-dioxanyl. aziridinyl, furyl, furanyl, pyridyl, pyridinyl, pyridazinyl, pyrimidinyl, benzoxazolyl, 1,2,4-oxadiazolyl, 1,3,4-oxadiazolyl, 1,3,4-thiadiazole, indazolyl, triazinayl, 1,3,5-triazinyl, thienyl, isothiazolyl, imidazolyl, tetrazolyl, pyrazinyl, benzofuranyl, quinolyl, isoquinolyl, benzothienyl, isobenzofuryl, pyrazolyl, indolyl, isoindolyl, benzimidazolyl, purinyl, carbazolyl, oxazolyl, thiazolyl, benzothiazolyl, isothiazolyl, 1,2,4-thiadiazolyl, isoxazolyl, 1,2,4-oxadiazolyl, 1,3,4-oxadiazolyl, pyrrolyl, quinazolinyl, quinoxalinyl, benzoxazolyl, quinolinyl, isoquinolinyl, cinnolinyl, phthalazinyl, xanthinyl, hypoxanthinyl, pyrazole, imidazole, 1,2,3-triazole, 1,2,4-triazole, 1,2,3-oxadiazole, thiazine, pyridazine, triazolopyridinyl or pteridinyl wherein said heteroaryl or heterocyclic group can be optionally substituted with one or more substituent selected from the same substituents as set out above for aryl groups. Functional oxygen and nitrogen groups on the heteroaryl group can be protected as necessary or desired. Suitable protecting groups can include trimethylsilyl, dimethylhexylsilyl, t-butyldimethylsilyl, and t-butyldiphenylsilyl, trityl or substituted trityl, alkyl groups, acyl groups such as acetyl and propionyl, methanesulfonyl, and p-toluenesulfonyl.

The terms "thienyl" and "thien", alone or in combination, refers to a five member cyclic group wherein the ring contains one sulfur atom and two double bonds.

The term "benzothienyl", alone or in combination, refers to a five member cyclic group wherein the ring contains one sulfur atom and two double bonds fused to a phenyl ring.

The term "aryloxy", alone or in combination, refers to an aryl group bound to the molecule through an oxygen atom.

The term "heteroaryloxy", alone or in combination, refers to a heteroaryl group bound to the molecule through an oxygen atom.

The term "aralkoxy", alone or in combination, refers to an aryl group attached to an alkyl group which is attached to the molecule through an oxygen atom.

The term "heterocyclearalkoxy" refers to a heterocyclic group attached to an aryl group attached to an alkyl-O— group. The heterocyclic, aryl and alkyl groups can be optionally substituted as described above.

The terms "halo" and "halogen", alone -or in combination, refer to chloro, bromo, iodo and fluoro.

The terms "alkoxy" or "alkylthio", alone or in combination, refers to an alkyl group as defined above bonded through an oxygen linkage (—O—) or a sulfur linkage (—S—), respectively. The terms "lower alkoxy" or "lower alkylthio", alone or in combination, refers to a lower alkyl group as defined above bonded through an oxygen linkage (—O—) or a sulfur linkage (—S—), respectively.

The term “acyl”, alone or in combination, refers to a group of the formula C(O)R', wherein R' is an alkyl, aryl, alkaryl or aralkyl group, or substituted alkyl, aryl, aralkyl or alkaryl, wherein these groups are as defined above.

The term “acetyl”, alone or in combination, refers to the radical $—C(O)CH_3$.

The term “amino”, alone or in combination, denotes the radical $—NH_2$ or —NH—.

The term “nitro”, alone or in combination, denotes the radical $—NO_2$.

The term “substituted”, means that one or more hydrogen on the designated atom or substituent is replaced with a selection from the indicated group, provided that the designated atom’s normal valency is not exceeded, and the that the substitution results in a stable compound. When a subsitutent is “oxo” (keto) (i.e., ═O), then 2 hydrogens on the atom are replaced.

As used herein, the term “patient” refers to warm-blooded animals or mammals, and in particular humans, who are in need of the therapy described herein. The term “host”, as used herein, refers to a unicellular or multicellular organism, including cell lines and animals, and preferably a human.

Synthesis of the Active Compounds

The compounds of the present invention can be readily prepared by those skilled in the art of organic synthesis using commonly known methods, many of which are described by J, March, in *Advanced Organic Chemistry,* 4$^{th}$ Edition (Wiley-Interscience, New York, 1992) and D. N. Dnar in *The Chemistry of Chalcones and Related Compounds* (Wiley-Interscience, New York, 1981), incorporated herein by reference.

Compounds of the invention may be isolated as either mixtures of cis (Z) and trans (E) geometric isomers or pure trans (E) isomers. If desired, either the mixtures or the pure trans isomers may be isomerized to the corresponding predominantly cis (Z) iomers using methods well known in the literature.

The following schemes and examples will prove useful to those skilled in the art in manufacturing the compounds of the invention:

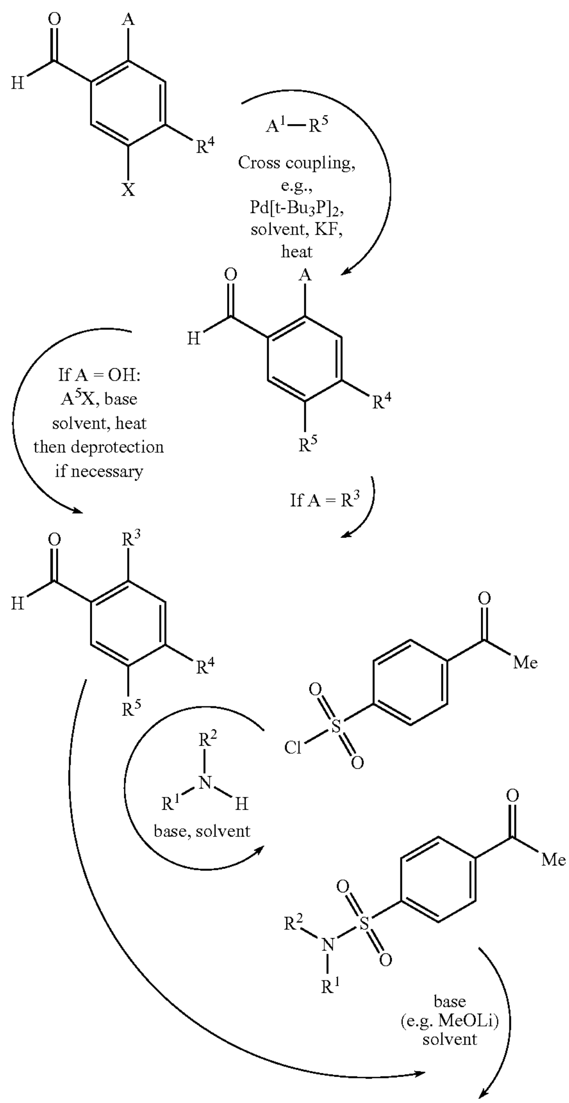

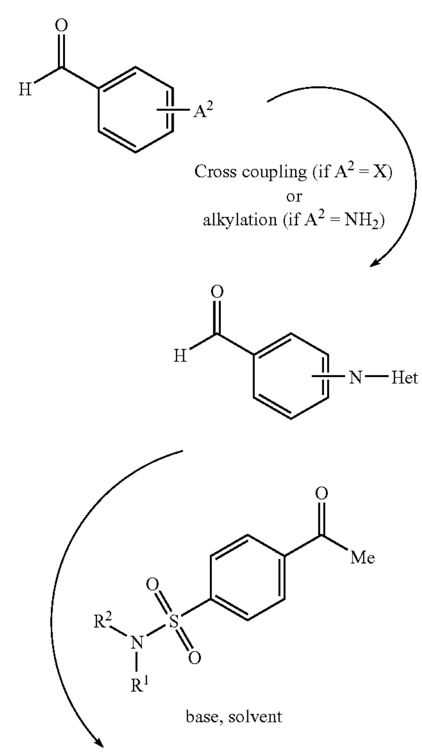

-continued
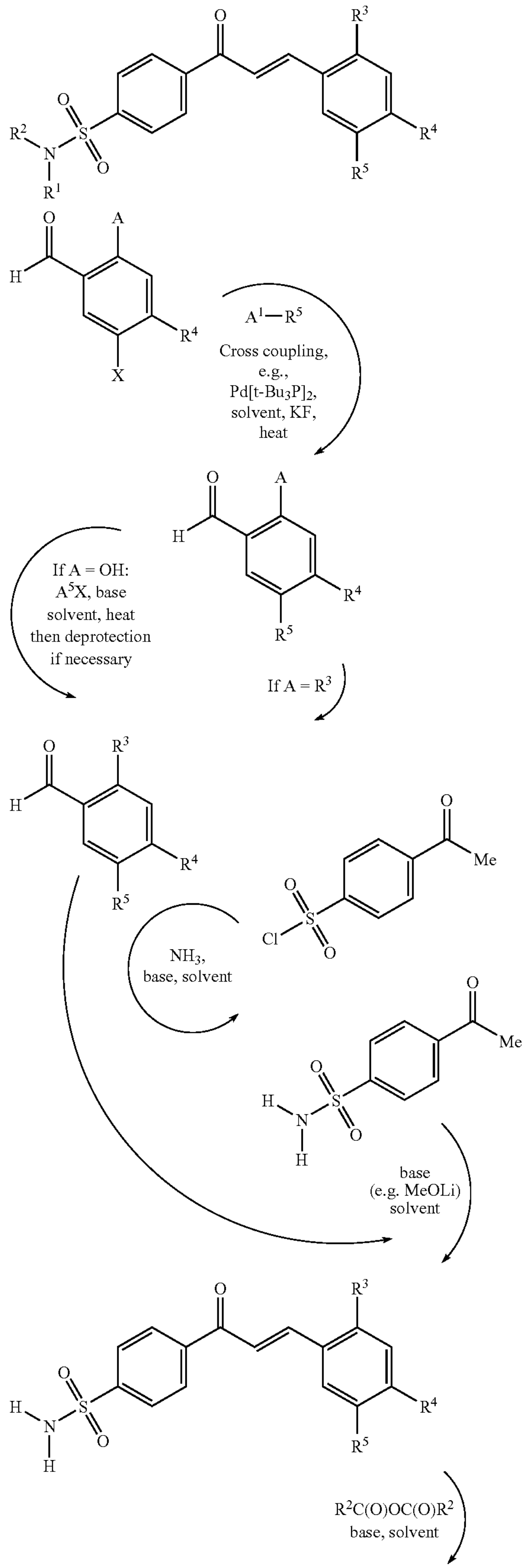
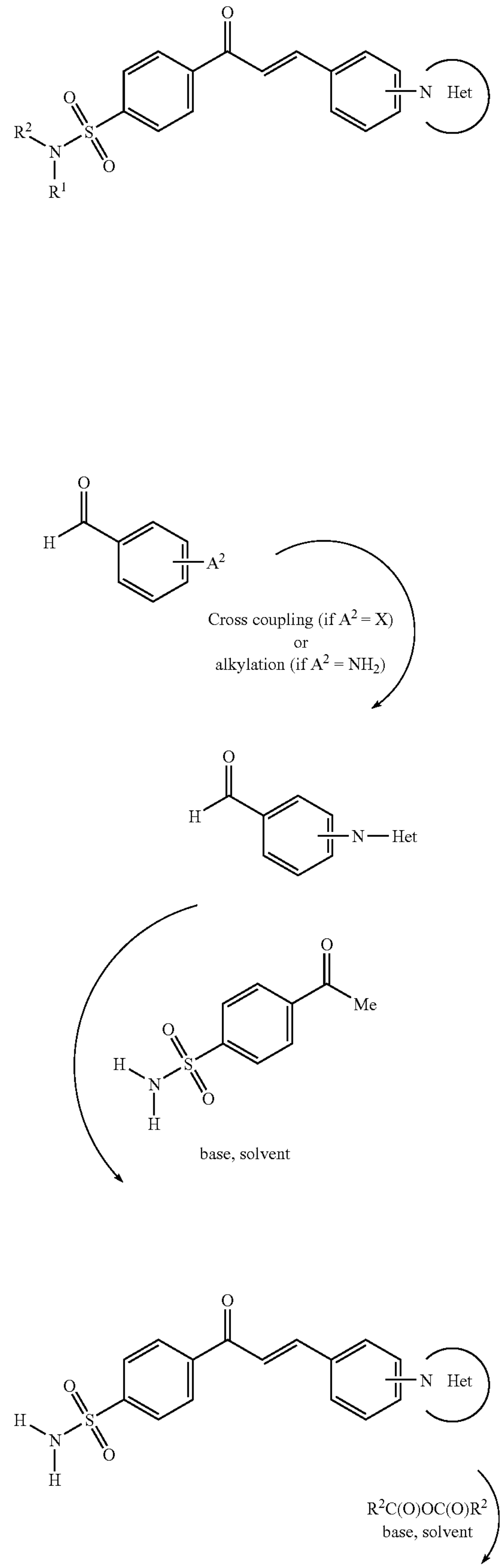

-continued
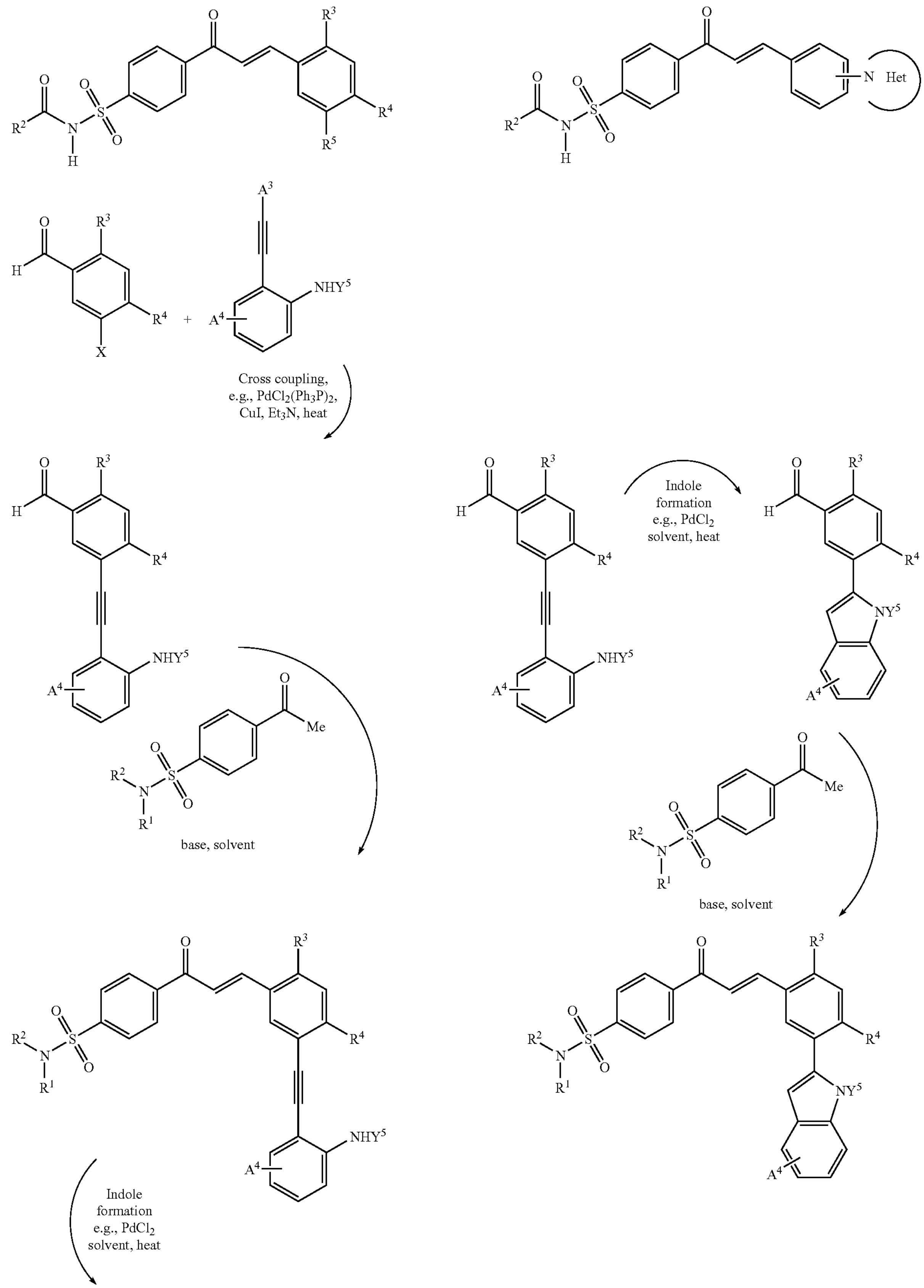

-continued

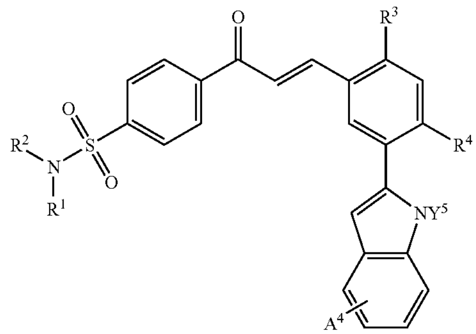

Legend:
A = OH or $R^3$
$A^1$ = —$B(OH)_2$, —$B(alkyl)_2$, or —$Sn(alkyl)_3$;
or H (when $R^5$ = amino or alkylamino)
$A^2$ = X or $NH_2$
$A^3$ = H or silyl
$A^4$ = Single or multiple $R^1$
$A^5$ = alkyl, substituted alkyl, or equivalent
Het = Heterocyclic (aliphatic or aromatic)
Each R, $R^1$, $R^2$, $R^3$, $R^4$, and $R^5$ are independent and defined herein
X = Br, Cl, or I
$Y^5$ is defined herein.

EXAMPLES

The following examples are understood to be illustrative only and are not intended to limit the scope of the present invention in any way. All intermediates and final products have been characterized by conventional proton NMR, mass spectral analyses and/or standard analytical methods known to those skilled in the art.

Example 1

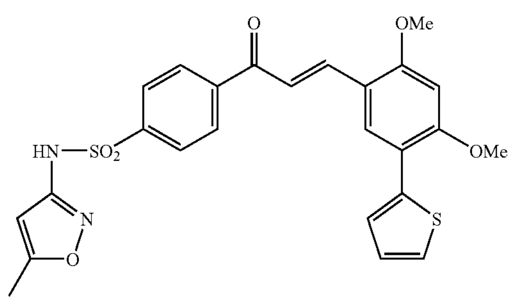

4-[3E-(2,4-Dimethoxy-5-thien-2-yl-phenyl)acryloyl]-N-(5-methylisoxazol-3-yl)benzenesulfonamide Ex-1A: 5-bromo-2,4-dimethoxybenzaldehyde (20.3 g, 83 mmol), thiophene-2-boronic acid (11.6 g, 91 mmol) and THF (200 mL) were sequentially charged into a clean reaction vessel fitted with a reflux condenser, mechanical stirrer and nitrogen inlet adapter. Nitrogen was bubbled into the resulting solution for 20 min followed by the sequential addition of KF (10.1 g, 174 mmol), and $Pd(^tBu_3P)_2$ (0.424 g, 0.83 mmol). The solution was immediately heated to 60° C. and aged for 1.5 h. The reaction was diluted with $H_2O$ (200 mL) and transferred to a separatory funnel containing EtOAc (200 mL) and $H_2O$ (200 mL). The layers were cut and the aqueous layer was extracted with EtOAc (100 mL). The combined organic cuts were filtered through a pre-washed pad of solka floc (5 g). The pad of solka floc and spent catalyst were washed with fresh EtOAc (200 mL) and this wash combined with the batch. The resultant filtrate was concentrated to dryness. The crude product was dissolved in THF (38 mL) and crystallized upon heptane (152 mL) addition. The product was filtered and then dried to a constant weight in the vacuum oven (38° C., 20 in Hg) affording 19.32 g (94%) of the desired 2,4-dimethoxy-5-thien-2-ylbenzaldehyde as a light off-white solid, mp 125–126° C. $^1$H-NMR (300 MHz, $CDCl_3$): 10.34 (s, 1 H), 8.12 (s, 1 H), 7.44 (dd, 1 H, J=3.5 and 1.5 Hz), 7.31 (dd, 1 H, J=5.2 and 1.5 Hz), 7.07 (dd, 1 H, J=5.2 and 3.5 Hz), 6.51 (s, 1 H), 4.02 (s, 3 H), 3.99 (s, 3 H). HRMS (EI) Calcd. for $C_{13}H_{12}O_3S$: 248.0507 ($M^+$); Found: 248.0504.

Ex-1B: To a solution of 3-amino-5-methylisoxazole (0.27 g, 2.75 mmol) in pyridine (1 mL) at 0° C. was added a solution of 4-acetylbenzenesulfonyl chloride (0.50 g, 2.29 mmol) in 1 mL pyridine dropwise to the reaction. The resulting solution was stirred at 0° C. for 30 min and then warmed to room temperature and stirred for an additional 18 h. The mixture was diluted with water (100 mL), cooled to 0° C., and stirred for 1 h. The resulting precipitate was collected on filter paper and rinsed with several portions of water. The filtrate was acidified with 3 N HCl and the resulting precipitate was collected and rinsed with water. The solids were combined and dried in vacuo to afford 0.50 g (80%) of 4-acetyl-N-(5-methylisoxazole-3-yl)benzenesulfonamide as a pale green solid, mp 189–190° C. $^1$H-NMR (300 MHz, DMSO-$d_6$) δ 8.14 (d, 2H, J=8.1 Hz), 7.98 (d, 2H, J=8.1 Hz), 6.16 (s, 1H), 2.62 (s, 3H), 2.30 (s, 3H). HRMS (EI) Calcd. for $C_{12}H_{12}N_2O_4S$: 280.0518 ($M^+$); Found: 280.0514. Anal. Calcd. for $C_{12}H_{12}N_2O_4S$: C, 51.42; H, 4.32; N, 9.99; S, 11.44; Found: C, 51.73; H, 4.39; N, 10.12; S, 11.30.

4-Acetyl-N-(5-methylisoxazole-3-yl)benzenesulfonamide (Ex-1B, 2.50 g, 8.9 mmol) and 2,4-dimethoxy-5-thien- 2-ylbenzaldehyde (Ex-1A, 2.20 g, 8.9 mmol) were dissolved in a dimethylformamide-methanol solution (55 mL, 7:3). After complete dissolution, lithium methoxide (1.35 g, 35.6 mmol) was added and the resulting orange slurry was stirred in the dark at room temperature for 1 h. Upon completion, as determined by HPLC, the mixture was diluted with water (80 mL), acidified with a 1 N hydrochloric acid solution, and extracted with ethyl acetate (3×40 mL). The combined organic extracts were dried over sodium sulfate and evaporated to dryness. The crude oil was taken up in ethanol (20 mL) and warmed to 60° C. to obtain complete dissolution and allowed to cool to room temperature. The resulting precipitate was collected on filter paper and dried in vacuo to yield 3.78 g (83%) of the title compound as an orange solid, mp 202–203° C. $^1$H-NMR (300 MHz, DMSO-$d_6$) δ8.31 (d, 2H, J=8.1 Hz), 8.27 (s, 1H), 8.08 (d, 1H, J=15.9 Hz), 8.01 (d, 2H, J=8.1 Hz), 7.88 (d, 1H, J=15.9 Hz), 7.66 (d, 1H, J=3.3 Hz), 7.53 (d, 1H, J=5.1 Hz), 7.13 (dd, 1H, J=5.1, 3.3 Hz), 6.84 (s, 1H), 6.18 (s, 1H), 4.02 (s, 3H), 4.00 (s, 3H), 2.31 (s, 3H). Anal. Calcd. for $C_{25}H_{22}N_2O_6S_2$: C, 58.81; H, 4.34; N, 5.49; S, 12.56; Found: C, 58.68; H, 4.40; N, 5.61; S, 12.62. HRMS (EI) Calcd. for $C_{25}H_{22}N_2O_6S_2$: 511.0997 ($M^+$); Found: 511.0983.

Example 2

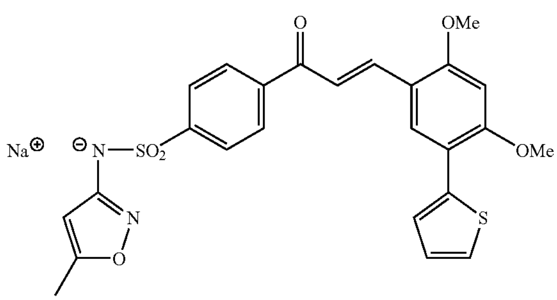

4-[3E-(2,4-Dimethoxy-5-thien-2-ylphenyl)acryloyl]-N-(5-methylisoxazol-3-yl)benzenesulfonamide sodium salt To a solution of 4-[3E-(2,4-dimethoxy-5-thien-2-ylphenyl)acryloyl]-N-(5-methyl-isoxazol-3-yl)benzenesulfonamide (Ex-1, 0.50 g, 0.98 mmol) in tetrahydrofuran (8 mL) was added sodium methoxide (0.061 g, 1.07 mmol) and the reaction was stirred in the dark at room temperature for 1 h. The resulting yellow solid was collected on filter paper and rinsed with fresh portions of THF. The wet filtercake was dried in a vacuum desiccator for 1 h then transferred to a flask and dried further in vacuo for 18 h. The crude orange solid was taken up in ethanol (6 mL) and stirred for 4 h at room temperature in the dark. The solid was collected on filter paper and dried in vacuo to yield 0.30 g (60%) of the title compound as a yellow solid, mp>260° C. $^1$H-NMR (300 MHz, DMSO-$d_6$) δ8.26 (s, 1H), 8.11 (d, 2H, J=8.1 Hz), 8.04 (d, 1H, J=15.7 Hz), 7.88 (d, 1H, J=15.7 Hz), 7.80 (d, 2H, J=8.1 Hz), 7.69 (d, 1H, J=3.3 Hz), 7.51 (d, 1H, J=5.1 Hz), 7.13 (dd, 1H, J=5.1, 3.3 Hz), 6.83 (s, 1H), 5.80 (s, 1H), 4.01 (s, 3H), 4.00 (s, 3H), 2.11 (s, 3H). Anal. Calcd. for $C_{25}H_{21}N_2NaO_6S_2$.¼$H_2O$: C, 55.91; H, 4.04; N, 5.22; S, 11.94; Found: C, 55.92; H, 3.98; N, 5.21; S, 11.95.

Example 3

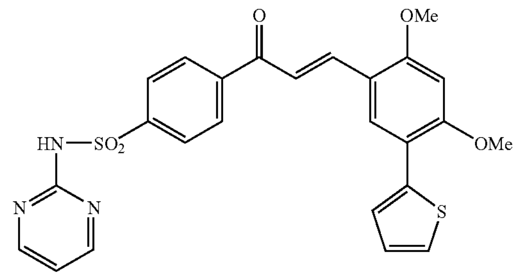

4-[3E-(2,4-Dimethoxy-5-thien-2-ylphenyl)acryloyl]-N-pyrimidin-2-ylbenzenesulfonamide Ex-3A: 4-Acetyl-N-pyrimidin-2-ylbenzenesulfonamide was prepared in an analogous fashion as Ex-1B using 2-aminopyrimidine, 30% yield, pale yellow solid, mp>240° C. (dec). $^1$H-NMR (300 MHz, DMSO-$d_6$) δ 8.50 (d, 2H, J=4.8 Hz), 8.07–8.14 (m, 4H), 7.05 (t, 1H, J=4.5 Hz), 2.61 (s, 3H). HRMS (ESI) Calcd. for $C_{12}H_{11}N_3O_3S$: 278.0599 $(M+H)^+$; Found: 278.0608.

The title compound was prepared in an analogous fashion as Ex-1 using 4-acetyl-N-pyrimidin-2-ylbenzenesulfonamide (Ex-3A), 70% yield, yellow solid, mp 215° C. (dec). $^1$H-NMR (300 MHz, DMSO-$d_6$) δ8.27 (s, 1H), 8.12–8.16 (m, 4H), 8.06 (d, 1H, J=15.6 Hz), 7.95 (d, 2H, J=8.1 Hz), 7.90 (d, 1H, J=15.6 Hz), 7.68 (d, 1H, J=3.6 Hz), 7.52 (d, 1H, J=4.8 Hz), 7.12–7.15 (m, 1H), 6.84 (s, 1H), 6.50 (t, 1H, J=5.1 Hz), 4.02 (s, 3H), 4.00 (s, 3H). Anal. Calcd. for $C_{25}H_{21}N_3O_5S_2$.3$H_2O$: C, 53.46; H, 4.85; N, 7.48; S, 11.42; Found: C, 53.67; H, 4.71; N, 7.38; S, 11.76. HRMS (ESI) Calcd. for $C_{25}H_{21}N_3O_5S_2$: 508.1001 $(M+H)^+$; Found: 508.1005.

Example 4

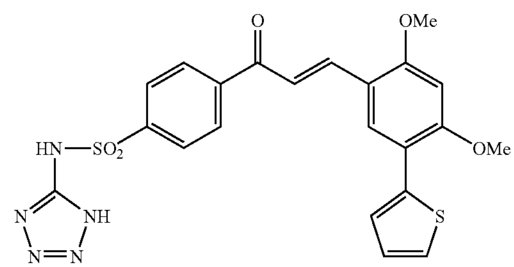

4-[3E-(2,4-Dimethoxy-5-thien-2-ylphenyl)acryloyl]-N-(1-H-tetrazol-5-yl)benzenesulfonamide Ex-4A: 4-Acetyl-N-(1-H-tetrazol-5-yl)benzenesulfonamide was prepared in an analogous fashion as Ex-1B using 5-aminotetrazole, 50% yield, off-white solid, mp 150–151° C. $^1$H-NMR (300 MHz, DMSO-$d_6$) δ 8.98 (brs, 1 H), 8.11 (d, 2H, J=8.1 Hz), 8.02 (d, 2H, J=8.1 Hz), 7.91 (brs, 1H), 2.64 (s, 3H). HRMS (EI) Calcd. for $C_9H_9N_5O_3S$: 267.0426 ($M^+$); Found: 267.04

The title compound was prepared in an analogous fashion as Ex-1 using 4-acetyl-N-(1-H-tetrazol-5-yl)benzenesulfonamide (Ex-4A), 55% yield, dark yellow solid, mp 185–186° C. $^1$H-NMR (300 MHz, DMSO-$d_6$) δ8.29 (d, 2H, J=8.1 Hz), 8.27 (s, 1H), 8.07 (d, 1H, J=15.9 Hz), 8.03 (d, 2H, J=8.1 Hz), 7.88 (d, 1H, J=15.9 Hz), 7.66 (d, 1H, J=3.6 Hz), 7.52 (dd, 1H, J=5.4, 1.5 Hz), 7.13 (dd, 1H, J=5.4, 3.6 Hz), 6.85 (s, 1H), 4.02 (s, 3H), 4.00 (s, 3H). Anal. Calcd. for $C_{22}H_{19}N_5O_5S_2$.¼EtOH: C, 53.09; H, 4.06; N, 13.76; S, 12.60; Found: C, 53.39; H, 3.95; N, 13.51; S, 12.72. HRMS (ESI) Calcd. for $C_{22}H_{19}N_5O_5S_2$: 498.0906 $(M+H)^+$; Found: 498.0920.

Example 5

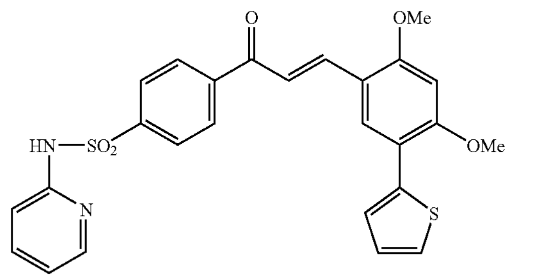

4-[3E-(2,4-Dimethoxy-5-thien-2-ylphenyl)acryloyl]-N-pyridin-2-ylbenzenesulfonamide Ex-5A: 4-Acetyl-N-pyridin-2-ylbenzenesulfonamide was prepared in an analogous fashion as Ex-1B using 2-aminopyridine, 77% yield, off-white solid, mp 198–199° C. $^1$H-NMR (300 MHz, DMSO-$d_6$) δ 8.07 (d, 2H, J=8.1 Hz), 7.97 (d, 3H, J=8.1 Hz), 7.75–7.80 (m, 1H), 7.22 (d, 1H, J=8.7 Hz), 6.86 (t, 1H, J=6.9 Hz), 2.60 (s, 3H). HRMS (EI) Calcd. for $C_{13}H_{12}N_2O_3S$: 276.0569 $(M^+)$; Found: 276.0563.

The title compound was prepared in an analogous fashion as Ex-1 using 4-acetyl-N-pyridin-2-ylbenzenesulfonamide (Ex-5A), 54% yield, yellow solid, mp 141–143° C. $^1$H-NMR (300 MHz, DMSO-$d_6$) δ8.26 (s, 1H), 8.24 (d, 2H, J=8.1 Hz), 8.06 (d, 1H, J=15.6 Hz), 8.01 (d, 2H, J=8.1 Hz), 7.96–7.99 (m, 1H), 7.87 (d, 1H, J=15.6 Hz), 7.75 (ddd, 1H, J=8.7, 6.7, 1.8 Hz), 7.66 (dd, 1H, J=3.5, 1.5 Hz), 7.52 (d, 1H, J=5.4 Hz), 7.21 (d, 1H, J=8.7 Hz), 7.13 (dd, 1H, J=5.4, 3.5 Hz), 6.82–6.86 (m, 2H), 4.02 (s, 3H), 4.00 (s, 3H). Anal. Calcd. for $C_{26}H_{22}N_2O_5S_2.½H_2O$: C, 60.78; H, 4.81; N, 5.35; S, 12.25; Found: C, 60.63; H, 4.55; N, 5.74; S, 12.32. HRMS (ESI) Calcd. for $C_{26}H_{22}N_2O_5S_2$: 507.1048 $(M+H)^+$; Found: 507.1051.

Example 6

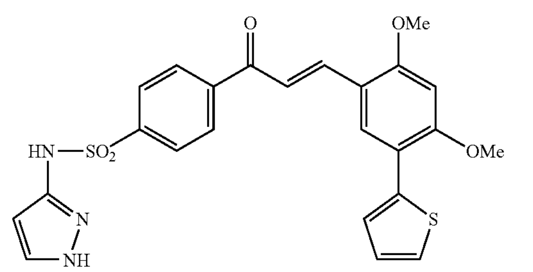

4-[3E-(2,4-Dimethoxy-5-thien-2-ylphenyl)acryloyl]-N-(1H-pyrazol-3-yl)benzenesulfonamide Ex-6A: 4-Acetyl-N-(1H-pyrazol-3-yl)benzenesulfonamide was prepared in an analogous fashion as Ex-1B using 3-aminopyrazole except that silica gel chromatography (ethyl acetate/hexanes, 1:1 to 3:1) was used, 15% yield, white solid. $^1$H-NMR (300 MHz, DMSO-$d_6$) δ 10.60 (s, 1H), 8.09 (d, 2H, J=8.7 Hz), 7.90 (d, 2H, J=8.7 Hz), 7.56 (s, 1H), 5.98 (s, 1H), 2.61 (s, 3H). HRMS (EI) Calcd. for $C_{11}H_{11}N_3O_3S$: 265.0521 $(M^+)$; Found: 265.0526.

The title compound was prepared in an analogous fashion as Ex-1 using 4-acetyl-N-(1H-pyrazol-3-yl)benzenesulfonamide (Ex-6A), 40% yield, yellow solid, mp 142–145° C. $^1$H-NMR (300 MHz, DMSO-$d_6$) δ10.60 (s, 1H), 8.25 (d, 3H, J=8.4 Hz), 8.08 (d, 1H, J=15.6 Hz), 7.93 (d, 2H, J=8.7 Hz), 7.87 (d, 1H, J=15.6 Hz), 7.67 (d, 1H, J=–3.6 Hz), 7.56 (d, 1H, J=2.1 Hz), 7.52 (d, 1H, J=5.4 Hz), 7.13 (dd, 1H, J=5.4, 3.6 Hz), 6.84 (s, 1H), 6.00 (d, 1H, J=1.8 Hz), 4.02 (s, 3H), 4.00 (s, 3H). HRMS (ESI) Calcd. for $C_{24}H_{21}N_3O_5S_2$: 496.1001 $(M+H)^+$; Found: 496.1022.

Example 7

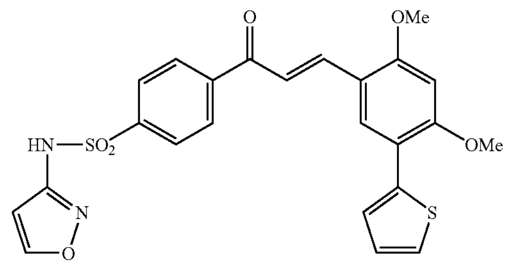

4-[3E-(2,4-Dimethoxy-5-thien-2-ylphenyl)acryloyl]-N-isoxazol-3-ylbenzenesulfonamide Ex-7A: 4-Acetyl-N-isoxazol-3-ylbenzenesulfonamide was prepared in an analogous fashion as Ex-1B using 3-aminoisoxazole, 71% yield, off-white solid, mp 165–166° C. $^1$H-NMR (300 MHz, DMSO-$d_6$) δ 8.75 (d, 1H, J=1.5 Hz), 8.14 (d, 2H, J=8.1 Hz), 8.00 (d, 2H, J=8.1 Hz), 6.45 (d, 1H, J=1.5 Hz), 2.62 (s, 3H). Anal. Calcd. for $C_{11}H_{10}N_2O_4S$: C, 49.62; H, 3.79; N, 10.52; S, 12.04. Found: C, 49.58; H, 3.63; N, 10.45; S, 12.14. HRMS (EI) Calcd. for $C_{11}H_{10}N_2O_4S$: 266.0361 $(M^+)$; Found: 266.0365.

The title compound was prepared in an analogous fashion as Ex-1 using 4-acetyl-N-isoxazol-3-ylbenzenesulfonamide (Ex-7A), 77% yield, orange solid, mp 198–199° C. $^1$H-NMR (300 MHz, DMSO-$d_6$) δ8.76 (d, 1H, J=2.7 Hz), 8.31 (d, 2H, J=8.1 Hz), 8.27 (s, 1H), 8.07 (d, 1H, J=15.6 Hz), 8.02 (d, 2H, J=8.1 Hz), 7.88 (d, 1H, J=15.6 Hz), 7.67 (d, 1H, J=3.6 Hz), 7.53 (d, 1H, J=5.4 Hz), 7.13 (dd, 1H, J=5.4, 3.6 Hz), 6.84 (s, 1H), 6.48 (d, 1H, J=2.7 Hz), 4.02 (s, 3H), 4.00 (s, 3H). Anal. Calcd. for $C_{24}H_{20}N_2O_6S_2$: C, 58.05; H, 4.06; N, 5.64; S, 12.91; Found: C, 57.91; H, 4.16; N, 5.63; S, 12.71. HRMS (EI) Calcd. for $C_{24}H_{20}N_2O_6S_2$: 496.0763 $(M^+)$; Found: 496.0770.

Example 8

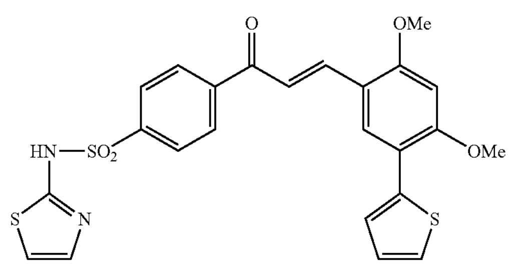

4-[3E-(2,4-Dimethoxy-5-thien-2-ylphenyl)acryloyl]-N-thiazol-2-ylbenzenesulfonamide Ex-8A: 4-Acetyl-N-thiazol-2-ylbenzenesulfonamide was prepared in an analogous fashion as Ex-1B using 2-aminothiazole, 68% yield, tan solid, mp 194–195° C. $^1$H-NMR (300 MHz, DMSO-$d_6$) δ 8.08 (d, 2H, J=8.4 Hz), 7.92 (d, 2H, J=8.4 Hz), 7.29 (d, 1H, J=4.5 Hz), 6.87 (d, 1H, J=4.5 Hz), 2.60 (s, 3H). HRMS (EI) Calcd. for $C_{11}H_{10}N_2O_3S_2$: 282.0133 $(M^+)$; Found: 282.0131.

The title compound was prepared in an analogous fashion as Ex-1 using 4-acetyl-N-thiazol-2-ylbenzenesulfonamide (Ex-8A), 83% yield, yellow solid, mp 220–221° C. $^1$H-NMR (300 MHz, DMSO-$d_6$) δ8.24–8.26 (m, 3H), 8.06 (d, 1H, J=15.8 Hz), 7.95 (d, 2H, J=7.8 Hz), 7.88 (d, 1H, J=15.8 Hz), 7.66 (d, 1H, J=3.6 Hz), 7.52 (d, 1H, J=5.4 Hz), 7.29 (d, 1H, J=4.2 Hz), 7.13 (dd, 1H, J=5.4, 3.6 Hz), 6.88 (d, 1H, J=4.5 Hz), 6.84 (s, 1H), 4.02 (s, 3H), 4.00 (s, 3H). HRMS (ESI) Calcd. for $C_{24}H_{20}N_2O_5S_3$: 513.0612 (M+H)$^+$; Found: 513.0633.

Example 9

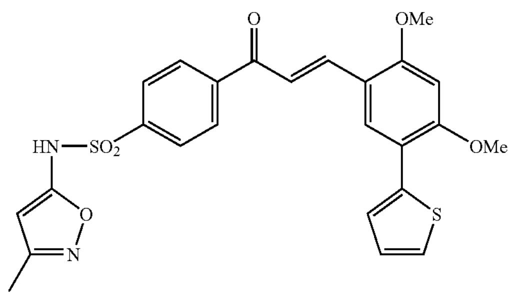

4-[3E-(2,4-Dimethoxy-5-thien-2-ylphenyl)acryloyl]-N-(3-methylisoxazol-5-ylbenzenesulfonamide Ex-9A: 4-Acetyl-N-(3-methylisoxazol-5-yl)benzenesulfonamide was prepared in an analogous fashion as Ex-1B using 5-amino-3-methylisoxazole, 64% yield, tan solid, mp 144–145° C. $^1$H-NMR (300 MHz, DMSO-$d_6$) δ 8.15 (d, 2H, J=8.7 Hz), 7.99 (d, 2H, J=8.7 Hz), 5.77 (s, 1H), 2.63 (s, 3H), 2.01 (s, 3H). HRMS (EI) Calcd. for $C_{12}H_{12}N_2O_4S$: 280.0518 (M$^+$); Found: 280.0525.

The title compound was prepared in an analogous fashion as Ex-1 using 4-acetyl-N-(3-methylisoxazol-5-yl)benzenesulfonamide (Ex-9A), 30% yield, orange solid, mp 138–140° C. $^1$H-NMR (300 MHz, DMSO-$d_6$) δ8.28–8.34 (m, 3H), 8.08 (d, 1H, J=15.3 Hz), 8.02 (d, 2H, J=8.1 Hz), 7.90 (d, 1H, J=15.3 Hz), 7.66 (d, 1H, J=–3.0 Hz), 7.51 (d, 1H, J=5.4 Hz), 7.13 (dd, 1H, J=5.4, 3.6 Hz), 6.85 (s, 1H), 5.80 (s, 1H), 4.02 (s, 3H), 4.00 (s, 3H), 2.11 (s, 3H). HRMS (ESI) Calcd. for $C_{25}H_{22}N_2O_6S_2$: 510.0997 (M+H)$^+$; Found: 511.0991.

Example 10

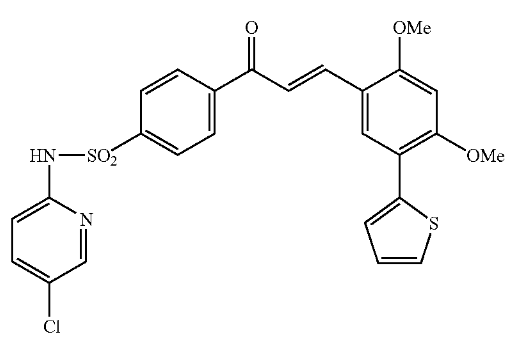

N-(5—Chloropyridin-2-yl)-4-[3E-(2,4-dimethoxy-5-thien-2-ylphenyl)acryloyl]benzenesulfonamide Ex-10A: 4-Acetyl-N-(5-chloropyridin-2-yl)benzenesulfonamide was prepared in an analogous fashion as Ex-1B using 2-amino-5-chloropyridine, 78% yield, tan solid, mp 181–182° C. $^1$H-NMR (300 MHz, DMSO-$d_6$) δ 8.20 (d, 1H, J=3.3 Hz), 8.11 (d, 2H, J=8.4 Hz), 8.03 (d, 2H, J=8.4 Hz), 7.82 (dd, 1H, J=9.0, 3.3 Hz), 7.09 (d, 1H, J=9.0 Hz), 2.62 (s, 3H). Anal. Calcd. for $C_{13}H_{11}ClN_2O_3S$: C, 50.24; H, 3.57; Cl, 11.41; N, 9.01; S, 10.32. Found: C, 50.59; H, 3.62; Cl, 11.49; N, 9.34; S, 10.02. HRMS (ESI) Calcd. for $C_{13}H_{11}ClN_2O_3S$: 311.0257 (M+H)$^+$; Found: 311.0264.

The title compound was prepared in an analogous fashion as Ex-1 using 4-acetyl-N-(5-chloropyridin-2-yl)benzenesulfonamide (Ex-10A), 85% yield, orange solid, mp 228–229° C. $^1$H-NMR (300 MHz, DMSO-$d_6$) δ8.27–8.30 (m, 3H), 8.22 (d, 1H, J=2.4 Hz), 8.05–8.10 (m, 3H), 7.87 (d, 1H, J=16.0 Hz), 7.83 (dd, 1H, J=9.0, 2.4 Hz), 7.65 (d, 1H, J=3.6 Hz), 7.53 (d, 1H, J=5.4 Hz), 7.10–7.15 (m, 2H), 6.84 (s, 1H), 4.02 (s, 3H), 4.00 (s, 3H). Anal. Calcd. for $C_{26}H_{21}ClN_2O_5S_2 \cdot \frac{1}{6}H_2O$: C, 57.40; H, 3.95; Cl, 6.52; N, 5.15; S, 11.79. Found: C, 57.18; H, 4.05; Cl, 6.25; N, 5.51; S, 11.60. HRMS (ESI) Calcd. for $C_{26}H_{21}ClN_2O_5S_2$: 541.0658 (M+H)$^+$; Found: 541.0642.

Example 11

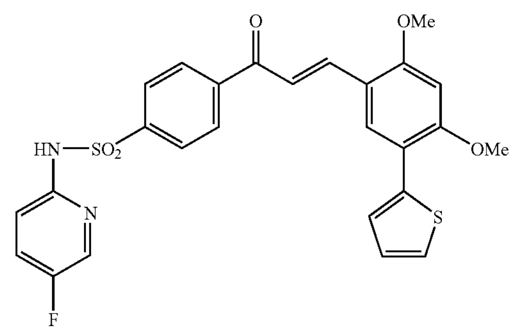

4-[3E-(2,4-Dimethoxy-5-thien-2-ylphenyl)acryloyl]-N-(5-fluoropyridin-2-yl)benzenesulfonamide Ex-11A: 4-Acetyl-N-(5-fluoropyridin-2-yl)benzenesulfonamide was prepared in an analogous fashion as Ex-1B using 2-amino-5-fluoropyridine, 91% yield, light red solid, mp 151–152° C. $^1$H-NMR (300 MHz, DMSO-$d_6$) δ 8.17 (d, 1H, J=3.0 Hz), 8.11 (d, 2H, J=8.4 Hz), 8.02 (d, 2H, J=8.4 Hz), 7.82 (dt, 1H, J=9.1, 3.3 Hz), 7.09 (dd, 1H, J=9.1, 3.3 Hz), 2.61 (s, 3H). HRMS (ESI) Calcd. for $C_{13}H_{11}FN_2O_3S$: 295.0552 (M+H)$^+$; Found: 295.0563.

The title compound was prepared in an analogous fashion as Ex-1 using 4-acetyl-N-(5-fluoropyridin-2-yl)benzenesulfonamide (Ex-11A), 81% yield, an orange solid, mp 194–195° C. $^1$H-NMR (300 MHz, DMSO-$d_6$) δ8.29–8.31 (m, 3H), 8.18 (d, 1H, J=2.1 Hz), 8.03–8.10 (m, 3H), 7.87 (d, 1H, J=15.6 Hz), 7.66–7.72 (m, 2H), 7.52 (d, 1H, J=3.0 Hz), 7.12–7.17 (m, 2H), 6.84 (s, 1H), 4.02 (s, 3H), 4.00 (s, 3H). Anal. Calcd. for $C_{26}H_{21}FN_2O_5S_2 \cdot \frac{1}{5}H_2O$: C, 59.12; H, 4.08; F, 3.60; N, 5.30; S, 12.14. Found: C, 59.07; H, 4.07; F, 3.55; N, 5.53; S, 12.17. HRMS (ESI) Calcd. for $C_{26}H_{21}FN_2O_5S_2$: 525.0954 (M+H)+; Found: 525.0967.

Example 12

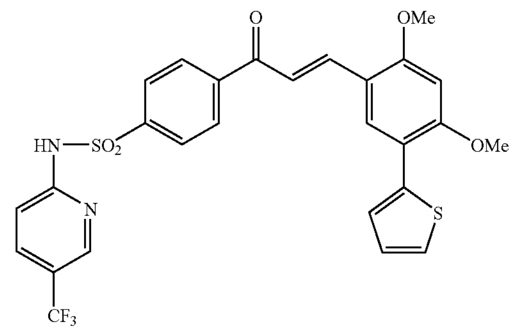

4-[3E-(2,4-Dimethoxy-5-thien-2-ylphenyl)acryloyl]-N-(5-trifluoromethylpyridin-2-yl)benzenesulfonamide Ex-12A: 4-Acetyl-N-(5-trifluoromethylpyridin-2-yl)benzenesulfonamide was prepared in an analogous fashion as Ex-1B using 2-amino-5-(trifluoromethyl)pyridine, 75% yield, off-white solid, mp 179–180° C. $^1$H-NMR (300 MHz, DMSO-$d_6$) δ 8.52 (brs, 1H), 8.06–8.14 (m, 5H), 7.23 (d, 1H, J=9.0 Hz), 2.61 (s, 3H). HRMS (ESI) Calcd. for $C_{14}H_{11}F_3N_2O_3S$: 345.0520 $(M+H)^+$; Found: 345.0531.

The title compound was prepared in an analogous fashion as Ex-1 using 4-acetyl-N-(5-trifluoromethylpyridin-2-yl) benzenesulfonamide (Ex-12A), 85% yield, orange solid, mp 228–229° C. $^1$H-NMR (300 MHz, DMSO-$d_6$) δ8.54 (brs, 1H), 8.29 (d, 2H, J=8.4 Hz), 8.26 (s, 1H), 8.05–8.13 (m, 4H), 7.88 (d, 1H, J=15.9 Hz), 7.65 (d, 1H, J=3.6 Hz), 7.52 (d, 1H, J=5.1 Hz), 7.24 (d, 1H, J=8.7 Hz), 7.13 (dd, 1H, J=5.1, 3.6 Hz), 6.84 (s, 1H), 4.02 (s, 3H), 4.00 (s, 3H). Anal. Calcd. for $C_{27}H_{21}F_3N_2O_5S_2$.¼$H_2O$: C, 56.00; H, 3.74; F, 9.84; N, 4.84; S, 11.07. Found: C, 55.90; H, 3.90; F, 9.81; N, 5.09; S, 11.08. HRMS (ESI) Calcd. for $C_{27}H_{21}F_3N_2O_5S_2$: 575.0922 $(M+H)^+$; Found: 575.0925.

Example 13

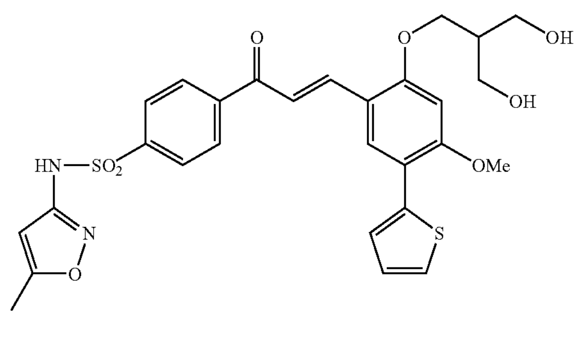

4-{3E-[2-(3-Hydroxy-2-hydroxymethylpropoxy)-4-methoxy-5-thien-2-ylphenyl]acryloyl}-N-(5-methyl-isoxazol-3-yl)benzenesulfonamide Ex-13A: To a solution of 3-(tert-butyldimethylsilanyloxy)-2-(tert-butyldimethylsilanyloxymethyl)propan-1-ol (25.0 g, 74.3 mmol) and triethylamine (22.6 g, 223 mmol) in dichloromethane (150 mL) at 0° C. was added methanesulfonyl chloride (12.8 g, 111 mmol) and the resulting slurry was stirred at 0° C. for 15 min and allowed to warm to room temperature. The solution was stirred for an additional 3 h at room temperature and diluted with water (130 mL) and ethyl acetate (350 mL). The layers were separated and the aqueous was extracted with ethyl acetate (150 mL). The combined organic extracts were washed with a saturated sodium bicarbonate (200 mL), a 50% sodium chloride solution (2×200 mL), dried over sodium sulfate and concentrated to afford 29.5 g (97%) of methanesulfonic acid 3-(tert-butyldimethylsilanyloxy)-2-(tert-butyldimethylsilanyloxymethyl)propyl ester as a yellow oil. $^1$H-NMR (300 MHz, $CDCl_3$) δ 4.29 (d, 2H, J=5.7 Hz), 3.61–3.68 (m, 4H), 2.99 (s, 3H), 2.04–2.11 (m, 1H), 0.88 (s, 18H), 0.049 (s, 12H). HRMS (ESI) Calcd. for $C_{17}H_{40}O_5SSi_2$: 413.2213 $(M+H)^+$; Found: 413.2226.

Ex-13B: 2-Hydroxy-4-methoxybenzaldehyde (6.0 g, 39 mmol) was dissolved in dichloromethane (50 mL) and cooled to 0° C. using an ice-water bath. Bromine (6.8 g, 43 mmol) in dichloromethane (2 mL) was added dropwise to the cooled solution and stirred for 2 h at 0° C. The mixture was warmed to room temperature and stirred for an additional 1 h and the resulting yellow precipitate was collected. Recrystallization (ethyl acetate/hexanes) yielded 7.1 g (80%) of 5-bromo-2-hydroxy-4-methoxybenzaldehyde as white needles, mp 63–64° C. $^1$H-NMR (300 MHz, $CDCl_3$) δ 11.43 (s, 1H), 9.69 (s, 1H), 7.68 (s, 1H), 6.48 (s, 1H), 3.95 (s, 3H). Anal. Calcd. for $C_8H_7BrO_3$: C, 41.59; H, 3.05; Found: C, 41.86; H, 3.05.

Ex-13C: 5-Bromo-2-hydroxy-4-methoxybenzaldehyde (Ex-13B, 1.5 g, 6.5 mmol) and thiophene-2-boronic acid (0.91 g, 7.1 mmol) were dissolved in tetrahydrofuran (15 mL). Nitrogen was bubbled into the solution for 10 min followed by the sequential addition of potassium fluoride (0.80 g, 14 mmol, spray-dried) and bis(tri-t-butylphosphine) palladium (0) (0.033 g, 0.065 mmol). The solution was immediately heated to 60° C. and aged for 1.5 h. Upon completion, as determined by HPLC, the reaction was diluted with water (25 mL) and extracted with ethyl acetate (3×30 mL). The combined organic extracts were dried over sodium sulfate and concentrated to a brown solid. Silica gel chromatography (ethyl acetate/hexanes, 1:3) gave 1.46 g (97%) of 2-hydroxy-4-methoxy-5-thien-2-ylbenzaldehyde as a yellow solid, mp 118–119° C. $^1$H-NMR (300 MHz, $CDCl_3$) δ 11.48 (s, 1H), 9.79 (s, 1H), 7.72 (s, 1H), 7.37 (d, 1H, J=3.6 Hz), 7.31 (dd, 1H, J=5.1, 1.5 Hz), 7.08 (dd, 1H, J=5.1, 3.6 Hz), 6.54 (s, 1H), 3.98 (s, 3H). MS (ESI) m/z 235 ($[M+H]^+$, 100%). Anal. Calcd. for $C_8H_7O_3S$: C, 61.52; H, 4.30; S, 13.69; Found: C, 61.12; H, 4.34; S, 13.56.

Ex-13D: To a solution of 2-hydroxy-4-methoxy-5-thien-2-ylbenzaldehyde (Ex-13C, 0.10 g, 0.43 mmol) in N,N-dimethylformamide (3 mL) was added potassium carbonate (0.18 g, 1.3 mmol) and the resulting yellow slurry was heated to 80° C. Methanesulfonic acid 3-(tert-butyldimethylsilanyloxy)-2-(tert-butyldimethylsilanyloxymethyl)propyl ester (Ex-13A, 0.24 g, 1.3 mmol) was then added dropwise in three equal portions with stirring at 1 h intervals. After the last addition, the reaction was stirred for an additional 1 h at 80° C. and cooled to room temperature. The mixture was diluted with water (15 mL) and extracted with ethyl acetate (3 x 15 mL). The combined organic phase was sequentially washed with a saturated ammonium chloride solution (15 mL), water (15 mL), and brine (15 mL), dried over sodium sulfate, and concentrated to a brown oil. Silica gel chromatography (ethyl acetate/hexanes, 1:6) gave 0.78 g (90%) of 2-[3-(tert-butyldimethylsilanyloxy)-2-(tert-butyldimethylsilanyloxymethyl)propoxy]-4-methoxy-5-thien-2-ylbenzaldehyde as a pale green solid, mp 91–92° C. $^1$H-NMR (300 MHz, $CDCl_3$) δ 10.34 (s, 1H), 8.13 (s, 1H), 7.41 (dd, 1H, J=3.6, 1.2 Hz), 7.28 (dd, 1H, J=5.1, 1.2 Hz), 7.05 (dd, 1H, J=5.1, 3.6 Hz), 6.54 (s, 1H), 4.22 (d, 2H, J=5.7 Hz), 3.96 (s, 3H), 3.80 (d, 4H, J=5.7 Hz), 2.33 (pentet, 1H, J=5.7 Hz), 0.88 (s, 18H), 0.012 (s, 12H). HRMS (EI) Calcd. for $C_{28}H_{46}O_5SSi_2$: 550.2604 $(M^+)$; Found: 550.2593.

Ex-13E: To a solution of 2-[3-(tert-butyldimethylsilanyloxy)-2-(tert-butyldimethylsilanyloxymethyl)propoxy]-4-methoxy-5-thien-2-ylbenzaldehyde (Ex-13D, 0.78 g, 1.41 mmol) in tetrahydrofuran (5 mL) was added tetrabutylammonium fluoride (1 M in tetrahydrofuran, 3.0 mL, 2.9 mmol) and the mixture was stirred at room temperature for 30 min. The reaction was diluted with ethyl acetate (50 mL) and washed sequentially with a 50% ammonium chloride solution (30 mL), water (2×30 mL), brine (30 mL), dried over sodium sulfate and concentrated to a crude yellow solid. Silica gel chromatography afforded 0.37 g (99%) of 2-(3-hydroxy-2-hydroxymethylpropoxy)-4-methoxy-5-thien-2-ylbenzaldehyde as a pale yellow solid, mp 144–145° C. $^1$H-NMR (300 MHz, $CDCl_3$) δ 10.33 (s, 1H), 8.10 (s, 1H), 7.38 (dd, 1H, J=3.6, 1.5 Hz), 7.30 (dd, 1H, J=5.1, 1.5 Hz), 7.07 (dd, 1H, J=5.1, 3.6 Hz), 6.59 (s, 1H), 4.35 (d, 2H, J=6.0 Hz), 4.02 (t, 4H, J=4.8 Hz), 3.96 (s, 3H), 2.33 (pentet, 1H, J=6.0 Hz), 1.89 (t, 2H, J=4.8 Hz). Anal. Calcd. for $C_{16}H_{18}O_5S$: C, 59.61; H, 5.63; S, 9.95; Found: C, 59.34; H, 5.75; S, 9.82.

The title compound was prepared in an analogous fashion as Ex-1 using 4-acetyl-N-(5-methylisoxazole-3-yl)benzenesulfonamide (Ex-13E), 57% yield, orange solid, mp 165–166° C. $^1$H-NMR (300 MHz, DMSO-$d_6$) δ8.29 (d, 2H, J=8.7 Hz), 8.25 (s, 1H), 8.08 (d, 1H, J=15.9 Hz), 8.02 (d, 2H, J=8.7 Hz), 7.90 (d, 1H, J=15.9 Hz), 7.65 (d, 1H, J=3.6 Hz), 7.52 (d, 1H, J=5.1 Hz), 7.13 (dd, 1H, J=5.1, 3.6 Hz), 6.87 (s, 1H), 6.18 (s, 1H), 4.67 (brs, 2H), 4.23 (d, 2H, J=5.7 Hz), 4.01 (s, 3H), 3.57–3.59 (m, 4H), 2.31 (s, 3H), 2.11 (pentet, 1H, J=5.7 Hz). Anal. Calcd. for $C_{28}H_{28}N_2O_8S_2$: C, 57.52; H, 4.83; N, 4.79; S, 10.97. Found: C, 57.58; H, 4.77; N, 4.67; S, 11.01. HRMS (ESI) Calcd. for $C_{28}H_{28}N_2O_8S_2$: 585.1365 $(M+H)^+$; Found: 585.1367.

Example 14

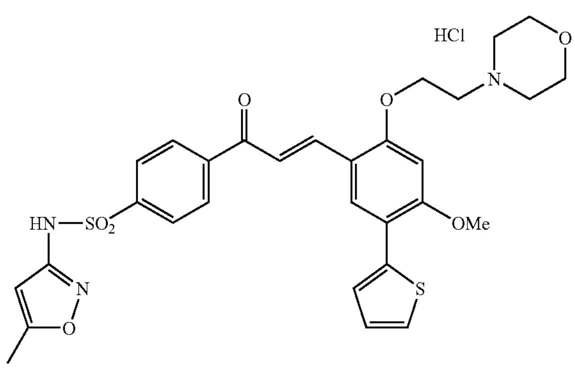

4-{3E-[4-Methoxy-2-(2-morpholin-4-yl-ethoxy)-5-thien-2-ylphenyl]acryloyl}-N-(5-methyl-isoxazol-3-yl)benzenesulfonamide hydrochloride Ex-14A: 4-Methoxy-2-(2-morpholin-4-ylethoxy)-5-thien-2-ylbenzaldehyde was prepared in an analogous fashion as Ex-13D using 4-(2-chloroethyl)morpholine hydrochloride, 93% yield after silica gel chromatography (80 to 100% ethyl acetate/hexanes then 5% methanol/methylene chloride), off-white solid, mp 130–131° C. $^1$H-NMR (300 MHz, $CDCl_3$) δ 10.36 (s, 1H), 8.12 (s, 1H), 7.44 (dd, 1H, J=3.6, 1.5 Hz), 7.30 (dd, 1H, J=5.1, 1.5 Hz), 7.07 (dd, 1H, J=5.1, 3.6 Hz), 6.53 (s, 1H), 4.27 (t, 2H, J=6.3 Hz), 4.00 (s, 3H), 3.72–3.76 (m, 4H), 2.89 (t, 2H, J=6.3 Hz), 2.60–2.63 (m, 4H). HRMS (EI) Calcd. for $C_{18}H_{21}NO_4S$: 347.1191 $(M^+)$; Found: 347.1188.

4-Acetyl-N-(5-methylisoxazole-3-yl)benzenesulfonamide (Ex-1B, 0.30 g, 0.86 mmol) and 4-methoxy-2-(2-morpholin-4-ylethoxy)-5-thien-2-ylbenzaldehyde (Ex-14A, 0.24 g, 0.86 mmol) were dissolved in a dimethylformamide-methanol solution (6.0 mL, 7:3). After complete dissolution, lithium methoxide (0.13 g, 3.4 mmol) was added and the resulting orange slurry was stirred in the dark at room temperature for 1 h. Upon completion, as determined by HPLC, the mixture was diluted with water (8.0 mL), acidified with a 1 N hydrochloric acid solution, and extracted with ethyl acetate:tetrahydrofuran (1:1, 3×20 mL). The combined organic extracts were evaporated to dryness. The crude oil was taken up in ethanol (10 mL) and warmed to 60° C. to obtain complete dissolution and allowed to cool to room temperature. The resulting precipitate was collected on filter paper and dried in vacuo to yield 0.46 g (88%) of the title compound as a pale orange solid, mp>260° C. $^1$H-NMR (300 MHz, DMSO-$d_6$) δ8.34 (d, 2H, J=9.0 Hz), 8.32 (s, 1H), 8.12 (d, 1H, J=15.9 Hz), 8.03 (d, 2H, J=9.0 Hz), 7.93 (d, 1H, J=15.9 Hz), 7.69 (d, 1H, J=3.3 Hz), 7.56 (d, 1H, J=5.4 Hz), 7.15 (dd, 1H, J=5.4, 3.3 Hz), 6.92 (s, 1H), 6.18 (s, 1H), 4.65 (brs, 2H), 4.03 (s, 3H), 3.97 (brs, 4H), 3.69 (brs, 2H), 3.50–3.23 (brs, 4H), 2.31 (s, 3H). Anal. Calcd. for $C_{30}H_{32}ClN_3O_7S_2.H_2O$: C, 54.25; H, 5.16; N, 6.33; S, 9.66; Found: C, 54.10; H, 4.91; N, 6.39; S, 9.68. HRMS (ESI) Calcd. for $C_{30}H_{32}ClN_3O_7S_2$: 610.1681 (—HCl) $(M+H)^+$. Found: 610.1673.

Example 15

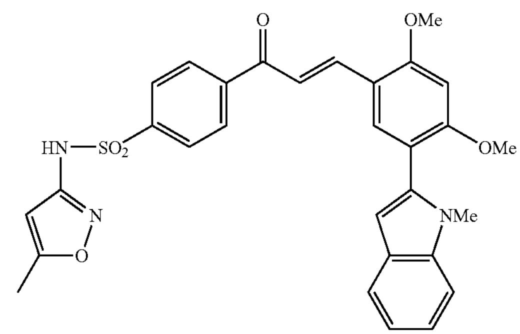

4-{3E-[2,4-Dimethoxy-5-(l-methyl-1H-indol-2-yl)phenyl]acryloyl}-N-(5-methylisoxazol-3-yl)benzenesulfonamide Ex-15A: 1-Methylindole (5.0 g, 38.1 mmol) was dissolved in tetrahydrofuran (190 mL) and nitrogen was bubbled into the solution for 15 min. The solution was then cooled to 0° C. and tert-butyllithium (1.6 M solution in pentane, 23.5 mL, 40.0 mmol) was added dropwise and the mixture was stirred for 30 min at 0° C. and then warmed to room temperature and stirred for an additional 1 h. Triethylborane (1.0 M solution in THF, 45.7 mL, 45.7 mmol) was added, and the reaction mixture was stirred for 1 h at room temperature. To the crude indolylborate, generated in situ, was added 5-bromo-2,4-dimethoxybenzaldehyde (9.3 g, 38.1 mmol) and bis(tri-t-butylphosphine)palladium (0) (0.48 g, 0.95 mmol). The solution was immediately heated to 60° C. and aged for 30 min. Upon completion, as determined by HPLC, the reaction was treated with 10% aqueous sodium hydroxide (190 mL) and 30% hydrogen peroxide (38 mL) with ice-cooling for 20 min. The mixture was extracted with ethyl acetate (3×100 mL), and the combined organic extracts were washed with brine (2×75 mL), dried over sodium sulfate and concentrated to a brown oil. Silica gel chromatography (ethyl acetate/hexanes, 1:3 to 3:1) gave 7.69 g (77%) of 2,4-dimethoxy-5-(1-methyl-1H-indol-2-yl)benzaldehyde as a yellow solid, mp 153–153° C. $^1$H-NMR (300

MHz, $CDCl_3$) δ 10.36 (s, 1H), 7.87 (s, 1H), 7.37 (d, 1H, J=7.5 Hz), 7.31 (d, 1H, J=9.0 Hz), 7.20–7.28 (m, 1H), 7.12 (t, 1H, J=6.8 Hz), 6.55 (s, 1H), 6.48 (s, 1H), 4.03 (s, 3H), 3.91 (s, 3H), 3.55 (s, 3H). Anal. Calcd. for $C_{18}H_{17}NO_3$: C, 73.20; H, 5.80; N, 4.74; Found: C, 72.98; H, 5.89; N, 4.73.

The title compound was prepared in an analogous fashion as Ex-1 using 2,4-dimethoxy-5-(1-methyl-1H-indol-2-yl) benzaldehyde (Ex-15A), 66% yield, pale orange solid, mp 220° C. $^1$H-NMR (300 MHz, DMSO-$d_6$) δ8.29 (d, 2H, J=8.7 Hz), 8.12 (d, 1H, J=15.8 Hz), 8.04 (s, 1H), 7.96 (d, 2H, J=8.7 Hz), 7.84 (d, 1H, J=15.8 Hz), 7.55 (d, 1H, J=7.5 Hz), 7.46 (d, 1H, J=8.1 Hz), 7.17 (t, 1H, J=7.5 Hz), 7.06 (t, 1H, J=7.8 Hz), 6.89 (s, 1H), 6.45 (s, 1H), 6.15 (s, 1H), 4.05 (s, 3H), 3.91 (s, 3H), 3.54 (s, 3H), 2.28 (s, 3H). Anal. Calcd. for $C_{30}H_{27}N_3O_6S$: C, 64.62; H, 4.88; N, 7.54; S, 5.75. Found: C, 64.42; H, 5.26; N, 7.46; S, 5.61. HRMS (ESI) Calcd. for $C_{30}H_{27}N_3O_6S$: 558.1699 $(M+H)^+$; Found: 558.1685.

Example 16

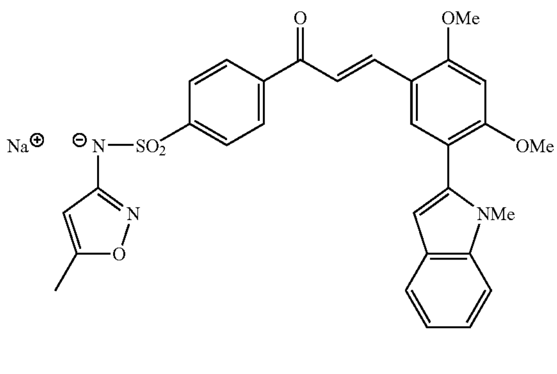

4-{3E-[2,4-Dimethoxy-5-(1-methyl-1H-indol-2-yl) phenyl]acryloyl}-N-(5-methylisoxazol-3-yl)benzenesulfonamide sodium salt The title compound was prepared in an analogous fashion as Ex-2 from 4-{3-[2,4-dimethoxy-5-(1-methyl-1H-indol-2-yl)phenyl]acryloyl}-N-(5-methylisoxazol-3-yl)benzenesulfonamide (Ex-15) as a yellow solid, mp 202–206° C. $^1$H-NMR (300 MHz, DMSO-$d_6$) δ8.03–8.10 (m, 4H), 7.88 (d, 1H, J=15.9 Hz), 7.75 (d, 2H, J=8.1 Hz), 7.55 (d, 1H, J=7.5 Hz), 7.46 (d, 1H, J=8.4 Hz), 7.17 (t, 1H, J=7.5 Hz), 7.06 (t, 1H, J=7.8 Hz), 6.88 (s, 1H), 6.46 (s, 1H), 5.77 (s, 1H), 4.04 (s, 3H), 3.91 (s, 3H), 3.54 (s, 3H), 2.09 (s, 3H). Anal. Calcd. for $C_{30}H_{26}N_3NaO_6S.H_2O.⅓EtOH$: C, 60.09; H, 4.93; N, 6.86; S, 5.23; Found: C, 59.86; H, 4.89; N, 6.80; S, 5.14.

Example 17

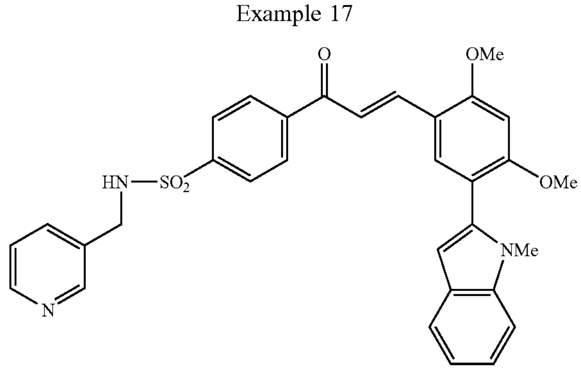

4-{3E-[2,4-Dimethoxy-5-(1-methyl-1H-indol-2-yl) phenyl]acryloyl}-N-pyridin-3-ylmethy-benzenesulfonamide Ex-17A: To a solution of 4-acetylbenzenesulfonyl chloride (0.50 g, 2.3 mmol) in tetrahydrofuran (10 mL) was added 3-(aminomethyl)pyridine (0.58 g, 5.7 mmol) and the reaction was stirred for 30 min at room temperature. The mixture was then diluted with water (30 mL) and extracted with ethyl acetate (3×20 mL). The combined organic layers were washed with brine (2×25 mL), dried over sodium sulfate, and the solvent was removed under reduced pressure. The resulting solid was dried in vacuo to afford 0.67 g (99%) of 4-acetyl-N-pyridin-3-ylmethylbenzenesulfonamide as a white solid, mp 143–144° C. $^1$H-NMR (300 MHz, $CDCl_3$) δ 8.50–8.52 (m, 1H), 8.41 (d, 1H, J=2.7 Hz), 8.06 (d, 2H, J=8.7 Hz), 7.95 (d, 2H, J=8.4 Hz), 7.6–7.63 (m, 1H), 7.21–7.25 (m, 1H), 5.05 (brs, 1H), 4.22 (d, 2H, J=5.7 Hz), 2.66 (s, 3H). HRMS (EI) Calcd. for $C_{14}H_{14}N_2O_3S$: 290.0725 $(M^+)$; Found: 290.0726.

The title compound was prepared in an analogous fashion as Ex-1 using 4-acetyl-N-(5-methylisoxazole-3-yl)benzenesulfonamide (Ex-17A) and 2,4-dimethoxy-5-(1-methyl-1H-indol-2-yl)benzaldehyde (Ex-15A), 80% yield, yellow solid, mp 202–203° C. $^1$H-NMR (300 MHz, DMSO-$d_6$) δ8.39–8.43 (m, 3H), 8.26 (d, 2H, J=8.0 Hz), 8.13 (d, 1H, J=15.9 Hz), 8.06 (s, 1H), 7.89 (d, 2H, J=8.0 Hz), 7.85 (d, 1H, J=15.9 Hz), 7.60–7.63 (m, 1H), 7.56 (d, 1H, J=6.9 Hz), 7.46 (d, 1H, J=8.1 Hz), 7.27 (dd, 1H, J=7.2, 4.2 Hz), 7.17 (t, 1H, J=7.2 Hz), 7.06 (t, 1H, J=8.1 Hz), 6.90 (s, 1H), 6.46 (s, 1H), 4.07 (s, 2H), 4.06 (s, 3H), 3.93 (s, 3H), 3.55 (s, 3H). Anal. Calcd. for $C_{32}H_{29}N_3O_5S.¼H_2O$: C, 67.17; H, 5.20; N, 7.34; S, 5.60; Found: C, 67.39; H, 5.41; N, 7.38; S, 5.54. HRMS (ESI) Calcd. for $C_{32}H_{29}N_3O_5S$: 568.1906 $(M+H)^+$; Found: 568.1895.

Example 18

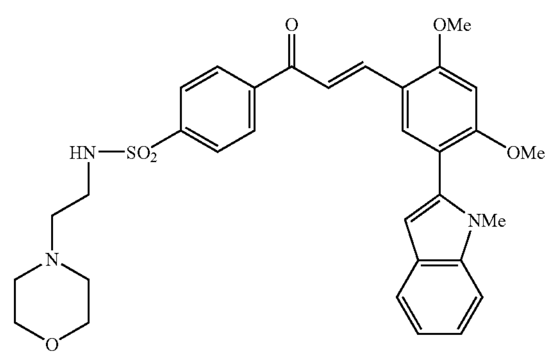

4-{3E-[2,4-Dimethoxy-5-(1-methyl-1H-indol-2-yl) phenyl]acryloyl}-N-(2-morpholin-4-yl-ethyl)benzenesulfonamide Ex-18A: 4-Acetyl-N-(2-morpholin-4-ylethyl)benzenesulfonamide was prepared in an analogous fashion as Ex-17A using 4-(2-aminoethyl)morpholine, 99% yield, off-white solid, mp 128–129° C. $^1$H-NMR (300 MHz, $CDCl_3$) δ 8.08 (d, 2H, J=8.7 Hz), 7.98 (d, 2H, J=8.7 Hz), 5.28 (brs, 1H), 3.61–3.64 (m, 4H), 3.05 (t, 2H, J=5.4 Hz), 2.66 (s, 3H), 2.42 (t, 2H, J=5.7 Hz), 2.27–2.31 (m, 4H). HRMS (ESI) Calcd. for $C_{14}H_{20}N_2O_4S$: 313.1222 $(M+H)^+$; Found: 313.1215.

The title compound was prepared in an analogous fashion as Ex-1 using 4-acetyl-N-(5-methylisoxazole-3-yl)benzenesulfonamide (Ex-18A) and 2,4-dimethoxy-5-(1-methyl-1H-indol-2-yl)benzaldehyde (Ex-15A), 80% yield, yellow solid, mp 167–168° C. $^1$H-NMR (300 MHz, DMSO-$d_6$) δ8.29 (d, 2H, J=8.7 Hz), 8.14 (d, 1H, J=15.3 Hz), 8.06 (s, 1H), 7.93 (d, 2H, J=8.7 Hz), 7.86 (d, 1H, J=15.3 Hz), 7.77 (brs, 1H), 7.56 (d, 1H, J=7.2 Hz), 7.46 (d, 1H, J=8.1 Hz), 7.18 (t, 1H, J=7.8Hz), 7.06 (t, 1H, J=7.2Hz), 6.90 (s, 1H), 6.46 (s, 1H), 4.06 (s, 3H), 3.93 (s, 3H), 3.55 (s, 3H), 3.42–3.48 (m, 4H), 2.89 (t, 2H, J=7.5 Hz), 2.22–2.31 (m, 6H). Anal. Calcd. for $C_{32}H_{35}N_3O_6S$: C, 65.18; H, 5.98; N, 7.13; S, 5.44; Found: C, 65.05; H, 6.11; N, 7.09; S, 5.42. HRMS (ESI) Calcd. for $C_{32}H_{35}N_3O_6S$: 590.2325 $(M+H)^+$; Found: 590.2334.

Example 19

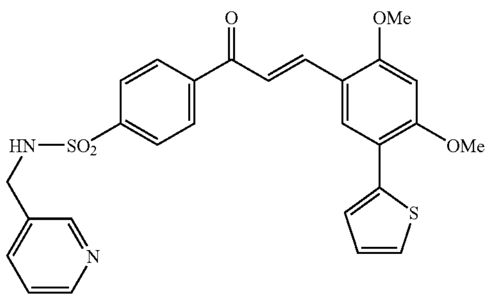

4-[3E-(2,4-Dimethoxy-5-thien-2-ylphenyl)acryloyl]-N-pyridin-3-ylmethylbenzenesulfonamide The title compound was prepared in an analogous fashion as Ex-1 using 4-acetyl-N-pyridin-3-ylmethylbenzenesulfonamide (Ex-17A), 85% yield, yellow solid, mp 167–168° C. $^1$H-NMR (300 MHz, DMSO-$d_6$) δ8.47 (brs, 1H), 8.40–8.43 (m, 2H), 8.27 (d, 3H, J=8.4 Hz), 8.10 (d, 1H, J=15.6 Hz), 7.94 (d, 2H, J=8.4 Hz), 7.90 (d, 1H, J=15.6 Hz), 7.62–7.68 (m, 2H), 7.53 (d, 1H, J=5.4 Hz), 7.29 (dd, 1H, J=7.5, 4.8 Hz), 7.14 (dd, 1H, J=5.4, 3.6 Hz), 6.85 (s, 1H), 4.10 (s, 2H), 4.02 (s, 3H), 4.01 (s, 3H). Anal. Calcd. for $C_{27}H_{24}N_2O_5S_2$: C, 62.29; H, 4.65; N, 5.38; S, 12.32; Found: C, 62.03; H, 4.87; N, 5.39; S, 12.10.

Example 20

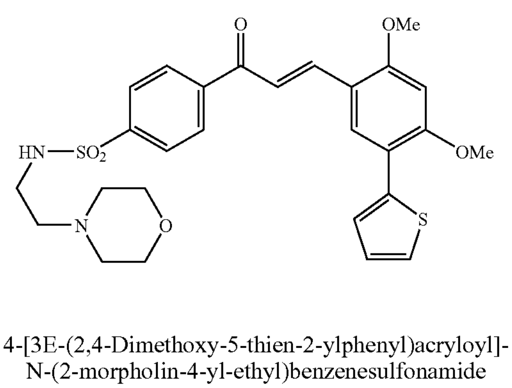

4-[3E-(2,4-Dimethoxy-5-thien-2-ylphenyl)acryloyl]-N-(2-morpholin-4-yl-ethyl)benzenesulfonamide The title compound was prepared in an analogous fashion as Ex-1 using 4-acetyl-N-(2-morpholin-4-ylethyl)benzenesulfonamide (Ex-18A), 90% yield, yellow solid, mp 171–172° C. $^1$H-NMR (300 MHz, DMSO-$d_6$) δ8.31 (d, 2H, J=9.0 Hz), 8.28 (s, 1H), 8.09 (d, 1H, J=15.6 Hz), 7.97 (d, 2H, J=9.0 Hz), 7.91 (d, 1H, J=15.6 Hz), 7.80 (brs, 1H), 7.67 (d, 1H, J=3.6 Hz), 7.53 (d, 1H, J=5.4 Hz), 7.13 (dd, 1H, J=5.4, 3.6 Hz), 6.85 (s, 1H), 4.02 (s, 3H), 4.01 (s, 3H), 3.47–3.50 (m, 4H), 2.91 (t, 2H, J=7.2 Hz), 2.24–2.33 (m, 6H). Anal. Calcd. for $C_{27}H_{30}N_2O_6S_2$: C, 59.76; H, 5.57; N, 5.16; S, 11.82; Found: C, 59.39; H, 5.65; N, 5.11; S, 11.53.

Example 21

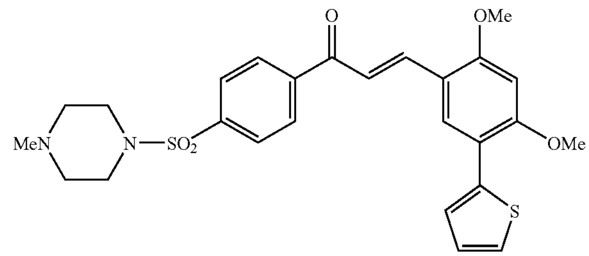

3E-(2,4-Dimethoxy-5-thien-2-ylphenyl)-1-[4-(4-methylpiperazine-1-sulfonyl)phenyl]propenone Ex-21A: 1-[4-(4-Methylpiperazine-1-sulfonyl)phenyl]ethanone was prepared in an analogous fashion as Ex-17A using 4-methylpiperazine, 99% yield, pale yellow solid, mp 118–119° C. $^1$H-NMR (300 MHz, $CDCl_3$) δ 8.09 (d, 2H, J=9.3 Hz), 7.85 (d, 2H, J=9.3 Hz), 3.67 (t, 4H, J=4.8 Hz), 2.66 (s, 3H), 2.48 (t, 4H, J=4.8 Hz), 2.27 (s, 3H). HRMS (EI) Calcd. for $C_{13}H_{18}N_2O_3S$: 282.1038 $(M^+)$; Found: 282.1038.

The title compound was prepared in an analogous fashion as Ex-1 using 1-[4-(4-methylpiperazine-1-sulfonyl)phenyl]ethanone (Ex-21A), 30% yield after silica gel chromatography (methanol/methylene chloride, 1:10), dark yellow solid, mp 133–135° C. $^1$H-NMR (300 MHz, DMSO-$d_6$) δ8.31 (d, 2H, J=8.7 Hz), 8.25 (s, 1H), 8.06 (d, 1H, J=15.0 Hz), 7.89 (d, 2H, J=8.7 Hz), 7.82 (d, 1H, J=15.0 Hz), 7.63 (d, 1H, J=3.9 Hz), 7.48 (d, 1H, J=5.4 Hz), 7.09 (dd, 1H, J=5.4, 3.9 Hz), 6.81 (s, 1H), 4.00 (s, 3H), 3.98 (s, 3H), 3.90 (brs, 4H), 2.32–2.34 (m, 4H), 2.07 (s, 3H). HRMS (EI) Calcd. for $C_{26}H_{28}N_2O_5S_2$: 512.1440 $(M^+)$; Found: 512.1427.

Example 22

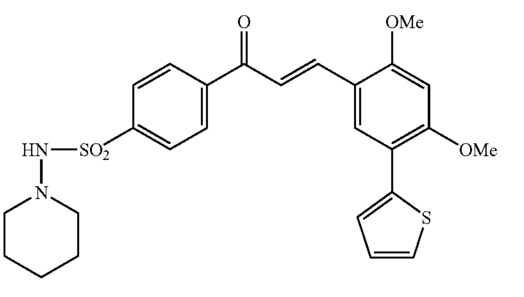

4-[3E-(2,4-Dimethoxy-5-thien-2-ylphenyl)acryloyl]-N-piperidin-1-ylbenzenesulfonamide Ex-22A: 4-Acetyl-N-piperidin-1-ylbenzenesulfonamide was prepared in an analogous fashion as Ex-17A using 1-aminopiperidine, 98% yield, pale yellow solid, mp 137–139° C. $^1$H-NMR (300 MHz, $CDCl_3$) δ 8.07 (s, 4H), 5.38 (brs, 1H), 2.67 (s, 3H), 2.54 (t, 4H, J=5.4 Hz), 1.47–1.55 (m, 4H), 1.30–1.33 (m, 2H). Anal. Calcd. for $C_{13}H_{18}N_2O_3S$: C, 55.30; H, 6.43; N, 9.92; S, 11.36; Found: C, 55.22; H, 6.40; N, 9.50; S, 11.38.

The title compound was prepared in an analogous fashion as Ex-1 using 4-acetyl-N-piperidin-1-ylbenzenesulfonamide (Ex-22A), 71% yield, orange solid, mp 174–176° C. $^1$H-NMR (300 MHz, DMSO-$d_6$) δ8.94 (s, 1H), 8.32 (d, 2H, J=8.7 Hz), 8.29 (s, 1H), 8.10 (d, 1H, J=15.0 Hz), 8.00 (d, 2H, J=8.7 Hz), 7.93 (d, 1H, J=15.0 Hz), 7.67 (dd, 1H, J=3.6, 1.5 Hz), 7.53 (dd, 1H, J=5.4, 1.5 Hz), 7.14 (dd, 1H, J=5.4, 3.6 Hz), 6.85 (s, 1H), 4.02 (s, 3H), 4.01 (s, 3H), 2.44–2.47 (m, 4H), 1.38 (brs, 4H), 1.21–1.23 (m, 2H). Anal. Calcd. for $C_{26}H_{28}N_2O_5S_2$: C, 60.92; H, 5.51; N, 5.46; S, 12.51; Found: C, 61.13; H, 5.71; N, 5.38; S, 12.35.

Example 23

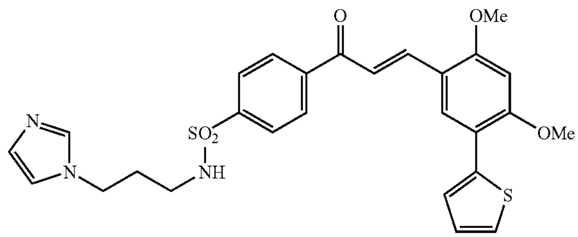

4-[3E-(2,4-Dimethoxy-5-thien-2-ylphenyl)acryloyl]-N-(3-imidazol-1-ylpropyl)benzenesulfonamide Ex-23A: 4-Acetyl-N-(3-imidazol-1-ylpropyl)benzenesulfonamide was prepared in an analogous fashion as Ex-17A using 1-(3-aminopropyl)imidazole, 89% yield, white solid, mp 142–144° C. $^1$H-NMR (300 MHz, DMSO-$d_6$) δ 8.14 (d, 2H, J=8.1 Hz), 7.89 (d, 2H, J=8.1 Hz), 7.54 (s, 1 H), 7.09 (s, 1H), 6.85 (s, 1H), 3.96 (t, 2H, J=7.2 Hz), 3.31 (s, 3H), 2.70 (t, 2H, J=7.8 Hz), 1.80 (pentet, 2H, J=7.8 Hz). HRMS (EI) Calcd. for $C_{14}H_{17}N_3O_3S$: 307.0991 ($M^+$); Found: 307.0986.

The title compound was prepared in an analogous fashion as Ex-1 using 4-acetyl-N-(3-imidazol-1-ylpropyl)benzenesulfonamide (Ex-23A), 70% yield, yellow solid, mp 160–162° C. $^1$H-NMR (300 MHz, DMSO-$d_6$) δ8.31 (d, 2H, J=8.7 Hz), 8.29 (s, 1H), 8.10 (d, 1H, J=15.9 Hz), 7.93 (d, 3H, J=8.7 Hz), 7.91 (d, 1H, J=15.9 Hz), 7.67 (dd, 1H, J=3.6, 1.5 Hz), 7.55 (s, 1H), 7.54 (d, 1H, J=5.4 Hz), 7.13 (dd, 1H, J=5.4, 3.6 Hz), 7.10 (s, 1H), 6.85 (s, 1H), 4.02 (s, 3H), 4.01 (s, 3H), 3.97 (t, 2H, J=6.3 Hz), 2.70–2.76 (m, 2H), 1.81 (pentet, 2H, J=6.3 Hz). Anal. Calcd. for $C_{27}H_{27}N_3O_5S_2$: C, 60.32; H, 5.06; N, 7.82; S, 11.93; Found: C, 59.76; H, 5.06; N, 7.60; S, 12.00.

Example 24

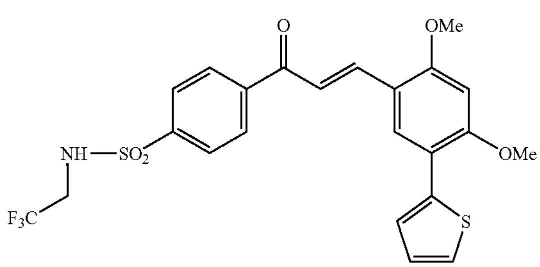

4-[3E-(2,4-Dimethoxy-5-thien-2-ylphenyl)acryloyl]-N-(2,2,2-trifluoroethyl)benzenesulfonamide Ex-24A: 4-Acetyl-N-(2,2,2-trifluoroethyl)benzenesulfonamide was prepared in an analogous fashion as Ex-17A using 2,2,2-trifluoroethylamine hydrochloride and triethylamine in a tetrahydrofuran:water mixture (9:1), 73% yield, white solid, mp 180–181° C. $^1$H-NMR (300 MHz, DMSO-$d_6$) δ 8.85 (brs, 1H), 8.14 (d, 2H, J=8.1 Hz), 7.96 (d, 2H, J=8.1 Hz), 7.75 (q, 2H, J=10.0 Hz), 6.64 (s, 3H). HRMS (EI) Calcd. for $C_{10}H_{10}F_3NO_3S$: 281.0333 ($M^+$); Found: 281.0342.

The title compound was prepared in an analogous fashion as Ex-1 using 4-acetyl-N-(2,2,2-trifluoroethyl)benzenesulfonamide (Ex-24A), 43% yield, yellow solid, mp 167–168° C. $^1$H-NMR (400 MHz, DMSO-$d_6$) δ8.87 (s, 1H), 8.31 (d, 2H, J=5.6 Hz), 8.29 (s, 1H), 8.10 (d, 1H, J=10.4 Hz), 8.00 (d, 2H, J=5.6 Hz), 7.92 (d, 1H, J=10.4 Hz), 7.67 (d, 1H, J=2.8 Hz), 7.53 (d, 1H, J=3.6 Hz), 7.14 (dd, 1H, J=3.6, 2.8 Hz), 6.85 (s, 1H), 4.02 (s, 3H), 4.01 (s, 3H), 3.78 (q, 2H, J=6.8 Hz). HRMS (ESI) Calcd. for $C_{23}H_{20}F_3NO_5S_2$: 512.0813 $(M+H)^+$; Found: 512.0798.

Example 25

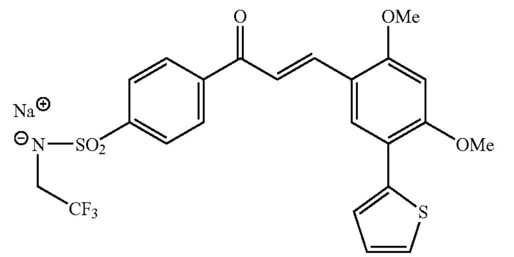

4-[3E-(2,4-Dimethoxy-5-thien-2-ylphenyl)acryloyl]-N-(2,2,2-trifluoroethyl)benzenesulfonamide sodium salt The title compound was prepared in an analogous fashion as Ex-2, from 4-[3E-(2,4-Dimethoxy-5-thien-2-ylphenyl)acryloyl]-N-(2,2,2-trifluoroethyl)benzenesulfonamide (Ex-24, 45% yield, yellow solid, mp 160–170° C. $^1$H-NMR (300 MHz, DMSO-$d_6$) δ8.27 (s, 1H), 8.10 (d, 2H, J=8.1 Hz), 8.05 (d, 1H, J=15.7 Hz), 7.90 (d, 1H, J=15.7 Hz), 7.71 (d, 3H, J=8.1 Hz), 7.52 (d, 1H, J=5.4 Hz), 7.13 (dd, 1H, J=3.3, 5.4 Hz), 6.84 (s, 1H), 4.02 (s, 3H), 4.01 (s, 3H), 3.28 (q, 2H, J=10.5 Hz). Anal. Calcd. for $C_{23}H_{19}F_3NNaO_5S_2.⅔H_2O.⅓EtOH$: C, 50.68; H, 4.01; N, 2.50; S, 11.43; Found: C, 50.88; H, 4.35; N, 2.49; S, 10.99.

Example 26

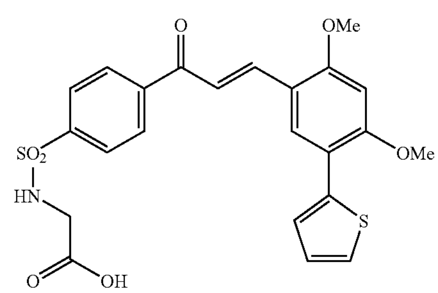

{4-[3E-(2,4-Dimethoxy-5-thien-2-ylphenyl)acryloyl]benzenesulfonylamino}acetic acid Ex-26A: To a solution of 4-acetylbenzenesulfonyl chloride (0.50 g, 2.3 mmol) in acetone (7.5 mL) was added a solution of glycine (0.42 g, 5.7 mmol) in 5% aqueous sodium hydroxide (2.5 mL) and the reaction was stirred for 30 min at room temperature. The mixture was diluted with water (10 mL), acidified with a 1 N hydrochloric acid solution, and extracted with ethyl acetate (3×15 mL). The combined organic layers were washed with brine (2×20 mL), dried over sodium sulfate, and the solvent was removed under reduced pressure. The resulting solid was dried in vacuo to afford 0.55 g (94%) of (4-acetylbenzenesulfonylamino)acetic acid as a white solid, mp 213–215° C. $^1$H-NMR (300 MHz, DMSO-$d_6$) δ 8.28 (t, 1H, J=5.4 Hz), 8.12 (d, 2H, J=8.4 Hz), 7.92 (d, 2H, J=8.4 Hz), 3.64 (d, 2H, J=5.1 Hz), 2.64 (s, 3H). Anal. Calcd. for $C_{10}H_{11}NO_5S$: C, 46.69; H, 4.31; N, 5.44; S, 12.46; Found: C, 46.76; H, 4.43; N, 5.39; S, 12.16.

The title compound was prepared in an analogous fashion as Ex-1 using (4-acetylbenzenesulfonylamino)acetic acid (Ex-26A), 82% yield, orange solid, mp 100–101° C. $^1$H-NMR (300 MHz, DMSO-$d_6$) δ8.30 (d, 3H, J=8.1 Hz), 8.29(s, 1H), 8.10 (d, 1H, J=15.0 Hz), 7.96 (d, 2H, J=8.1 Hz), 7.92 (d, 1H, J=15.0 Hz), 7.67 (dd, 1H, J=3.6, 1.2 Hz), 7.53 (d, 1H, J=5.4 Hz), 7.14 (dd, 1H, J=5.4, 3.6 Hz), 6.85 (s, 1H), 4.02 (s, 3H), 4.01 (s, 3H), 3.66 (d, 2H, J=5.7 Hz). HRMS (ESI) Calcd. for $C_{23}H_{21}NO_7S_2$: 488.0837 $(M+H)^+$; Found: 488.0847.

Example 27

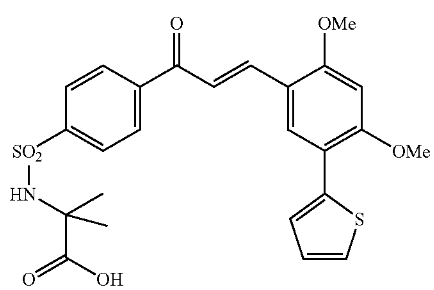

2-{4-[3E-(2,4-Dimethoxy-5-thien-2-yl-phenyl)acryloyl]benzenesulfonylamino}-2-methylpropionic acid Ex-27A: 2-(4-Acetylbenzenesulfonylamino)-2-methylpropionic acid was prepared in an analogous fashion as Ex-26A using 2-aminoisobutyric acid, 70% yield, white solid, mp 157–158° C. $^1$H-NMR (300 MHz, DMSO-$d_6$) δ 8.21 (s, 1H), 8.10 (d, 2H, J=8.7 Hz), 7.92 (d, 2H, J=8.7 Hz), 3.63 (s, 3H), 1.27 (s, 6H). Anal. Calcd. for $C_{12}H_{15}NO_5S.\frac{1}{30}H_2O$: C, 50.40; H, 5.31; N, 4.90; S, 11.21; Found: C, 50.12; H, 5.25; N, 5.15; S, 11.65. HRMS (ESI) Calcd. for $C_{12}H_{15}NO_5S$: 286.0749 $(M+H)^+$; Found: 286.0756.

The title compound was prepared in an analogous fashion as Ex-1 using 2-(4-acetylbenzenesulfonylamino)-2-methylpropionic acid (Ex-27A), 80% yield, yellow solid, mp 205° C. (dec). $^1$H-NMR (300 MHz, DMSO-$d_6$) δ8.29 (d, 2H, J=8.4 Hz), 8.28(s, 1H), 8.23 (s, 1H), 8.10 (d, 1H, J=15.3 Hz), 7.96 (d, 2H, J=8.4 Hz), 7.92 (d, 1H, J=15.3 Hz), 7.67 (d, 1H, J=3.6 Hz), 7.53 (d, 1H, J=5.4 Hz), 7.14 (dd, 1H, J=5.4, 3.6 Hz), 6.85 (s, 1H), 4.02 (s, 3H), 4.01 (s, 3H), 1.30 (s, 6H). Anal. Calcd. for $C_{25}H_{25}NO_7S_2.\frac{1}{5}H_2O$: C, 57.83; H, 4.93; N, 2.70; S, 12.35; Found: C, 57.81; H, 4.98; N, 3.08; S, 12.45.

Example 28

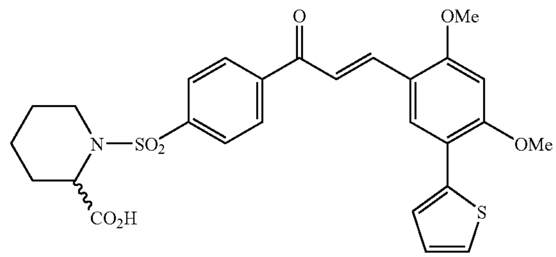

1-{4-[3E-(2,4-Dimethoxy-5-thien-2-ylphenyl)acryloyl]benzenesulfonyl}piperidine-2-carboxylic acid Ex-28A: 1-(4-Acetylbenzenesulfonyl)piperidine-2-carboxylic acid was prepared in an analogous fashion as Ex-26A using 2-pipecolinic acid, 67% yield, white foam. $^1$H-NMR (300 MHz, $CDCl_3$) δ 8.06 (d, 2H, J=8.4 Hz), 7.90 (d, 2H, J=8.4 Hz), 4.83 (d, 1H, J=3.9 Hz), 3.76–3.83 (m, 2H), 3.19 (dt, 1H, J=12.7, 3.0 Hz), 2.66 (s, 3H), 2.19–2.24 (m, 1H), 1.60–1.82 (m, 4H). HRMS (ESI) Calcd. for $C_{14}H_{17}NO_5S$: 312.0905 $(M+H)^+$; Found: 312.0915.

The title compound was prepared in an analogous fashion as Ex-1 using 1-(4-acetylbenzenesulfonyl)piperidine-2-carboxylic acid (Ex-28A), 66% yield, yellow foam. $^1$H-NMR (300 MHz, $CDCl_3$) δ8.08 (d, 1H, J=15.6 Hz), 8.05 (d, 2H, J=8.7 Hz), 8.00 (s, 1H), 7.91 (d, 2H, J=8.7 Hz), 7.86 (s, 1H), 7.51 (d, 1H, J=15.7 Hz), 7.41 (d, 1H, J=3.6 Hz), 7.31 (d, 1H, J=5.7 Hz), 7.09 (dd, 1H, J=5.7, 3.6 Hz), 6.54 (s, 1H), 4.81 (d, 1H, J=4.2 Hz), 3.99 (s, 3H), 3.98 (s, 3H), 3.80–3.83 (m, 2H), 3.23 (dt, 1H, J=12.0, 2.1 Hz), 2.17–2.21 (m, 1H), 1.65–1.73 (m, 4H). HRMS (ESI) Calcd. for $C_{27}H_{27}NO_7S_2$: 542.1307 $(M+H)^+$; Found: 542.1298.

Example 29

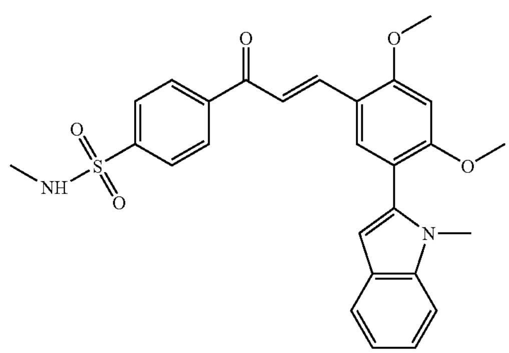

4-{3E-[2,4-Dimethoxy-5-(1-methyl-1H-indol-2-yl)phenyl]acryloyl}-N-methyl-benzenesulfonamide Ex-29A: To a solution of 4-acetylbenzenesulfonyl chloride (1.1 g, 5.0 mmol) in 25 ml of THF, methylamine (0.44 ml of 40% solution in $H_2O$, 5 mmol) was added dropwise, and the mixture was stirred for 30 min. The reaction mixture was poured into water, and the precipitate was filtered. Recrystallization from EtOAc/hexanes gave 0.67 g (62.6%) of 4-acetyl-N-methyl-benzenesulfonamide as a white solid. $^1$H-NMR (300 MHz, $CDCl_3$) δ 8.09 (d, J=8 Hz, 2H), 7.96 (d, J=8 Hz, 2H), 4.48 (br, 1H), 2.70 (d, J=4 Hz, 1H), 2.66 (s, 3H).

The title compound was prepared using in an analogous way as Ex-1 using 4-acetyl-N-methyl-benzenesulfonamide (Ex-29A) and 2,4-dimethoxy-5-(1-methyl-1H-indol-2-yl) benzaldehyde (Ex-15A), 57% yield, yellow solid, mp 129–131° C. $^{1}$H-NMR (300 MHz, $CDCl_3$) δ 8.17 (d, J=16 Hz, 1H), 8.10 (d, J=9 Hz, 2H), 7.95 (d, J=9 Hz, 2H), 7.68 (s, 1H), 7.64 (d, J=7 Hz), 1H), 7.47 (d, J=16 Hz, 1H), 7.36 (d, J=8 Hz, 1H), 7.22–7.26 (m, 1H), 7.14–7.16 (m, 1H), 6.59 (s, 1H), 6.51 (s, 1H), 4.42 (br s, 1H) 4.03 (s, 3H), 3.90 (s, 3H), 3.58 (s, 3H), 2.69 (d, J=6 Hz, 3H). HRMS (ESI) Calcd. for $C_{27}H_{26}N_2O_5S$: 491.1641 $(M+H)^+$; Found: 491.1646.

Example 30

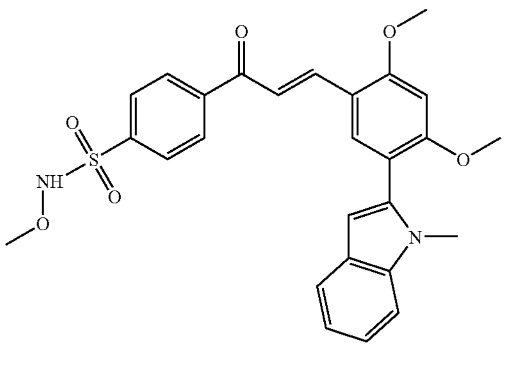

4-{3E-[2,4-Dimethoxy-5-(1-methyl-1H-indol-2-yl) phenyl]acryloyl}-N-methoxybenzenesulfonamide Ex-30A: To a solution of 4-acetylbenzenesulfonyl chloride (2.18 g, 10.0 mmol) in 100 ml of THF at 0° C., $Et_3N$ (2.5 g, 25 mmol) was added followed by O-methyl hydroxyamine hydrochloride (0.84 g, 10 mmol). The mixture was stirred for 1 hr at room temperature and then poured into water, and the precipitate was filtered and dried. Recrystallization from THF/hexanes gave 1.5 g (65.8%) of 4-acetyl-N-methoxybenzenesulfonamide as a white solid. $^{1}$H-NMR (300 MHz, $CDCl_3$) δ 8.10 (d, J=8 Hz, 2H), 8.03 (d, J=8 Hz, 2H), 7.23 (brs, 1H), 3.82 (s, 3H), 2.66 (s, 3H).

The title compound was prepared in an analogous way as Ex-1 using 4-acetyl-N-methoxy-benzenesulfonamide (Ex-30A) and 2,4-dimethoxy-5-(1-methyl-1H-indol-2-yl)benzaldehyde (Ex-15A), 94% yield, yellow solid, mp 214–216° C. $^{1}$H-NMR (300 MHz, $CDCl_3$) δ 8.17 (d, J=16 Hz, 1H), 8.11 (d, J=8 Hz, 2H), 8.03 (d, J=8 Hz, 2H), 7.68 (s, 1H), 7.64 (d, J=7 Hz, 1H), 7.48 (d, J=16 Hz, 1H), 7.36 (d, J=8 Hz, 1H), 7.25–7.26 (m, 1H), 7.11–7.16 (m, 2H), 6.59 (s, 1H), 6.50 (s, 1H), 4.03 (s, 3H) 3.90 (s, 3H), 3.84 (s, 3H), 3.58 (s, 3H). MS m/z: 506 ($[M]^+$, 30%), 476 (100%).

Example 31

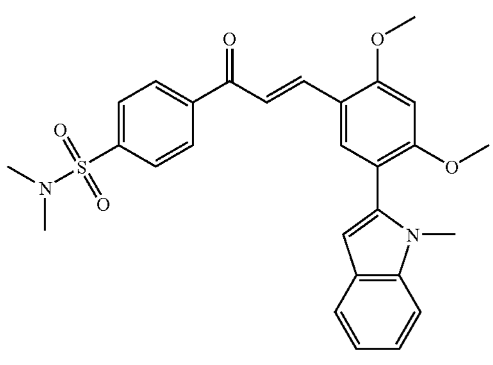

4-{3E-[2,4-Dimethoxy-5-(1-methyl-1H-indol-2-yl) phenyl]acryloyl}-N,N-dimethylbenzenesulfonamide Ex-31A: 4-Acetyl-N,N-dimethylbenzenesulfonamide was prepared in an analogous manner as Ex-29A using dimethylamine, 93% yield, white solid. $^{1}$H-NMR (300 MHz, $CDCl_3$) δ 8.10 (d, J=8 Hz, 2H), 7.87 (d, J=8 Hz, 2H), 2.74 (s, 6H), 2.66 (s, 3H).

The title compound was prepared in an analogous manner as Ex-1 using 4-acetyl-N,N-dimethyl-benzenesulfonamide (Ex-31A) and 2,4-dimethoxy-5-(1-methyl-1H-indol-2-yl) benzaldehyde (Ex-15A), 64% yield, yellow solid, mp 120–122° C. $^{1}$H-NMR (300 MHz, $CDCl_3$) δ 8.18 (d, J=16 Hz, 1H), 8.12 (d, J=8 Hz, 2H), 7.88 (d, J=8 Hz, 2H), 7.69 (s, 1H), 7.64 (d, J=8 Hz, 1H), 7.48 (d, J=16 Hz, 1H), 7.36 (d, J=8 Hz, 1H), 7.22–7.27 (m, 1H), 7.11–7.16 (m, 1H), 6.59 (s, 1H), 6.50 (s, 1H), 4.11 (s, 3H), 3.90 (s, 3H), 3.59 (s, 3H), 2.74 (s, 6H). HRMS (ESI) Calcd. for $C_{28}H_{28}N_2O_5S$: 505.1797 $(M+H)^+$; Found: 505.1797.

Example 32

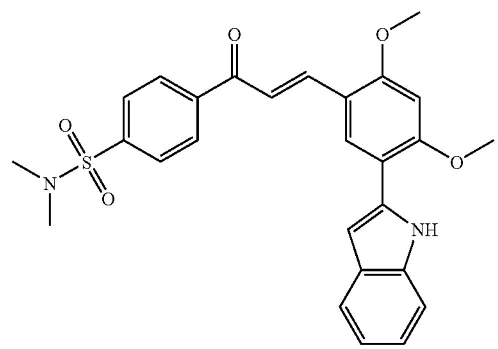

4-{3E-[5-(1H-Indol-2-yl)-2,4-dimethoxyphenyl] acryloyl}-N,N-dimethylbenzenesulfonamide Ex-32A: 2-(5-Formyl-2,4-dimethoxyphenyl)indole-l-carboxylic acid tert-butyl ester was prepared from 5-bromo-2, 4-dimethoxybenzaldehyde and N-Boc-indole-2-boronic acid in a similar manner as Ex-1A, 79% yield, yellow oil. $^{1}$H-NMR (300 MHz, CDCl3) δ 10.36 (s, 1H), 8.15 (d, J=8 Hz, 1H), 7.88 (s, 1H), 7.45 (d, J=8 Hz, 3H), 7.27–7.35 (m, 1H), 7.19–7.27 (m, 1H), 6.52 (s, 1H), 6.47 (s, 1H), 4.00 (s, 3H), 3.86 (s, 3H), 1.42 (s, 9H).

Ex-32B: 2-(5-Formyl-2,4-dimethoxyphenyl)indole-1-carboxylic acid tert-butyl ester (Ex-32A, 2.0 g, 5.2 mmol) was dissolved in 100 ml of THF, and $Bu_4NF$ (6.86 g, 26 mmol) was added. The reaction mixture was stirred at room temperature overnight. No significant reaction occurred under these conditions by HPLC. Then, additional $Bu_4NF$ (6.86 g, 26 mmol) was added to the mixture, and the mixture was stirred at reflux for 4 days. The reaction reached about 50% completion (HPLC). The reaction mixture was poured into $CH_2Cl_2$, and washed with water and brine. The organic phase was dried over $MgSO_4$, and concentrated. The residue was purified by column chromatography (EtOAc/hexanes, 2:1) to give 0.45 g (30%) of 5-(1H-indol-2-yl)-2,4-dimethoxybenzaldehyde. $^{1}$H-NMR (300 MHz, $CDCl_3$) δ 10.37 (s, 1H), 9.25 (br, 1H), 8.28 (s, 1H), 7.63(d, J=8 Hz, 1H), 7.39 (d, J=8 Hz, 1H), 7.08–7.20 (m, 2H), 6.92(d, J=2 Hz, 1H), 6.56 (s, 1H) 4.11(s, 3H), 4.00 (s, 3H). HMRS (EI) calcd. for $C_{17}H_{15}NO_3$: 281.1052 $(M^+)$; Found: 281.1049.

The title compound was prepared in an analogous manner as Ex-1 using 5-(1H-indol-2-yl)-2,4-dimethoxybenzaldehye (Ex-32B) and 4-acetyl-N,N-dimethylbenzenesulfonamide (Ex-31A), 12% yield after silica gel column chromatography (hexane/EtOAc, 2:1), yellow solid, mp 158–162° C. $^{1}$H-NMR (300 MHz, $CDCl_3$) δ 9.39 (br, 1H), 8.15 (m, 2H), 8.08 (d, J=9 Hz, 2H), 7.91 (d, J=9Hz, 2H), 7.64 (d, J=7 Hz, 1H), 7.57 (d, J=15 Hz, 1H), 7.42 (d, J=8 Hz, 1H), 7.09–7.21 (m, 2H), 6.87 (d, J=2Hz, 1H), 6.60 (s, 1H), 4.10 (s, 3H), 4.01

(s, 3H), 2.76 (s, 6H). HRMS (ESI) Calcd. for $C_{27}H_{26}N_2O_5S$: 491.1641 $(M+H)^+$; Found: 491.1638.

Example 33

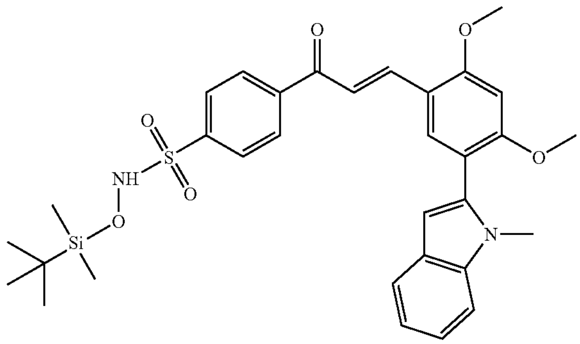

4-{3E-[2,4-Dimethoxy-5-(1-methyl-1H-indol-2-yl) phenyl]acryloyl}-N-(tert-butyldimethylsiloxy)benzenesulfonamide Ex-33A: To a solution of O-(tert-butyldimethylsilyl)hydroxylamine (0.74 g, 5 mmol) and triethylamine (1.01 g, 10 mmol) in 25 ml THF, 4-acetylbenzenesulfonyl chloride(1.1 g, 5 mmol) was added at 0° C. The mixture was stirred overnight and then poured into $H_2O$. The precipitate was filtered, dried, and recrystallized from EtOAc/Hexene to give 1.3 g (76.8%) of 4-acetyl-N-(tert-butyldimethylsiloxy) benzenesulfonamide as a white solid. $^1$H-NMR (300 MHz, $CDCl_3$) δ 8.11 (d, J=9 Hz, 2H), 8.01 (d, J=9 Hz, 2H), 6.59 (b, 1H), 2.67 (s, 3H), 0.89 (s, 9H), 0.20 (s, 6H).

The title compound was prepared in an analogous manner as Ex-1 using 4-acetyl-N-(tert-butyldimethylsiloxy)benzenesulfonamide (Ex-33A) and 2,4-dimethoxy-5-(1-methyl-1H-indol-2-yl)benzaldehyde (Ex-15A), 19% yield after preparative TLC ($MeOH/CH_2Cl_2$, 1:10), yellow solid, mp 129–131° C. $^1$H-NMR (300 MHz, $CDCl_3$) δ 8.18 (d, J=15 Hz, 1H), 8.12 (d, J=8 Hz, 2H), 8.02 (d, J=8 Hz, 2H), 7.69 (s, 1H), 7.64 (d, J=8 Hz, 1H), 7.47 (d, J=15 Hz, 1H), 7.36 (d, J=7 Hz, 1H), 7.22–7.26 (m, 1H), 7.11–7.16 (m, 1H), 6.58 (s, 1H), 6.50–6.51 (m, 2H), 4.03 (s, 3H), 3.90 (s, 3H), 3.59 (s, 3H), 0.90 (s, 9H), 0.20 (s, 6H). HRMS (ESI) Calcd. for $C_{32}H_{39}N_2O_6SSi$: 607.2298 $(M+H)^+$; Found: 607.2306.

Example 34

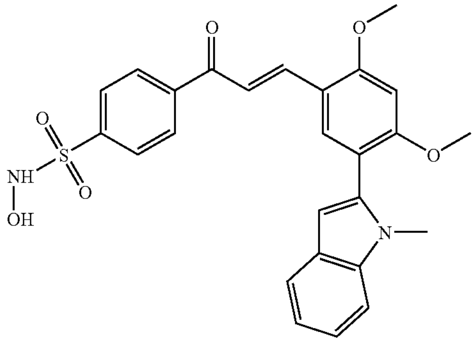

4-{3E-[2,4-Dimethoxy-5-(1-methyl-1H-indol-2-yl) phenyl]acryloyl}-N-hydroxybenzenesulfonamide The title compound was obtained as a side product from Ex-33 (37% yield after preparative TLC) as a yellow solid, mp>260° C. $^1$H-NMR (300 MHz, $CD_3OD$) δ 8.01–8.14 (m, 3H), 7.65–7.78 (m, 4H), 7.52 (d, J=7 Hz, 1H), 7.33 (d, J=8 Hz, 1H), 7.11–7.17 (m, 1H), 6.80(s, 1H), 6.40 (s, 1H), 4.05 (s, 3H), 3.91 (s, 3H), 3.55 (s, 3H). HRMS Calcd. for $C_{26}H_{24}N_2O_6S$: 492.1355 $(M^+)$; Found: 493.1423.

Example 35

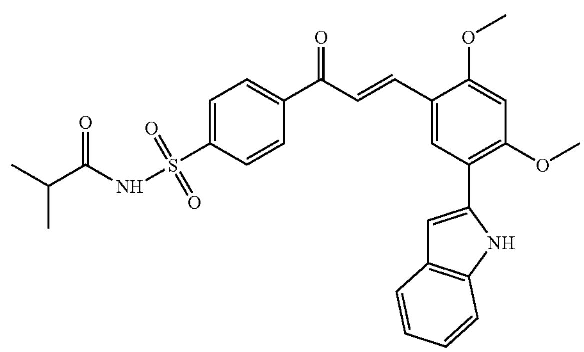

4-{3E-[5-(1H-Indol-2-yl)-2,4-dimethoxyphenyl] acryloyl}-N-isobutyrylbenzenesulfonamide Ex-35A: To a solution of 4-acetylbenzenesulfonyl chloride in acetone (30 mL) was added ammonia (28% in water, 8.2 mL, 57.3 mmol) dropwise at 0° C. The reaction mixture was allowed to stir at 0° C. for 30 min. The precipitate was filtered and the residue was washed with water and dried in vacuo to afford 4-acetylbenzenesulfonamide as a white solid (3.54 g, 93%), mp 176–177° C. $^1$H NMR (DMSO-$d_6$) δ 8.10 (d, J=9 Hz, 2H), 8.03 (d, J=9 Hz, 2H), 4.86 (brs, 2H), 2.65 (s, 3H). HRMS Calcd. for $C_8H_9NO_3S$: 199.0303 $(M^+)$; Found: 199.0300.

Ex-35B: To a solution of 2.4-dimethoxybenzaldehye (20.0 g, 120.4 mmol) in methanol (550 mL) was added iodine monochloride (23.5 g in 60 mL methanol) dropwise over 20 min at ambient temperature. The solution was allowed to stir at this temperature. HPLC showed about 94% conversion after 3 hours. The reaction mixture was then poured into a solution of HCl (0.5M, 600 mL). The precipitate was collected by filtration, washed with water, dried in vacuo (40° C.) to give crude product of 33.02 g. The crude product was further purified by recrystallization from THF/heptane (1:1) to give 5-iodo-2,4-dimethoxybenzaldehyde as an off-white solid (27.5 g, m.p 170–172° C.). The mother liquid was concentrated to dryness. The residual material was dissolved in EtOH (100 mL) and acetone (20 mL) followed by addition of water (20 mL) to give additional product (3.12 g, m.p. 169–171° C.). Overall isolated yield of this reaction was 87.5%. $^1$H NMR ($CDCl_3$) δ 10.20 (s, 1H), 8.22 (s, 1H), 6.39 (s, 1H), 3.97 (s, 3H), 3.95 (s, 3H). HRMS Calcd. for $C_9H_9IO_3$: 291.9596 $(M^+)$; Found: 291.9602. Anal. Calcd. for $C_8H_9NO_3S$: C, 37.01; H, 3.11; 1, 43.33; Found: C, 37.12; H, 3.15; I, 43.33.

Ex-35C: To a solution of 5-iodo-2,4-dimethoxybenzaldehyde (Ex-35B, 11.7 g, 40 mmol) in 250 ml of THF, $PdCl_2(PPh_3)_2$ (0.56 g, 0.8 mmol), CuI (0.3 g, 1.6 mmol), $Et_3N$ (6.06 g, 60 mmol), and 2-[(trimethylsilyl)ethynyl]aniline (7.92 g, 42 mmol) were added. The mixture was stirred to a homogeneous solution, and then TBAF (10.4 g, 40 mmol) was added. The reaction mixture was aged at room temperature for 4 h and then filtered. The filtrate was concentrated to about 50 ml, and the precipitate was filtered to give first portion of 5-(2-aminophenylethynyl)-2,4-dimethoxybenzaldehyde (8.5 g), as light yellow crystals. The filtrate was concentrated, and the residue was recrystallized from EtOAc/hexanes to give 1.85 g of additional product (total 10.35 g, 92%), mp 180–181° C. $^1$H-NMR (300 MHz, $CDCl_3$) δ 10.30 (s, 1H), 7.99 (s, 1H), 7.36 (d, J=8 Hz, 1H), 7.11–7.17 (m, 1H), 6.69–6.75 (m, 2H), 6.46 (s, 1H), 4.41 (brs, 2H), 4.02 (s, 3H), 4.00 (s, 3H). HRMS Calcd. for $C_{17}H_{15}NO_3$: 281.1052 ($M^+$); Found: 281.1056. Anal. Calcd. for $C_{17}H_{15}NO_3$: C, 72.58; H, 5.37; N, 4.98; Found: C, 72.74; H, 5.38; N, 4.93.

Ex-35D: 4-{3E-[5-(2-Amino-phenylethynyl)-2,4-dimethoxyphenyl]acryloyl}benzenesulfonamide was prepared in a similar manner as Ex-1 using 4-acetylbenzenesulfonamide (Ex-35A) and 5-(2-amino-phenylethynyl)-2,4-dimethoxybenzaldehyde (Ex-35C), 82.6% yield, yellow solid, mp 167–169° C. $^1$H-NMR (300 MHz, DMSO-$d_6$) δ 8.27 (d, J=8 Hz, 2H), 8.20(s, 1H), 8.01 (d, J=16Hz, 1H), 7.94 (d, J=8 Hz, 2H), 7.84 (d, J=16 Hz, 1H), 7.53 (s, 2H), 7.15–7.17 (m, 1H), 7.02–7.08 (m, 1H), 6.77 (s, 1H), 6.72 (d, J=8 Hz, 1H), 6.49–6.54 (m, 1H), 5.46 (br, 1H) 3.97 (s, 3H), 3.96 (s, 3H). MS m/z: 462 ($[M+H]^+$, 100%).

Ex-35E: 4-{3E-[5-(2-Aminophenylethynyl)-2,4-dimethoxyphenyl]acryloyl}benzenesulfonamide (Ex-35D, 0.91 g, 1.97 mmol) was dissolved in acetonitrile (100 ml), heated to reflux, and then $PdCl_2$ (0.035 g, 0.197 mmol) was added. The reaction mixture was kept at reflux for 10 min and cooled to room temperature. Upon cooling, the mixture was filtered to remove any solid material and the filtrate was treated with 3-mercaptopropyl-functionalized silica gel (1.0 g) under stirring for 0.5 h. The mixture was then filtered and concentrated to give crude product, which was recrystallized from EtOAc/hexanes to yield 0.75 g (83%) of 4-{3E-[5-(1H-indol-2-yl)-2,4-dimethoxyphenyl] acryloyl}benzenesulfonamide as a yellow solid, mp 185–187° C. $^1$H-NMR (DMSO-$d_6$) δ 11.15 (brs, 1H), 8.33(s, 1H), 8.24 (d, J=8 Hz, 2H), 8.07 (d, J=15 Hz, 1H), 7.98 (d, J=8 Hz, 2H), 7.80 (d, J=15 Hz, 1H), 7.41–7.55 (m, 4H), 7.03–7.08 (m, 1H), 6.93–6.99 (m, 2H), 6.83 (s, 1H), 4.04 (s, 3H), 3.99(s, 3H), MS m/z: 463 $[M+H]^+$.

To a suspension of 4-{3E-[5-(1H-indol-2-yl)-2,4-dimethoxyphenyl]acryloyl}benzenesulfonamide (Ex-35E, 1.84 g, 4 mmol) in 100 ml of THF, isobutyric anhydride (1.26 g, 8 mmol), triethylamine (0.42 g, 4.2 mmol) and N-dimethylaminopyridine (0.049 g, 0.4 mmol) were added. The mixture was aged at room temperature overnight and then poured into water (100 ml) and extracted with $CH_2Cl_2$ (3×100 ml). The combined organic phases were washed with 0.5 N HCl, $H_2O$ and brine, and concentrated. Recrystallization from EtOAc/hexanes gave 1.8 g (87%) of the title compound as a red solid, mp 243–245° C. (dec.). $^1$H-NMR (300 MHz, $CD_3COCD_3$) δ 10.54 (brs, 1H), 8.35(s, 1H), 8.27 (d, J=8 Hz, 2H), 8.18 (d, J=16Hz, 1H), 8.15 (d, J=8 Hz, 2H), 7.90 (d, J=16 Hz, 1H), 7.52 (d, J=8 Hz, 1H), 7.38 (d, J=8 Hz, 1H), 6.91–7.07 (m, 4H), 4.10 (s, 3H), 4.05 (s, 3H), 2.58 (septet, J=6 Hz, 1H), 1.02 (d, J=6 Hz, 6H). HRMS (ESI) Calcd. for $C_{29}H_{28}N_2O_6S$: 533.1746 $(M+H)^+$; Found: 533.1746.

Example 36

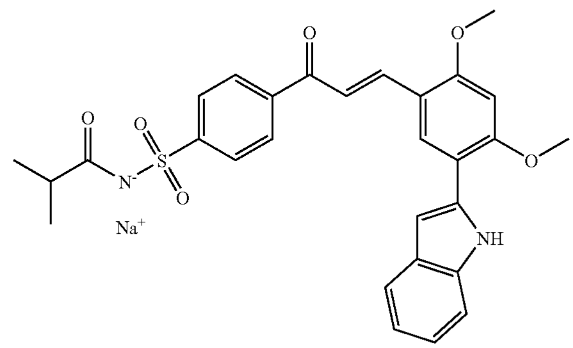

4-{3E-[5-(1H-Indol-2-yl)-2,4-dimethoxyphenyl] acryloyl}-N-isobutyrylbenzenesulfonamide sodium salt To a solution of 4-{3E-[5-(1H-indol-2-yl)-2,4-dimethoxyphenyl]acryloyl}-N-isobutyrylbenzenesulfonamide (Ex-35, 2.44 g, 4.6 mmol) in 100 ml of THF, NaOMe (0.24 g, 4.4 mmol) was added. The mixture was stirred at room temperature overnight. The resulting thick yellow mixture was diluted with 150 ml of EtOAc/hexanes (1:1) and filtered. The yellow solid was then dried in vacuo to afford 2.35 g (93%) of the title compound as a red solid, mp 249–251° C. (dec.). $^1$H-NMR (300 MHz, DMSO-$d_6$) δ 11.16 (brs, 1H), 8.32 (s, 1H), 8.05 (d, J=8 Hz, 2H), 8.04 (d, J=15 Hz, 1H), 7.84 (d, J=15 Hz, 1H), 7.83 (d, J=8 Hz, 2H), 7.49 (d, J=8 Hz, 1H), 7.42 (d, J=8 Hz, 1H), 7.02–7.07(m, 1H), 6.93–6.97 (m, 2H), 6.83(s, 1H), 4.03 (s, 3H), 3.99 (s, 3H), 2.10 (septet, J=8 Hz, 1H), 0.84 (d, J=8 Hz, 6H). HRMS (ESI) Calcd. for $C_{29}H_{27}N_2O_6SNa$: 531.1595 $(M-Na)^+$; Found: 531.1611.

Example 37

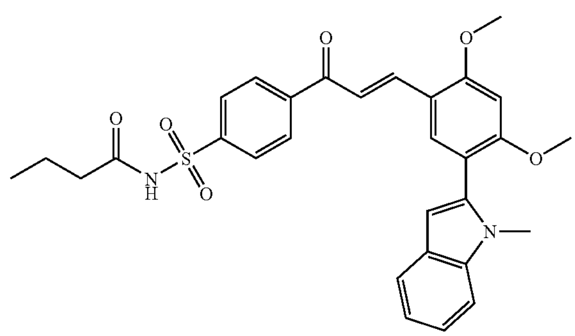

N-Butyryl-4-{3E-[2,4-dimethoxy-5-(1-methyl-1H-indol-2-yl)phenyl]acryloyl}benzenesulfonamide Ex-37A: To a solution of 4-acetylbenzenesulfonamide (Ex-35A, 0.20 g, 1 mmol) and 2,4-dimethoxy-5-(1-methyl-1H-indol-2-yl)benzaldehyde (Ex-15A, 0.30 g, 1 mmol) in DMF (25 ml) was added lithium methoxide (4 ml, 1.0 M in methanol). The mixture was stirred at room temperature overnight. It was poured into water (50 ml) and acidified to pH=1 with 3 N HCl. The yellow precipitate was filtered, washed with water, and dried. Crystallization from EtOAc/hexanes gave 4-{3-[2,4-dimethoxy-5-(1-methyl-1H-indol-2-yl)phenyl]acryloyl}benzenesulfonamide (0.43 g, 90%) as a yellow solid, mp 148–150° C. $^1$H-NMR (300 MHz, $CDCl_3$) δ 8.17 (d, J=16 Hz, 1H), 8.09 (d, J=9 Hz, 2H), 8.01 (d, J=9 Hz, 2H), 7.68 (s, 1H), 7.64 (d, J=8 Hz, 1H), 7.47 (d, J=16 Hz, 1H), 7.35 (d, J=8 Hz, 1H), 7.22–7.26 (m, 1H), 7.11–7.16 (m, 1H), 6.58 (s, 1H), 6.50 (s, 1H), 4.92 (brs, 2H), 4.02 (s, 3H), 3.90 (s, 3H), 3.58 (s, 3H). MS m/z=477 ($[M+H]^+$, 100%).

To a suspension of 4-{3-[2,4-dimethoxy-5-(1-methyl-1H-indol-2-yl)phenyl]acryloyl}benzenesulfonamide (Ex-37A, 1.5 g, 3.15 mmol) in 100 ml of THF, butyric anhydride (1.0 g, 6.3 mmol), triethylamine (0.33 g, 3.3 mmol) and 4-dimethylaminopyridine (0.038 g, 0.32 mmol) were added. The mixture was aged at room temperature overnight. The mixture was poured into water (100 ml) and extracted with 3×100 ml of $CH_2Cl_2$. The combined organic phase was washed with 0.5 N HCl, $H_2O$, and brine, and concentrated to give crude product. Crystallization from EtOAc/hexanes gave 0.95 g (55%) of the title compound as a yellow solid, mp 144–146° C. $^1$H-NMR (300 MHz, $CD_3COCD_3$) δ 8.27 (d, J=9 Hz, 2H), 8.21 (d, J=16 Hz, 1H), 8.10 (d, J=9 Hz, 2H), 7.89 (s, 1H), 7.87 (d, J=16 Hz, 1H), 7.54 (d, J=8 Hz, 1H), 7.37 (d, J=8 Hz, 1H), 7.13–7.18 (m, 1H), 7.01–7.06 (m, 1H), 6.91 (s, 1H), 6.41 (s, 1H), 4.08 (s, 3H), 3.94 (s, 3H), 3.57 (s, 3H), 2.27 (t, J=7 Hz, 2H), 1.45–1.53 (m, 2H), 0.79 (t, J=8 Hz, 3H). HRMS (ESI) Calcd. for $C_{30}H_{30}N_2O_6S$: 547.1903 $(M+H)^+$; Found: 547.1905.

Example 38

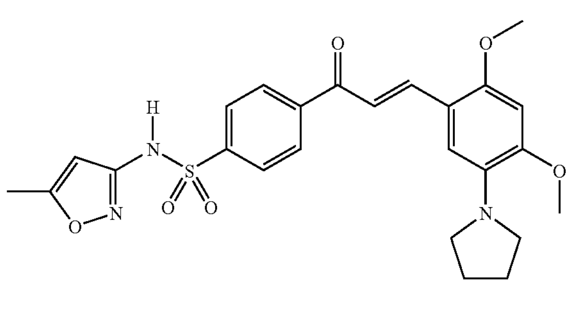

4-[3E-(2,4-Dimethoxy-5-pyrrolidin-1-yl-phenyl) acryloyl]-N-(5-methyl-isoxazol-3-yl)benzene-sulfonamide Ex-38A: Method A: A mixture of 2,4-dimethoxyaniline (1.0 g, 6.53 mmol), 1,4-dibromobutane (1.41 g, 6.53 mmol) and potassium carbonate (3.61 g, 26.1 mmol) in N,N-dimethylformamide (70 mL) was heated at 150° C. overnight. The reaction mixture was concentrated under reduced pressure. The residue was taken up in a mixture of water and ethyl acetate. After the mixture was partitioned, the aqueous solution was extracted with ethyl acetate. The combined solution of ethyl acetate was washed with saturated sodium bicarbonate, brine, dried over sodium sulfate and concentrated. The residue was purified by flash chromatography. Elution with ethyl acetate and hexane (1:2, v/v) gave 1-pyrrolidin-1-yl-2,4-dimethoxybenzene as a brown oil (0.85 g, 63%). $^1$H-NMR (300 MHz, $CDCl_3$) δ 6.76 (d, J=8.9 Hz, 1H), 6.49 (d, J=2.7 Hz, 1H), 6.41 (dd, J=2.7, 8.9 Hz, 1H), 3.84 (s, 3H), 3.78 (s, 3H), 3.18–3.14 (m, 4H), 1.95–1.90 (m, 4H). Method B: Sodium tert-butoxide was charged to a mixture of 1-bromo-2,4-dimethoxybenzene (3.03 g, 14.0 mmol), pyrrolidine (1.75 mL, 20.9 mmol), tris(dibenzylideneacetone)dipalladium ($Pd_2(dba)_3$) (0.26 g, 0.28 mmol) and rac-2,2'-bis(diphenylphosphino)-1,1'-binaphthyl (BINAP) (0.35 g, 0.56 mmol) in degassed toluene (60 mL). The reaction mixture was heated at 100° C. under $N_2$ for 17 h. After cooling to room temperature, the reaction mixture was diluted with water (60 mL) and partitioned. The aqueous solution was further extracted with ethyl acetate. The combined ethyl acetate and toluene was washed with saturated sodium bicarbonate, brine, dried over sodium sulfate and concentrated. The crude product was purified by flash chromatography with ethyl acetate and hexane (1:2, v/v) to give 1-pyrrolidin-1-yl-2,4-dimethoxybenzene as a brown oil (1.82 g, 63%).

Ex-38B: To a solution of 1-pyrrolidin-1-yl-2,4-dimethoxybenzene (Ex-38A, 1.82 g, 8.78 mmol) and α,α-dichloromethyl methyl ether (1.6 mL, 17.6 mmol) in dichloromethane (50 mL) was added titanium tetrachloride (1.0 M in dichloromethane, 26.3 mL, 26.3 mmol) dropwise at 0° C. The solution was allowed to stir for 16 h at ambient temperature and poured into ice/water. The aqueous solution was extracted with dichloromethane. The combined dichloromethane was washed with saturated sodium bicarbonate, brine, dried over sodium sulfate and concentrated to give a crude product (0.67 g). The aqueous solution was further treated with solid sodium hydroxide to pH 8. The suspension was mixed with ethyl acetate. The insoluble solid was removed by filtering through a pad of Celite. The filtrate was then partitioned. The aqueous solution was further extracted with ethyl acetate. The combined ethyl acetate was washed with saturated sodium bicarbonate, brine, dried over sodium sulfate and concentrated. The combined crude product (1.71 g) was purified by flash chromatography. Elution with ethyl acetate and hexane (1:1, v/v) gave 2,4-dimethoxy-5-pyrrolidin-1-yl-benzaldehyde as a brown oil (1.03 g, 50%): $^1$H-NMR (300 MHz, $CDCl_3$) δ 10.25 (s, 1H), 7.26 (s, 3H), 6.44 (s, 1H), 3.93 (s, 3H), 3.89 (s, 3H), 3.20–3.16 (m, 4H), 1.93–1.89 (m, 4H). MS m/z: 235 ($M^+$), 100%.

The title compound was prepared in a similar manner as Ex-1 using 4-acetyl-N-(5-methyl-isoxazol-3-yl)benzenesulfonamide (Ex-1B, 0.30 g, 1.07 mmol) and 2,4-dimethoxy-5-pyrrolidin-1-ylbenzaldehyde (Ex-38B, 0.25 g, 1.07 mmol) as a dark red solid, mp 164–165° C. $^1$H-NMR (300 MHz, $CDCl_3$) δ 8.09–7.93 (m, 4H), 7.35 (d, J=15.3 Hz, 1H), 7.05 (s, 1H), 6.48 (s, 1H), 6.24 (s, 1H), 3.92 (s, 3H), 3.90 (s, 3H), 3.29–3.18 (m, 4H), 2.38 (s, 3H), 2.02–1.91 (s, 4H). MS m/z: 498 ($M^+$), 100%.

Example 39

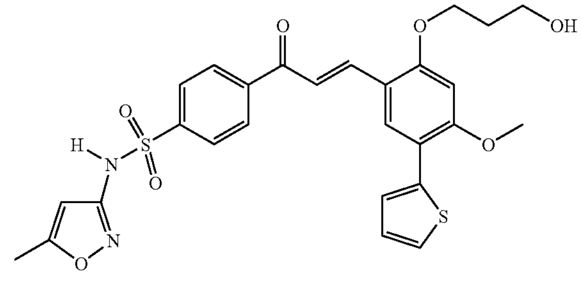

4-{3E-[2-(3-Hydroxy-propoxy)-4-methoxy-5-thien-2-ylphenyl]acryloyl}-N-(5-methylisoxazol-3-yl) benzenesulfonamide Ex-39A: A solution of 2-hydroxy-4-methoxy-5-thiophen-2-yl-benzaldehyde (Ex-13C, 500 mg, 2.13 mmol) in DMF (20 mL) was treated with potassium carbonate (589 mg, 4.26 mmol) followed by the addition of 3-bromo-propan-1-ol (356 mg, 2.56 mmol). The reaction mixture was heated to 80° C. for 2 h followed by another addition of potassium carbonate (294 mg, 2.13 mmol) and 3-bromo-propan-1-ol (296 mg, 2.13 mmol). The reaction mixture was stirred for an additional 45 minutes, quenched with water (15 mL), and extracted with ethyl acetate (2×25 ml). The organic phase was washed with brine, dried over sodium sulfate, and concentrated to a beige oil. The oil was purified by column chromatography (elution: 30, 50, and 80% ethyl acetate in hexane) to yield 240 mg (38%) of 2-(3-hydroxypropoxy)-4-methoxy-5-thiophen-2-ylbenzaldehyde as an off-white solid. $^{1}$H-NMR (300 MHz, $CDCl_3$) δ10.21 (s, 1H), 8.02 (s, 1H), 7.41 (br d, 1H, J=3.9 Hz), 7.28 (d, 1H, J=5.10 Hz), 7.06 (dd, 1H, J=3.0, 5.7 Hz), 6.48 (s, 1H), 4.24 (t, 2H, J=7.0 Hz), 3.92 (s, 3H), 3.88 (br s, 2H), 2.11 (q, 2H, J=7.0 Hz).

The title compound was prepared in a analogous way as Ex-1 from 2-(3-hydroxypropoxy)-4-methoxy-5-thien-2-yl-benzaldehyde (Ex-39A), 78% yield, red solid, mp 178–182° C. $^{1}$H-NMR (300 MHz, DMSO-$d_6$) δ11.63 (brs, 1H), 8.23 (m, 3H), 8.04 (d, 1H, J=16.0 Hz), 7.98 (d, 2H, J=9.0 Hz), 7.86 (d, 1H, J=16.0 Hz), 7.61 (d, 1H, J=4 Hz), 7.48 (d, 1H, J=5 Hz,), 7.09 (t, 1H), 6.81 (s, 1H), 6.14 (s, 1H), 4.62 (m, 1H), 4.62 (m, 1H), 4.24 (t, 2H), 3.96 (s, 3H), 3.59 (s, 2H), 2.27 (s, 3H), 1.95 (quintet, 2H). HRMS (ESI) Calcd. for $C_{27}H_{26}N_2O_7S_2$: 555.1260 $(M+H)^+$; Found: 555.1261.

Example 40

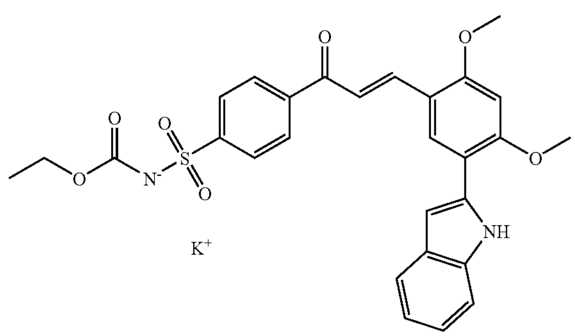

N-Ethoxycarbonyl-4-{3E-[5-(1H-indol-2-yl)-2,4-dimethoxyphenyl]acryloyl}benzenesulfonamide potassium salt To a solution of 4-{3E-[5-(1 H-indol-2-yl)-2,4-dimethoxyphenyl]acryloyl}benzenesulfonamide (Ex-35E, 3.0 g, 6.5 mmol) in 250 mL of acetone were added ethyl chloroformate (0.93 g, 8.6 mmol) and $K_2CO_3$ (2.3 g, 16.7 mmol). The mixture was heated to reflux overnight. The yellow precipitate formed was filtered and washed with cold water to give 2.6 g (70%) of the title compound as a yellow solid, mp 220–222° C. $^{1}$H-NMR (300 MHz, DMSO-$d_6$) δ 11.23 (br, 1H), 8.35 (s, 1H), 8.01–8.09 (m, 3H), 7.83–7.89 (m, 3H), 7.49 (d, J=7 Hz, 1H), 7.42 (d, J=8 Hz, 1H), 7.02–7.07(m, 1H), 6.92–6.97 (m, 2H), 6.83 (s, 1H), 4.03 (s, 3H), 3.99 (s, 3H), 3.67 (q, J=8 Hz, 2H), 0.98(t, J=8 Hz, 3H). HRMS Calcd for $C_{28}H_{25}KN_2O_7S$: 533.1382 $([M-K]^+)$; Found: 533.1378. Anal. Calcd for $C_{28}H_{25}KN_2O_7S$: C, 58.72; H, 4.40; N, 4.89; S, 5.60; Found: C, 58.62; H, 4.34; N, 4.83; S, 5.62.

Example 41

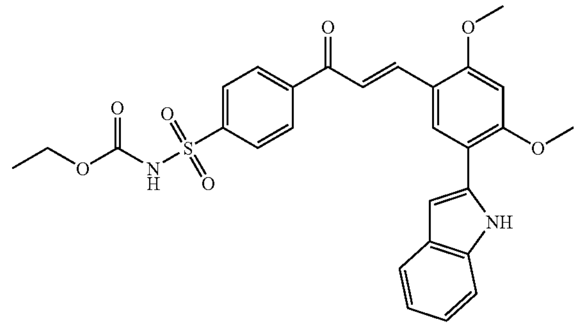

N-Ethoxycarbonyl-4-{3E-[5-(1H-indol-2-yl)-2,4-dimethoxyphenyl]acryloyl}benzenesulfonamide To a solution of 4-{3E-[5-(1H-indol-2-yl)-2,4-dimethoxyphenyl]acryloyl}benzenesulfonamide (Ex-35E, 3.0 g, 6.5 mmol) in 250 mL of acetone were added ethyl chloroformate (0.93 g, 8.6 mmol) and $K_2CO_3$ (2.3 g, 16.7 mmol). The mixture was heated to reflux overnight. The yellow precipitate-formed was filtered. The filtrate was acidified to pH=1 with 3N HCl and extracted with $CH_2Cl_2$. The organic phase was washed with water, dried over $MgSO_4$, and concentrated. The residue was further purified by passing a short silica gel column eluted with EtOAc/hexenes (1:1) to give 30 mg of the title compound as a yellow solid, mp 165–175° C. $^{1}$H-NMR (300 MHz, $CDCl_3$) δ 9.39 (br, 1H), 8.04–8.20 (m, 6H), 7.64 (d, J=7 Hz, 1H), 7.57 (d, J=15 Hz, 1H), 7.42 (d, J=8 Hz, 1H), 7.12–7.07(m, 2H), 6.87 (s, 1H), 6.59 (s, 1H), 4.16 (q, J=7 Hz, 2H), 4.10 (s, 3H), 4.01 (s, 3H), 1.24 (t, J=7 Hz, 3H).

Example 42

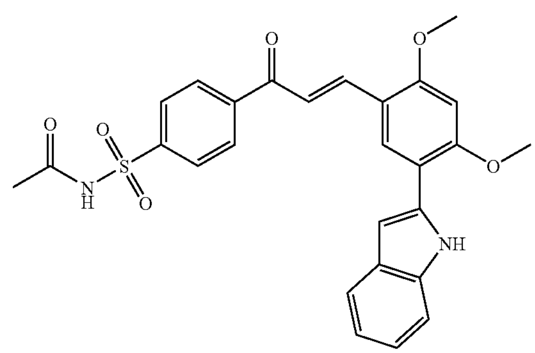

N-Acetyl-4-{3E-[5-(1H-indol-2-yl)-2,4-dimethoxyphenyl]acryloyl}benzenesulfonamide To a solution of 4-{3E-[5-(1H-indol-2-yl)-2,4-dimethoxyphenyl]acryloyl}benzenesulfonamide (Ex-35E, 0.462 g, 1 mmol), DMAP (0.012 g, 0.1 mmol), and $Et_3N$ (0.1 g, 1.05 mmol) in 50 ml of THF, was added $Ac_2O$ (0.204 g, 2 mmol). The reaction mixture was stirred at room temperature overnight. The yellow solid precipitated was filtered and redissolved in 50% ethanol in water (50 mL). The clear solution was then adjusted to pH1, and the solid formed was filtered and washed with water to give 0.31 g (62%) the title compound as a red solid, mp 218–220° C. $^1$H-NMR (300 MHz, DMSO-$d_6$) δ 12.26 (br, 1H), 11.15 (s, 1H), 8.32 (s, 1H), 8.25 (d, J=8 Hz, 2H), 8.04–8.09 (m, 3H), 7.83 (d, J=15 Hz, 1H), 7.49 (d, J=7 Hz, 1H), 7.42 (d, J=8 Hz, 1H), 7.02–7.07 (m, 1H), 6.93–6.97(m, 2H), 6.82 (s, 1H), 4.03 (s, 3H), 3.99 (s, 3H), 1.94 (s, 3H). HRMS (EI) Calcd for $C_{27}H_{24}N_2O_6S$: 504.1335 ([M]$^+$); Found: 504.1365.

Example 43

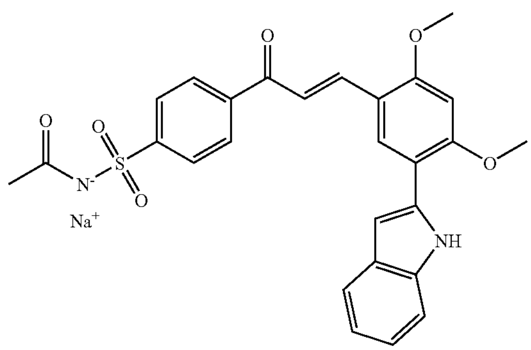

N-Acetyl-4-{3E-[5-(1H-indol-2-yl)-2,4-dimethoxyphenyl]acryloyl}benzenesulfonamide sodium salt To a solution of N-acetyl-4-{3E-[5-(1H-indol-2-yl)-2,4-dimethoxyphenyl]acryloyl}benzenesulfonamide (Ex-42, 0.17 g, 0.34mmol) in THF (30 mL) was added NaOMe (0.0174 g, 0.32 mmol). The solution was stirred overnight. The reaction mixture was concentrated to about 5 mL and filtered to give 0.17 g (96%) of the title compound as a red solid, mp 240–250° C. $^1$H-NMR (300 MHz, DMSO-$d_6$) δ 11.17 (s, 1H), 8.30 (s, 1H), 8.00–8.06 (m, 3H), 7.80–7.86 (m, 3H), 7.49 (d, J=7 Hz, 1H), 7.42 (d, J=7 Hz, 1H), 7.02–7.04 (m, 1H), 6.93–6.96(m, 2H), 6.81 (s, 1H), 4.02 (s, 3H), 3.97 (s, 3H), 1.63 (s, 3H). Anal. Calcd for $C_{27}H_{23}N_2NaO_6S.5/4H_2O$: C, 59.06; H, 4.68; N, 5.10; S, 5.84; Found: C, 59.17; H, 4.86; N, 5.04; S, 5.54.

Example 44

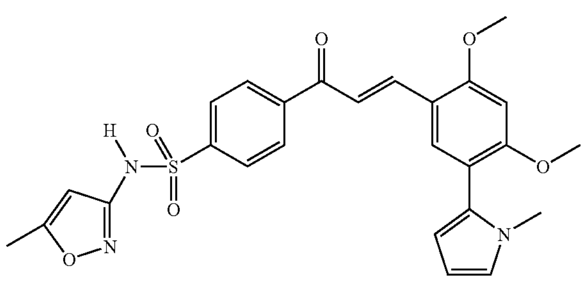

4-{3E-[2,4-Dimethoxy-5-(1-methyl-1H-pyrrol-2-yl)phenyl]acryloyl}-N-(5-methyl-isoxazol-3-yl)benzenesulfonamide Ex-44A: A solution of 5-bromo-2,4-dimethoxybenzaldehyde (1.90 g, 7.77 mmol) and trans-dichlorobis(triphenylphosphine)palladium(II) in dioxane (150 mL) was treated with 1-methyl-2-(tributylstannyl)-1H-pyrrole and then refluxed for 68 h. The reaction mixture was quenched with 10% potassium fluoride/ether (300 mL/100 mL) and filtered through Celite. The organic phase was extracted with saturated ammonium chloride solution (4×25 mL), dried over magnesium sulfate, and concentrated to a brown solid. The solid was purified by column chromatography (30% ethyl acetate/hexane) to yield 0.87 g (46%) of 2,4-dimethoxy-5-(1-methyl-1H-pyrrol-2-yl)benzaldehyde as a white solid. $^1$H-NMR (300 MHz, $CDCl_3$) δ 10.34 (s, 1 H), 7.78 (s, 1H), 6.72 (m, 1H), 6.51 (s, 1H), 6.20 (m, 1H), 6.13 (m, 1H), 4.01 (s, 3H), 3.92 (s, 3H), 3.46 (s, 3H).

The title compound was prepared in a similar manner as Ex-1 using 2,4-dimethoxy-5-(1-methyl-1H-pyrrol-2-yl)benzaldehyde (Ex-44A), yellow solid, mp 113–115° C. $^1$H-NMR (300 MHz, DMSO-$d_6$) δ 8.13 (d, 1H, J=16.0 Hz), 8.05 (d, 2H, J=9.0 Hz), 7.95 (d, 2H, J=9.0 Hz), 7.57 (s, 1H), 7.41 (d, 1H, J=16.0 Hz,), 7.26 (s, 1H), 6.73 (t, 1H, J=3 Hz), 6.52 (s, 1H), 6.22 (m, 2H), 6.13 (m, 1H), 3.98 (s, 3H), 3.88 (s, 3H), 3.47 (s, 3H), 2.38 (s, 3H), HRMS (ESI) Calcd. for $C_{26}H_{25}N_3O_6S$: 507.1464 (M+H)$^+$; Found: 507.1477.

Example 45

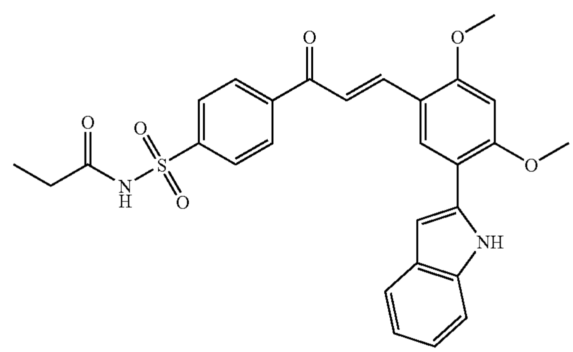

4-{3E-[5-(1H-Indol-2-yl)-2,4-dimethoxyphenyl]acryloyl}-N-propionyl-benzenesulfonamide To a solution of 4-{3E-[5-(1H-indol-2-yl)-2,4-dimethoxyphenyl]acryloyl}benzenesulfonamide (Ex-35E, 0.462 g, 1 mmol), DMAP (0.012 g, 0.1 mmol) and $Et_3N$ (0.1 g, 1.05 mmol) in THF (50 mL) was added propionic anhydride (0.26 g, 2 mmol). The reaction mixture was stirred at room temperature overnight. The clear solution was poured into 100 ml of $H_2O$ and extracted with $CH_2Cl_2$. The combined organic phase was washed with water, dried over $MgSO_4$, and concentrated to dryness. Recrystallization from EtOAc/hexenes gave 0.42 g (81%) of the title compound as a red solid, mp 223–225° C. $^1$H-NMR (300 MHz, Acetone-$d_6$) δ 10.54 (br, 1H), 8.35 (s, 1H), 8.27 (d, J=9 Hz, 2H), 8.13–8.20 (m, 3H), 7.89 (d, J=15 Hz, 1H), 7.52 (d, J=7 Hz, 1H), 7.39 (d, J=8 Hz, 1H), 6.97–7.05(m, 3H), 6.90 (s, 1H), 4.09 (s, 3H), 404 (s, 3H), 2.35 (q, J=8 Hz, 2H), 0.97(t, J=8 Hz, 3H). HRMS (EI) Calcd for $C_{28}H_{26}N_2O_6S$: 518.1512 ([M]$^+$); Found: 518.1516.

Example 46

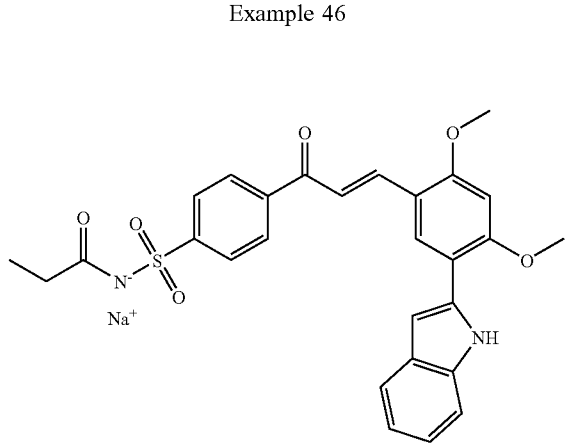

4-{3E-[5-(1H-Indol-2-yl)-2,4-dimethoxyphenyl] acryloyl}-N-propionylbenzenesulfonamide sodium salt To a solution of 4-{3E-[5-(1H-Indol-2-yl)-2,4-dimethoxyphenyl]acryloyl}-N-propionylbenzenesulfonamide (Ex-45, 0.39 g, 0.75 mmol) in THF (50 mL) was added NaOMe (0.039 g, 0.72 mmol). The solution was stirred overnight. The reaction mixture was concentrated to about 5 mL, and filtered to give 0.34 g (83%) of the title compound as a red solid, mp>250° C. $^1$H-NMR (300 MHz, $DMSO_6$) δ 11.18 (s, 1H), 8.30 (s, 1H), 8.00–8.06 (m, 3H), 7.80–7.86 (m, 3H), 7.49 (d, J=7 Hz, 1H), 7.42 (d, J=8 Hz, 1H), 7.02–7.04 (m, 1H), 6.93–6.96(m, 2H), 6.81 (s, 1H), 4.02 (s, 3H), 3.97 (s, 3H), 1.90 (q, J=8 Hz, 2H), 0.82 (t, J=8 Hz, 3H). Anal. Calcd for $C_{28}H_{25}N_2NaO_6S.¾H_2O$: C, 60.72; H, 4.78; N, 5.06; S, 5.79 ; Found: C, 60.63; H, 4.76; N, 5.03; S, 5.68.

Example 47

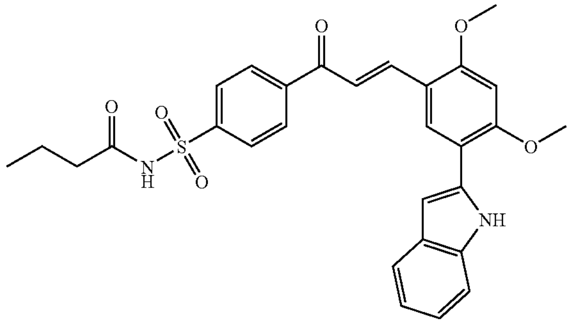

N-Butyryl-4-{3E-[5-(1H-indol-2-yl)-2,4-dimethoxyphenyl]acryl}benzenesulfonamide

To a solution of 4-{3E-[5-(1H-indol-2-yl)-2,4-dimethoxyphenyl]acryloyl}benzenesulfonamide (Ex-35E, 0.92 g, 2 mmol), DMAP(0.024 g, 0.2 mmol) and $Et_3N$ (0.2 g, 2.1 mmol) in 100 ml o THF was added butyric anhydride (0.64 g, 4 mmol). The reaction mixture was stirred at room temperature overnight. The clear solution was then poured into 150 ml of $H_2O$ and extracted with $CH_2Cl_2$. The combined organic phase was washed with water, dried over $MgSO_4$, and concentrated to dryness. Recrystallization from EtOAc/hexenes gave 0.80 g (75%) of the title compound as a red solid, mp 155–165° C. $^1$H-NMR (300 MHz, Acetone-$d_6$) δ 10.55 (br, 1H), 8.35 (s, 1H), 8.27 (d, J=8 Hz, 2H), 8.13–8.20 (m, 3H), 7.89 (d, J=16 Hz, 1H), 7.52 (d, J=7 Hz, 1H), 7.39 (d, J=8 Hz, 1H), 7.02–7.07(m, 1H), 6.95–7.00 (m, 2H), 6.90 (s, 1H), 4.10 (s, 3H), 4.04 (s, 3H), 2.29 (t, J=8 Hz, 2H), 1.48–1.56 (m, 2H), 0.81(t, J=8 Hz, 3H).

Example 48

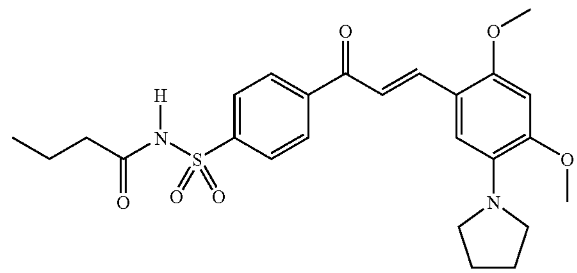

N-Butyryl-4-[3E-(2,4-dimethoxy-5-pyrrolidin-1-ylphenyl)acryloyl]benzenesulfonamide Ex-48A: To a solution of 4-acetylbenzenesulfonamide (Ex-35A, 0.13 g, 0.64 mmol) and 2,4-dimethoxy-5-pyrrolidin-1-yl-benzaldehyde (Ex-38B, 0.15 g, 0.64 mmol) in N,N-dimethylformamide (5 mL) was added lithium methoxide (1.0 M in methanol, 1.6 mL, 1.6 mmol). The solution was allowed to stir at ambient temperature for 13 h and then at 40° C. for 2 h. HPLC indicated no further change of starting materials. The reaction mixture was then diluted with water, acidified to pH 5. The resulting precipitate was collected by filtration, washed with water, dried in vacuo. The crude product was slurried in ethanol overnight. The solid was collected by filtration, washed with ethanol, dried in vacuo to give 4-[3E-(2,4-dimethoxy-5-pyrrolidin-1-ylphenyl)acryloyl]benzenesulfonamide (0.16 g, 59%) as a red solid, m.p. 220–222° C. $^1$H-NMR (300 MHz, DMSO-$d_6$) δ 8.22 (d, J=8.7 Hz, 2H), 8.04 (d, J=16.1 Hz, 1H), 7.93 (d, J=8.7 Hz, 2H), 7.64 (d, J=16.1 Hz, 1H), 7.52 (s, 2H), 7.18 (s, 1H), 6.67 (s, 1H), 3.86 (s, 6H), 3.19–3.17 (m, 4H), 1.84–1.83 (m, 4H). HRMS Calcd for $C_{21}H_{24}N_2O_5S$: 416.1408 ($M^+$); Found: 416.1408.

The title compound was synthesized by reacting 4-[3E-(2,4-dimethoxy-5-pyrrolidin-1-ylphenyl)acryloyl]benzenesulfonamide (Ex-48A, 137 mg, 0.33 mmol) with butyric anhydride (0.11 mL, 0.66 mmol) in the presence of triethylamine (0.048 mL, 0.35 mmol) and 4-(dimethylamino)pyridine (4 mg, 0.03 mmol) in a mixture of THF (5 mL) and DMF (0.7 mL) in a similar manner as Ex-35, dark red solid (98 mg, 61%), mp 193–195° C. $^1$H NMR (300 MHz, DMSO-$d_6$) δ 12.23 (brs, 1H), 8.26 (d, J=8.5 Hz, 2H), 8.11–8.03 (m, 3H), 7.66 (d, J=15.2 Hz, 1H), 7.02 (s, 1H), 6.71 (s, 1H), 3.90 (s, 6H), 3.15–3.25 (m, 4H), 2.20 (t, J=7.6 Hz, 2H), 1.92–1.81 (m, 4H), 1.46–1.39 (m, 2H), 0.76 (t, J=7.3 Hz, 3H).

Example 49

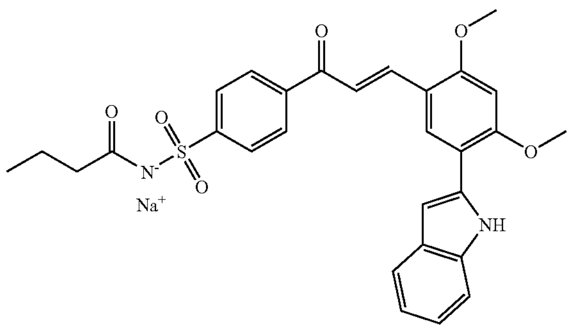

N-Butyryl-4-{3E-[5-(1H-indol-2-yl)-2,4-dimethoxyphenyl]acryloyl}benzenesulfonamide sodium salt To a solution of N-butyryl-4-{3E-[5-(1H-indol-2-yl)-2,4-dimethoxyphenyl]acryloyl}benzenesulfonamide (Ex-47, 0.40 g, 0.75 mmol) in 50 ml THF, was added NaOMe (0.039 g, 0.72 mmol). The solution was stirred overnight. The reaction mixture was concentrated to about 5 mL and filtered to give 0.36 g (86%) of the title compound as a red solid, mp 191–193° C. $^1$H-NMR (300 MHz, $DMSO_6$) δ 11.18 (s, 1H), 8.30 (s, 1H), 8.00–8.06 (m, 3H), 7.80–7.85 (m, 3H), 7.49 (d, J=7 Hz, 1H), 7.42 (d, J=8 Hz, 1H), 7.02–7.04 (m, 1H), 6.93–6.96(m, 2H), 6.81 (s, 1H), 4.02 (s, 3H), 3.97 (s, 3H), 1.86 (t, J=7 Hz, 2H), 0.73 (t, J=8 Hz, 3H). Anal. Calcd for $C_{29}H_{27}N_2NaO_6S.2H_2O$: C, 58.97; H, 5.29; N, 4.74; S, 5.43; Found: C, 59.08; H, 5.52; N, 4.64; S, 5.16.

Example 50

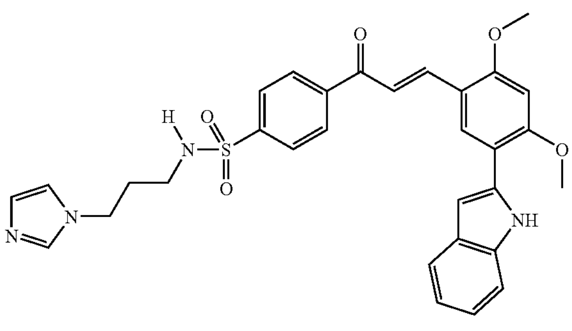

N-(3-Imidazol-1-yl-propyl)-4-{3E-[5-(1H-indol-2-yl)-2,4-dimethoxy-phenyl]acryloyl}benzenesulfonamide Ex-50A: A solution of 4-acetyl-N-(3-imidazol-1-ylpropyl)benzenesulfonamide (Ex-23A, 312 mg, 1.02 mmol) and 5-(2-amino-phenylethynyl)-2,4-dimethoxybenzaldehyde (Ex-35C, 287 mg, 1.02 mmol) in DMF (4.4 mL) and MeOH (1.9 mL) was treated with lithium methoxide (155 mg, 4.08 mmol). The reaction mixture was stirred at room temperature for 16 h under nitrogen. The reaction mixture was quenched with water (25 mL) and extracted with (3:1) ethyl acetate/THF (3×25 mL). The organic phase was brined, dried over sodium sulfate, and concentrated to a yellow oil. The crude material was purified by column chromatography (0–7.5% MeOH in dichloromethane) to give 4-{3E-[5-(2-amino-phenylethynyl)-2,4-dimethoxy-phenyl]acryloyl}-N-(3-imidazol-1-ylpropyl)benzenesulfonamide (309 mg, 53%) as a yellow oil. $^1$H-NMR (3.00 MHz, DMSO-$d_6$) δ8.28 (d, 2H, J=7.80), 8.20 (s, 1H), 8.01 (d, 1H, J=15.0 Hz), 7.86 (m, 5 H), 7.51 (s, 1H), 7.16 (d, 1H, J=7.5 Hz), 7.23 (m, 2H), 6.79 (d, 2H, J=10.8 Hz), 6.72 (d, 1H, J=8.1 Hz), 6.52 (t, 1H, J=7.2 Hz), 5.45 (m, 1H), 3.97 (s, 3H), 3.96 (s, 3H), 3.92 (m, 4H), 1.77 (quintet, 2H, J=6.6 Hz).

A suspension of 4-{3E-[5-(2-amino-phenylethynyl)-2,4-dimethoxyphenyl]acryloyl}-N-(3-imidazol-1-ylpropyl)benzenesulfonamide (Ex-50A, 210 mg, 0.37 mmol) in acetonitrile (130 mL) was purged with nitrogen gas for 10 minutes. Palladium(II) chloride (5.0 mg, 0.029 mmol) was added to the reaction vessel. The reaction mixture was refluxed for 16 hrs. The cooled reaction mixture was stirred with 3-mercaptopropyl functionalized silica gel (500 mg) for 5 minutes. The filtrate was collected via suction filtration and concentrated to an orange solid to give 210 mg (100%) of the title compound, mp 197–200° C. $^1$H-NMR (300 MHz, DMSO-$d_6$) δ11.19 (br s, 1H), 8.28 (m, 3H), 8.11 (m, 2H), 7.95 (m, 4H), 7.45 (m, 3H), 7.00 (m, 5H), 4.08 (s, 3H), 4.03 (s, 3H), 3.89 (m, 2H), 2.69 (br s, 2H), 1.78 (br s, 2H). HRMS (ESI) Calcd. for $C_{31}H_{30}N_4O_5S$: 571.2015 [$(M+H)^+$]; Found: 571.2016.

Example 51

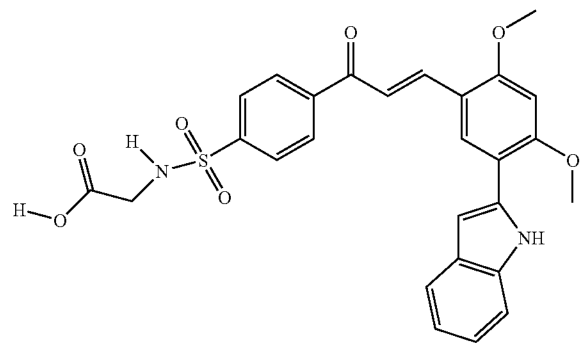

(4-{3E-[5-(1H-Indol-2-yl)-2,4-dimethoxyphenyl]acryloyl}benzenesulfonylamino)acetic acid Ex-51A: A solution (4-acetylbenzenesulfonylamino)acetic acid (Ex-26A, 238 mg, 1.01 mmol) in DMF (4.4 mL) and MeOH (1.9 mL) was treated with lithium methoxide (153 mg, 4.04 mmol), followed by the addition of 5-(2-amino-phenylethynyl)-2,4-dimethoxybenzaldehyde (Ex-35C, 300 mg, 1.07 mmol). The reaction mixture was stirred at room temperature for 23 h under nitrogen. It was quenched with water (10 mL) and extracted with ethyl acetate (25 mL). The aqueous phase was acidified with 6N HCl to pH3 and was extracted with (3:1) ethyl acetate/THF (5×25 mL). The organic phase was brined, dried over sodium sulfate, and concentrated to a yellow oil. The crude material was purified by column chromatography (0–7.5% MeOH in dichloromethane) to give (4-{3E-[5-(2-amino-phenylethynyl)-2,4-dimethoxyphenyl]acryloyl}benzenesulfonylamino)acetic acid (188 mg, 36%) as an orange solid. $^1$H-NMR (300 MHz, DMSO-$d_6$) δ8.23 (d, 2H, J=8.7), 8.19 (s, 1H), 7.99 (d, 1H, J=15.9 Hz), 7.92 (d, 2H, J=7.80 Hz), 7.82 (d, 1H, J=16.5 Hz), 7.16 (d, 1H, J=6.6 Hz), 7.05 (t, 1H, J=8.1 Hz), 6.76 (s, 1H), 6.71 (d, 1H, J=7.8 Hz), 6.52 (t, 1H, J=7.2 Hz), 5.72 (s, 1H), 5.45 (br s, 1H), 3.96 (s, 3H), 3.95 (s, 3H), 3.41 (m, 2H).

A suspension of (4-{3E-[5-(2-amino-phenylethynyl)-2,4-dimethoxyphenyl]acryloyl}benzenesulfonylamino)acetic acid (Ex-51A, 153 mg, 0.294 mmol) in acetonitrile (130 mL) was purged with nitrogen gas for 10 minutes. Palladium (II) chloride (5.2 mg, 0.029 mmol) was added to the reaction vessel. The reaction mixture was refluxed for 2 h. The reaction mixture was gravity filtered and yielded a red solid. The crude was swished in ethanol to give 35 mg (23%) of the title compound as a red solid, mp 189–190° C. $^1$H-NMR (300 MHz, DMSO-$d_6$) δ11.18 (br s, 1H), 8.25 (m, 3H), 8.06 (d, 1H, J=15.3 Hz), 7.89 (m, 5H), 7.49 (d, 1H, J=7.8 Hz), 7.41 (d, 1H, J=8.1 Hz), 7.03 (t, 1H, J=6.6 (m, 1H), 6.83 (s, 1H), 4.04 (s, 3H), 3.99 (s, 3H). MS (ESI, for $C_{27}H_{24}N_2O_7S$) Found: 520 [(M+H)$^+$].

Example 52

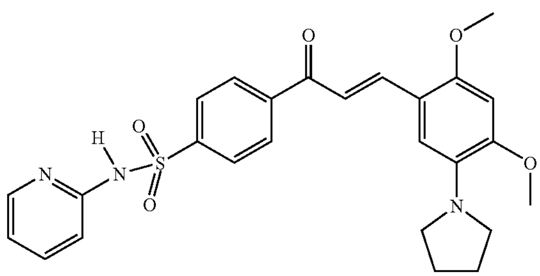

4-[3E-(2,4-Dimethoxy-5-pyrrolidin-1-yl-phenyl)-acryloyl]-N-pyridin-2-yl-benzenesulfonamide A solution 4-acetyl-N-pyridin-2-ylbenzenesulfonamide (Ex-5A, 588 mg, 2.13 mmol) and 2,4-dimethoxy-5-pyrrolidin-1-yl-benzaldehyde (Ex-38B, 500 mg, 2.13 mmol) in DMF (9.3 mL) and MeOH (4.0 mL) was treated with lithium methoxide (243 mg, 6.39 mmol) and stirred for 20 h at room temperature under nitrogen. The reaction mixture was quenched with water (25 mL) and extracted ethyl acetate (3×50 mL). The product precipitated out of the organic phase to give 535 mg (51%) of the title compound as a red solid, mp 124–128° C. $^1$H-NMR (300 MHz, DMSO-$d_6$) δ8.16 (d, 2H, J=8.7), 8.02 (d, 1H, J=15.9 Hz), 7.95 (m, 3H), 7.70 (t, 1H, J=7.80 Hz), 7.61 (d, 1H, J=16.2 Hz), 7.18 (d, 1H, J=8.70 Hz), 7.15 (s, 1H), 6.83 (t, 1H, J=6.0 Hz), 6.66 (s, 1H), 3.84 (s, 6H), 3.13 (m, 4H), 1.18 (m, 4H). HRMS (ESI) Calcd. for $C_{26}H_{27}N_3O_5S$: 494.1750 [(M+H)$^+$]; Found: 494.1750.

Example 53

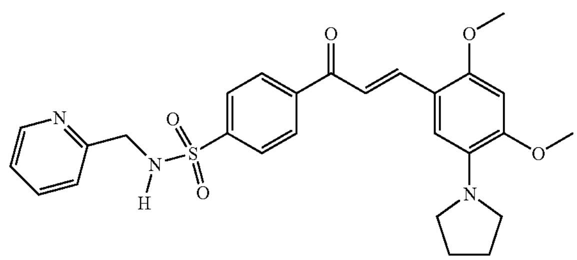

4-[3E-(2,4-Dimethoxy-5-pyrrolidin-1-ylphenyl)acryloyl]-N-pyridin-2-ylmethylbenzenesulfonamide Ex-53A: A solution of 4-acetyl-benzenesulfonyl chloride (1.94 g, 8.89 mmol) and triethylamine (1.85 mL, 13.3 mmol) in anhydrous THF (15 mL) was treated with 2-(aminomethyl)pyridine (1.01 g, 9.34 mmol) at room temperature under nitrogen. The reaction mixture was stirred for 5 minutes and a precipitate formed. The reaction mixture was diluted with water (10 mL) and suction filtration gave 4-acetyl-N-pyridin-2-ylmethylbenzenesulfonamide as a yellow solid (1.36 g, 65%). $^1$H-NMR (300 MHz, DMSO-$d_6$) δ8.38 (m, 3H), 8.06 (d, 2H, J=9.0 Hz), 7.87 (d, 2H, J=7.8 Hz), 7.58 (d, 1H, J=8.7 Hz), 7.25 (dd, 1H, J=5.4, 4.5 Hz), 4.04 (d, 2H, J=3.9 Hz), 2.60 (s, 3H).

A solution 4-acetyl-N-pyridin-2-ylmethyl-benzenesulfonamide (Ex-53A, 617 mg, 2.13 mmol) and 2,4-dimethoxy-5-pyrrolidin-1-yl-benzaldehyde (Ex-38B, 500 mg, 2.13 mmol) in DMF (9.3 mL) and MeOH (4.0 mL) was treated with lithium methoxide (162 mg, 4.26 mmol) and stirred for 20 h at room temperature under nitrogen. The reaction mixture was quenched with water (20 mL) and extracted ethyl acetate (3×50 mL). The organic phase was brined, dried over sodium sulfate, and concentrated to a red solid. Crystallization from hot ethanol (25 mL) and water (50 mL) gave the title compound as a red solid (626 mg, 58%), mp 112–116° C. $^1$H-NMR (300 MHz, DMSO-$d_6$) δ8.40 (m, 3H), 8.19 (d, 2H, J=9.0 Hz), 8.05 (d, 1H, J=15.9 Hz), 7.89 (d, 2H, J=9.0 Hz), 7.62 (m, 2H), 7.25 (dd, 1H, J=4.5, 5.7 Hz), 7.17 (s, 1H), 6.67 (s, 1H), 4.05 (d, 2H, J=5.7 Hz), 3.86 (s, 3H), 3.85 (s, 3H), 3.16 (br s, 4H), 1.82 (br s, 4H). HRMS (ESI) Calcd. for $C_{27}H_{29}N_3O_5S$: 508.1906 [(M+H)$^+$]; Found: 508.1902.

Example 54

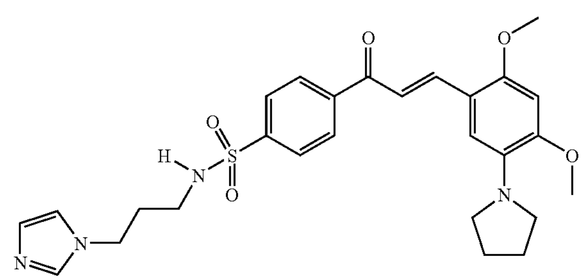

4-[3E-(2,4-Dimethoxy-5-pyrrolidin-1-ylphenyl)acryloyl]-N-(3-imidazol-1-ylpropyl)benzenesulfonamide A solution 4-acetyl-N-(3-imidazol-1-ylpropyl)benzenesulfonamide (Ex-23A, 653 mg, 2.13 mmol) and 2,4-dimethoxy-5-pyrrolidin-1-yl-benzaldehyde (Ex-38B, 500 mg, 2.13 mmol) in DMF (9.3 mL) and MeOH (4.0 mL) was treated with lithium methoxide (162 mg, 4.26 mmol) and stirred for 20 h at room temperature under nitrogen atmosphere. The reaction mixture was quenched with water (75 mL) and extracted ethyl acetate (3×50 mL). The organic phase was brined, dried over sodium sulfate, and concentrated to a red solid. Crystallization from hot ethanol (10 mL) and water (12 mL) gave 461 mg (41%) of the title compound as a red solid, mp 140–143° C. $^{1}$H-NMR (300 MHz, DMSO-$d_6$) δ8.23 (d, 2H, J=8.7 Hz), 8.05 (d, 1H, J=15.3 Hz), 7.88 (d, 2H, J=9.3 Hz), 7.64 (d, 1H, J=15.3 Hz), 7.51 (s, 1H), 7.17 (s, 1H), 7.05 (s, 1H), 6.81 (s, 1H), 6.67 (s, 1H), 3.92 (t, 2H, J=6.9 Hz), 3.86 (s, 6H), 3.15 (m, 4H), 2.68 (t, 2H, J=6.3 Hz), 1.80 (m, 6H). HRMS (ESI) Calcd. for $C_{27}H_{32}N_4O_5S$: 525.2172 $(M+H)^+$; Found; 525.2179.

Example 55

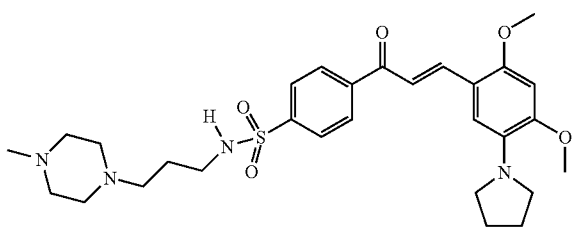

4-[3E-(2,4-Dimethoxy-5-pyrrolidin-1-ylphenyl)acryloyl]-N-[3-(4-methyl-piperazin-1-yl)propyl]benzenesulfonamide Ex-55A: A chilled solution of 4-acetyl-benzenesulfonyl chloride (1.0 g, 4.57 mmol) and triethylamine (0.955 mL, 6.86 mmol) in anhydrous THF (5 mL) was treated with 1-(3-amiopropyl)-4-methylpiperazine (755 mg, 4.80 mmol) under nitrogen. The reaction mixture was stirred for 30 minutes, quenched with water (30 mL) and extracted with ethyl acetate (3×25 mL). The combined organic phase was brined, dried over sodium sulfate, and concentrated to 4-acetyl-N-[3-(4-methylpiperazin-1-yl)propyl]benzenesulfonamide as a brown solid (1.18 g, 76%). $^{1}$H-NMR (300 MHz, DMSO-$d_6$) δ8.10 (d, 2H, J=8.1 Hz), 7.86 (d, 2H, J=8.4 Hz) 7.77 (br s, 1H), 2.74 (quartet, 2H, J=5.4 Hz), 2.60 (s, 3H), 2.20–2.13 (m, 10H), 2.09 (s, 3H), 1.45 (quintet, 2H, J=7.2 Hz).

A solution 4-acetyl-N-[3-(4-methylpiperazin-1-yl)propyl]benzenesulfonamide (Ex-55A, 830 mg, 2.44 mmol) and 2,4-dimethoxy-5-pyrrolidin-1-ylbenzaldehyde (Ex-38B, 575 mg, 2.44 mmol) in DMF (10.8 mL) and MeOH (4.4 mL) was treated with lithium methoxide (278 mg, 7.32 mmol) and stirred for 20 h at room temperature under nitrogen atmosphere. The reaction mixture was quenched with water (75 mL) and extracted ethyl acetate (3×50 mL). The combined organic phase was brined, dried over sodium sulfate, and concentrated to a red solid. Column chromatography (5% MeOH in dichloromethane) gave 772 mg (57%) of the title compound as a brown solid, mp 64–68° C. $^{1}$H-NMR (300 MHz, DMSO-$d_6$) δ8.23 (d, 2H, J=8.7), 8.05 (d, 1H, J=15.3 Hz), 7.88 (d, 2H, J=7.5 Hz), 7.76 (t, 1H, J=4.8 Hz), 7.63 (d, 1H, J=15.3 Hz), 7.16 (s, 1H), 6.67 (s, 1H), 3.86 (s, 6H), 3.16 (br s, 4H), 2.76 (quartet, 2H, J=6.9 Hz), 2.15 (m, 10H), 2.06 (s, 3H), 1.80 (br s, 4H), 1.45 (quintet, 2H, J=6.9 Hz). HRMS (ESI) Calcd. for $C_{29}H_{40}N_4O_5S$: 557.2798 $[(M+H)^+]$; Found: 557.2798.

Example 56

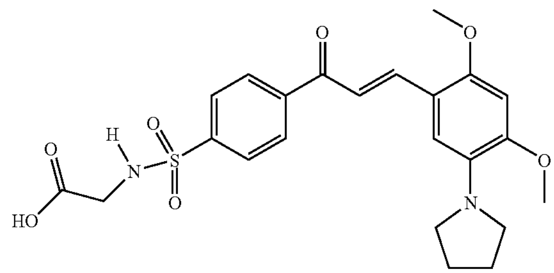

{4-[3E-(2,4-Dimethoxy-5-pyrrolidin-1-ylphenyl)acryloyl]benzenesulfonylamino}acetic acid A solution of (4-acetylbenzenesulfonylamino)acetic acid (Ex-26A, 226 mg, 0.878 mmol) and 2,4-dimethoxy-5-pyrrolidin-1-ylbenzaldehyde (Ex-38B, 216 mg, 0.922 mmol) in DMF (8.0 mL) and MeOH (3.6 mL) was treated with lithium methoxide (140 mg, 3.69 mmol) and stirred for 21 h at room temperature under nitrogen. The reaction mixture was quenched with water (10 mL) and extracted ethyl acetate (2×20 mL). The aqueous phase was acidified with 6N HCl to pH3 and was extracted with (3:1) ethyl acetate/THF (6×25 mL). The organic phase was brined, dried over sodium sulfate, and concentrated to a red solid. Precipitation from dichloromethane (5 mL) gave the title compound (33 mg, 8%) as a brown solid, mp 155–158° C. $^{1}$H-NMR (300 MHz, DMSO-$d_6$) δ12.06 (br s, 1), 8.22 (m, 3H), 8.04 (d, 1H, J=15.3 Hz), 7.89 (d, 2H, J=7.8 Hz), 7.64 (d, 1H, J=15.3 Hz), 7.18 (s, 1H), 6.67 (s, 1H), 3.86 (s, 6H), 3.29 (br s, 2H), 3.16 (br s, 4H), 1.82 (br s, 4H). HRMS (ESI) Calcd. for $C_{23}H_{26}N_2O_7S$: 475.1539 [(M+H)+]; Found: 475.1547.

Example 57

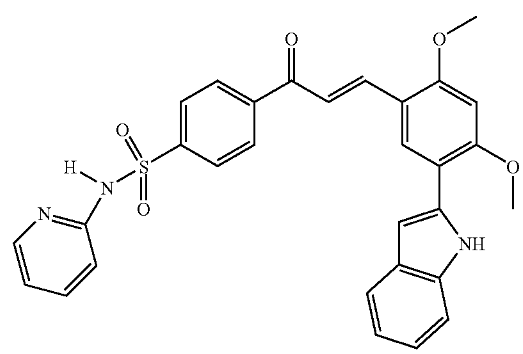

4-{3E-[5-(1H-Indol-2-yl)-2,4-dimethoxyphenyl]acryloyl}-N-pyridin-2-ylbenzenesulfonamide Ex-57A: A solution of 4-acetyl-N-pyridin-2-ylbenzenesulfonamide (Ex-5A, 451 mg, 1.63 mmol) and 5-(2-aminophenylethynyl)-2,4-dimethoxybenzaldehyde (Ex-35C, 459 mg, 1.63 mmol) in DMF (10.0 mL) and MeOH (5.0 mL) was treated with lithium methoxide (248 mg, 6.52 mmol). The reaction mixture was stirred at room temperature for 3 h under nitrogen, quenched with water (50 mL), and extracted with (3:1) ethyl acetate/THF (4×30 mL). The combined organic phase was brined, dried over sodium sulfate, and concentrated to a yellow oil. The crude material was purified by column chromatography (2–5% MeOH in dichloromethane) to give 735 mg (65%) of 4-{3E-[5-(2-amino-phenylethynyl)-2,4-dimethoxyphenyl]acryloyl}-N-pyridin-2-yl-benzenesulfonamide as a yellow oil. $^1$H-NMR (300 MHz, DMSO-$d_6$) δ8.21 (d, 2H, J=7.5), 8.18 (s, 1H), 8.00 (m, 4H), 7.81 (d, 1H, J=15.0 Hz), 7.74 (t, 2H, J=7.5 Hz), 7.17 (m, 2H), 7.05 (t, 2H, J=7.2 Hz), 6.80 (m, 3H), 6.52 (t, 1H), J=7.5 Hz), 5.43 (d, 1H, J=6.9 Hz), 3.96 (s, 3H), 3.95 (s, 3H).

Ex-57B:

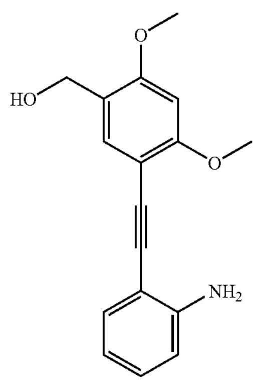

A solution of 5-(2-aminophenylethynyl)-2,4-dimethoxy-benzaldehyde (Ex-35C, 10.3 g, 36.7 mmol) in 500 ml of THF and 500 ml of MeOH was cooled to 0° C. with an ice bath. To this solution was added $NaBH_4$ (2.8 g, 73.4 mmol) portion-wise. The mixture was stirred at 0° C. for 1 h. The reaction was quenched with 1N $H_2SO_4$ slowly until no gas bubbling was observed.

The mixture was filtered and the filtrate was concentrated to about 100 ml. The precipitate was filtered to give 9.65 g (92.3%) of [5-(2-aminophenylethynyl)-2,4-dimethoxyphenyl]methanol as a white solid. $^1$H-NMR (300 MHz, Acetone-$d_6$) δ 7.44 (s, 1H), 7.19 (dd, J=8, 1 Hz, 1H), 7.00–7.5 (m, 1H), 6.74 (d, J=8 Hz, 1H), 6.70 (s, 1H), 6.52–6.57 (m, 1H), 5.15 (br, 2H), 4.53 (d, J=5 Hz, 2H), 3.92 (s, 3H), 3.87 (s, 3H).

Ex-57C:

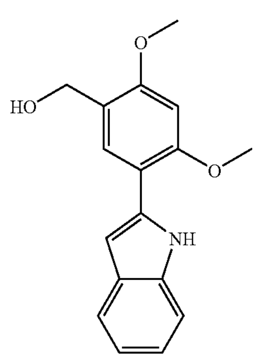

To a solution of [5-(2-aminophenylethynyl)-2,4-dimethoxyphenyl]methanol (Ex-57B, 9.65 g, 34 mmol) in 1 L of acetonitrile, was added $PdCl_2$ (0.6 g, 3.4 mmol). The mixture was heated to reflux for about 0.5 h and the reaction was complete as indicated by HPLC. The mixture was cooled to room temperature and filtered. The filtrate was treated with 20 g of 3-mercaptopropyl functional silica gel with stirring for 30 min and then filtered. The filtrate was concentrated and the residue was recrystallized from EtOAc/hexanes to give 6.25 g (67.8%) of [5-(1H-indol-2-yl)-2,4-dimethoxyphenyl]methanol as off-white solid. $^1$H-NMR (Acetone-$d_6$) δ 10 50 (br, 1H), 7.84 (s, 1H), 7.48 (d, J=7 Hz, 1H), 7.37 (d, J=8 Hz, 1H),6.91–7.03 (m, 2H), 6.79 (d, J=2 Hz, 1H), 6.77 (s, 1H), 4.59 (s, 2H), 3.98 (s, 3H), 3.88 (s, 3H).

Ex-57D:

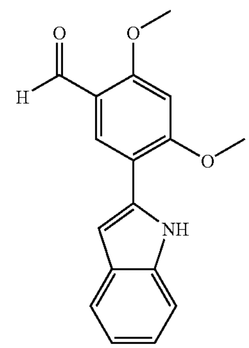

To a solution of [5-(1H-indol-2-yl)-2,4-dimethoxyphenyl] methanol (Ex-57C, 5.8 g, 20 mmol) in 250 ml of THF and 250 ml of $CH_2Cl_2$, was added $MnO_2$ (1.8 g, 20 mmol). The mixture was heated to reflux. The reaction was pushed to completion by adding two more portions of $MnO_2$ (1.8 g each ) within 48 h. The mixture was then cooled to room temperature and filtered. The filtrate was concentrated and the residue was recrystallized from EtOAc/Hexane to give 5.1 g (88%) of 5-(1H-indol-2-yl)-2,4-dimethoxybenzaldehyde. $^1$H-NMR (300 MHz, DMSO-$d_6$) δ 11.29 (br s, 1H), 10 24 (s, 1H), 8.10 (s, 1H), 7.47 (d, J=8 Hz, 1H), 7.37 (d, J=7 Hz, 1H), 7.01–7.05 (m, 1H), 6.91–6.95 (m, 1H), 6.85–6.86 (m, 2H), 4.06 (s, 3H), 3.99 (s, 3H). HRMS (EI) Calcd. for $C_{17}H_{15}NO_3$: 281.1052 ($M^+$); Found: 281.1046.

Ex-57DD:

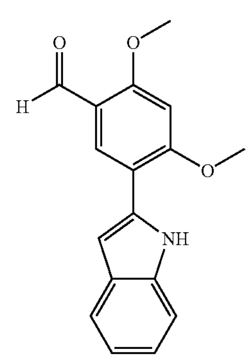

A solution of $PdCl_2$ (0.066 g, 0.373 mmol) in 200 ml of acetonitrile was heated to reflux. To this solution was added 5-(2-amino-phenylethynyl)-2,4-dimethoxybenzaldehyde (Ex-35C, 1.4 g, 5 mmol) portion by portion slowly so that no cloudiness of the solution occurred. After the addition, the reaction was kept at reflux for another 10 min. Then the mixture was cooled to room temperature and filtered. The filtrate was treated with 5 g of 3-mercaptopropyl functional silica gel with stirring for 30 min and filtered. The filtrate was concentrated and the residue was recrystallized from EtOAc/Hexane to give 0.84 g (60%) of 5-(1H-indol-2-yl)-2,4-dimethoxybenzaldehyde, analytical dada identical as in Ex-57D.

Ex-57E:

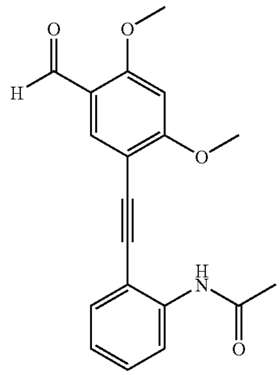

Pyridine (453 μL, 5.61 mmol) was added to a suspension of 5-(2-amino-phenylethynyl)-2,4-dimethoxybenzaldehyde (Ex-35C, 750 mg, 2.67 mmol) in anhydrous methylene chloride (20 mL) and chilled to 0° C. The reaction mixture was treated dropwise with acetyl chloride (9.25 mL, 75.1 mmol). Upon completion the reaction was quenched with IN HCl (10 mL) and the layers were separated. The organic layer was washed with brine, dried over sodium sulfate, and concentrated to dryness. The crude solid was purified by silica gel chromatography (5% MeOH/$CH_2Cl_2$) to yield 671 mg (78%) of N-[2-(5-formyl-2,4-dimethoxyphenylethynyl) phenyl]acetamide as an off-white solid. $^1$H-NMR (300 MHz, DMSO-$d_6$) δ10.15 (s, 1H), 9.23 (br s, 1H), 7.82 (m, 2H), 7.80 (s, 1H), 7.50 (dd, 1H, J=0.9, 7.8 Hz), 7.35 (dt, 1H, J=1.8, 9.3 Hz), 7.12 (t, 1H, J=7.8 Hz), 6.82 (s, 1H), 4.00 (s, 3.99 (s, 3H), 2.10 (s, 3H).

Ex-57F:

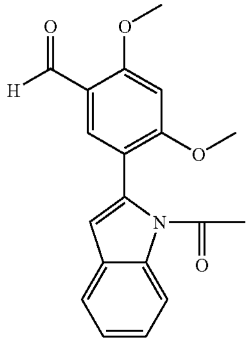

N-[2-(5-Formyl-2,4-dimethoxy-phenyl ethynyl)phenyl] acetamide (Ex-57E, 535 mg, 1.6 mmol) was added to 150 mL of DMF (nitrogen purged) at room temperature and the resulting solution was heated to 80° C. Palladium(II) chloride (22 mg) was added in one portion. After 6 h the reaction mixture was poured into water (50 mL) and EtOAc (50 mL), and the layers were cut. The organic layer was filtered through Celite, washed with brine, and concentrated to an orange solid. The crude was purified by silica gel chromatography (25% ethyl acetate/hexane) to yield 210 mg (39%) of 5-(1-acetyl-1H-indol-2-yl)-2,4-dimethoxybenzaldehyde as a white solid. $^1$H-NMR (300 MHz, DMSO-$d_6$) δ10.22 (s, 1H), 8.13 (d, 1H, J=8.1 Hz), 7.71 (s, 1H), 7.55 (d, 1H, J=6.3 Hz), 7.25 (m, 2H, J=6.9 Hz), 6.84 (s, 1H), 6.64 (s, 1H), 4.01 (s, 3H), 3.87 (s, 3H), 2.13 (s, 3H).

Ex-57G:

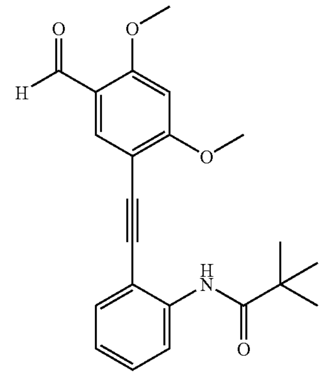

Pyridine (12.6 mL, 156.24 mmol) was added to a suspension of 5-(2-aminophenylethynnyl)-2,4-dimethoxybenzaldehyde (Ex-35C, 20.90 g, 74.4 mmol) in anhydrous methylene chloride (572 mL) and chilled to 0° C. The reaction mixture was treated dropwise with pivaloyl chloride (9.25 mL, 75.1 mmol) and then aged at room temperature for 2 h. The reaction was quenched with 1N HCl (200 mL) and the layers were cut. The organic layer was washed with brine, dried over sodium sulfate, and concentrated to dryness to afford 21.47 g (79%) of N-[2-(5-formyl-2,4-dimethoxyphenylethynyl)phenyl]-2,2-dimethylpropionamide as a light brown solid. $^1$H-NMR (300 MHz, DMSO-$d_6$) δ10.14 (s, 1H), 8.74 (br s, 1H), 7.89 (d, 1H, J=8.1 Hz), 7.80 (s, 1H), 7.50 (dd, 1H, J=1.2, 7.8 Hz), 7.35 (dt, 1H, 1.8, 9.3 Hz), 7.12 (t, 1H, J=9.0 Hz), 6.82 (s, 1H), 3.99 (s, 3H), 3.98 (s, 3H), 1.23 (s, 9H).

Ex-57H:

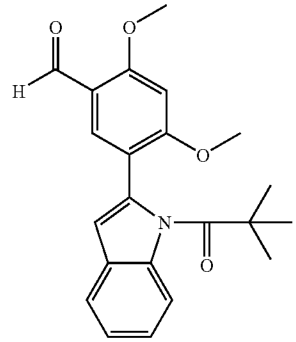

N-[2-(5-Formyl-2,4-dimethoxy-phenylethynyl)phenyl]-2,2-dimethylpropionamide (Ex-57G, 19.86 g, 54.4 mmol) was dissolved in nitrogen-purged DMF(189 mL) and heated to 80° C., followed by the addition of palladium(II) chloride (754 mg). After 1 h, the reaction mixture was diluted with water (300 mL) and extracted with EtOAc (2×200 mL). The combined organic phase was brined, dried over sodium sulfate, and concentrated to brown oil. The oil was purified by silica gel chromatography (30 to 50% ethyl acetate/hexane) to yield 14.31 g (72%) of 5-[1-(2,2-dimethylpropionyl)-1H-indol-2-yl]-2,4-dimethoxybenzaldehyde as a light yellow solid. $^1$H-NMR (300 z, $CDCl_3$) δ10.21 (s, 1H), 7.69 (s, 1H), 7.57 (d, 1H, J=37.8 Hz), 7.30 (d, 1H, J=8.10 Hz), 7.20 (t, 1H, J=6.9 Hz), 7.12 (t, 2H, J=6.9 Hz), 6.85 (s, 1H), 6.70 (s, 1H), 4.00 (s, 3H), 3.87 (s, 3H), 0.95 (s, 9H).

A suspension of 4-{3E-[5-(2-amino-phenylethynyl)-2,4-dimethoxyphenyl]acryloyl}-N-pyridin-2-ylbenzenesulfonamide (Ex-57A, 735 mg, 1.36 mmol) in acetonitrile (100 mL) was purged with nitrogen for 10 minutes. Palladium(II)

chloride (24 mg, 0.14 mmol) was added and the reaction mixture was refluxed for 3.5 hrs. The cooled reaction mixture was stirred with 3-mercaptopropyl functionalized silica gel (500 mg) for 5 minutes, filtered, and concentrated. The crude material was purified by column chromatography (2% MeOH in dichloromethane) to give 320 mg (44%) of the title compound as a red solid, mp 206–208° C. $^1$H-NMR (300 MHz, DMSO-$d_6$) δ 11.13 (br s, 1H), 8.31 (s, 1H), 8.19 (d, 2H, J=7.80 Hz), 8.05 (m, 3H), 7.94 (br s, 1H), 7.82 (d, 1H, J=15.0 Hz), 7.74 (t, 2H, J=7.2 Hz), 7.49 (d, 1H, J=8.1 Hz), 7.41 (d, 1H, J=7.5 Hz), 7.21 (d, 1H, J=8.4 Hz), 7.05 (t, 1H, J=7.5 Hz), 6.95 (m, 2H), 6.82 (s, 2H), 4.03 (s, 3H), 3.98 (s, 3H). HRMS (ESI) Calcd. for $C_{30}H_{25}N_3O_5S$: $(M+H)^+$; Found: 540.1576.

Alternatively, 4-Acetyl-N-pyridin-2-ylbenzenesulfonamide (Ex-5A, 1.52 g, 5.50 mmol), 5-[1-(2,2-dimethylpropionyl)-1H-indol-2-yl]-2,4-dimethoxybenzaldehyde (Ex-57H, 2.0 g, 5.47 mmol), MeOH (7 mL) and DMF (14 mL) were sequentially charged into a clean reaction vessel fitted with a stir bar and nitrogen inlet adapter. LiOMe (0.42 g, 11.1 mmol) was added and the resulting solution was aged for 45 min at room temperature. The reaction was diluted with sat.

$NH_4Cl$ (25 mL) and transferred to a separatory funnel containing THF (50 mL), EtOAc (50 mL) and $H_2O$ (50 mL). The layers were cut and the organic layer was concentrated to dryness. The crude product was suspended in EtOH (50 mL), filtered and then dried under vacuum to afford 2.5 g (85% yield) of the title compound, analytical dada identical as above. Similarly, the title compound could be prepared from 4-acetyl-N-pyridin-2-ylbenzenesulfonamide (Ex-5A) and 5-(1-acetyl-1H-indol-2-yl)-2,4-dimethoxybenzaldehyde (Ex-57F) or 5-(1H-indol-2-yl)-2,4-dimethoxybenzaldehyde (Ex-57D or Ex-57DD).

Using one or more of the preceding procedures or methods, additional compounds of the inventions listed in the following Tables can be prepared by one skilled in the art.

TABLE 1a

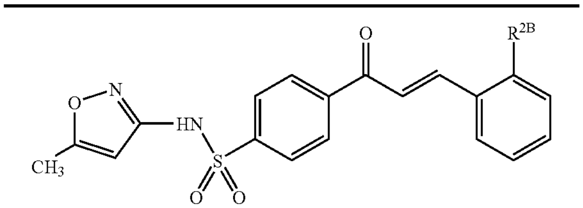

| Ex. No. | $R^{2B}$ |
|---|---|
| 100 | 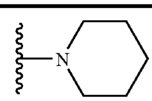 |
| 101 | 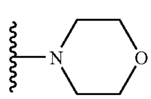 |
| 102 | 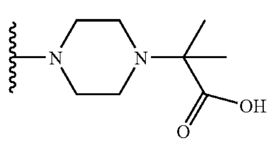 |
| 103 | 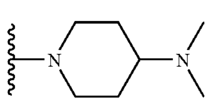 |

TABLE 1a-continued

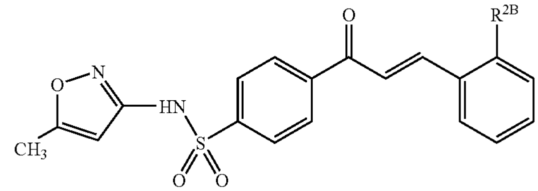

| Ex. No. | $R^{2B}$ |
|---|---|
| 104 | 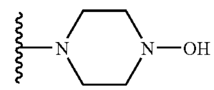 |
| 105 | 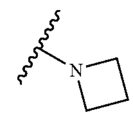 |
| 106 | 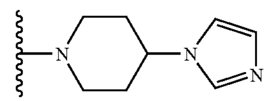 |
| 107 | 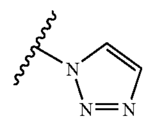 |
| 108 | 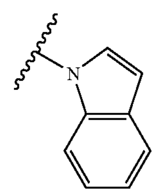 |
| 109 | 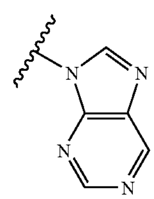 |
| 110 | 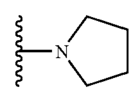 |
| 111 | 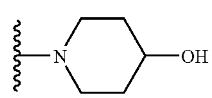 |
| 112 | 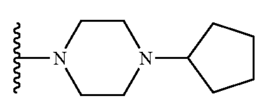 |
| 113 | 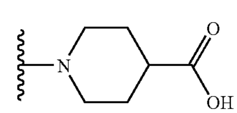 |

TABLE 1a-continued
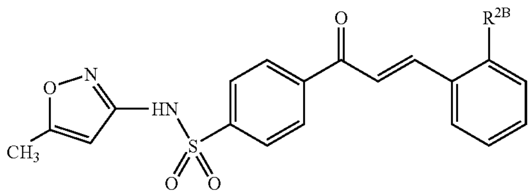
| Ex. No. | $R^{2B}$ |
|---|---|
| 114 | 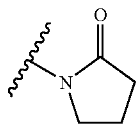 |
| 115 | 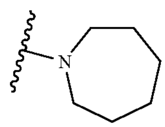 |
| 116 | 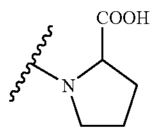 |
| 117 | 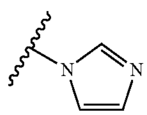 |
| 118 | 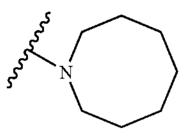 |
| 119 | 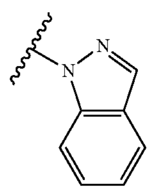 |
| 120 | 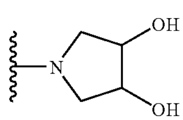 |
| 121 | 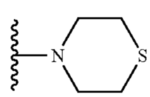 |
| 122 | 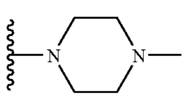 |
| 123 | 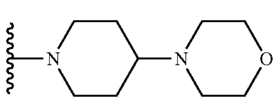 |
TABLE 1a-continued
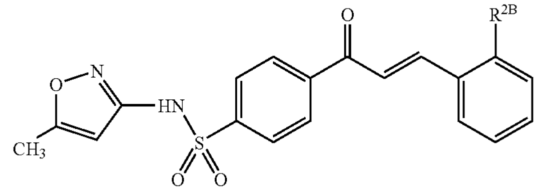
| Ex. No. | $R^{2B}$ |
|---|---|
| 124 | 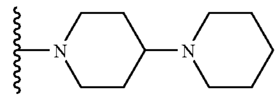 |
| 125 | 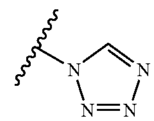 |
| 126 | 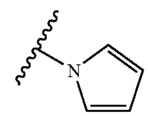 |
| 127 | 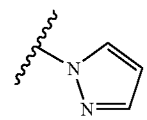 |
| 128 | 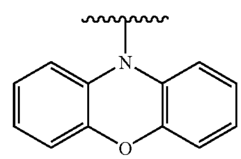 |
| 129 | 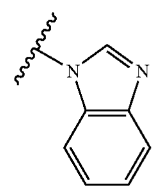 |
TABLE 1b
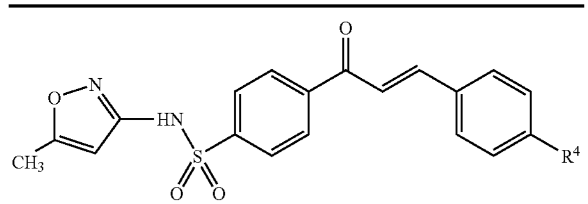
| Ex. No. | $R^4$ |
|---|---|
| 130 | 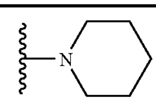 |
| 131 | 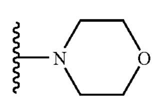 |

TABLE 1b-continued
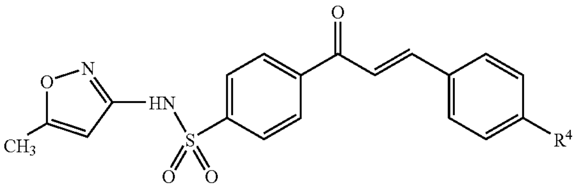
| Ex. No. | $R^4$ |
|---|---|
| 132 | 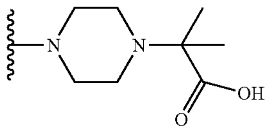 |
| 133 | 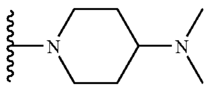 |
| 134 | 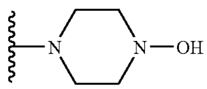 |
| 135 | 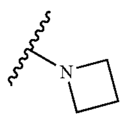 |
| 136 | 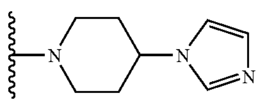 |
| 137 | 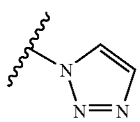 |
| 138 | 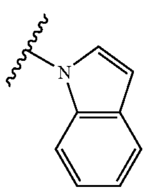 |
| 139 | 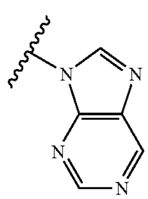 |
| 140 | 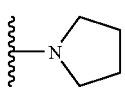 |
| 141 | 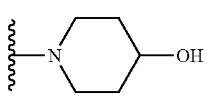 |
TABLE 1b-continued
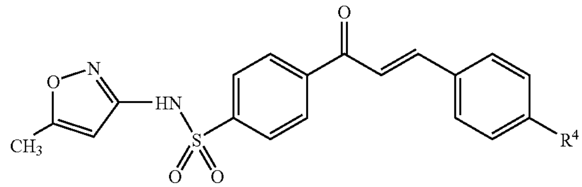
| Ex. No. | $R^4$ |
|---|---|
| 142 | 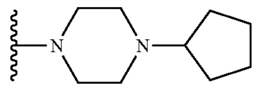 |
| 143 | 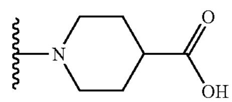 |
| 144 | 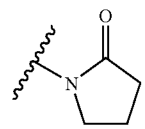 |
| 145 | 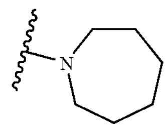 |
| 146 | 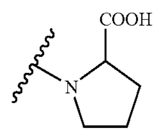 |
| 147 | 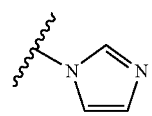 |
| 148 | 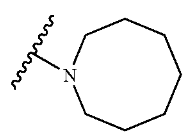 |
| 149 | 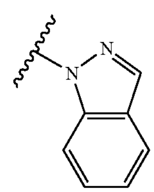 |
| 150 | 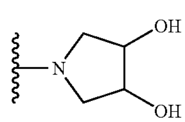 |
| 151 | 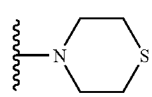 |

TABLE 1b-continued
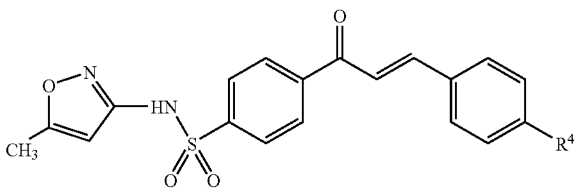
| Ex. No. | $R^4$ |
|---|---|
| 152 | 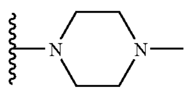 |
| 153 | 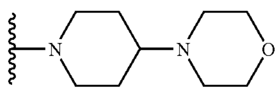 |
| 154 | 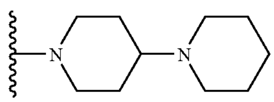 |
| 155 | 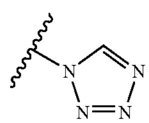 |
| 156 | 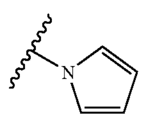 |
| 157 | 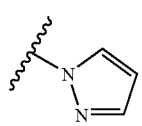 |
| 158 | 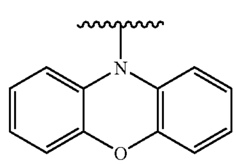 |
| 159 | 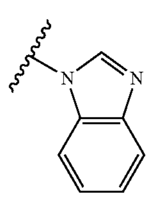 |
TABLE 1c
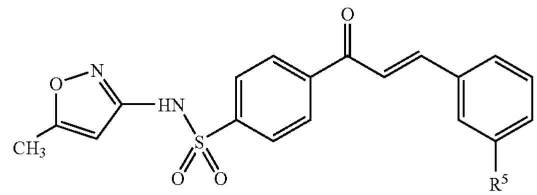
| Ex. No. | $R^5$ |
|---|---|
| 160 | 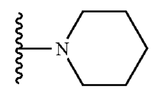 |
| 161 | 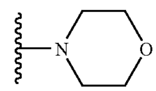 |
| 162 | 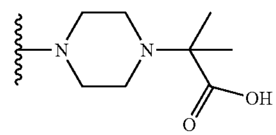 |
| 163 | 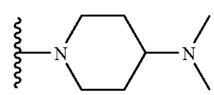 |
| 164 | 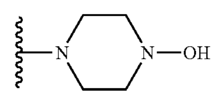 |
| 165 | 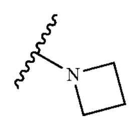 |
| 166 | 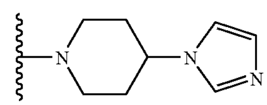 |
| 167 | 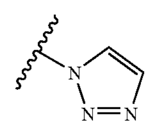 |
| 168 | 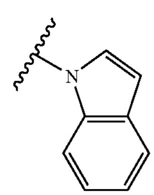 |
| 169 | 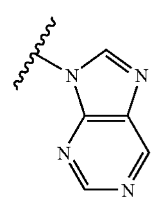 |

TABLE 1c-continued
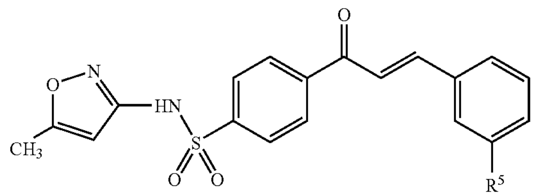
| Ex. No. | $R^5$ |
|---|---|
| 170 | 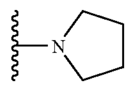 |
| 171 | 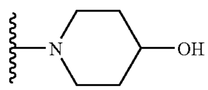 |
| 172 | 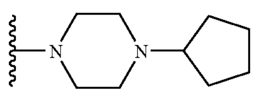 |
| 173 | 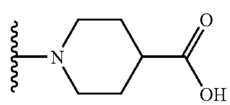 |
| 174 | 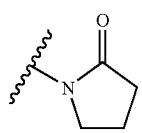 |
| 175 | 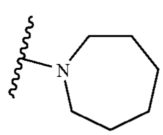 |
| 176 | 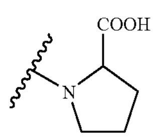 |
| 177 | 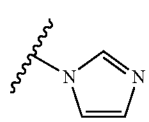 |
| 178 | 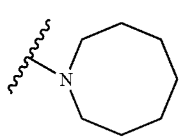 |
| 179 | 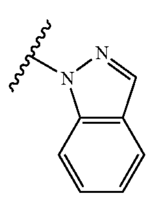 |
TABLE 1c-continued
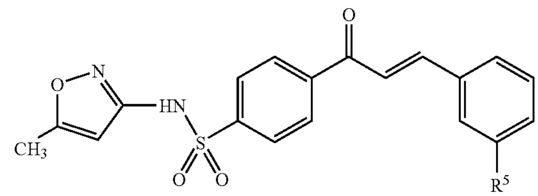
| Ex. No. | $R^5$ |
|---|---|
| 180 | 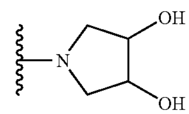 |
| 181 | 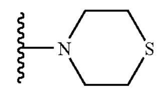 |
| 182 | 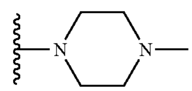 |
| 183 | 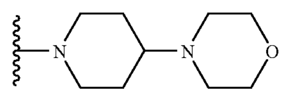 |
| 184 | 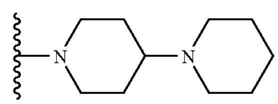 |
| 185 | 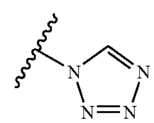 |
| 186 | 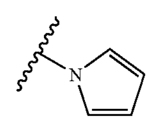 |
| 187 | 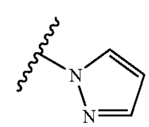 |
| 188 | 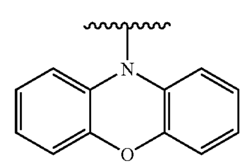 |
| 189 | 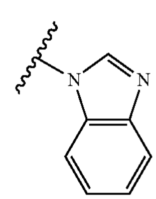 |

TABLE 1d
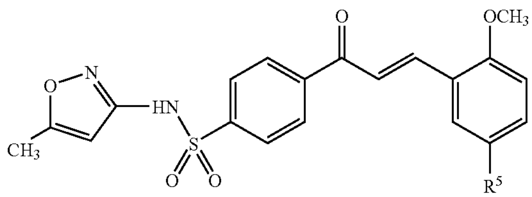
| Ex. No. | $R^5$ |
|---|---|
| 190 | 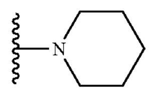 |
| 191 | 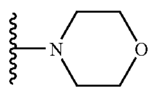 |
| 192 | 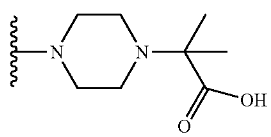 |
| 193 | 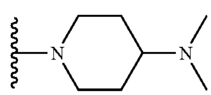 |
| 194 | 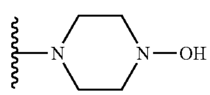 |
| 195 | 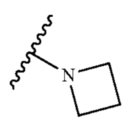 |
| 196 | 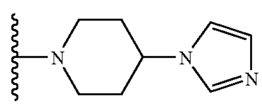 |
| 197 | 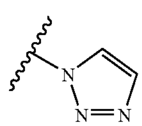 |
| 198 | 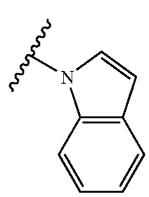 |
| 199 | 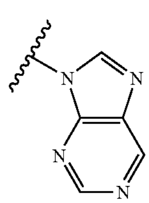 |
TABLE 1d-continued
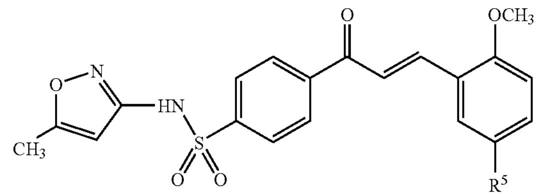
| Ex. No. | $R^5$ |
|---|---|
| 200 | 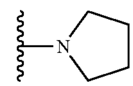 |
| 201 | 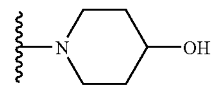 |
| 202 | 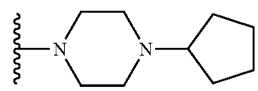 |
| 203 | 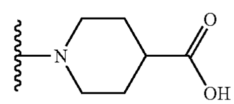 |
| 204 | 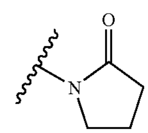 |
| 205 | 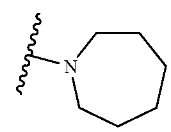 |
| 206 | 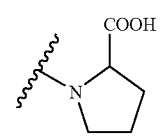 |
| 207 | 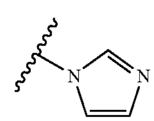 |
| 208 | 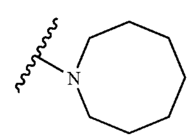 |
| 209 | 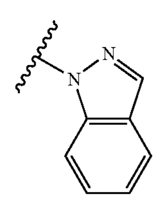 |

TABLE 1d-continued
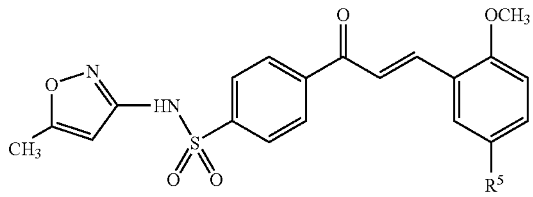
| Ex. No. | $R^5$ |
| --- | --- |
| 210 | 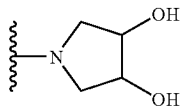 |
| 211 | 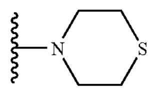 |
| 212 | 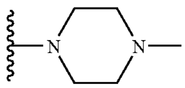 |
| 213 | 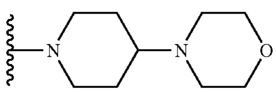 |
| 214 | 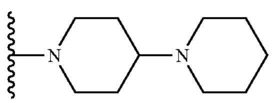 |
| 215 | 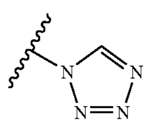 |
| 216 | 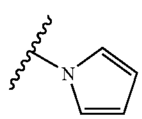 |
| 217 | 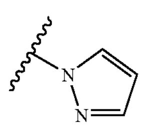 |
| 218 | 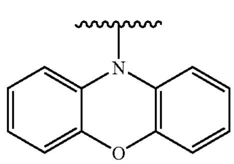 |
| 219 | 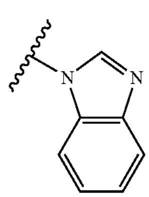 |
TABLE 1e
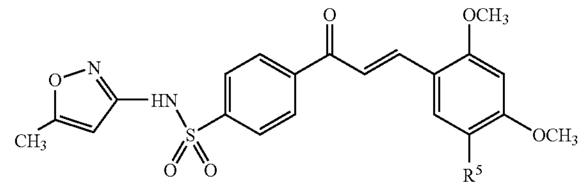
| Ex. No. | $R^5$ |
| --- | --- |
| 220 | 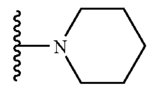 |
| 221 | 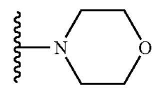 |
| 222 | 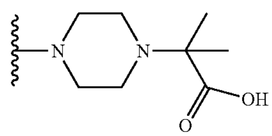 |
| 223 | 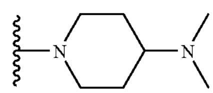 |
| 224 | 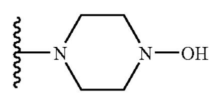 |
| 225 | 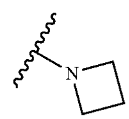 |
| 226 | 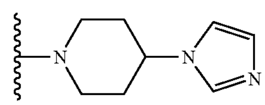 |
| 227 | 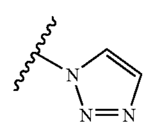 |
| 228 | 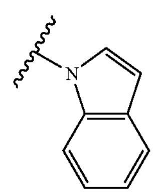 |
| 229 | 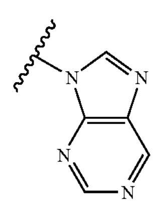 |

TABLE 1e-continued
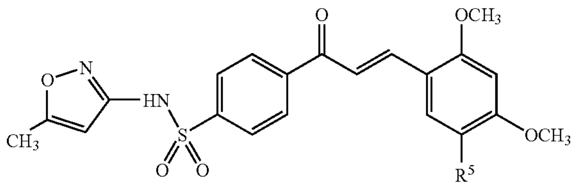
| Ex. No. | $R^5$ |
|---|---|
| 230 | 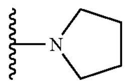 |
| 231 | 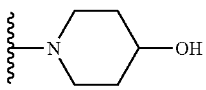 |
| 232 | 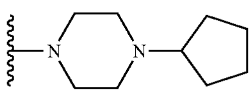 |
| 233 | 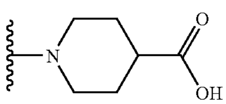 |
| 234 | 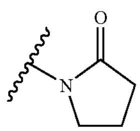 |
| 235 | 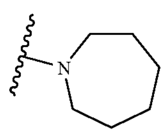 |
| 236 | 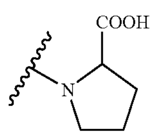 |
| 237 | 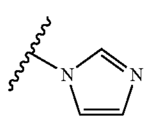 |
| 238 | 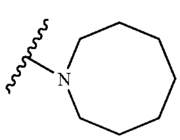 |
| 239 | 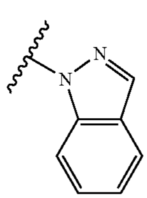 |
TABLE 1e-continued
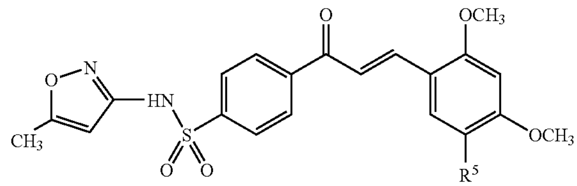
| Ex. No. | $R^5$ |
|---|---|
| 240 | 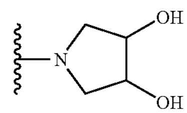 |
| 241 | 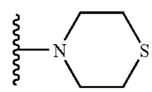 |
| 242 | 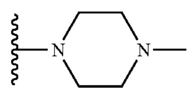 |
| 243 | 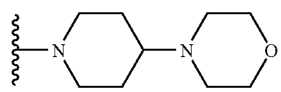 |
| 244 | 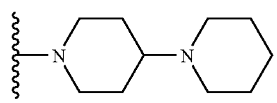 |
| 245 | 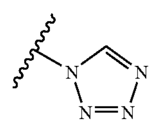 |
| 246 | 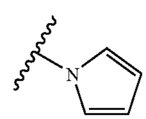 |
| 247 | 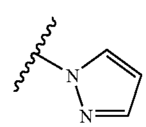 |
| 248 | 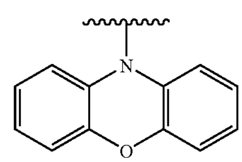 |
| 249 | 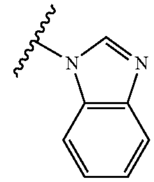 |

TABLE 1f
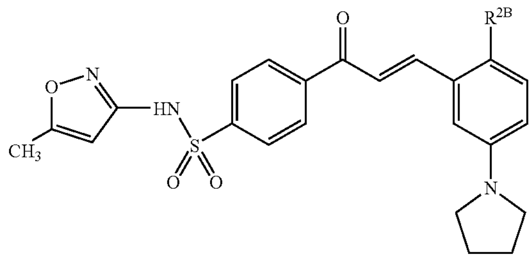
| Ex. No. | $R^{2B}$ |
|---|---|
| 250 | 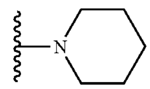 |
| 251 | 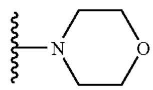 |
| 252 | 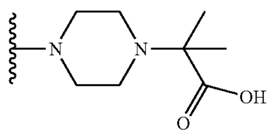 |
| 253 | 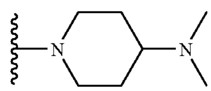 |
| 254 | 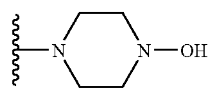 |
| 255 | 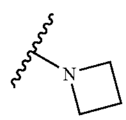 |
| 256 | 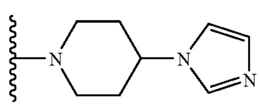 |
| 257 | 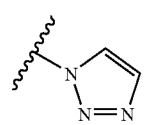 |
| 258 | 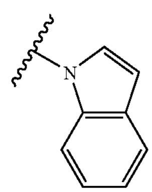 |
| 259 | 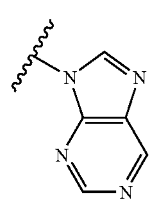 |
TABLE 1f-continued
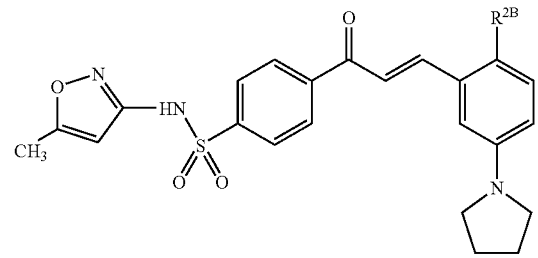
| Ex. No. | $R^{2B}$ |
|---|---|
| 260 | 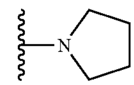 |
| 261 | 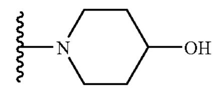 |
| 262 | 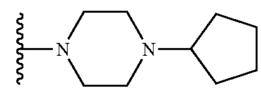 |
| 263 | 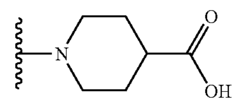 |
| 264 | 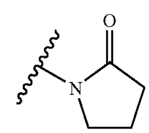 |
| 265 | 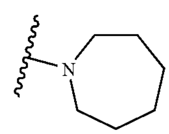 |
| 266 | 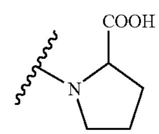 |
| 267 | 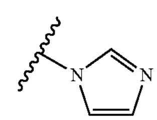 |
| 268 | 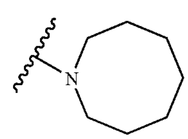 |
| 269 | 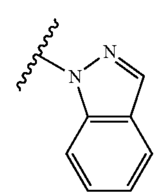 |

TABLE 1f-continued
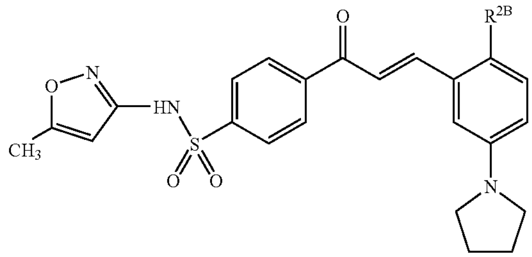
| Ex. No. | $R^{2B}$ |
|---|---|
| 270 | 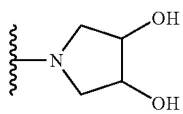 |
| 271 | 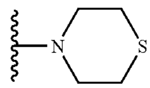 |
| 272 | 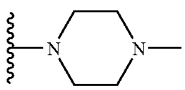 |
| 273 | 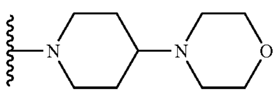 |
| 274 | 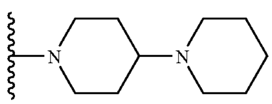 |
| 275 | 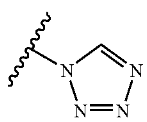 |
| 276 | 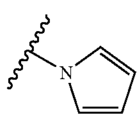 |
| 277 | 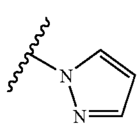 |
| 278 | 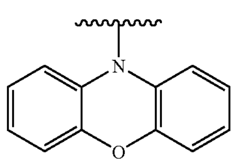 |
| 279 | 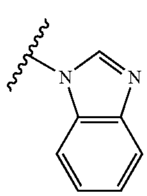 |
TABLE 1g
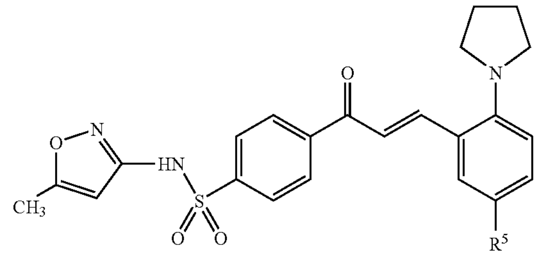
| Ex. No. | $R^5$ |
|---|---|
| 280 | 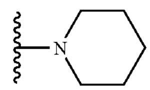 |
| 281 | 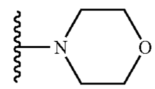 |
| 282 | 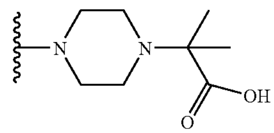 |
| 283 | 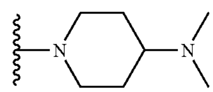 |
| 284 | 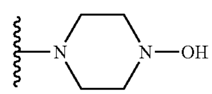 |
| 285 | 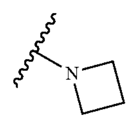 |
| 286 | 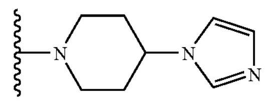 |
| 287 | 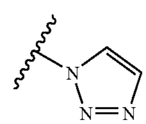 |
| 288 | 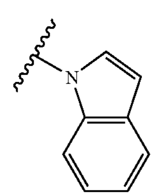 |
| 289 | 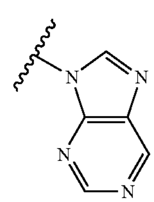 |

TABLE 1g-continued
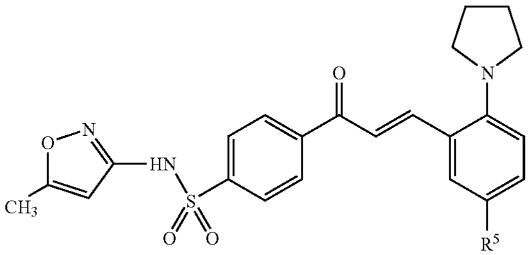
| Ex. No. | $R^5$ |
|---|---|
| 290 | 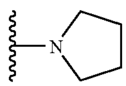 |
| 291 | 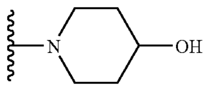 |
| 292 | 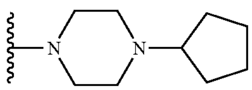 |
| 293 | 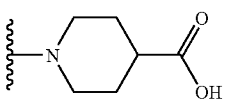 |
| 294 | 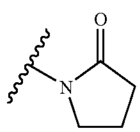 |
| 295 | 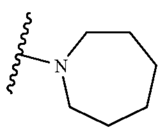 |
| 296 | 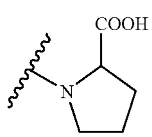 |
| 297 | 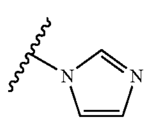 |
| 298 | 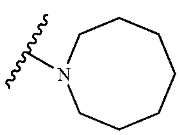 |
| 299 | 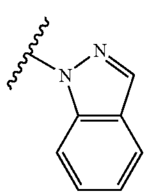 |
TABLE 1g-continued
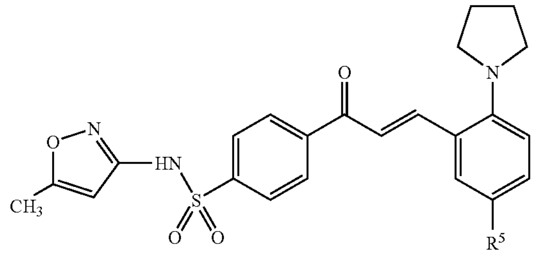
| Ex. No. | $R^5$ |
|---|---|
| 300 | 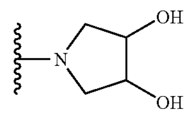 |
| 301 | 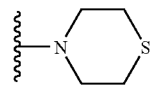 |
| 302 | 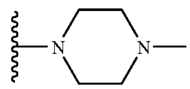 |
| 303 | 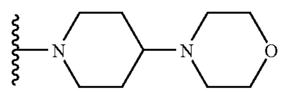 |
| 304 | 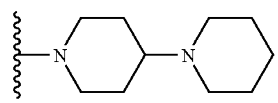 |
| 305 | 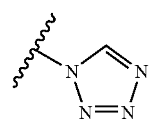 |
| 306 | 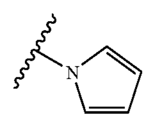 |
| 307 | 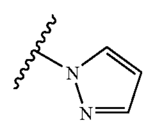 |
| 308 | 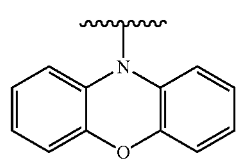 |
| 309 | 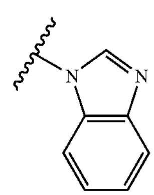 |

TABLE 2a
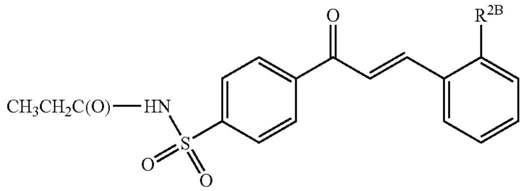
| Ex. No. | $R^{2B}$ |
|---|---|
| 310 | 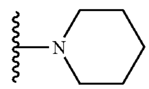 |
| 311 | 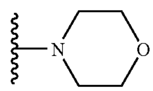 |
| 312 | 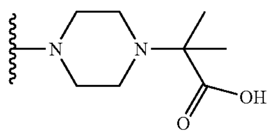 |
| 313 | 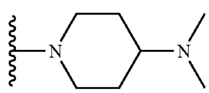 |
| 314 | 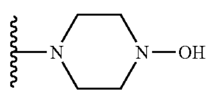 |
| 315 | 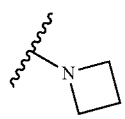 |
| 316 | 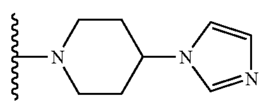 |
| 317 | 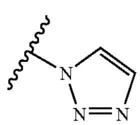 |
| 318 | 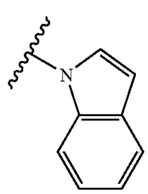 |
| 319 | 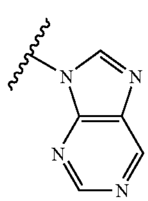 |
TABLE 2a-continued
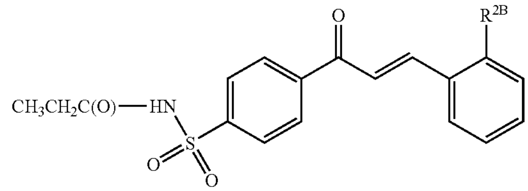
| Ex. No. | $R^{2B}$ |
|---|---|
| 320 | 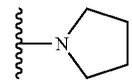 |
| 321 | 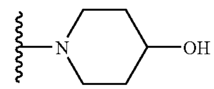 |
| 322 | 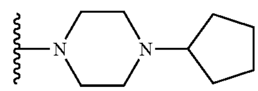 |
| 323 | 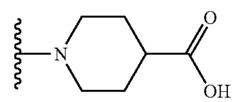 |
| 324 | 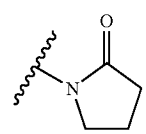 |
| 325 | 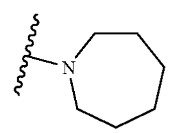 |
| 326 | 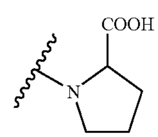 |
| 327 | 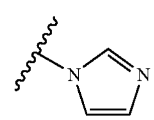 |
| 328 | 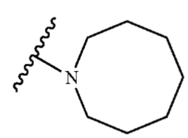 |
| 329 | 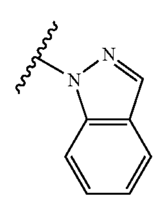 |

TABLE 2a-continued
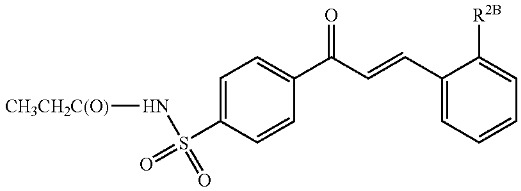
| Ex. No. | $R^{2B}$ |
| --- | --- |
| 330 | 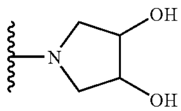 |
| 331 | 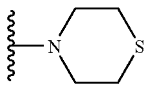 |
| 332 | 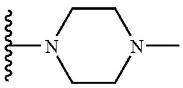 |
| 333 | 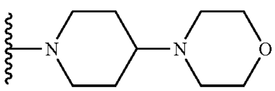 |
| 334 | 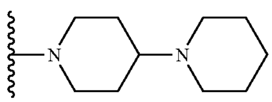 |
| 335 | 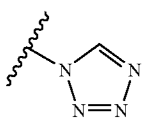 |
| 336 | 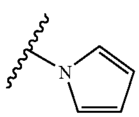 |
| 33 | 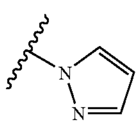 |
| 338 | 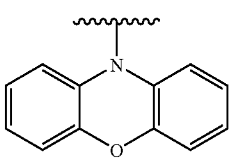 |
| 339 | 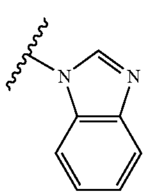 |
TABLE 2b
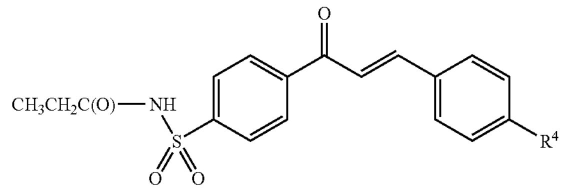
| Ex. No. | $R^4$ |
| --- | --- |
| 340 | 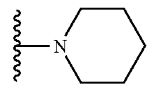 |
| 341 | 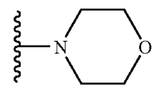 |
| 342 | 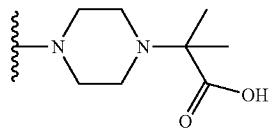 |
| 343 | 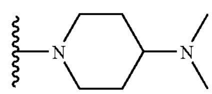 |
| 344 | 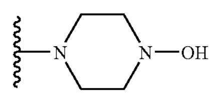 |
| 345 | 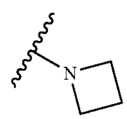 |
| 346 | 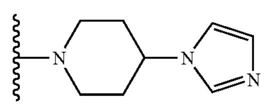 |
| 347 | 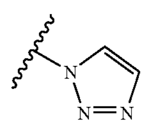 |
| 348 | 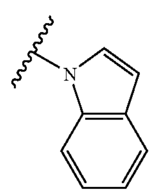 |
| 349 | 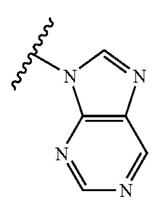 |

TABLE 2b-continued
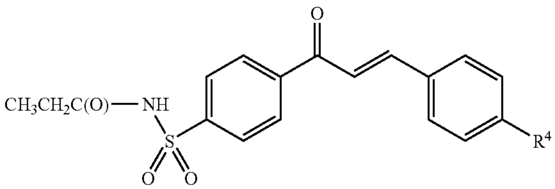
| Ex. No. | $R^4$ |
|---|---|
| 350 | 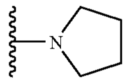 |
| 351 | 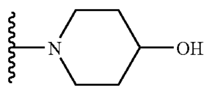 |
| 352 | 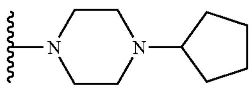 |
| 353 | 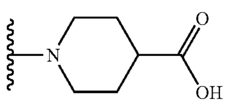 |
| 354 | 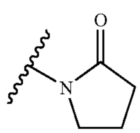 |
| 355 | 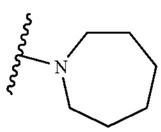 |
| 356 | 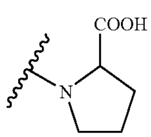 |
| 357 | 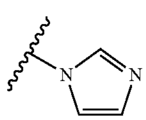 |
| 358 | 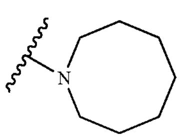 |
| 359 | 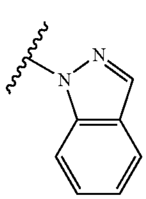 |
TABLE 2b-continued
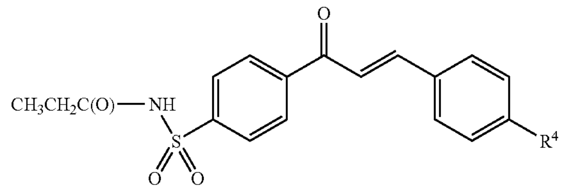
| Ex. No. | $R^4$ |
|---|---|
| 360 | 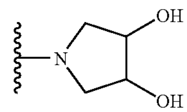 |
| 361 | 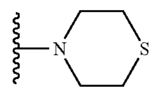 |
| 362 | 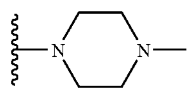 |
| 363 | 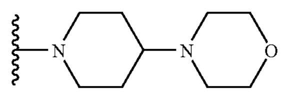 |
| 364 | 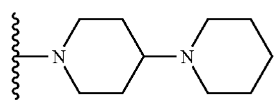 |
| 365 | 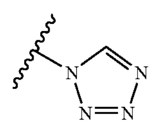 |
| 366 | 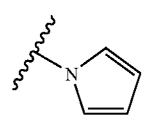 |
| 367 | 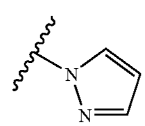 |
| 368 | 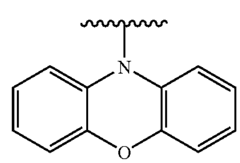 |
| 369 | 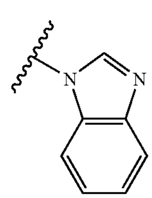 |

TABLE 2c
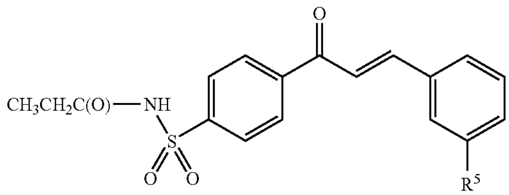
| Ex. No. | $R^5$ |
|---|---|
| 370 | 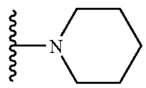 |
| 371 | 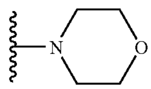 |
| 372 | 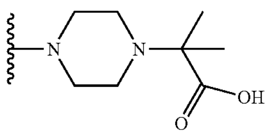 |
| 373 | 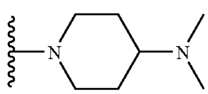 |
| 374 | 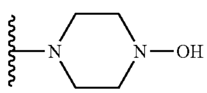 |
| 375 | 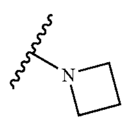 |
| 376 | 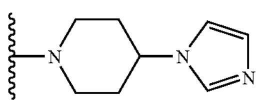 |
| 377 | 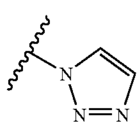 |
| 378 | 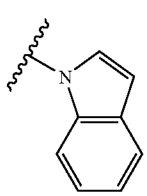 |
| 379 | 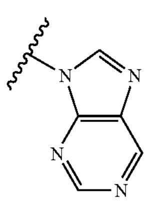 |
TABLE 2c-continued
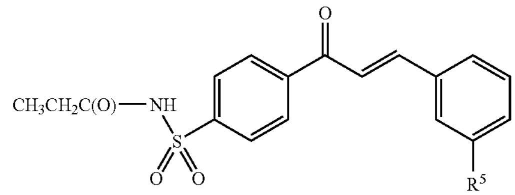
| Ex. No. | $R^5$ |
|---|---|
| 380 | 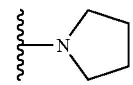 |
| 381 | 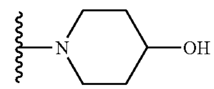 |
| 382 | 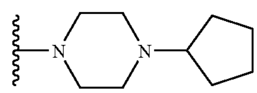 |
| 383 | 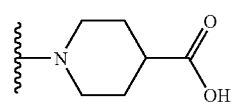 |
| 384 | 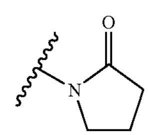 |
| 385 | 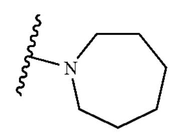 |
| 386 | 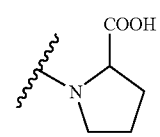 |
| 387 | 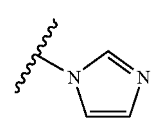 |
| 388 | 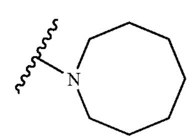 |
| 389 | 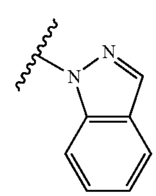 |

TABLE 2c-continued
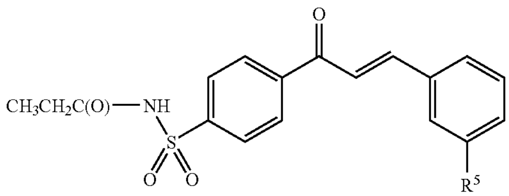
| Ex. No. | $R^5$ |
|---|---|
| 390 | 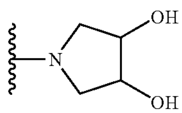 |
| 391 | 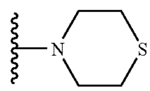 |
| 392 | 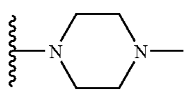 |
| 393 | 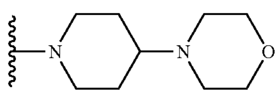 |
| 394 | 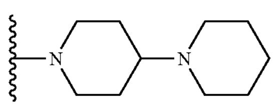 |
| 395 | 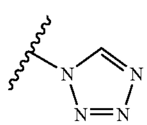 |
| 396 | 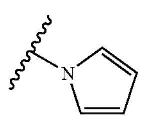 |
| 397 | 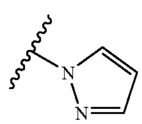 |
| 398 | 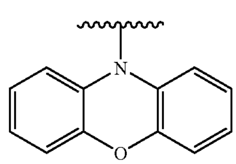 |
| 399 | 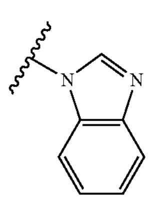 |
TABLE 2d
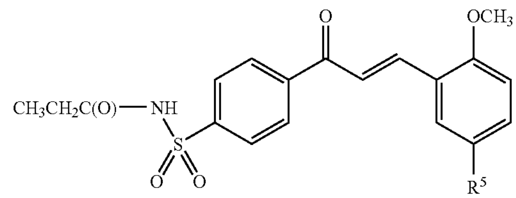
| Ex. No. | $R^5$ |
|---|---|
| 400 | 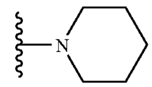 |
| 401 | 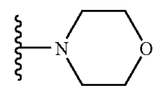 |
| 402 | 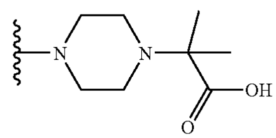 |
| 403 | 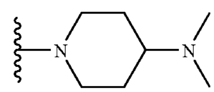 |
| 404 | 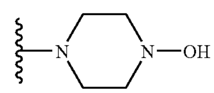 |
| 405 | 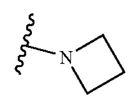 |
| 406 | 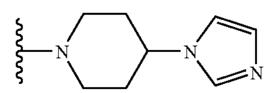 |
| 407 | 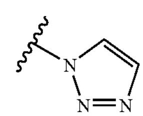 |
| 408 | 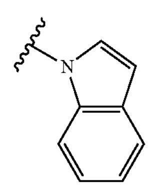 |
| 409 | 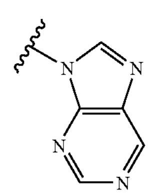 |
| 410 | 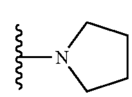 |

TABLE 2d-continued
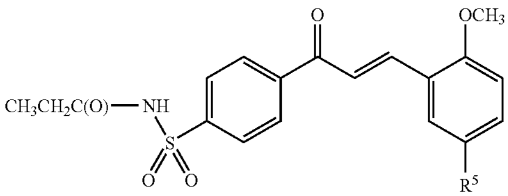
| Ex. No. | $R^5$ |
| --- | --- |
| 411 | 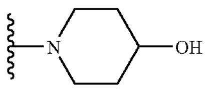 |
| 412 | 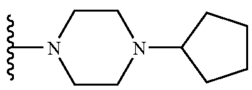 |
| 413 | 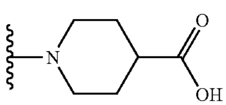 |
| 414 | 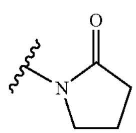 |
| 415 | 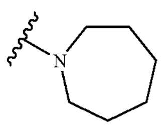 |
| 416 | 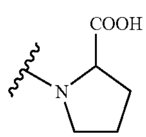 |
| 417 | 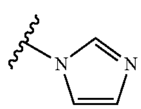 |
| 418 | 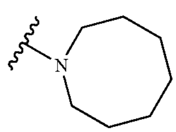 |
| 419 | 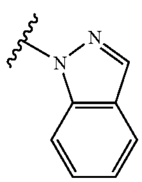 |
| 420 | 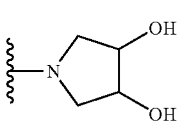 |
TABLE 2d-continued
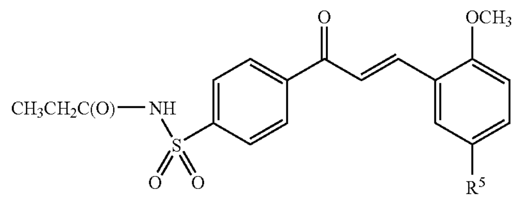
| Ex. No. | $R^5$ |
| --- | --- |
| 421 | 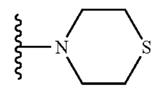 |
| 422 | 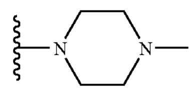 |
| 423 | 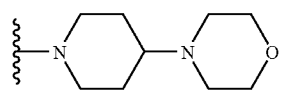 |
| 424 | 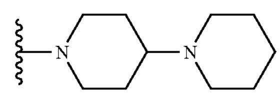 |
| 425 | 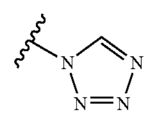 |
| 426 | 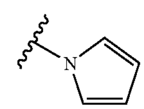 |
| 427 | 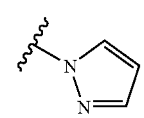 |
| 428 | 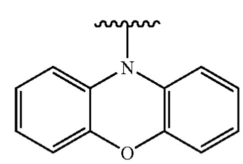 |
| 429 | 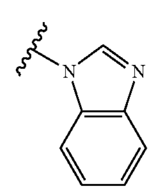 |

TABLE 2e
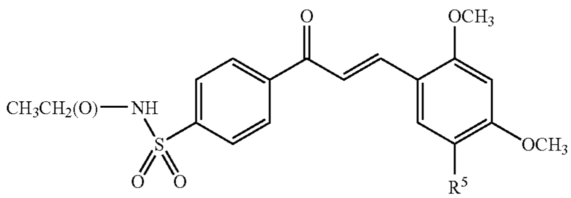
| Ex. No. | $R^5$ |
|---|---|
| 430 | 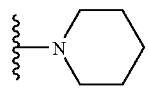 |
| 431 | 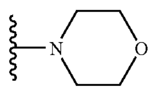 |
| 432 | 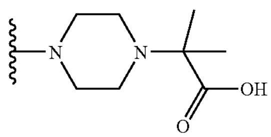 |
| 433 | 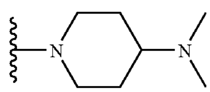 |
| 434 | 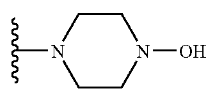 |
| 435 | 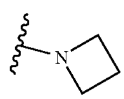 |
| 436 | 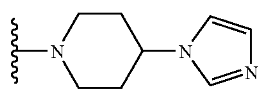 |
| 437 | 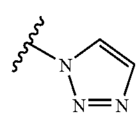 |
| 438 | 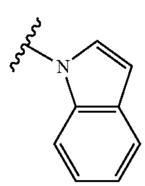 |
| 439 | 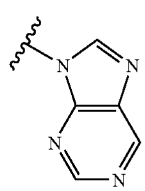 |
| 440 | 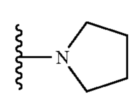 |
TABLE 2e-continued
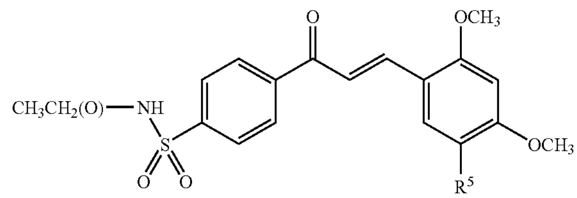
| Ex. No. | $R^5$ |
|---|---|
| 441 | 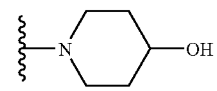 |
| 442 | 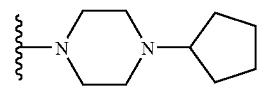 |
| 443 | 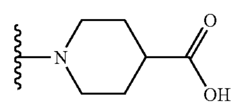 |
| 444 | 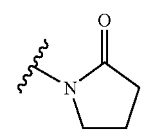 |
| 445 | 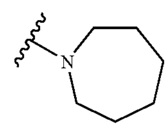 |
| 446 | 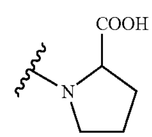 |
| 447 | 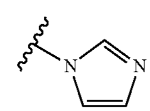 |
| 448 | 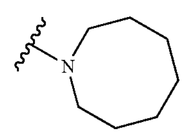 |
| 449 | 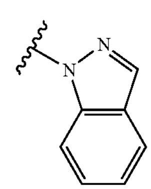 |
| 450 | 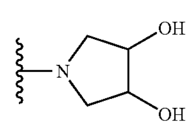 |

TABLE 2e-continued
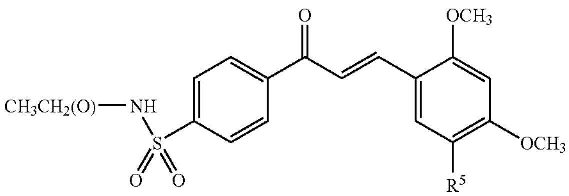
| Ex. No. | $R^5$ |
|---|---|
| 451 | 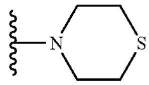 |
| 452 | 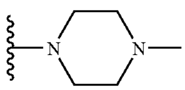 |
| 453 | 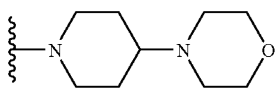 |
| 454 | 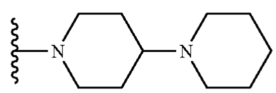 |
| 455 | 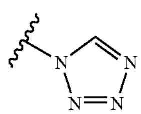 |
| 456 | 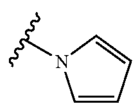 |
| 457 | 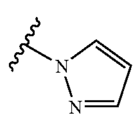 |
| 458 | 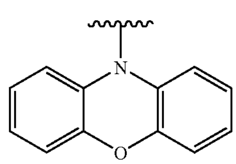 |
| 459 | 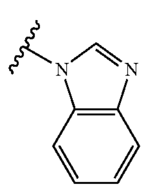 |
TABLE 2f
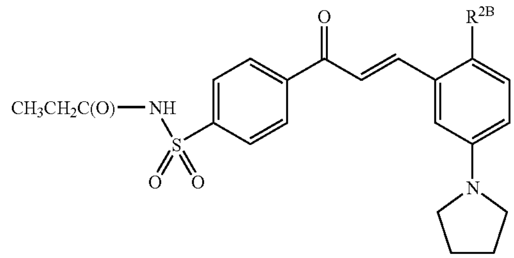
| Ex. No. | $R^{2B}$ |
|---|---|
| 460 | 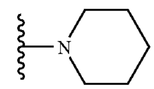 |
| 461 | 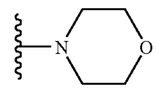 |
| 462 | 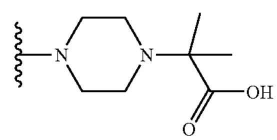 |
| 463 | 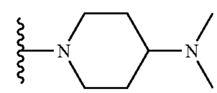 |
| 464 | 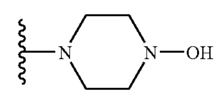 |
| 465 | 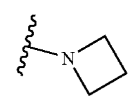 |
| 466 | 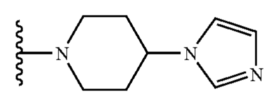 |
| 467 | 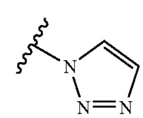 |
| 468 | 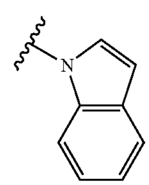 |
| 469 | 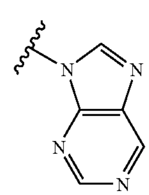 |

TABLE 2f-continued
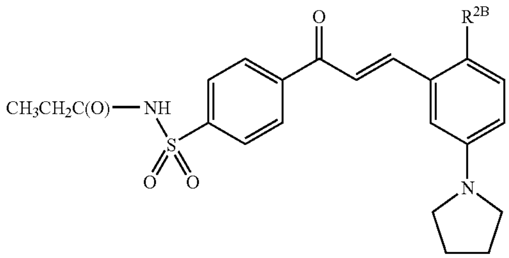
| Ex. No. | $R^{2B}$ |
|---|---|
| 470 | 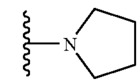 |
| 471 | 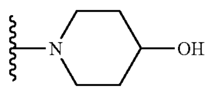 |
| 472 | 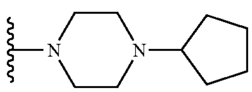 |
| 473 | 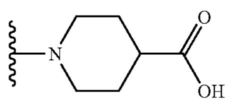 |
| 474 | 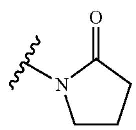 |
| 475 | 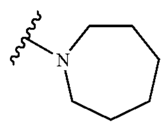 |
| 476 | 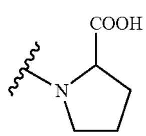 |
| 477 | 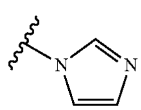 |
| 478 | 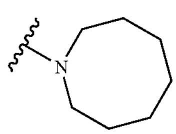 |
| 479 | 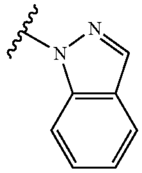 |
TABLE 2f-continued
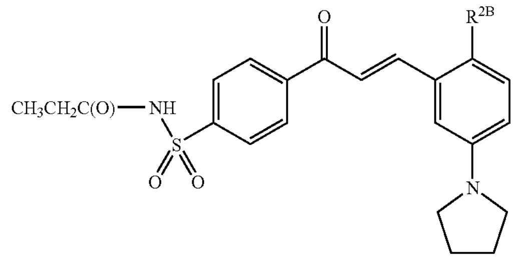
| Ex. No. | $R^{2B}$ |
|---|---|
| 480 | 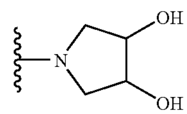 |
| 481 | 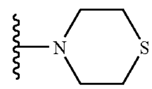 |
| 482 | 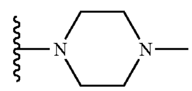 |
| 483 | 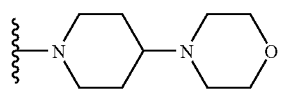 |
| 484 | 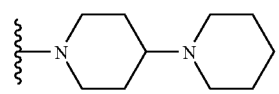 |
| 485 | 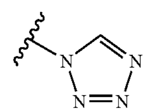 |
| 486 | 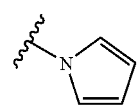 |
| 487 | 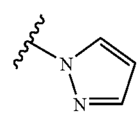 |
| 488 | 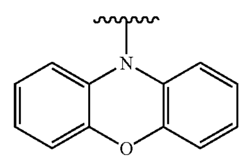 |
| 489 | 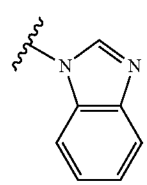 |

TABLE 2g
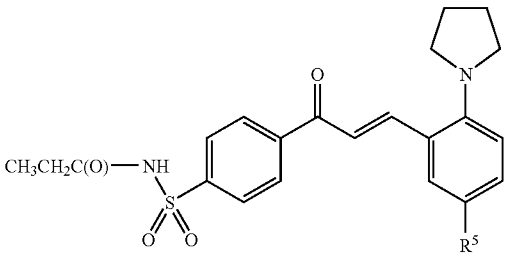
| Ex. No. | $R^5$ |
| --- | --- |
| 490 | 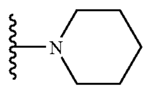 |
| 491 | 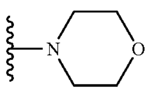 |
| 492 | 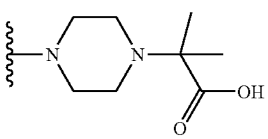 |
| 493 | 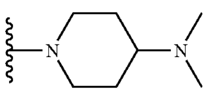 |
| 494 | 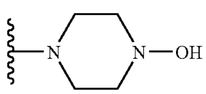 |
| 495 | 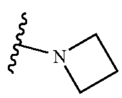 |
| 496 | 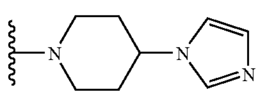 |
| 497 | 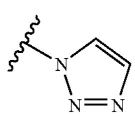 |
| 498 | 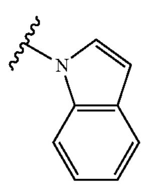 |
| 499 | 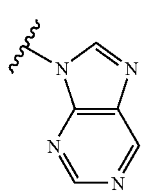 |
TABLE 2g-continued
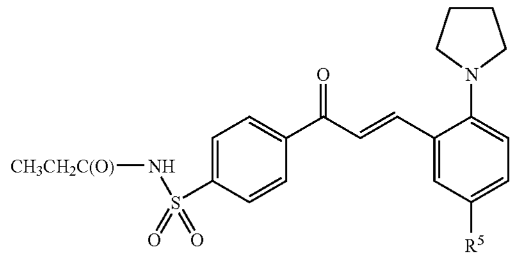
| Ex. No. | $R^5$ |
| --- | --- |
| 500 | 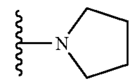 |
| 501 | 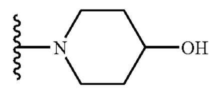 |
| 502 | 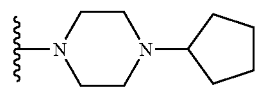 |
| 503 | 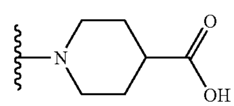 |
| 504 | 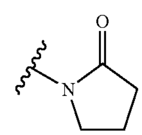 |
| 505 | 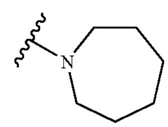 |
| 506 | 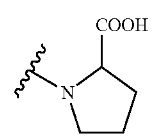 |
| 507 | 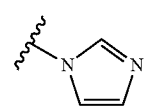 |
| 508 | 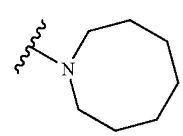 |
| 509 | 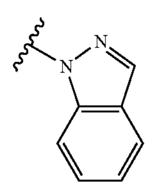 |

TABLE 2g-continued
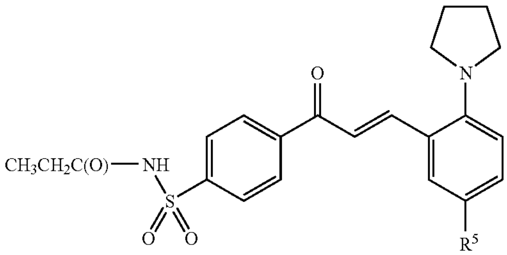
| Ex. No. | $R^5$ |
|---|---|
| 510 | 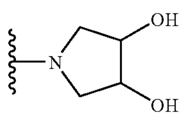 |
| 511 | 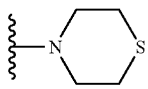 |
| 512 | 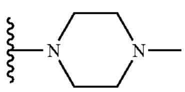 |
| 513 | 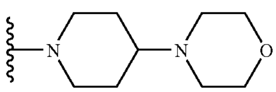 |
| 514 | 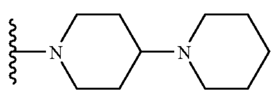 |
| 515 | 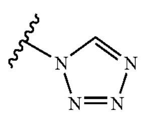 |
| 516 | 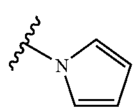 |
| 517 | 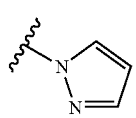 |
| 518 | 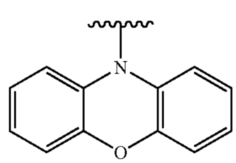 |
| 519 | 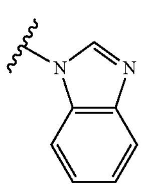 |
TABLE 3a
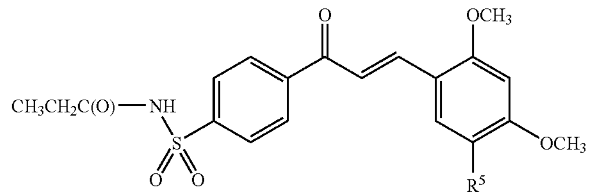
| Ex. No. | $R^5$ |
|---|---|
| 730 | 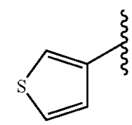 |
| 731 | 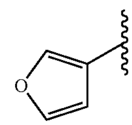 |
| 732 | 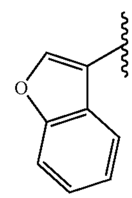 |
| 733 | 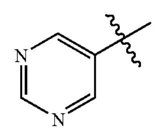 |
| 734 | 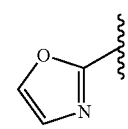 |
| 735 | 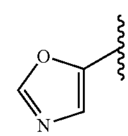 |
| 736 | 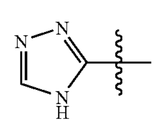 |
| 737 | 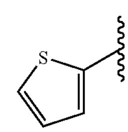 |
| 738 | 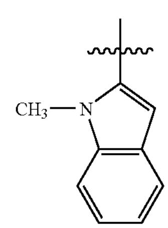 |

TABLE 3a-continued
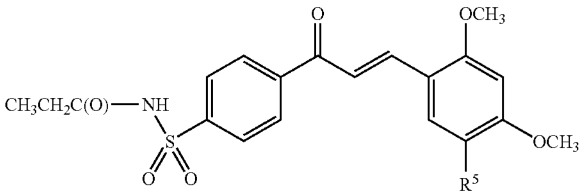
| Ex. No. | $R^5$ |
| --- | --- |
| 739 | 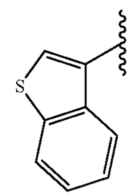 |
| 740 | 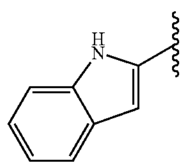 |
| 741 | 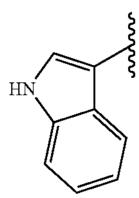 |
| 742 | 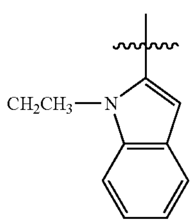 |
| 743 | 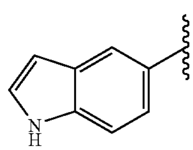 |
| 744 | 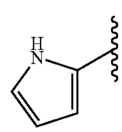 |
| 745 | 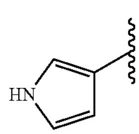 |
TABLE 3a-continued
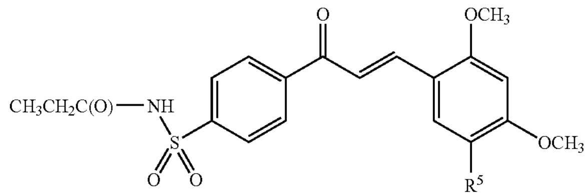
| Ex. No. | $R^5$ |
| --- | --- |
| 746 | 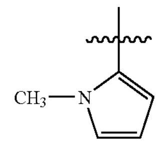 |
| 747 | 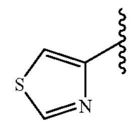 |
| 748 | 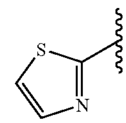 |
| 749 | 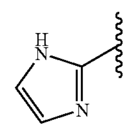 |
| 750 | 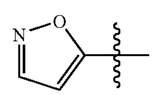 |
TABLE 3b
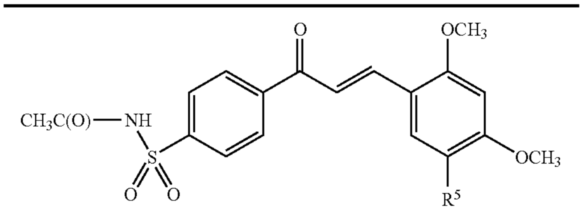
| Ex. No. | $R^5$ |
| --- | --- |
| 751 | 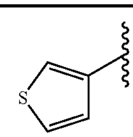 |
| 752 | 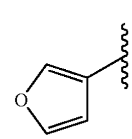 |

TABLE 3b-continued
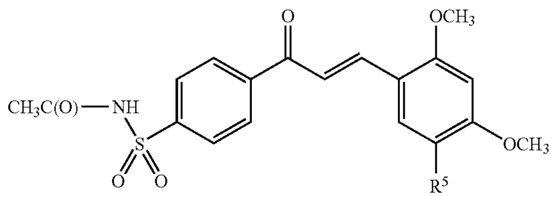
| Ex. No. | $R^5$ |
|---|---|
| 753 | 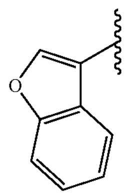 |
| 754 | 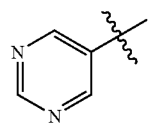 |
| 755 | 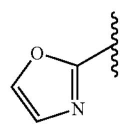 |
| 756 | 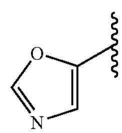 |
| 757 | 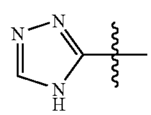 |
| 758 | 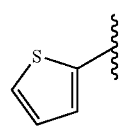 |
| 759 | 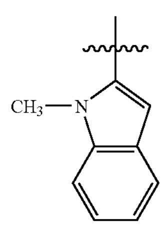 |
| 760 | 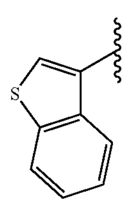 |
TABLE 3b-continued
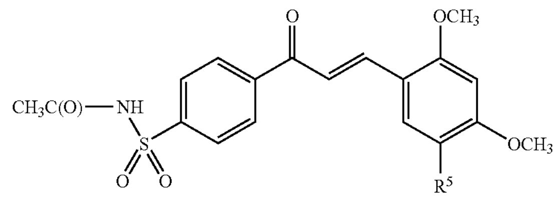
| Ex. No. | $R^5$ |
|---|---|
| 761 | 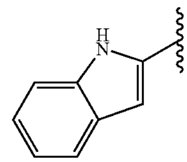 |
| 762 | 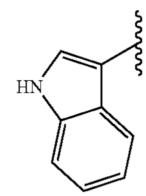 |
| 763 | 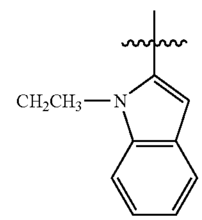 |
| 764 | 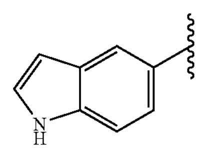 |
| 765 | 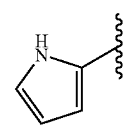 |
| 766 | 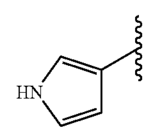 |
| 767 | 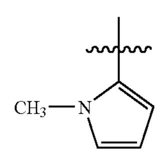 |
| 768 | 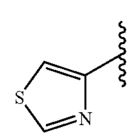 |

TABLE 3b-continued
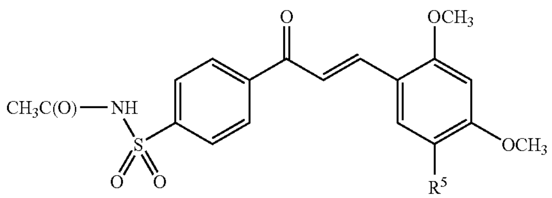
| Ex. No. | $R^5$ |
|---|---|
| 769 | 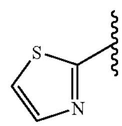 |
| 770 | 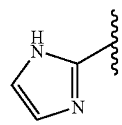 |
| 771 | 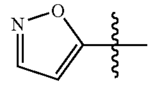 |
TABLE 3c
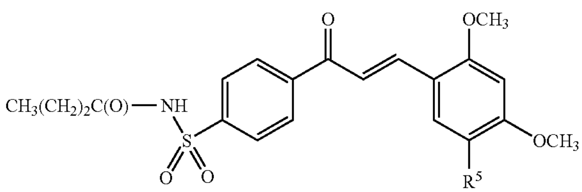
| Ex. No. | $R^5$ |
|---|---|
| 772 | 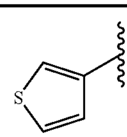 |
| 773 | 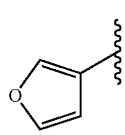 |
| 774 | 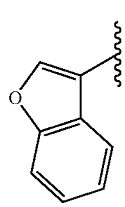 |
| 775 | 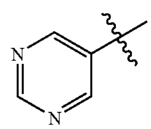 |
TABLE 3c-continued
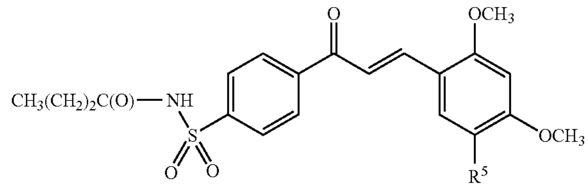
| Ex. No. | $R^5$ |
|---|---|
| 776 | 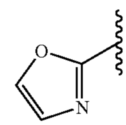 |
| 777 | 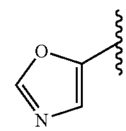 |
| 778 | 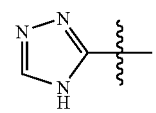 |
| 779 | 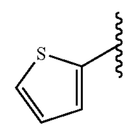 |
| 780 | 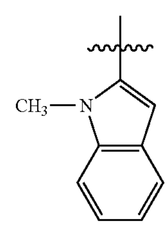 |
| 781 | 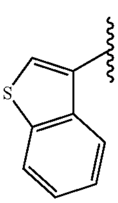 |
| 782 | 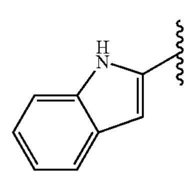 |
| 783 | 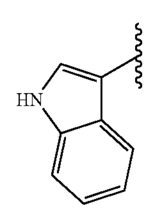 |

TABLE 3c-continued
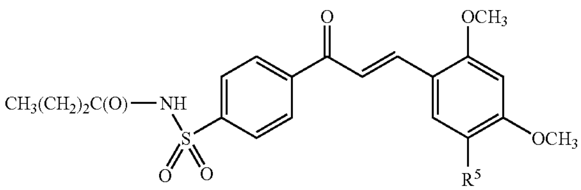
| Ex. No. | $R^5$ |
| --- | --- |
| 784 | 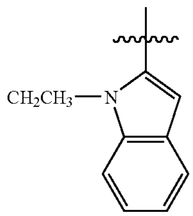 |
| 785 | 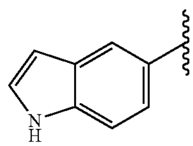 |
| 786 | 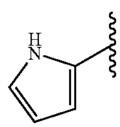 |
| 787 | 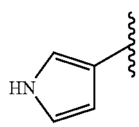 |
| 788 | 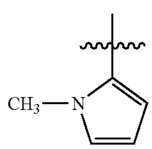 |
| 789 | 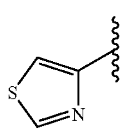 |
| 790 | 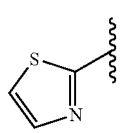 |
| 791 | 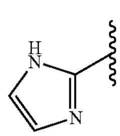 |
| 792 | 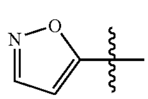 |
TABLE 3d
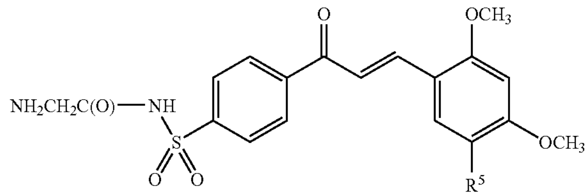
| Ex. No. | $R^5$ |
| --- | --- |
| 793 | 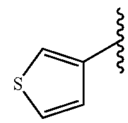 |
| 794 | 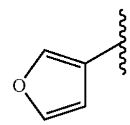 |
| 795 | 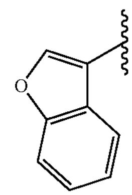 |
| 796 | 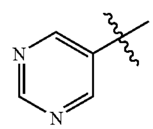 |
| 797 | 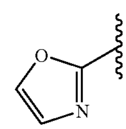 |
| 798 | 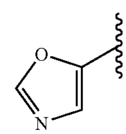 |
| 799 | 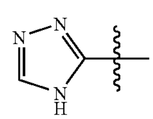 |
| 800 | 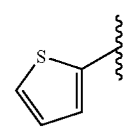 |
| 801 | 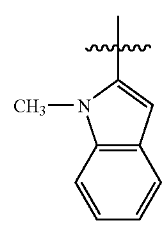 |

TABLE 3d-continued
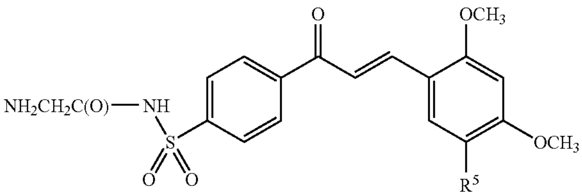
| Ex. No. | $R^5$ |
|---|---|
| 802 | 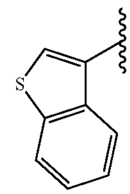 |
| 803 | 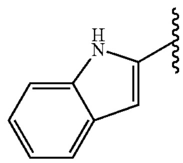 |
| 804 | 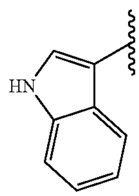 |
| 805 | 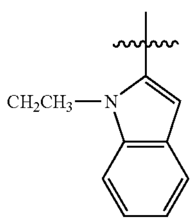 |
| 806 | 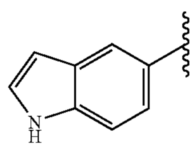 |
| 807 | 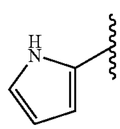 |
| 808 | 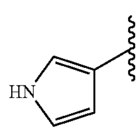 |
| 809 | 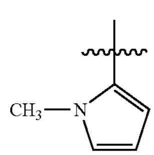 |
TABLE 3d-continued
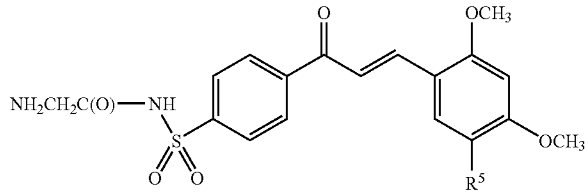
| Ex. No. | $R^5$ |
|---|---|
| 810 | 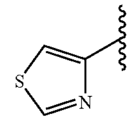 |
| 811 | 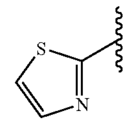 |
| 812 | 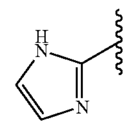 |
| 813 | 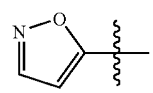 |
TABLE 3e
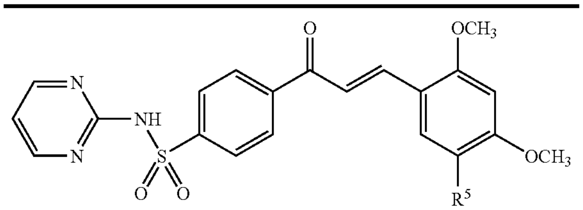
| Ex. No. | $R^5$ |
|---|---|
| 814 | 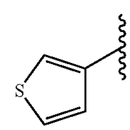 |
| 815 | 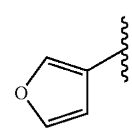 |
| 816 | 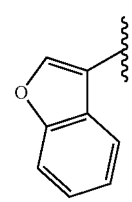 |

TABLE 3e-continued
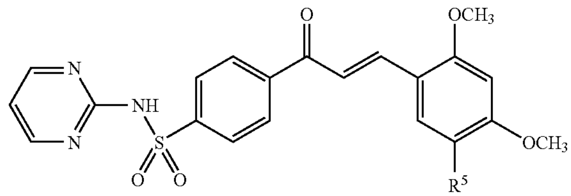
| Ex. No. | $R^5$ |
|---|---|
| 817 | 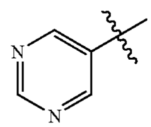 |
| 818 | 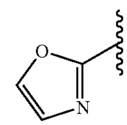 |
| 819 | 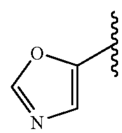 |
| 820 | 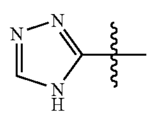 |
| 821 | 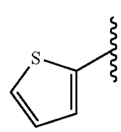 |
| 822 | 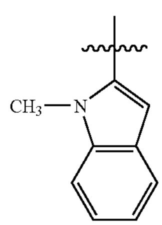 |
| 823 | 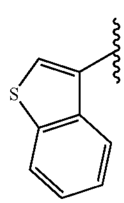 |
| 824 | 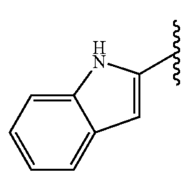 |
TABLE 3e-continued
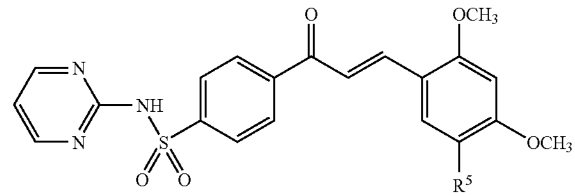
| Ex. No. | $R^5$ |
|---|---|
| 825 | 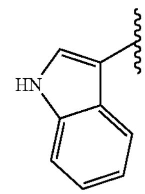 |
| 826 | 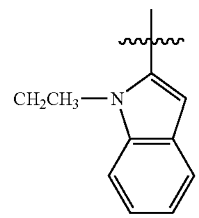 |
| 827 | 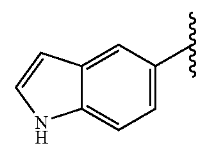 |
| 828 | 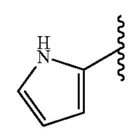 |
| 829 | 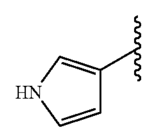 |
| 830 | 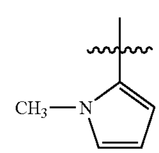 |
| 831 | 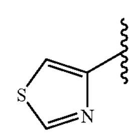 |
| 832 | 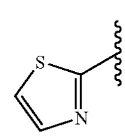 |

TABLE 3e-continued
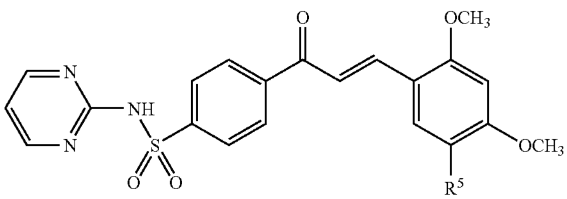
| Ex. No. | $R^5$ |
| --- | --- |
| 833 | 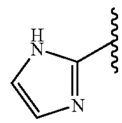 |
| 834 | 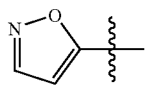 |
TABLE 3f
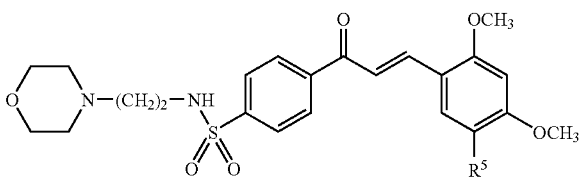
| Ex. No. | $R^5$ |
| --- | --- |
| 835 | 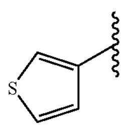 |
| 836 | 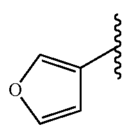 |
| 837 | 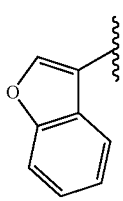 |
| 838 | 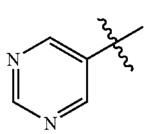 |
| 839 | 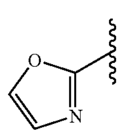 |
TABLE 3f-continued
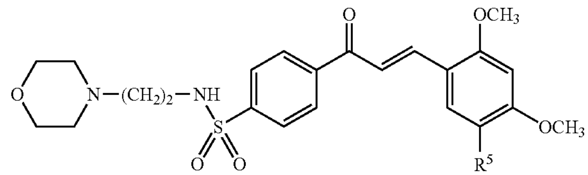
| Ex. No. | $R^5$ |
| --- | --- |
| 840 | 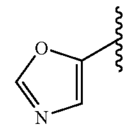 |
| 841 | 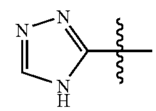 |
| 842 | 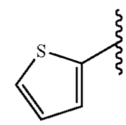 |
| 843 | 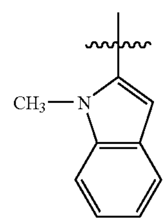 |
| 844 | 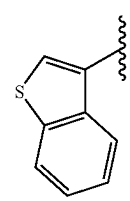 |
| 845 | 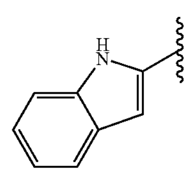 |
| 846 | 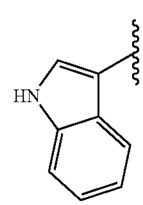 |

TABLE 3f-continued
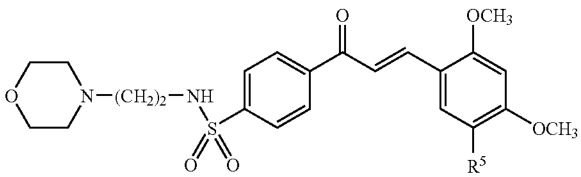
| Ex. No. | $R^5$ |
|---|---|
| 847 | 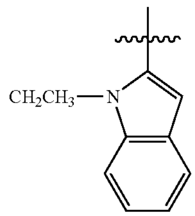 |
| 848 | 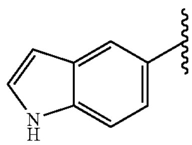 |
| 849 | 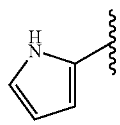 |
| 850 | 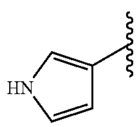 |
| 851 | 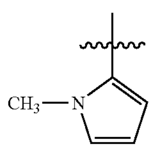 |
| 852 | 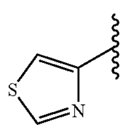 |
| 853 | 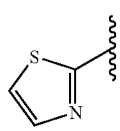 |
| 854 | 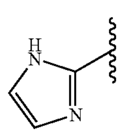 |
| 855 | 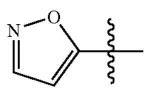 |
TABLE 3g
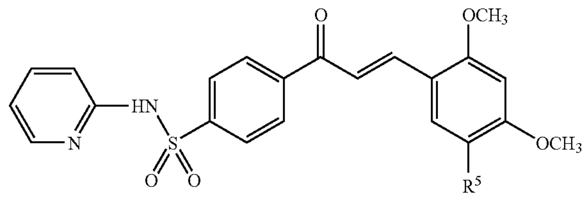
| Ex. No. | $R^5$ |
|---|---|
| 856 | 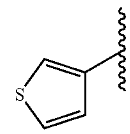 |
| 857 | 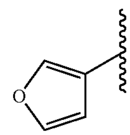 |
| 858 | 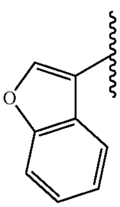 |
| 859 | 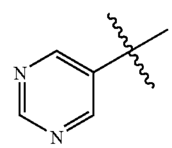 |
| 860 | 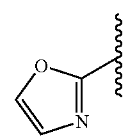 |
| 861 | 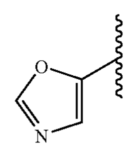 |
| 862 | 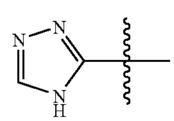 |
| 863 | 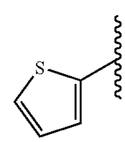 |

TABLE 3g-continued
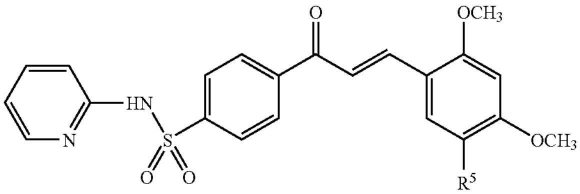
| Ex. No. | $R^5$ |
|---|---|
| 864 | 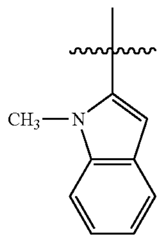 |
| 865 | 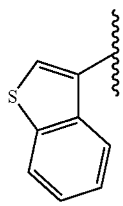 |
| 866 | 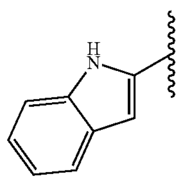 |
| 867 | 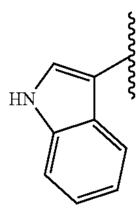 |
| 868 | 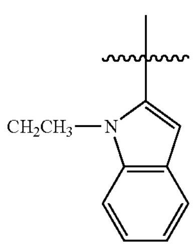 |
| 869 | 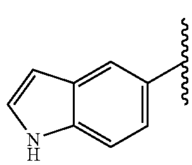 |
TABLE 3g-continued
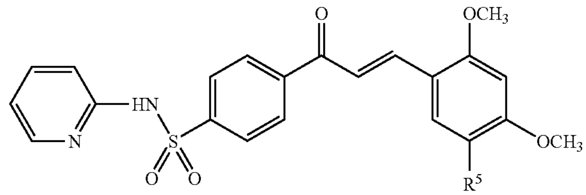
| Ex. No. | $R^5$ |
|---|---|
| 870 | 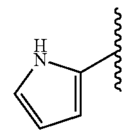 |
| 871 | 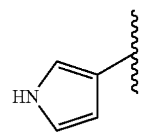 |
| 872 | 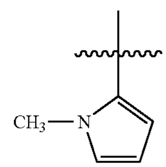 |
| 873 | 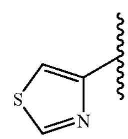 |
| 874 | 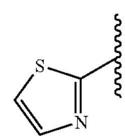 |
| 875 | 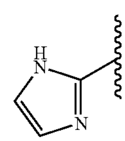 |
| 876 | 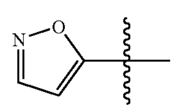 |

TABLE 3h
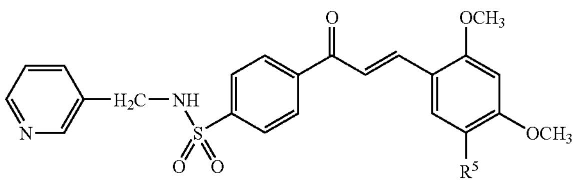
| Ex. No. | $R^5$ |
|---|---|
| 877 | 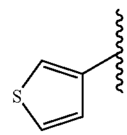 |
| 878 | 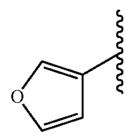 |
| 879 | 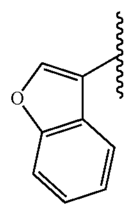 |
| 880 | 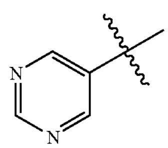 |
| 881 | 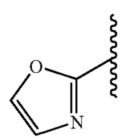 |
| 882 | 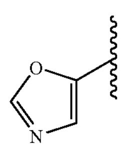 |
| 883 | 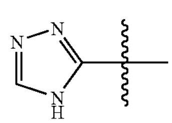 |
| 884 | 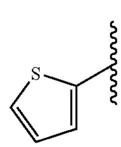 |
TABLE 3h-continued
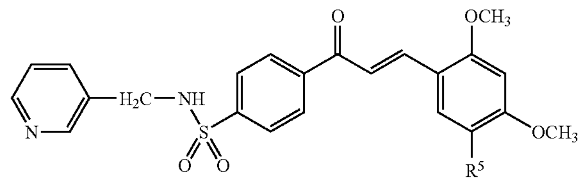
| Ex. No. | $R^5$ |
|---|---|
| 885 | 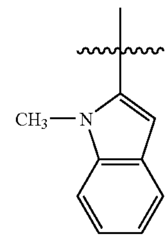 |
| 886 | 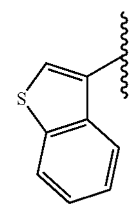 |
| 887 | 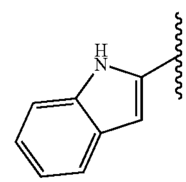 |
| 888 | 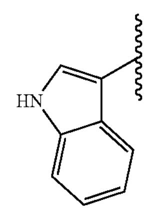 |
| 889 | 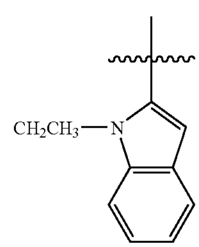 |
| 890 | 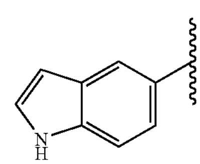 |
| 891 | 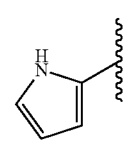 |

TABLE 3h-continued
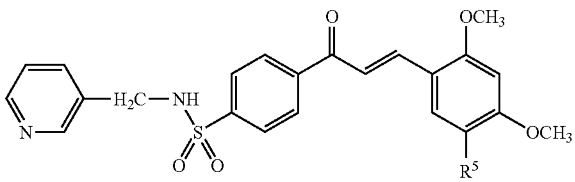
| Ex. No. | $R^5$ |
|---|---|
| 892 | 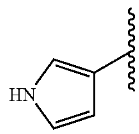 |
| 893 | 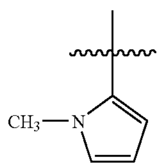 |
| 894 | 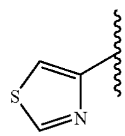 |
| 895 | 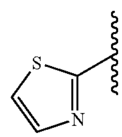 |
| 896 | 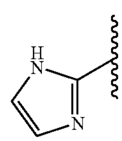 |
| 897 | 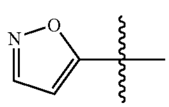 |
TABLE 3i
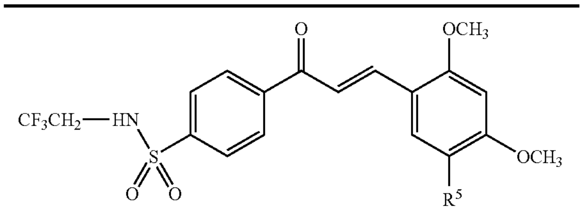
| Ex. No. | $R^5$ |
|---|---|
| 898 | 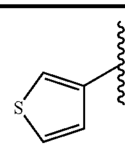 |
TABLE 3i-continued
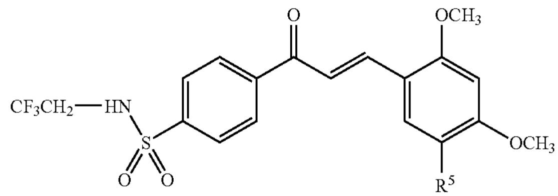
| Ex. No. | $R^5$ |
|---|---|
| 899 | 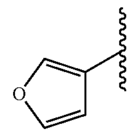 |
| 900 | 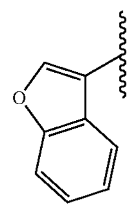 |
| 901 | 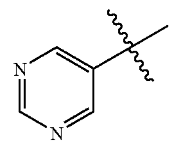 |
| 902 | 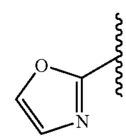 |
| 903 | 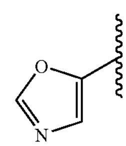 |
| 904 | 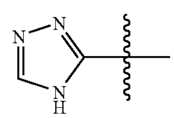 |
| 905 | 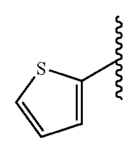 |
| 906 | 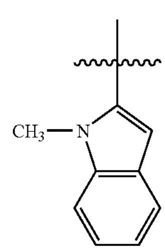 |

TABLE 3i-continued

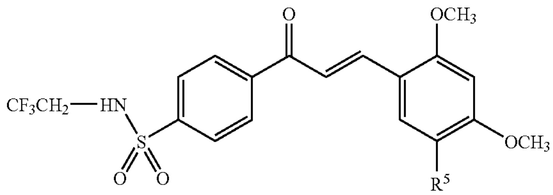

| Ex. No. | $R^5$ |
|---|---|
| 907 | 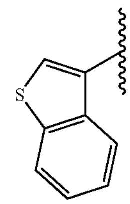 |
| 908 | 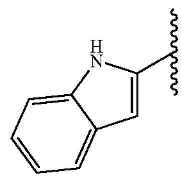 |
| 909 | 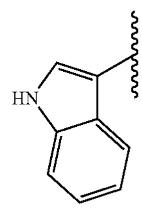 |
| 910 | 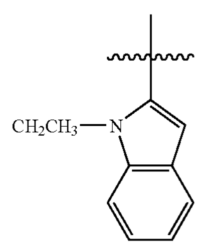 |
| 911 | 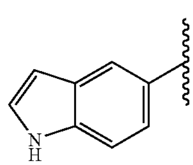 |
| 912 | 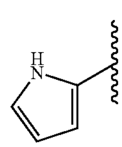 |
| 913 | 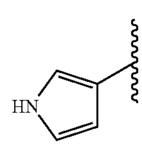 |

TABLE 3i-continued

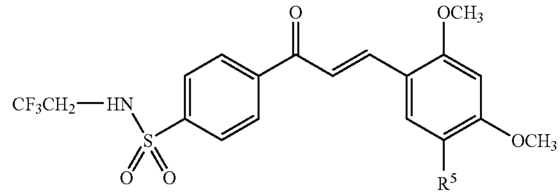

| Ex. No. | $R^5$ |
|---|---|
| 914 | 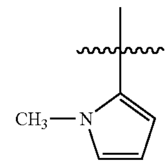 |
| 915 | 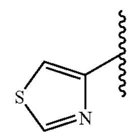 |
| 916 | 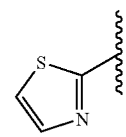 |
| 917 | 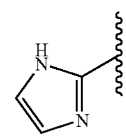 |
| 918 | 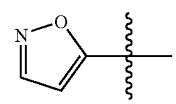 |

Stereoisomerism and Polymorphism

It is appreciated that compounds of the present invention having a chiral center may exist in and be isolated in optically active and racemic forms. Some compounds may exhibit polymorphism. It is to be understood that the present invention encompasses any racemic, optically-active, diastereomeric, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase).

Examples of methods to obtain optically active materials are known in the art, and include at least the following.

i) physical separation of crystals—a technique whereby macroscopic crystals of the individual enantiomers are manually separated. This technique can be used if crystals of the separate enantiomers exist, i.e., the material is a conglomerate, and the crystals are visually distinct;

ii) simultaneous crystallization—a technique whereby the individual enantiomers are separately crystallized from a solution of the racemate, possible only if the latter is a conglomerate in the solid state;

iii) enzymatic resolutions—a technique whereby partial or complete separation of a racemate by virtue of differing rates of reaction for the enantiomers with an enzyme;

iv) enzymatic asymmetric synthesis—a synthetic technique whereby at least one step of the synthesis uses an enzymatic reaction to obtain an enantiomerically pure or enriched synthetic precursor of the desired enantiomer;

v) chemical asymmetric synthesis—a synthetic technique whereby the desired enantiomer is synthesized from an achiral precursor under conditions that produce asymmetry (i.e., chirality) in the product, which may be achieved using chiral catalysts or chiral auxiliaries;

vi) diastereomer separations—a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations—a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors—a synthetic technique whereby the desired enantiomer is obtained from non-chiral starting materials and where the stereochemical integrity is not or is only minimally compromised over the course of the synthesis;

x) chiral liquid chromatography—a technique whereby the enantiomers of a racemate are separated in a liquid mobile phase by virtue of their differing interactions with a stationary phase. The stationary phase can be made of chiral material or the mobile phase can contain an additional chiral material to provoke the differing interactions;

xi) chiral gas chromatography—a technique whereby the racemate is volatilized and enantiomers are separated by virtue of their differing interactions in the gaseous mobile phase with a column containing a fixed non-racemic chiral adsorbent phase;

xii) extraction with chiral solvents—a technique whereby the enantiomers are separated by virtue of preferential dissolution of one enantiomer into a particular chiral solvent;

xiii) transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one enantiomer of the racemate to pass through.

Pharmaceutically Acceptable Salt Formulations

In cases where compounds are sufficiently basic or acidic to form stable nontoxic acid or base salts, administration of the compound as a pharmaceutically acceptable salt may be appropriate. The term "pharmaceutically acceptable salts" or "complexes" refers to salts or complexes that retain the desired biological activity of the compounds of the present invention and exhibit minimal undesired toxicological effects.

Examples of pharmaceutically acceptable salts are organic acid addition salts formed with acids, which form a physiological acceptable anion, for example, tosylate, methanesulfonate, acetate, citrate, malonate, tartarate, succinate, benzoate, ascorbate, α-ketoglutarate and α-glycerophosphate. Suitable inorganic salts may also be formed, including, sulfate, nitrate, bicarbonate and carbonate salts. Alternatively, the pharmaceutically acceptable salts may be made with sufficiently basic compounds such as an amine with a suitable acid affording a physiologically acceptable anion. Alkali metal (for example, sodium, potassium or lithium) or alkaline earth metal (for example calcium) salts of carboxylic acids can also be; made.

Nonlimiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalcturonic acid; (b) base addition salts formed with metal cations such as zinc, calcium, bismuth, barium, magnesium, aluminum, copper, cobalt, nickel, cadmium, sodium, potassium, and the like, or with a cation formed from ammonia, N,N-dibenzylethylenediamine, D-glucosamine, tetraethylammonium, or ethylenediamine; or (c) combinations of (a) and (b); e.g., a zinc tannate salt or the like. Also included in this definition are pharmaceutically acceptable quaternary salts known by those skilled in the art, which specifically include the quaternary ammonium salt of the formula $—NR^+A^-$, wherein R is as defined above and A is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate).

Particular FDA-approved salts can be conveniently divided between anions and cations (Approved Drug Products with Therapeutic Equivalence Evaluations (1994) U.S. Department of Health and Human Services, Public Health Service, FDA, Center for Drug Evaluation and Research, Rockville, Md; L. D. Bighley, S. M. Berge and D. C. Monkhouse, Salt Forms of Drugs and Absorption, *Encyclopedia of Pharmaceutical Technology,* Vol. 13, J. Swarbridk and J. Boylan, eds., Marcel Dekker, NY (1996)). Among the approved anions include aceglumate, acephyllinate, acetamidobenzoate, acetate, acetylasparaginate, acetylaspartate, adipate, aminosalicylate, anhydromethylenecitrate, ascorbate, aspartate, benzoate, besylate, bicarbonate, bisulfate, bitartrate, borate, bromide, camphorate, camsylate, carbonate, chloride, chlorophenoxyacetate, citrate,closylate, cromesilate, cyclamate, dehydrocholate, dihydrochloride, dimalonate, edentate, edisylate, estolate, esylate, ethylbromide, ethylsulfate, fendizoate, fosfatex, fumarate, gluceptate, gluconate, glucuronate, glutamate, glycerophosphate, glysinate, glycollylarsinilate, glycyrrhizate, hippurate, hemisulfate, hexylresorcinate, hybenzate, hydrobromide, hydrochloride, hydroiodid, hydroxybenzenesulfonate, hydroxybenzoate, hydroxynaphthoate, hyclate, iodide, isethionate, lactate, lactobionate, lysine, malate, maleate, mesylate, methylbromide, methyliodide, methylnitrate, methylsulfate, monophosadenine, mucate, napadisylate, napsylate, nicotinate, nitrate, oleate, orotate, oxalate, oxoglurate, pamoate, pantothenate, pectinate, phenylethylbarbiturate, phosphate, pacrate, plicrilix, polistirex, polygalacturonate, propionate, pyridoxylphosphate, saccharinate, salicylate, stearate, succinate, stearylsulfate, subacetate, succinate, sulfate, sulfosalicylate, tannate, tartrate, teprosilate, terephthalate, teoclate, thiocyante, tidiacicate, timonacicate, tosylate, triethiodide, triethiodide, undecanoate, and xinafoate. The approved cations include ammonium, benethamine, benzathine, betaine, calcium, camitine, clemizole, chlorcyclizine, choline, dibenylamine, diethanolamine, diethylamine, diethylammonium diolamine, eglumine, erbumine, ethylenediamine, heptaminol, hydrabamine, hydroxyethylpyrrolidone, imadazole, meglumine, olamine, piperazine, 4-phenylcyclohexylamine, procaine, pyridoxine, triethanolamine, and tromethamine. Metallic cations include, aluminum, bismuth, calcium lithium, magnesium, neodymium, potassium, rubidium, sodium, strontium and zinc.

A particular class of salts can be classified as organic amine salts. The organic amines used to form these salts can be primary amines, secondary amines or tertiary amines, and the substituents on the amine can be straight, branched or cyclic groups, including ringed structures formed by attachment of two or more of the amine substituents. Of particular interest are organic amines that are substituted by one or more hydroxyalkyl groups, including alditol or carbohydrate moieties. These hydroxy substituted organic amines can be cyclic or acyclic, both classes of which can be primary amines, secondary amines or tertiary amines. A common class of cyclic hydroxy substituted amines are the amino sugars.

A particular class of acyclic organic amines are represented by the formula

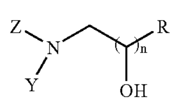

wherein Y and Z are independently hydrogen or lower alkyl or, may be taken together to form a ring, R is hydrogen, alkyl or hydroxyloweralkyl, and n is 1, 2, 3, 4, or 5. Among these hydroxyl amines are a particular class characterized when n is 4. A representative of this group is meglumine, represented when Y is hydrogen, Z is methyl and R is methoxy. Meglumine is also known in the art as N-methylglucamine, N-MG, and 1-deoxy-1-(methylamino)-D-glucitol.

The invention also includes pharmaceutically acceptable prodrugs of the compounds. Pharmaceutically acceptable prodrugs refer to a compound that is metabolized, for example hydrolyzed or oxidized, in the host to form the compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound.

Any of the compounds described herein can be administered as a prodrug to increase the activity, bioavailability, stability or otherwise alter the properties of the compound. A number of prodrug ligands are known. In general, alkylation, acylation or other lipophilic modification of the compound will increase the stability of the chalcone. Examples of substituent groups that can replace one or more hydrogens on the compound are alkyl, aryl, steroids, carbohydrates, including sugars, 1,2-diacylglycerol and alcohols. Many are described in R. Jones and N. Bischofberger, *Antiviral Research,* 27 (1995) 1–17. Any of these can be used in combination with the disclosed compounds to achieve a desired effect.

The compounds of the present invention can be used to treat any disorder that is mediated by VCAM-1. Inflammatory disorders that are mediated by VCAM-1 include, but are not limited to arthritis, asthma, dermatitis, psoriasis, cystic fibrosis, post transplantation late and chronic solid organ rejection, multiple sclerosis, systemic lupus erythematosis, inflammatory bowel diseases, autoimmune diabetes, diabetic retinopathy, diabetic nephropathy, diabetic vasculopathy, ocular inflammation, uveitis, rhinitis, ischemia-reperfusion injury, post-angioplasty restenosis, chronic obstructive pulmonary disease (COPD), glomerulonephritis, Graves disease, gastrointestinal allergies, conjunctivitis, atherosclerosis, coronary artery disease, angina and small artery disease.

The compounds disclosed herein can be used in the treatment of inflammatory skin diseases that are mediated by VCAM-1, and in particular, human endothelial disorders that are mediated by VCAM-1, which include, but are not limited to, psoriasis, dermatitis, including eczematous dermatitis, and Kaposi's sarcoma, as well as proliferative disorders of smooth muscle cells.

In yet another embodiment, the compounds disclosed herein can be selected to treat anti-inflammatory conditions that are mediated by mononuclear leucocytes.

In yet another embodiment, the compounds of the present invention can be selected for the prevention or treatment of tissue or organ transplant rejection. Treatment and prevention of organ or tissue transplant rejection includes, but are not limited to treatment of recipients of heart, lung, combined heart-lung, liver, kidney, pancreatic, skin, spleen, small bowel, or corneal transplants. They are also indicated for the prevention or treatment of graft-versus-host disease, which sometimes occurs following bone marrow transplantation.

In an alternative embodiment, the compounds described herein are useful in both the primary and adjunctive medical treatment of cardiovascular disease. The compounds are used in primary treatment of, for example, coronary disease states including atherosclerosis, post-angioplasty restenosis, coronary artery diseases and angina. The compounds can be administered to treat small vessel disease that is not treatable by surgery or angioplasty, or other vessel disease in which surgery is not an option. The compounds can also be used to stabilize patients prior to revascularization therapy.

In another aspect the invention the compounds can be used in compositions including pharmaceutical compositions for the treatment of diseases or disorders mediated by VCAM-1 wherein such compositions comprise a VCAM-1 inhibiting amount of a compound of the invention or a pharmaceutically acceptable salt thereof and/or a pharmaceutically acceptable carrier.

Another aspect of the invention provides a method for treating a disease or disorder mediated by VCAM-1 comprising administering to a patient a VCAM-1 inhibiting effective amount of a compound of the invention or a pharmaceutically acceptable salt thereof.

In another aspect the invention provides a method for treating cardiovascular and inflammatory disorders in a patient in need thereof comprising administering to said patient an VCAM-1 inhibiting effective amount of a compound of the invention or a pharmaceutically. acceptable salt thereof.

In another aspect the invention provides a method and composition for treating asthma or arthritis in a patient in need thereof comprising administering to said patient an effective amount of a compound of the invention or a pharmaceutically acceptable salt thereof.

Nonlimiting examples of arthritis include rheumatoid (such as soft-tissue rheumatism and non-articular rheumatism, fibromyalgia, fibrositis, muscular rheumatism, myofascil pain, humeral epicondylitis, frozen shoulder, Tietze's syndrome, fascitis, tendinitis, tenosynovitis, bursitis), juvenile chronic, spondyloarthropaties (ankylosing spondylitis), osteoarthritis, hyperuricemia and arthritis associated with acute gout, chronic gout and systemic lupus erythematosus.

Human endothelial disorders mediated by VCAM-1 include psoriasis, eczematous dermatitis, Kaposi's sarcoma, as well as proliferative disorders of smooth muscle cells.

In yet another embodiment, the compounds disclosed herein can be selected to treat anti-inflammatory conditions that are mediated by mononuclear leucocytes.

In one embodiment, the compounds of the present invention are selected for the prevention or treatment of tissue or organ transplant rejection. Treatment and prevention of organ or tissue transplant rejection includes, but are not limited to treatment of recipients of heart, lung, combined heart-lung, liver, kidney, pancreatic, skin, spleen, small bowel, or corneal transplants. The compounds can also be used in the prevention or treatment of graft-versus-host disease, such as sometimes occurs following bone marrow transplantation.

In an alternative embodiment, the compounds described herein are useful in both the primary and adjunctive medical treatment of cardiovascular disease. The compounds are used in primary treatment of, for example, coronary disease states including atherosclerosis, post-angioplasty restenosis, coronary artery diseases and angina. The compounds can be administered to treat small vessel disease that is not treatable by surgery or angioplasty, or other vessel disease in which surgery is not an option. The compounds can also be used to stabilize patients prior to revascularization therapy.

In addition to inhibiting the expression of VCAM-1, some of the compounds of the invention have the additional properties of inhibiting monocyte chemoattractant protein-1 (MCP-1) and/or smooth muscle proliferation. MCP-1 is a chemoattractant protein produced by endothelial cells, smooth muscle cells as well as macrophages. MCP-1 promotes integrin activation on endothelial cells thereby facilitating adhesion of leukocytes to VCAM-1, and MCP-1 is a chemoattractant for monocytes. MCP-1 has been shown to play a role in leukocyte recruitment in a number of chronic inflammatory diseases including atherosclerosis, rheumatoid arthritis, and asthma. Its expression is upregulated in these diseases and as such inhibition of MCP-1 expression represents a desirable property of anti-inflammatory therapeutics. Furthermore, smooth muscle cell hyperplasia and resulting tissue remodeling and decreased organ function is yet another characteristic of many chronic inflammatory diseases including atherosclerosis, chronic transplant rejection and asthma. Inhibition of the hyperproliferation of smooth muscle cells is another desirable property for therapeutic compounds.

Combination and Alternation Therapy

Any of the compounds disclosed herein can be administered in combination or alternation with a second biologically active agent to increase its effectiveness against the target disorder.

In combination therapy, effective dosages of two or more agents are administered together, whereas during alternation therapy an effective dosage of each agent is administered serially. The dosages will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

The efficacy of a drug can be prolonged, augmented, or restored by administering the compound in combination or alternation with a second, and perhaps third, agent that induces a different biological pathway from that caused by the principle drug. Alternatively, the pharmacokinetics, biodistribution or other parameter of the drug can be altered by such combination or alternation therapy. In general, combination therapy is typically preferred over alternation therapy because it induces multiple simultaneous stresses on the condition.

Any method of alternation can be used that provides treatment to the patient. Nonlimiting examples of alternation patterns include 1–6 weeks of administration of an effective amount of one agent followed by 1–6 weeks of administration of an effective amount of a second agent. The alternation schedule can include periods of no treatment. Combination therapy generally includes the simultaneous administration of an effective ratio of dosages of two or more active agents.

Illustrative examples of specific agents that can be used in combination or alternation with the compounds of the present invention are described below in regard to asthma and arthritis. The agents set out below or others can alternatively be used to treat a host suffering from any of the other disorders listed above or that are mediated by VCAM-1 or MCP-1. Illustrative second biologically active agents for the treatment of cardiovascular disease are also provided below.

Asthma

In one embodiment, the compounds of the present invention are administered in combination or alternation with heparin, frusemide, ranitidine, an agent that effects respiratory function, such as DNAase, or immunosuppressive agents, IV gamma globulin, troleandomycin, cyclosporin (Neoral), methotrexate, FK-506, gold compounds such as Myochrysine (gold sodium thiomalate), platelet activating factor (PAF) antagonists such as thromboxane inhibitors, leukotriene-$D_4$-receptor antagonists such as Accolate (zafirlukast), Ziflo (zileuton), leukotriene $C_1$ or $C_2$ antagonists and inhibitors of leukotriene synthesis such as zileuton for the treatment of asthma, or an inducible nitric oxide synthase inhibitor.

In another embodiment, the active compound is administered in combination or alternation with one or more other prophylactic agent(s). Examples of prophylactic agents that can be used in alternation or combination therapy include but are not limited to sodium cromoglycate, Intal (cromolyn sodium, Nasalcrom, Opticrom, Crolom, Ophthalmic Crolom), Tilade (nedocromil, nedocromil sodium) and ketotifen.

In another embodiment, the active compound is administered in combination or alternation with one or more other $\beta_2$-adrenergic agonist(s) (β agonists). Examples of β2-adrenergic agonists (β agonists) that can be used in alternation or combination therapy include but are not limited to albuterol (salbutamol, Proventil, Ventolin), terbutaline, Maxair (pirbuterol), Serevent (salmeterol), epinephrine, metaproterenol (Alupent, Metaprel), Brethine (Bricanyl, Brethaire, terbutaline sulfate), Tornalate (bitolterol), isoprenaline, ipratropium bromide, bambuterol hydrochloride, bitolterol meslyate, broxaterol, carbuterol hydrochloride, clenbuterol hydrochloride, clorprenaline hydrochloride, efirmoterol fumarate, ephedra (source of alkaloids), ephedrine (ephedrine hydrochloride, ephedrine sulfate), etafedrine hydrochloride, ethylnoradrenaline hydrochloride, fenoterol hydrochloride, hexoprenaline hydrochloride, isoetharine hydrochloride, isoprenaline, mabuterol, methoxyphenamine hydrochloride, methylephedrine hydrochloride, orciprenaline sulphate, phenylephrine acid tartrate, phenylpropanolamine (phenylpropanolamine polistirex, phenylpropanolamine sulphate), pirbuterol acetate, procaterol hydrochloride, protokylol hydrochloride, psuedoephedrine (psuedoephedrine polixtirex, psuedoephedrine tannate, psuedoephedrine hydrochloride, psuedoephedrine sulphate), reproterol hydrochloride, rimiterol hydrobromide, ritodrine hydrochloride, salmeterol xinafoate, terbutaline sulphate, tretoquinol hydrate and tulobuterol hydrochloride.

In another embodiment, the active compound is administered in combination or alternation with one or more other corticosteriod(s). Examples of corticosteriods that can be used in alternation or combination therapy include but are not limited to glucocorticoids (GC), Aerobid (Aerobid-M, flunisolide), Azmacort (triamcinolone acetonide), Beclovet (Vanceril, beclomethasone dipropionate), Flovent (fluticasone), Pulmicort (budesonide), prednisolone, hydrocortisone, adrenaline, Alclometasone Dipropionate, Aldosterone, Amcinonide, Beclomethasone Dipropionate, Bendacort, Betamethasone (Betamethasone Acetate, Betamethasone Benzoate, Betamethasone Dipropionate, Betamethasone Sodium Phosphate, Betamethasone Valerate), Budesonide, Ciclomethasone, Ciprocinonide, Clobetasol Propionate, Clobetasone Butyrate, Clocortolone Pivalate, Cloprednol, Cortisone Acetate, Cortivazol, Deflazacort, Deoxycortone Acetate (Deoxycortone Pivalate), Deprodone, Desonide, Desoxymethasone, Dexamethasone (Dexamethasone Acetate, Dexamethasone Isonicotinate, Dexamethasone Phosphate, Dexamethasone Sodium Metasulphobenzoate, Dexamethasone Sodium Phosphate), Dichlorisone Acetate, Diflorasone Diacetate, Diflucortolone Valerate, Difluprednate, Domoprednate, Endrysone, Fluazacort, Fluclorolone Acetonide, Fludrocortisone Acetate, Flumethasone (Flumethasone Pivalate), Flunisolide, Fluocinolone Acetonide, Fluocinonide, Fluocortin Butyl, Fluocortolone (Fluocortolone Hexanoate, Fluocortolone Pivalate), Fluorometholone (Fluorometholone Acetate), Fluprednidene Acetate, Fluprednisolone, Flurandrenolone, Fluticasone Propionate, Formocortal, Halcinonide, Halobetasol Propionate, Halometasone, Hydrocortamate Hydrochloride, Hydrocortisone (Hydrocortisone Acetate, Hydrocortisone Butyrate, Hydrocortisone Cypionate, Hydrocortisone Hemisuccinate, Hydrocortisone Sodium Phosphate, Hydrocortisone Sodium Succinate, Hydrocortisone Valerate), Medrysone, Meprednisone, Methylprednisolone (Methylprednisolone Acetate, Methylprednisolone, Hemisuccinate, Methylprednisolone Sodium Succinate), Mometasone Furoate, Paramethasone Acetate, Prednicarbate, Prednisolamate Hydrochloride, Prednisolone (Prednisolone Acetate, Prednisolone Hemisuccinate, Prednisolone Hexanoate, Prednisolone Pivalate, Prednisolone Sodium Metasulphobenzoate, Prednisolone Sodium Phosphate, Prednisolone Sodium Succinate, Prednisolone Steaglate, Prednisolone Tebutate), Prednisone (Prednisone Acetate), Prednylidene, Procinonide, Rimexolone, Suprarenal Cortex, Tixocortol Pivalate, Triamcinolone (Triamcinolone Acetonide, Triamcinolone Diacetate and Triamcinolone Hexacetonide).

In another embodiment, the active compound is administered in combination or alternation with one or more other antihistimine(s) ($H_1$ receptor antagonists). Examples of antihistimines ($H_1$ receptor antagonists) that can be used in alternation or combination therapy include alkylamines, ethanolamines ethylenediamines, piperazines, piperidines or phenothiazines. Some non-limiting examples of antihistimes are Chlortrimeton (Teldrin, chlorpheniramine), Atrohist (brompheniramine, Bromarest, Bromfed, Dimetane), Actidil (triprolidine), Dexchlor (Poladex, Polaramine, dexchlorpheniramine), Benadryl (diphen-hydramine), Tavist (clemastine), Dimetabs (dimenhydrinate, Dramamine, Marmine), PBZ (tripelennamine), pyrilamine, Marezine (cyclizine), Zyrtec (cetirizine), hydroxyzine, Antivert (meclizine, Bonine), Allegra (fexofenadine), Hismanal (astemizole), Claritin (loratadine), Seldane (terfenadine), Periactin (cyproheptadine), Nolamine (phenindamine, Nolahist), Phenameth (promethazine, Phenergan), Tacaryl (methdilazine) and Temaril (trimeprazine).

Alternatively, the compound of the present invention may be administered in combination or alternation with (a) xanthines and methylxanthines, such as Theo-24 (theophylline, Slo-Phylline, Uniphyllin, Slobid, Theo-Dur), Choledyl (oxitriphylline), aminophylline;

(b) anticholinergic agents (antimuscarinic agents) such as belladonna alkaloids, Atrovent (ipratropium bromide), atropine, oxitropium bromide;

(c) phosphodiesterase inhibitors, including phosphodiesterase IV inhibitors such as zardaverine;

(d) calcium antagonists such as nifedipine;

(e) potassium activators such as cromakalim for the treatment of asthma;

(f) B-eotaxin chemokine receptor, CCR3, antagonists; or (g) IL-5 antibodies, IL-13 antibodies, IL-13 antagonists, IL-4 receptor antagonists, and IgE antibodies.

Arthritic Disorders

In one embodiment, the compound of the present invention can also be administered in combination or alternation with apazone, amitriptyline, chymopapain, collegenase, cyclobenzaprine, diazepam, fluoxetine, pyridoxine, ademetionine, diacerein, glucosamine, hylan (hyaluronate), misoprostol, paracetamol, superoxide dismutase mimics, IL-1 receptor antagonists, IL-2 receptor antagonists, IL-6 receptor antagonists, TNFα receptor antagonists, TNFα antibodies, P38 MAP Kinase inhibitors, tricyclic antidepressents, cJun kinase inhibitors or immunosuppressive agents, IV gamma globulin, troleandomycin, cyclosporin (Neoral), methotrexate, FK-506, gold compounds such as Myochrysine (gold sodium thiomalate), platelet activating factor (PAF) antagonists such as thromboxane inhibitors, MAPKAPK2 (MK2) Kinase inhibitors, CCR5 Receptor antagonists, Interleukin Converting Enzyme (ICE) inhibitors, IKB Kinase (IKK1, IKK2) inhibitors, TNF-α Convertase Enzyme (TACE) inhibitors, ICK Kinase inhibitors, Janus Kinase 3 (JAK3) inhibitors, Kinase insert domain-containing Receptor (KdR) Kinase inhibitors, and inducible nitric oxide sythase (iNOS) inhibitors.

In another embodiment, the active compound is administered in combination or alternation with one or more other corticosteriod(s). Examples of corticosteriods that can be used in alternation or combination therapy include but are not limited to glucocorticoids (GC), Aerobid (Aerobid-M, flunisolide), Azmacort (triamcinolone acetonide), Beclovet (Vanceril, beclomethasone dipropionate), Flovent (fluticasone), Pulmicort (budesonide), prednisolone, hydrocortisone, adrenaline, Alclometasone Dipropionate, Aldosterone, Amcinonide, Beclomethasone Dipropionate, Bendacort, Betamethasone (Betamethasone Acetate, Betamethasone Benzoate, Betamethasone Dipropionate, Betamethasone Sodium Phosphate, Betamethasone Valerate), Budesonide, Ciclomethasone, Ciprocinonide, Clobetasol Propionate, Clobetasone Butyrate, Clocortolone Pivalate, Cloprednol, Cortisone Acetate, Cortivazol, Deflazacort, Deoxycortone Acetate (Deoxycortone Pivalate), Deprodone, Desonide, Desoxymethasone, Dexamethasone (Dexamethasone Acetate, Dexamethasone Isonicotinate, Dexamethasone Phosphate, Dexamethasone Sodium Metasulphobenzoate, Dexamethasone Sodium Phosphate), Dichlorisone Acetate, Diflorasone Diacetate, Diflucortolone Valerate, Difluprednate, Domoprednate, Endrysone, Fluazacort, Fluclorolone Acetonide, Fludrocortisone Acetate, Flumethasone (Flumethasone Pivalate), Flunisolide, Fluocinolone Acetonide, Fluocinonide, Fluocortin Butyl, Fluocortolone (Fluocortolone Hexanoate, Fluocortolone Pivalate), Fluorometholone (Fluorometholone Acetate), Fluprednidene Acetate, Fluprednisolone, Flurandrenolone, Fluticasone Propionate, Formocortal, Halcinonide, Halobetasol Propionate, Halometasone, Hydrocortamate Hydrochloride, Hydrocortisone (Hydrocortisone Acetate, Hydrocortisone Butyrate, Hydrocortisone Cypionate, Hydrocortisone Hemisuccinate, Hydrocortisone Sodium Phosphate, Hydrocortisone Sodium Succinate, Hydrocortisone Valerate), Medrysone, Meprednisone, Methylprednisolone (Methylprednisolone Acetate, Methylprednisolone, Hemisuccinate, Methylprednisolone Sodium Succinate), Mometasone Furoate, Paramethasone Acetate, Prednicarbate, Prednisolamate Hydrochloride, Prednisolone (Prednisolone Acetate, Prednisolone Hemisuccinate, Prednisolone Hexanoate, Prednisolone Pivalate, Prednisolone Sodium Metasulphobenzoate, Prednisolone Sodium Phosphate, Prednisolone Sodium Succinate Prednisolone Steaglate, Prednisolone Tebutate), Prednisone (Prednisone Acetate), Prednylidene, Procinonide, Rimexolone, Suprarenal Cortex, Tixocortol Pivalate, Triamcinolone (Triamcinolone Acetonide, Triamcinolone Diacetate and Triamcinolone Hexacetonide).

In another embodiment, the active compound is administered in combination or alternation with one or more other non-steroidal anti-inflammatory drug(s) (NSAIDS). Examples of NSAIDS that can be used in alternation or combination therapy are carboxylic acids, propionic acids, fenamates, acetic acids, pyrazolones, oxicans, alkanones, gold compounds and others that inhibit prostaglandin synthesis, preferably by selectively inhibiting cylcooxygenase-2 (COX-2). Some nonlimiting examples of COX-2 inhibitors are Celebrex (celecoxib), Bextra (valdecoxib), Dynastat (parecoxib sodium) and Vioxx (rofacoxib). Some non-limiting examples of NSAIDS are aspirin (acetylsalicylic acid), Dolobid (diflunisal), Disalcid (salsalate, salicylsalicylate), Trisilate (choline magnesium trisalicylate), sodium salicylate, Cuprimine (penicillamine), Tolectin (tolmetin), ibuprofen (Motrin, Advil, Nuprin Rufen), Naprosyn (naproxen, Anaprox, naproxen sodium), Nalfon (fenoprofen), Orudis (ketoprofen), Ansaid (flurbiprofen), Daypro (oxaprozin), meclofenamate (meclofanamic acid, Meclomen), mefenamic acid, Indocin (indomethacin), Clinoril (sulindac), tolmetin, Voltaren (diclofenac), Lodine (etodolac), ketorolac, Butazolidin (phenylbutazone), Tandearil (oxyphenbutazone), piroxicam (Feldene), Relafen (nabumetone), Myochrysine (gold sodium thiomalate), Ridaura (auranofin), Solganal (aurothioglucose), acetaminophen, colchicine, Zyloprim (allopurinol), Benemid (probenecid), Anturane (sufinpyrizone), Plaquenil (hydroxychloroquine), Aceclofenac, Acemetacin, Acetanilide, Actarit, Alclofenac, Alminoprofen, Aloxiprin, Aluminium Aspirin, Amfenac Sodium, Amidopyrine, Aminopropylone, Ammonium Salicylate, Ampiroxicam, Amyl Salicylate, Anirolac, Aspirin, Auranofin, Aurothioglucose, Aurotioprol, Azapropazone, Bendazac (Bendazac Lysine), Benorylate, Benoxaprofen, Benzpiperylone, Benzydamine, Hydrochloride, Bornyl Salicylate, Bromfenac Sodium, Bufexamac, Bumadizone Calcium, Butibufen Sodium, Capsaicin, Carbaspirin Calcium, Carprofen, Chlorthenoxazin, Choline Magnesium Trisalicylate, Choline Salicylate, Cinmetacin, Clofexamide, Clofezone, Clometacin, Clonixin, Cloracetadol, Cymene, Diacerein, Diclofenac (Diclofenac Diethylammonium Salt, Diclofenac Potassium, Diclofenac Sodium), Diethylamine Salicylate, Diethylsalicylamide, Difenpiramide, Diflunisal, Dipyrone, Droxicam, Epirizole, Etenzamide, Etersalate, Ethyl Salicylate, Etodolac, Etofenamate, Felbinac, Fenbufen, Fenclofenac, Fenoprofen Calcium, Fentiazac, Fepradinol, Feprazone, Floctafenine, Flufenamic, Flunoxaprofen, Flurbiprofen (Flurbiprofen Sodium), Fosfosal, Furprofen, Glafenine, Glucametacin, Glycol Salicylate, Gold Keratinate, Harpagophytum Procumbens, Ibufenac, Ibuprofen, Ibuproxam, Imidazole Salicylate, Indomethacin (Indomethacin Sodium), Indoprofen, Isamifazone, Isonixin, Isoxicam, Kebuzone, Ketoprofen, Ketorolac Trometamol, Lithium Salicylate, Lonazolac Calcium, Lornoxicam, Loxoprofen Sodium, Lysine Aspirin, Magnesium Salicylate, Meclofenamae Sodium, Mefenamic Acid, Meloxicam, Methyl Butetisalicylate, Methyl Gentisate, Methyl Salicylate, Metiazinic Acid, Metifenazone, Mofebutazone, Mofezolac, Morazone Hydrochloride, Morniflumate, Morpholine Salicylate, Nabumetone, Naproxen (Naproxen Sodium), Nifenazone, Niflumic Acid, Nimesulide, Oxametacin, Oxaprozin, Oxindanac, Oxyphenbutazone, Parsalmide, Phenybutazone, Phenyramidol Hydrochloride, Picenadol Hydrochloride, Picolamine Salicylate, Piketoprofen, Pirazolac, Piroxicam, Pirprofen, Pranoprofen, Pranosal, Proglumetacin Maleate, Proquazone, Protizinic Acid, Ramifenazone, Salacetamide, Salamidacetic Acid, Salicylamide, Salix, Salol, Salsalate, Sodium Aurothiomalate, Sodium Gentisate, Sodium Salicylate, Sodium Thiosalicylate, Sulindac, Superoxide Dismutase (Orgotein, Pegorgotein, Sudismase), Suprofen, Suxibuzone, Tenidap Sodium, Tenoxicam, Tetrydamine, Thurfyl Salicylate, Tiaprofenic, Tiaramide Hydrochloride, Tinoridine Hydrochloride, Tolfenamic Acid, Tometin Sodium, Triethanolamine Salicylate, Ufenamate, Zaltoprofen, Zidometacin and Zomepirac Sodium.

Cardiovascular Disease

Compounds useful for combining with the compounds of the present invention for the treatment of cardiovascular disease encompass a wide range of therapeutic compounds.

Ileal bile acid transporter (IBAT) inhibitors, for example, are useful in the present invention, and are disclosed in patent application no. PCT/US95/10863, herein incorporated by reference. More IBAT inhibitors are described in PCT/US97/04076, herein incorporated by reference. Still further IBAT inhibitors useful in the present invention are described in U.S. application Ser. No. 08/816,065, herein incorporated by reference. More IBAT inhibitor compounds useful in the present invention are described in WO 98/40375, and WO 00/38725, herein incorporated by reference. Additional IBAT inhibitor compounds useful in the present invention are described in U.S. application Ser. No. 08/816,065, herein incorporated by reference.

In another aspect, the second biologically active agent is a statin. Statins lower cholesterol by inhibiting of 3-hydroxy-3-methylglutaryl coenzyme A (HMG CoA) reductase, a key enzyme in the cholesterol biosynthetic pathway. The statins decrease liver cholesterol biosynthesis, which increases the production of LDL receptors thereby decreasing plasma total and LDL cholesterol (Grundy, S. M. *New Engl. J. Med.* 319, 24 (1988); Endo, A. *J. Lipid Res.* 33, 1569 (1992)). Depending on the agent and the dose used, statins may decrease plasma triglyceride levels and may increase HDLc. Currently the statins on the market are lovastatin (Merck), simvastatin (Merck), pravastatin (Sankyo and Squibb) and fluvastatin (Sandoz). A fifth statin, atorvastatin (Parke-Davis/Pfizer), is the most recent entrant into the statin market. Any of these statins or thers can be used in combination with the chalcones of the present invention.

MTP inhibitor compounds useful in the combinations and methods of the present invention comprise a wide variety of structures and functionalities. Some of the MTP inhibitor compounds of particular interest for use in the present invention are disclosed in WO 00/38725, the disclosure from which is incorporated by reference. Descriptions of these therapeutic compounds can be found in *Science,* 282, 23 Oct. 1998, pp. 751–754, herein incorporated by reference.

Cholesterol absorption antagonist compounds useful in the combinations and methods of the present invention comprise a wide variety of structures and functionalities. Some of the cholesterol absorption antagonist compounds of particular interest for use in the present invention are described in U.S. Pat. No. 5,767,115, herein incorporated by reference. Further cholesterol absorption antagonist compounds of particular interest for use in the present invention, and methods for making such cholesterol absorption antagonist compounds are described in U.S. Pat. No. 5,631,365, herein incorporated by reference.

A number of phytosterols suitable for the combination therapies of the present invention are described by Ling and Jones in "Dietary Phytosterols: A Review of Metabolism, Benefits and Side Effects," *Life Sciences,* 57 (3), 195–206 (1995). Without limitation, some phytosterols of particular use in the combination of the present invention are Clofibrate, Fenofibrate, Ciprofibrate, Bezafibrate, Gemfibrozil. The structures of the foregoing compounds can be found in WO 00/38725.

Phytosterols are also referred to generally by Nes (*Physiology and Biochemistry of Sterols,* American Oil Chemists' Society, Champaign, Ill., 1991, Table 7–2). Especially preferred among the phytosterols for use in the combinations of the present invention are saturated phytosterols or stanols. Additional stanols are also described by Nes (Id.) and are useful in the combination of the present invention. In the combination of the present invention, the phytosterol preferably comprises a stanol. In one preferred embodiment the stanol is campestanol. In another preferred embodiment the stanol is cholestanol. In another preferred embodiment the stanol is clionastanol. In another preferred embodiment the stanol is coprostanol. In another preferred embodiment the stanol is 22,23-dihydrobrassicastanol. In another embodiment the stanol is epicholestanol. In another preferred embodiment the stanol is fucostanol. In another preferred embodiment the stanol is stigmastanol.

Another embodiment the present invention encompasses a therapeutic combination of a compound of the present invention and an HDLc elevating agent. In one aspect, the second HDLc elevating agent can be a CETP inhibitor. Individual CETP inhibitor compounds useful in the present invention are separately described in WO 00/38725, the disclosure of which is herein incorporated by reference. Other individual CETP inhibitor compounds useful in the present invention are separately described in WO 99/14174, EP818448, WO 99/15504, WO 99/14215, WO 98/04528, and WO 00/17166, the disclosures of which are herein incorporated by reference. Other individual CETP inhibitor compounds useful in the present invention are separately described in WO 00/18724, WO 00/18723, and WO 00/18721, the disclosures of which are herein incorporated by reference. Other individual CETP inhibitor compounds useful in the present invention are separately described in WO 98/35937 as well as U.S. Pat. Nos. 6,313,142, 6,310,075, 6,197,786, 6,147,090, 6,147,089, 6,140,343, and 6,140,343, the disclosures of which is herein incorporated by reference.

In another aspect, the second biologically active agent can be a fibric acid derivative. Fibric acid derivatives useful in the combinations and methods of the present invention comprise a wide variety of structures and functionalities which have been reported and published in the art.

The compounds of the present invention may also be used in combination or alternation therapy with PPAR agonists including PPARα/γ dual agonists, PPARα agonists, and PPARγ agonists.

In another embodiment the present invention encompasses a therapeutic combination of a compound of the present invention and an antihypertensive agent. Hypertension is defined as persistently high blood pressure. In another embodiment, the chalcone is administered in combination with an ACE inhibitor, a beta andrenergic blocker, alpha andrenergic blocker, angiotensin II receptor antagonist, vasodilator and diuretic.

Pharmaceutical Compositions

Any host organism, including a patient, mammal, and specifically a human, suffering from any of the above-described conditions can be treated by the administration of a composition comprising an effective amount of the compound of the invention or a pharmaceutically acceptable salt thereof, optionally in a pharmaceutically acceptable carrier or diluent.

The composition can be administered in any desired manner, including oral, topical, parenteral, intravenous, intradermal, intra-articular, intra-synovial, intrathecal, intra-arterial, intracardiac, intramuscular, subcutaneous, intraorbital, intracapsular, intraspinal, intrasternal, topical, transdermal patch, via rectal, vaginal or urethral suppository, peritoneal, percutaneous, nasal spray, surgical implant, internal surgical paint, infusion pump, or via catheter. In one embodiment, the agent and carrier are administered in a slow release formulation such as an implant, bolus, microparticle, microsphere, nanoparticle or nanosphere. For standard information on pharmaceutical formulations, see Ansel, et al., *Pharmaceutical Dosage Forms and Drug Delivery Systems,* Sixth Edition, Williams & Wilkins (1995).

An effective dose for any of the herein described conditions can be readily determined by the use of conventional techniques and by observing results obtained under analogous circumstances. In determining the effective dose, a number of factors are considered including, but not limited to: the species of patient; its size, age, and general health; the specific disease involved; the degree of involvement or the severity of the disease; the response of the individual patient; the particular compound administered; the mode of administration; the bioavailability characteristics of the preparation administered; the dose regimen selected; and the use of concomitant medication. Typical systemic dosages for all of the herein described conditions are those ranging from 0.1 mg/kg to 500 mg/kg of body weight per day as a single daily dose or divided daily doses. Preferred dosages for the described conditions range from 5–1500 mg per day. A more particularly preferred dosage for the desired conditions ranges from 25–750 mg per day. Typical dosages for topical application are those ranging from 0.001 to 100% by weight of the active compound.

The compound is administered for a sufficient time period to alleviate the undesired symptoms and the clinical signs associated with the condition being treated.

The active compound is included in the pharmaceutically acceptable carrier or diluent in an amount sufficient to deliver to a patient a therapeutic amount of compound in vivo in the absence of serious toxic effects.

The concentration of active compound in the drug composition will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the dosage ranges set forth herein are exemplary only and are not intended to limit the scope or practice of the claimed composition. The active ingredient may be administered at once, or may be divided into a number of smaller doses to be administered at varying intervals of time.

A preferred mode of administration of the active compound for systemic delivery is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The compound or its salts can be administered as a component of an elixir, suspension, syrup, wafer, chewing gum or the like. A syrup may contain, in addition to the active compounds, sucrose as a sweetening agent and certain preservatives, dyes and colorings and flavors.

The compound can also be mixed with other active materials that do not impair the desired action, or with materials that supplement the desired action. The compounds can also be administered in combination with nonsteroidal antiinflammatories such as ibuprofen, indomethacin, fenoprofen, mefenamic acid, flufenamic acid, sulindac. The compound can also be administered with corticosteriods.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

If administered intravenously, preferred carriers are physiological saline, bacteriostatic water, Cremophor EL™ (BASF, Parsippany, N.J.) or phosphate buffered saline (PBS).

In a preferred embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) are also preferred as pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the compound is then introduced into the container. The container is then swirled by hand to free lipid material from the sides of the container and to disperse lipid aggregates, thereby forming the liposomal suspension.

Suitable vehicles or carriers for topical application can be prepared by conventional techniques, such as lotions, suspensions, ointments, creams, gels, tinctures, sprays, powders, pastes, slow-release transdermal patches, suppositories for application to rectal, vaginal, nasal or oral mucosa. In addition to the other materials listed above for systemic administration, thickening agents, emollients and stabilizers can be used to prepare topical compositions. Examples of thickening agents include petrolatum, beeswax, xanthan gum, or polyethylene, humectants such as sorbitol, emollients such as mineral oil, lanolin and its derivatives, or squalene.

Any of the compounds described herein for combination or alternation therapy can be administered as any derivative that upon administration to the recipient, is capable of providing directly or indirectly, the parent compound, or that exhibits activity itself. Nonlimiting examples are the pharmaceutically acceptable salts (alternatively referred to as "physiologically acceptable salts"), and a compound which has been alkylated or acylated at an appropriate position. The modifications can affect the biological activity of the compound, in some cases increasing the activity over the parent compound. This can easily be assessed by preparing the derivative and testing its anti-inflammatory activity according to known methods.

Biological Activity of Active Compounds

The ability of a compound described herein to inhibit the expression of VCAM-1 or in the treatment of diseases in a host can be assessed using any known method, including that described in detail below.

In Vitro VCAM-1 Assay

Cell Culture and compound dosing: Cultured primary human aortic (HAEC) or pulmonary (HPAEC) endothelial cells were obtained from Clonetics, Inc., and were used below passage 9. Cells were seeded in 96 well plates such that they would reach 90–95% confluency by the following day. On the following day the cells were stimulated with TNF-$\alpha$ (1 ng/ml) in the presence or absence of compounds dissolved in DMSO such that the final concentration of DMSO is 0.25% or less. To establish a dose curve for each compound, four concentrations in 2- to 5-fold increments were used. Cells were exposed to TNF-$\alpha$ and compounds for approximately 16 hours. The next day the cells were examined under microscope to score for visual signs of toxicity or cell stress.

Following 16 hr exposure to TNF-$\alpha$ and compound the media was discarded and the cells were washed once with Hanks Balanced Salt Solution (HBSS)/Phosphate buffered saline (PBS) (1:1). Primary antibodies against VCAM-1 (0.25 μg/ml in HBSS/PBS+5% FBS) were added and incubated for 30–60 minutes at 37° C. Cells were washed with HBSS/PBS three times, and secondary antibody Horse Radish Peroxidase (HRP)-conjugated goat anti-mouse IgG (1:500 in HBSS/PBS+5% FBS) were added and incubated for 30 minutes at 37° C. Cells were washed with HBSS/PBS four time and TMB substrate were added and incubated at room temperature in the dark until there was adequate development of blue color. The length of time of incubation was typically 5–15 minutes. 2N sulfuric acid was added to stop the color development and the data was collected by reading the absorbance on a BioRad ELISA plate reader at OD 450 nm. The results are expressed as $IC_{50}$ values (the concentration (micromolar) of compound required to inhibit 50% of the maximal response of the control sample stimulated by TNF-$\alpha$ only). Compounds exhibiting $IC_{50}$'s of less than 5 micromolar are tabulated in Biological Table 1.

BIOLOGICAL TABLE 1

| Example Number | VCAM-1 IC50 (μM) |
|---|---|
| 1 | <5 |
| 2 | <5 |
| 3 | <5 |
| 4 | >10 |
| 5 | <5 |
| 6 | <5 |
| 7 | <5 |
| 8 | <5 |
| 9 | <10 |
| 10 | <10 |
| 11 | <5 |
| 12 | <10 |
| 13 | >10 |
| 14 | <5 |
| 15 | <5 |
| 16 | <5 |
| 17 | <10 |
| 18 | <10 |
| 19 | <5 |
| 20 | <5 |
| 21 | <10 |
| 22 | >10 |
| 23 | <5 |
| 24 | <5 |
| 25 | <5 |
| 26 | >10 |
| 27 | <10 |
| 28 | <10 |
| 29 | <5 |
| 30 | <10 |
| 31 | <10 |
| 32 | <5 |
| 33 | >10 |
| 34 | >10 |
| 35 | <5 |
| 36 | <5 |
| 37 | <5 |
| 38 | <5 |
| 39 | <5 |
| 40 | <5 |
| 41 | <5 |
| 42 | >10 |
| 43 | <5 |
| 44 | <5 |
| 45 | <5 |
| 40 | <5 |
| 46 | <5 |
| 47 | <5 |
| 48 | <5 |
| 49 | <5 |
| 50 | >10 |
| 51 | >10 |
| 52 | <5 |
| 53 | <5 |
| 54 | >5 |
| 55 | >10 |
| 56 | >10 |
| 57 | <5 |

Modifications and variations of the present invention relating to compounds and methods of treating diseases will be obvious to those skilled in the art from the foregoing detailed description of the invention. Such modifications and variations are intended to come within the scope of the appended claims.

We claim:

1. A compound of Formula I (I)

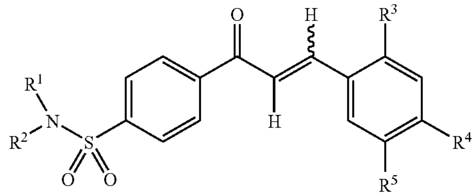

or its pharmaceutically acceptable salt, wherein:

$R^1$ is selected from the group consisting of hydrogen, alkyl, lower alkyl, carbocyclic, cycloalkyl, aryl, heteroaryl, heterocyclic, arylalkyl, heteroarylalkyl, acyl and heterocyclicalkyl, wherein all substituents may be optionally substituted by one or more selected from the group consisting of halo, alkyl, lower alkyl, alkenyl, cycloalkyl, haloalkyl, acyl, hydroxy, hydroxyalkyl, heterocyclic, amino, aminoalkyl, —$NR^7R^8$, alkoxy, oxo, cyano, carboxy, carboxyalkyl, alkoxycarbonyl, heteroaryl, —$C(O)NR^7R^8$, and —$C(O)N(R^2)_2$;

$R^2$ is independently selected from the group consisting of alkyl, lower alkyl, carbocyclic, cycloalkyl, hydroxy, alkoxy, lower alkoxy, trialkylsilyloxy, cycloalkyloxy, cycloalkylalkoxy, heterocyclicoxy, aryl, heteroaryl, heterocyclic, arylalkyl, heteroarylalkyl, acyl, alkoxycarbonyl, and heterocyclicalkyl, wherein all substituents may be optionally substituted by one or more selected from the group consisting of halo, alkyl, lower alkyl, alkenyl, cycloalkyl, haloalkyl, acyl, hydroxy, hydroxyalkyl, heterocyclic, amino, aminoalkyl, —$NR^7R^8$, alkoxy, oxo, cyano, carboxy, carboxyalkyl, alkoxycarbonyl, heteroaryl, —$C(O)NR^7R^8$, —$NR^1R^2$ and —$C(O)N(R^2)_2$;

$R^1$ and $R^2$ may be taken together to form a 4- to 12-membered saturated or unsaturated heterocyclic ring which can be optionally substituted by one or more selected from the group consisting of halo, alkyl, lower alkyl, alkenyl, cycloalkyl, haloalkyl, acyl, hydroxy, hydroxyalkyl, heterocyclic, amino, aminoalkyl, —$NR^7R^8$, alkoxy, oxo, cyano, carboxy, carboxyalkyl, alkoxycarbonyl, —$C(O)NR^7R^8$, and —$C(O)N(R^2)_2$;

$R^7$ and $R^8$ are independently selected from the group consisting of alkyl, alkenyl and aryl and linked together forming a 4- to 12-membered monocyclic, bicylic, tricyclic or benzofused ring, which may be optionally substituted by one or more selected from the group consisting of halo, alkyl, lower alkyl, alkenyl, cycloalkyl, haloalkyl, acyl, hydroxy, hydroxyalkyl, heterocyclic, amino, aminoalkyl, —$NR^7R^8$, alkoxy, oxo, cyano, carboxy, carboxyalkyl, alkoxycarbonyl, —$C(O)NR^7R^8$, and —$C(O)N(R^2)_2$;

$R^3$ and $R^4$ are independently selected from hydroxy, alkoxy, lower alkoxy, —$(O(CH_2)_2)_{1\text{-}3}$—O-lower alkyl, cycloalkyloxy, cycloalkylalkoxy, haloalkoxy, aryloxy, arylalkoxy, heteroaryloxy, heteroarylalkoxy, heteroaryl lower alkoxy, heterocyclicoxy, heterocyclicalkoxy, heterocyclic lower alkoxy, —$OC(R^1)_2C(O)N(R^2)_2$, and —$OC(R^1)_2C(O)NR^7R^8$, wherein all substituents may be optionally substituted by one or more selected from the group consisting of halo, alkyl, lower alkyl, alkenyl, cycloalkyl, haloalkyl, acyl, hydroxy, hydroxyalkyl, heterocyclic, amino, aminoalkyl, —$NR^7R^8$, alkoxy, oxo, cyano, carboxy, carboxyalkyl, alkoxycarbonyl, —$C(O)NR^7R^8$, and —$C(O)N(R^2)_2$;

$R^5$ is selected from the group consisting of a carbon-carbon linked heteroaryl and a carbon-carbon linked heterocyclic, which may be optionally substituted by one or more selected from the group consisting of halo, alkyl, lower alkyl, alkenyl, cycloalkyl, haloalkyl, acyl, hydroxy, hydroxyalkyl, heterocyclic, amino, aminoalkyl, —$NR^7R^8$, alkoxy, oxo, cyano, carboxy, carboxyalkyl, alkoxycarbonyl, —$C(O)NR^7R^8$, and —$C(O)N(R^2)_2$;

with the proviso that when $R^1$ is hydrogen and $R^2$ is 2-methyl propanoyl, then $R^5$ cannot be 5-benzo[b]thien-2-yl.

2. The compound of claim 1 or its pharmaceutically acceptable salt, wherein:

$R^1$ is selected from the group consisting of hydrogen, alkyl, and lower alkyl, wherein all substituents may be optionally substituted by one or more selected from the group consisting of halo, alkyl, lower alkyl, haloalkyl, heterocyclic, —$NR^7R^8$, alkoxy, carboxy, carboxyalkyl, alkoxycarbonyl and heteroaryl;

$R^2$ is independently selected from the group consisting of alkyl, lower alkyl, alkoxy, lower alkoxy, heteroaryl, heterocyclic, heteroarylalkyl, and heterocyclicalkyl, wherein all substituents may be optionally substituted by one or more selected from the group consisting of halo, alkyl, lower alkyl, haloalkyl, heterocyclic, —$NR^7R^8$, alkoxy, carboxy, carboxyalkyl, alkoxycarbonyl and heteroaryl;

$R^1$ and $R^2$ may be taken together to form a 5- to 7-membered saturated or unsaturated heterocyclic ring which can be optionally substituted by one or more selected from the group consisting of halo, alkyl, lower alkyl, haloalkyl, heterocyclic, —$NR^7R^8$, alkoxy, carboxy, carboxyalkyl and alkoxycarbonyl;

$R^7$ and $R^8$ are independently selected from the group consisting of alkyl, alkenyl and aryl and linked together forming a 5- to 10-membered monocyclic, bicylic or benzofused ring, which may be optionally substituted by one or more selected from the group consisting of halo, alkyl, lower alkyl, haloalkyl, heterocyclic, —$NR^7R^8$, alkoxy, carboxy, carboxyalkyl and alkoxycarbonyl;

$R^3$ and $R^4$ are independently selected from hydroxy, alkoxy, lower alkoxy, —$(O(CH_2)_2)_{1\text{-}3}$—O-lower alkyl, haloalkoxy, heteroaryloxy, heteroarylalkoxy, heteroaryl lower alkoxy, heterocyclicoxy, heterocyclicalkoxy, heterocyclic lower alkoxy, —$OC(R^1)_2C(O)N(R^2)_2$, and —$OC(R^1)_2C(O)NR^7R^8$, wherein all substituents may be optionally substituted by one or more selected from the group consisting of halo, alkyl, lower alkyl, hydroxy, hydroxyalkyl, heterocyclic, —$NR^7R^8$, alkoxy, —$C(O)NR^7R^8$, and —$C(O)N(R^2)_2$;

$R^5$ is selected from the group consisting of a carbon-carbon linked heteroaryl and a carbon-carbon linked heterocyclic, which may be optionally substituted by one or more selected from the group consisting of halo, alkyl, lower alkyl, haloalkyl, heterocyclic, —$NR^7R^8$ and alkoxy.

3. The compound of claim 1 or its pharmaceutically acceptable salt, wherein:

$R^1$ is selected from the group consisting of hydrogen and lower alkyl;

$R^2$ is independently selected from the group consisting of lower alkyl, lower alkoxy, heteroaryl, heterocyclic, heteroarylalkyl, and heterocyclicalkyl, wherein all substituents may be optionally substituted by one or more selected from the group consisting of halo, lower alkyl, haloalkyl, heterocyclic, —$NR^7R^8$ and carboxy;

$R^1$ and $R^2$ may be taken together to form a 5- to 6-membered heterocyclic saturated ring which can be optionally substituted by one or more selected from the group consisting of halo, lower alkyl and carboxy;

$R^7$ and $R^8$ are independently selected from the group consisting of alkyl and alkenyl, and linked together forming a 5- to 7-membered monocyclic ring, which may be optionally substituted by one or more selected from the group consisting of halo, lower alkyl, haloalkyl, heterocyclic and carboxy;

$R^3$ and $R^4$ are independently selected from hydroxy, lower alkoxy, $-(O(CH_2)_2)_{1-3}-$O-lower alkyl, heteroaryl lower alkoxy, heterocyclicoxy, heterocyclicalkoxy, heterocyclic lower alkoxy, $-OC(R^1)_2C(O)N(R^2)_2$, and $-OC(R^1)_2C(O)NR^7R^8$, wherein all substituents may be optionally substituted by one or more selected from the group consisting of hydroxy, hydroxyalkyl, heterocyclic, $-NR^7R^8$, $-C(O)NR^7R^8$, and $-C(O)N(R^2)_2$;

$R^5$ is selected from the group consisting of a carbon-carbon linked heteroaryl and a carbon-carbon linked heterocyclic, which may be optionally substituted by one or more lower alkyl.

4. The compound of claim 1 or its pharmaceutically acceptable salt, wherein:

$R^1$ is hydrogen;

$R^2$ is independently selected from the group consisting of lower alkyl, heteroaryl, heteroarylalkyl, and heterocyclicalkyl, wherein all substituents may be optionally substituted by one or more selected from the group consisting of halo and lower alkyl;

$R^1$ and $R^2$ may be taken together to form a 5- to 6-membered heterocyclic saturated ring;

$R^7$ and $R^8$ are independently alkyl and linked together forming a 5- to 7-membered saturated monocyclic ring;

$R^3$ and $R^4$ are independently selected from hydroxy, lower alkoxy and heterocyclic lower alkoxy;

$R^5$ is selected from the group consisting of a carbon-carbon linked heteroaryl and a carbon-carbon linked heterocyclic, which may be optionally substituted by one or more lower alkyl.

5. The compound of claim 1 or its pharmaceutically acceptable salt, wherein:

$R^1$ is hydrogen;

$R^2$ is independently selected from the group consisting of lower alkyl, heteroaryl, heteroarylalkyl, and heterocyclicalkyl, wherein all substituents may be optionally substituted by one or more selected from the group consisting of halo and lower alkyl;

$R^3$ and $R^4$ are independently selected from lower alkoxy and heterocyclic lower alkoxy;

$R^5$ is a carbon-carbon linked heteroaryl, which may be optionally substituted by one or more lower alkyl.

6. The compound of claim 1 or its pharmaceutically acceptable salt, wherein the compound is selected from the group consisting of:

4-[3E-(2,4-Dimethoxy-5-thien-2-yl-phenyl)acryloyl]-N-(5-methylisoxazol-3-yl)benzenesulfonamide;

3E-(2,4-Dimethoxy-5-thien-2-ylphenyl)acryloyl]-N-(5-methylisoxazol-3-yl)benzenesulfonamide sodium salt;

4-[3E-(2,4-Dimethoxy-5-thien-2-ylphenyl)acryloyl]-N-pyrimidin-2-ylbenzenesulfonamide;

4-[3E-(2,4-Dimethoxy-5-thien-2-ylphenyl)acryloyl]-N-(1-H-tetrazol-5-yl)benzenesulfonamide;

4-[3E-(2,4-Dimethoxy-5-thien-2-ylphenyl)acryloyl]-N-pyridin-2-ylbenzenesulfonamide;

4-[3E-(2,4-Dimethoxy-5-thien-2-ylphenyl)acryloyl]-N-(1H-pyrazol-3-yl)benzenesulfonamide;

4-[3E-(2,4-Dimethoxy-5-thien-2-ylphenyl)acryloyl]-N-isoxazol-3-ylbenzenesulfonamide;

4-[3E-(2,4-Dimethoxy-5-thien-2-ylphenyl)acryloyl]-N-thiazol-2-ylbenzenesulfonamide;

4-[3E-(2,4-Dimethoxy-5-thien-2-ylphenyl)acryloyl]-N-(3-methylisoxazol-5-ylbenzenesulfonamide;

N-(5-Chloropyridin-2-yl)-4-[3E-(2,4-dimethoxy-5-thien-2-ylphenyl)acryloyl]benzenesulfonamide;

4-[3E-(2,4-Dimethoxy-5-thien-2-ylphenyl)acryloyl]-N-(5-fluoropyridin-2-yl)benzenesulfonamide;

4-[3E-(2,4-Dimethoxy-5-thien-2-ylphenyl)acryloyl]-N-(5-trifluoromethylpyridin-2-yl)benzenesulfonamide;

4-{3E-[2-(3-Hydroxy-2-hydroxymethylpropoxy)-4-methoxy-5-thien-2-ylphenyl]acryloyl}-N-(5-methylisoxazol-3-yl)benzenesulfonamide;

4-{3E-[4-Methoxy-2-(2-morpholin-4-yl-ethoxy)-5-thien-2-ylphenyl]acryloyl}-N-(5methylisoxazol-3-yl)benzenesulfonamide hydrochloride;

4-{3E-[2,4-Dimethoxy-5-(1-methyl-1H-indol-2-yl)phenyl]acryloyl}-N-(5-methylisoxazol-3-yl)benzenesulfonamide;

4-{3E-[2,4-Dimethoxy-5-(1-methyl-1H-indol-2-yl)phenyl]acryloyl}-N-(5-methylisoxazol-3-yl)benzenesulfonamide sodium salt;

4-{3E-[2,4-Dimethoxy-5-(1-methyl-1H-indol-2-yl)phenyl]acryloyl}-N-pyridin-3-ylmethy-benzenesulfonamide;

4-{3E-[2,4-Dimethoxy-5-(1-methyl-1H-indol-2-yl)phenyl]acryloyl}-N-(2-morpholin-4-yl-ethyl)benzenesulfonamide;

4-[3E-(2,4-Dimethoxy-5-thien-2-ylphenyl)acryloyl]-N-pyridin-3-ylmethylbenzenesulfonamide 4-[3E-(2,4-Dimethoxy-5-thien-2-ylphenyl)acryloyl]-N-(2-morpholin-4-yl-ethyl)benzenesulfonamide;

3E-(2,4-Dimethoxy-5-thien-2-ylphenyl)-1-[4-(4-methylpiperazine-1-sulfonyl)phenyl]propenone;

4-[3E-(2,4-Dimethoxy-5-thien-2-ylphenyl)acryloyl]-N-piperidine-1-ylbenzenesulfonamide;

4-[3E-(2,4-Dimethoxy-5-thien-2-ylphenyl)acryloyl]-N-(3-imidazol-1-ylpropyl)benzenesulfonamide;

4-[3E-(2,4-Dimethoxy-5-thien-2-ylphenyl)acryloyl]-N-(2,2,2-trifluoroethyl)benzenesulfonamide;

4-[3E-(2,4-Dimethoxy-5-thien-2-ylphenyl)acryloyl]-N-(2,2,2-trifluoroethyl)benzenesulfonamide sodium salt;

{4-[3E-(2,4-Dimethoxy-5-thien-2-ylphenyl)acryloyl]benzenesulfonylamino}acetic acid;

2-{4-[3E-(2,4-Dimethoxy-5-thien-2-yl-phenyl)acryloyl]benzenesulfonylamino}-2-methylpropionic acid;

1-{4-[3E-(2,4-Dimethoxy-5-thien-2-ylphenyl)acryloyl]benzenesulfonyl}piperidine-2-carboxylic acid;

4-{3E-[2,4-Dimethoxy-5-(1-methyl-1H-indol-2-yl)phenyl]acryloyl}-N-methyl-benzenesulfonamide;

4-{3E-[2,4-Dimethoxy-5-(1-methyl-1H-indol-2-yl)phenyl]acryloyl}-N-methoxybenzenesulfonamide;

4-{3E-[2,4-Dimethoxy-5-(1-methyl-1H-indol-2-yl)phenyl]acryloyl}-N,N-dimethylbenzenesulfonamide;

4-{3E-[5-(1H-Indol-2-yl)-2,4-dimethoxyphenyl]acryloyl}-N,N-dimethylbenzenesulfonamide;

4-{3E-[2,4-Dimethoxy-5-(1-methyl-1H-indol-2-yl)phenyl]acryloyl}-N-(tert-butyldimethylsiloxy)benzenesulfonamide;

4-{3E-[2,4-Dimethoxy-5-(1-methyl-1H-indol-2-yl)phenyl]-acryloyl}-N-hydroxybenzenesulfonamide;

4-{3E-[2,4-Dimethoxy-5-(1-methyl-1H-pyrrol-2-yl)phenyl]acryloyl}-N-(5-methyl-isoxazol-3-yl)benzenesulfonamide;

4-{3E-[2-(3-Hydroxy-propoxy)-4-methoxy-5-thien-2-ylphenyl]acryloyl}-N-(5-methylisoxazol-3-yl)benzenesulfonamide;

4-{3E-[2,4-Dimethoxy-5-(1-methyl-1H-pyrrol-2-yl)phenyl]acryloyl}-N-(5-methyl-isoxazol-3-yl)benzenesulfonamide;

N-(3-Imidazol-1-yl-propyl)-4-{3E-[5-(1H-indol-2-yl)-2,4-dimethoxyphenyl]acryloyl}benzenesulfonamide;

(4-{3E-[5-(1H-Indol-2-yl)-2,4-dimethoxyphenyl]acryloyl}benzenesulfonylamino)acetic acid; and 4-{3E-[5-(1H-Indol-2-yl)-2,4-dimethoxyphenyl]acryloyl}-N-pyridin-2-ylbenzenesulfonamide.

7. A compound of Formula III

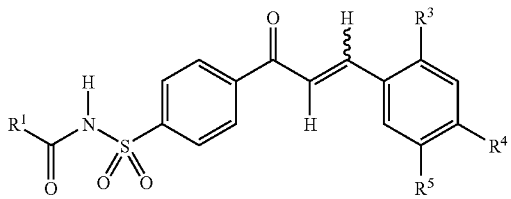

(III)

or its pharmaceutically acceptable salt, wherein:

$R^1$ is selected from the group consisting of hydrogen, alkyl, lower alkyl, carbocyclic, cycloalkyl, alkoxy, lower alkoxy, cycloalkyloxy, cycloalkylalkoxy, heterocyclicoxy, aryloxy, heteroaryloxy, aryl, heteroaryl, heterocyclic, arylalkyl, heteroarylalkyl, —$NR^7R^8$, —$NHR^2$, —$N(R^2)_2$, acyl and heterocyclicalkyl, wherein all substituents may be optionally substituted by one or more selected from the group consisting of halo, alkyl, lower alkyl, alkenyl, cycloalkyl, haloalkyl, acyl, hydroxy, hydroxyalkyl, heterocyclic, amino, aminoalkyl, —$NR^7R^8$, —$NHR^2$, —$N(R^2)_2$, alkoxy, oxo, cyano, carboxy, carboxyalkyl, alkoxycarbonyl, heteroaryl, —$C(O)NR^7R^8$, and —$C(O)N(R^2)^2$;

$R^2$ is independently selected from the group consisting of hydrogen, alkyl, lower alkyl, carbocyclic, cycloalkyl, aryl, heteroaryl, heterocyclic, arylalkyl, heteroarylalkyl, acyl, alkoxycarbonyl, and heterocyclicalkyl, wherein all substituents may be optionally substituted by one or more selected from the group consisting of halo, alkyl, lower alkyl, alkenyl, cycloalkyl, haloalkyl, acyl, hydroxy, hydroxyalkyl, heterocyclic, amino, aminoalkyl, —$NR^7R^8$, alkoxy, oxo, cyano, carboxy, carboxyalkyl, alkoxycarbonyl, heteroaryl, —$C(O)NR^7R^8$, —$NR^1R^2$ and —$C(O)N(R^2)_2$;

$R^7$ and $R^8$ are independently selected from the group consisting of alkyl, alkenyl and aryl and linked together forming a 4- to 12-membered monocyclic, bicylic, tricyclic or benzofused ring, which may be optionally substituted by one or more selected from the group consisting of halo, alkyl, lower alkyl, alkenyl, cycloalkyl, haloalkyl, acyl, hydroxy, hydroxyalkyl, heterocyclic, amino, aminoalkyl, —$NR^7R^8$, alkoxy, oxo, cyano, carboxy, carboxyalkyl, alkoxycarbonyl, —$C(O)NR^7R^8$, and —$C(O)N(R^2)_2$;

$R^3$, $R^4$ and $R^5$ are independently selected from hydrogen, hydroxy, alkoxy, lower alkoxy, —$(O(CH_2)_2)_{1-3}$—O-lower alkyl, cycloalkyloxy, cycloalkylalkoxy, haloalkoxy, aryloxy, arylalkoxy, heteroaryloxy, heteroarylalkoxy, heteroaryl lower alkoxy, heterocyclic, heteroaryl, $NR^7R^8$, heterocyclicoxy, heterocyclicalkoxy, heterocyclic lower alkoxy, —$OC(R^1)_2C(O)N(R^2)_2$, and —$OC(R^1)_2C(O)NR^7R^8$, wherein all substituents may be optionally substituted by one or more selected from the group consisting of halo, alkyl, lower alkyl, alkenyl, cycloalkyl, haloalkyl, acyl, hydroxy, hydroxyalkyl, heterocyclic, amino, aminoalkyl, N-linked heteroaryl, —$NR^7R^8$, alkoxy, oxo, cyano, carboxy, carboxyalkyl, alkoxycarbonyl, —$C(O)NR^7R^8$, and —$C(O)N(R^2)_2$;

with the proviso that at least one of $R^3$, $R^4$ or $R^5$ is an N-linked heteroaryl or —$NR^7R^8$.

8. The compound of claim 7 or its pharmaceutically acceptable salt, wherein:

$R^1$ is selected from the group consisting of hydrogen, alkyl, lower alkyl, alkoxy, lower alkoxy, cycloalkyloxy, cycloalkylalkoxy, heterocyclicoxy, aryloxy, heteroaryloxy, heterocyclic, heteroarylalkyl, acyl and heterocyclicalkyl, wherein all substituents may be optionally substituted by one or more selected from the group consisting of halo, alkyl, lower alkyl, haloalkyl, heterocyclic, amino, aminoalkyl, —$NR^7R^8$, —$NHR^2$, —$N(R^2)_2$, alkoxy, carboxy, carboxyalkyl, alkoxycarbonyl, and heteroaryl;

$R^2$ is independently selected from the group consisting of alkyl, lower alkyl, heteroaryl, heterocyclic, heteroarylalkyl, acyl and heterocyclicalkyl, wherein all substituents may be optionally substituted by one or more selected from the group consisting of halo, alkyl, lower alkyl, haloalkyl, heterocyclic, —$NR^7R^8$, alkoxy, carboxy, carboxyalkyl, alkoxycarbonyl and heteroaryl;

$R^7$ and $R^8$ are independently selected from the group consisting of alkyl, alkenyl and aryl and linked together forming a 5- to 10-membered monocyclic, bicylic or benzofused ring, which may be optionally substituted by one or more selected from the group consisting of halo, alkyl, lower alkyl, haloalkyl, heterocyclic, —$NR^7R^8$, alkoxy, carboxy, carboxyalkyl and alkoxycarbonyl;

$R^3$, $R^4$ and $R^5$ are independently selected from hydrogen, hydroxy, alkoxy, lower alkoxy, —$(O(CH_2)_2)_{1-3}$—O-lower alkyl, haloalkoxy, heteroaryloxy, heteroarylalkoxy, heteroaryl lower alkoxy, heterocyclic, heteroaryl, $NR^7R^8$, heterocyclicoxy, heterocyclicalkoxy, heterocyclic lower alkoxy, —$OC(R^1)_2C(O)N(R^2)_2$, and —$OC(R^1)_2C(O)NR^7R^8$, wherein all substituents may be optionally substituted by one or more selected from the group consisting of halo, alkyl, lower alkyl, hydroxy, hydroxyalkyl, heterocyclic, N-linked heteroaryl, —$NR^7R^8$, alkoxy, —$C(O)NR^7R^8$, and —$C(O)N(R)_2$;

with the proviso that at least one of $R^3$, $R^4$ or $R^5$ is an N-linked heteroaryl or —$NR^7R^8$.

9. The compound of claim 7 or its pharmaceutically acceptable salt, wherein:

$R^1$ is selected from the group consisting of alkyl, lower alkyl, alkoxy, and lower alkoxy, wherein all substituents may be optionally substituted by one or more selected from the group consisting of halo, alkyl, lower alkyl, amino, —$NR^7R^8$, —$NHR^2$, —$N(R^2)_2$, aminoalkyl, alkoxy, carboxy, carboxyalkyl, alkoxycarbonyl, and heteroaryl;

$R^2$ is independently selected from the group consisting of lower alkyl, heteroarylalkyl, and heterocyclicalkyl, wherein all substituents may be optionally substituted by one or more selected from the group consisting of halo, lower alkyl, haloalkyl, heterocyclic, —$NR^7R^8$ and carboxy;

$R^7$ and $R^8$ are independently selected from the group consisting of alkyl and alkenyl, and linked together forming a 5- to 7-membered monocyclic ring, which may be optionally substituted by one or more selected from the group consisting of halo, lower alkyl, haloalkyl, heterocyclic and carboxy;

$R^3$, $R^4$ and $R^5$ are independently selected from hydrogen, hydroxy, lower alkoxy, —$(O(CH_2)_2)_{1-3}$—O-lower alkyl, heteroaryl lower alkoxy, heterocyclic, heteroaryl, $NR^7R^8$, heterocyclicoxy, heterocyclic lower alkoxy, —$OC(R^1)_2C(O)N(R^2)_2$, and —$OC(R^1)_2C(O)NR^7R^8$, wherein all substituents may be optionally substituted by one or more selected from the group consisting of hydroxy, hydroxyalkyl, heterocyclic, N-linked heteroaryl, —$NR^7R^8$, —$C(O)NR^7R^8$, and —$C(O)N(R^2)_2$;

with the proviso that at least one of $R^3$, $R^4$ or $R^5$ is an N-linked heteroaryl or —$NR^7R^8$.

10. The compound of claim 7 or its pharmaceutically acceptable salt, wherein:

$R^1$ is selected from the group consisting of lower alkyl, and lower alkoxy, wherein all substituents may be optionally substituted by one or more selected from the group consisting of alkoxy, —$NR^7R^8$, —$NHR^2$, and —$N(R^2)_2$;

$R^2$ is lower alkyl;

$R^7$ and $R^8$ are independently alkyl and linked together forming a 5- to 7-membered saturated monocyclic ring;

$R^3$, $R^4$ and $R^5$ are independently selected from hydrogen, hydroxy, lower alkoxy, heterocyclic, heteroaryl, $NR^7R^8$ and heterocyclic lower alkoxy;

with the proviso that at least one of $R^3$, $R^4$ or $R^5$ is an N-linked heteroaryl or —$NR^7R^8$.

11. The compound of claim 7 or its pharmaceutically acceptable salt, wherein:

$R^1$ is selected from the group consisting of lower alkyl, and lower alkoxy;

$R^7$ and $R^8$ are independently alkyl and linked together forming a 5- to 7-membered saturated monocyclic ring;

$R^3$, $R^4$ and $R^5$ are independently selected from lower alkoxy, $NR^7R^8$ and heterocyclic lower alkoxy;

with the proviso that at least one of $R^3$, $R^4$ or $R^5$ is —$NR^7R^8$.

12. The compound of claim 7 or its pharmaceutically acceptable salt, wherein the compound is N-Butyryl-4-[3E-(2,4-dimethoxy-5-pyrrolidin-1-ylphenyl)acryloyl]benzenesulfonamide.

13. A compound of Formula III (III)

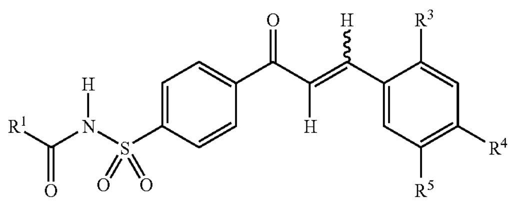

or its pharmaceutically acceptable salt, wherein:

$R^1$ is selected from the group consisting of hydrogen, alkyl, lower alkyl, carbocyclic, cycloalkyl, alkoxy, lower alkoxy, cycloalkyloxy, cycloalkylalkoxy, heterocyclicoxy, aryloxy, heteroaryloxy, aryl, heteroaryl, heterocyclic, arylalkyl, heteroarylalkyl, —$NR^7R^8$, —$NHR^2$, —$N(R^2)_2$, acyl and heterocyclicalkyl, wherein all substituents may be optionally substituted by one or more selected from the group consisting of halo, alkyl, lower alkyl, alkenyl, cycloalkyl, haloalkyl, acyl, hydroxy, hydroxyalkyl, heterocyclic, amino, aminoalkyl, —$NR^7R^8$, —$NHR^2$, —$N(R^2)_2$, alkoxy, oxo, cyano, carboxy, carboxyalkyl, alkoxycarbonyl, heteroaryl, —$C(O)NR^7R^8$, and —$C(O)N(R^2)_2$;

$R^2$ is independently selected from the group consisting of hydrogen, alkyl, lower alkyl, carbocyclic, cycloalkyl, aryl, heteroaryl, heterocyclic, arylalkyl, heteroarylalkyl, acyl, alkoxycarbonyl, and heterocyclicalkyl, wherein all substituents may be optionally substituted by one or more selected from the group consisting of halo, alkyl, lower alkyl, alkenyl, cycloalkyl, haloalkyl, acyl, hydroxy, hydroxyalkyl, heterocyclic, amino, aminoalkyl, —$NR^7R^8$, alkoxy, oxo, cyano, carboxy, carboxyalkyl, alkoxycarbonyl, heteroaryl, —$C(O)NR^7R^8$, —$NR^1R^2$ and —$C(O)N(R^2)_2$;

$R^7$ and $R^8$ are independently selected from the group consisting of alkyl, alkenyl and aryl and linked together forming a 4- to 12-membered monocyclic, bicylic, tricyclic or benzofused ring, which may be optionally substituted by one or more selected from the group consisting of halo, alkyl, lower alkyl, alkenyl, cycloalkyl, haloalkyl, acyl, hydroxy, hydroxyalkyl, heterocyclic, amino, aminoalkyl, —$NR^7R^8$, alkoxy, oxo, cyano, carboxy, carboxyalkyl, alkoxycarbonyl, —$C(O)NR^7R^8$, and —$C(O)N(R^2)_2$;

$R^3$ and $R^4$ are independently selected from hydrogen, hydroxy, alkoxy, lower alkoxy, —$(O(CH_2)_2)_{1-3}$—O-lower alkyl, cycloalkyloxy, cycloalkylalkoxy, haloalkoxy, aryloxy, arylalkoxy, heteroaryloxy, heteroarylalkoxy, heteroaryl lower alkoxy, heterocyclicoxy, heterocyclicalkoxy, heterocyclic lower alkoxy, —$OC(R^1)_2C(O)N(R^2)_2$, and —$OC(R^1)_2C(O)NR^7R^8$, wherein all substituents may be optionally substituted by one or more selected from the group consisting of halo, alkyl, lower alkyl, alkenyl, cycloalkyl, haloalkyl, acyl, hydroxy, hydroxyalkyl, heterocyclic, amino, aminoalkyl, N-linked heteroaryl, —$NR^7R^8$, alkoxy, oxo, cyano, carboxy, carboxyalkyl, alkoxycarbonyl, —$C(O)NR^7R^8$, and —$C(O)N(R^2)_2$;

$R^5$ is selected from the group consisting of a carbon-carbon linked heterocyclic and a carbon-carbon linked heteroaryl, which may be optionally substituted by one or more selected from the group consisting of halo, alkyl, lower alkyl, alkenyl, cycloalkyl, haloalkyl, acyl, hydroxy, hydroxyalkyl, heterocyclic, amino, aminoalkyl, —$NR^7R^8$, alkoxy, oxo, cyano, carboxy, carboxyalkyl, alkoxycarbonyl, —$C(O)NR^7R^8$, and —$C(O)N(R^2)_2$;

with the proviso that when $R^1$ is isopropyl, $R^5$ cannot be 5-benzo[b]thien-2-yl.

14. The compound of claim 13 or its pharmaceutically acceptable salt, wherein:

$R^1$ is selected from the group consisting of hydrogen, alkyl, lower alkyl, alkoxy, lower alkoxy, cycloalkyloxy, cycloalkylalkoxy, heterocyclicoxy, aryloxy, heteroaryloxy, heterocyclic, heteroarylalkyl, and heterocyclicalkyl, wherein all substituents may be optionally substituted by one or more selected from the group consisting of halo, alkyl, lower alkyl, haloalkyl, heterocyclic, amino, aminoalkyl, —$NR^7R^8$, —$NHR^2$, —$N(R^2)_2$, alkoxy, carboxy, carboxyalkyl, alkoxycarbonyl, and heteroaryl;

$R^2$ is independently selected from the group consisting of alkyl, lower alkyl, heteroaryl, heterocyclic, heteroarylalkyl, and heterocyclicalkyl, wherein all substituents may be optionally substituted by one or more selected from the group consisting of halo, alkyl, lower alkyl, haloalkyl, heterocyclic, —$NR^7R^8$, alkoxy, carboxy, carboxyalkyl, alkoxycarbonyl and heteroaryl;

$R^7$ and $R^8$ are independently selected from the group consisting of alkyl, alkenyl and aryl and linked together forming a 5- to 10-membered monocyclic, bicylic or benzofused ring, which may be optionally substituted by one or more selected from the group consisting of halo, alkyl, lower alkyl, haloalkyl, heterocyclic, —$NR^7R^8$, alkoxy, carboxy, carboxyalkyl and alkoxycarbonyl;

$R^3$ and $R^4$ are independently selected from hydroxy, alkoxy, lower alkoxy, —$(O(CH_2)_2)_{1-3}$—O-lower alkyl, haloalkoxy, heteroaryloxy, heteroarylalkoxy, heteroaryl lower alkoxy, heterocyclicoxy, heterocyclicalkoxy, heterocyclic lower alkoxy, —$OC(R^1)_2C(O)N(R^2)_2$, and —$OC(R^1)_2C(O)NR^7R^8$, wherein all substituents may be optionally substituted by one or more selected from the group consisting of halo, alkyl, lower alkyl, hydroxy, hydroxyalkyl, heterocyclic, —$NR^7R^8$, alkoxy, —$C(O)NR^7R^8$, and —$C(O)N(R^2)_2$;

$R^5$ is selected from the group consisting of a carbon-carbon linked heteroaryl and a carbon-carbon linked heterocyclic, which may be optionally substituted by one or more selected from the group consisting of halo, alkyl, lower alkyl, haloalkyl, heterocyclic, —$NR^7R^8$ and alkoxy;

with the proviso that when $R^1$ is isopropyl, $R^5$ cannot be 5-benzo[b]thien-2-yl.

15. The compound of claim 13 or its pharmaceutically acceptable salt, wherein:

$R^1$ is selected from the group consisting of alkyl, lower alkyl, alkoxy, and lower alkoxy, wherein all substituents may be optionally substituted by one or more selected from the group consisting of halo, alkyl, lower alkyl, amino, aminoalkyl, —$NR^7R^8$, —$NHR_2$, —$N(R^2)_2$, alkoxy, carboxy, carboxyalkyl, alkoxycarbonyl, and heteroaryl;

$R^2$ is independently selected from the group consisting of lower alkyl, heteroarylalkyl, and heterocyclicalkyl, wherein all substituents may be optionally substituted by one or more selected from the group consisting of halo, lower alkyl, haloalkyl, heterocyclic, —$NR^7R^8$ and carboxy;

$R^7$ and $R^8$ are independently selected from the group consisting of alkyl and alkenyl, and linked together forming a 5- to 7-membered monocyclic ring, which may be optionally substituted by one or more selected from the group consisting of halo, lower alkyl, haloalkyl, heterocyclic and carboxy;

$R^3$ and $R^4$ are independently selected from hydroxy, lower alkoxy, —$(O(CH_2)_2)_{1-3}$—O-lower alkyl, heteroaryl lower alkoxy, heterocyclicoxy, heterocyclicalkoxy, heterocyclic lower alkoxy, —$OC(R^1)_2C(O)N(R^2)_2$, and —$OC(R^1)_2C(O)NR^7R^8$, wherein all substituents may be optionally substituted by one or more selected from the group consisting of hydroxy, hydroxyalkyl, heterocyclic, —$NR^7R^8$, —$C(O)NR^7R^8$, and —$C(O)N(R^2)_2$;

$R^5$ is selected from the group consisting of a carbon-carbon linked heteroaryl and a carbon-carbon linked heterocyclic, which may be optionally substituted by one or more lower alkyl;

with the proviso that when $R^1$ is isopropyl, $R^5$ cannot be 5-benzo[b]thien-2-yl.

16. The compound of claim 13 or its pharmaceutically acceptable salt, wherein:

$R^1$ is selected from the group consisting of lower alkyl, and lower alkoxy, wherein all substituents may be optionally substituted by one or more selected from the group consisting of alkoxy, —$NR^7R^8$, —$NHR^2$, and —$N(R^2)_2$;

$R^2$ is lower alkyl;

$R^7$ and $R^8$ are independently alkyl and linked together forming a 5- to 7-membered saturated monocyclic ring;

$R^3$ and $R^4$ are independently selected from hydroxy, lower alkoxy and heterocyclic lower alkoxy;

$R^5$ is selected from the group consisting of a carbon-carbon linked heteroaryl and a carbon-carbon linked heterocyclic, which may be optionally substituted by one or more lower alkyl;

with the proviso that when $R^1$ is isopropyl, $R^5$ cannot be 5-benzo[b]thien-2-yl.

17. The compound of claim 13 or its pharmaceutically acceptable salt, wherein:

$R^1$ is selected from the group consisting of lower alkyl, and lower alkoxy;

$R^3$ and $R^4$ are independently selected from lower alkoxy and heterocyclic lower alkoxy;

$R^5$ is a carbon-carbon linked heteroaryl, which may be optionally substituted by one or more lower alkyl;

with the proviso that when $R^1$ is isopropyl, $R^5$ cannot be 5-benzo[b]thien-2-yl.

18. The compound of claim 13 or its pharmaceutically acceptable salt, wherein the compound is selected from the group consisting of:

4-{3E-[5-(1H-Indol-2-yl)-2,4-dimethoxyphenyl]acryloyl}-N-isobutyrylbenzenesulfonamide;

4-{3E-[5-(1H-Indol-2-yl)-2,4-dimethoxyphenyl]acryloyl}-N-isobutyrylbenzenesulfonamide sodium salt;

N-Butyryl-4-{3E-[2,4-dimethoxy-5-(1-methyl-1H-indol-2-yl)phenyl]acryloyl}benzenesulfonamide;

N-Ethoxycarbonyl-4-{3E-[5-(1H-indol-2-yl)-2,4-dimethoxyphenyl]acryloyl}benzenesulfonamide potassium salt;

N-Ethoxycarbonyl-4-{3E-[5-(1H-indol-2-yl)-2,4-dimethoxyphenyl]acryloyl}benzenesulfonamide;

N-Acetyl-4-{3E-[5-(1H-indol-2-yl)-2,4-dimethoxyphenyl]acryloyl}benzenesulfonamide;

N-Acetyl-4-{3E-[5-(1H-indol-2-yl)-2,4-dimethoxyphenyl]acryloyl}benzenesulfonamide sodium salt;

4-{3E-[5-(1H-Indol-2-yl)-2,4-dimethoxyphenyl]acryloyl}-N-propionyl-benzenesulfonamide;

4-{3E-[5-(1H-Indol-2-yl)-2,4-dimethoxyphenyl]acryloyl}-N-propionylbenzenesulfonamide sodium salt;

N-Butyryl-4-{3E-[5-(1H-indol-2-yl)-2,4-dimethoxyphenyl]acryloyl}benzenesulfonamide; and N-Butyryl-4-{3E-[5-(1H-indol-2-yl)-2,4-dimethoxyphenyl]acryloyl}benzenesulfonamide sodium salt.

19. A compound of Formula I

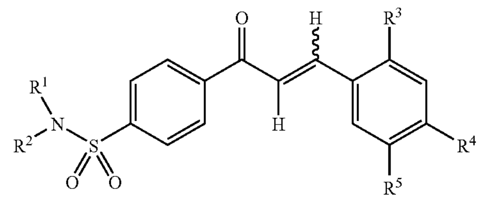

(I)

or its pharmaceutically acceptable salt, wherein:

$R^1$ is selected from the group consisting of hydrogen, alkyl, lower alkyl, carbocyclic, cycloalkyl, aryl, heteroaryl, heterocyclic, arylalkyl, heteroarylalkyl, acyl and heterocyclicalkyl, wherein all substituents may be optionally substituted by one or more selected from the group consisting of halo, alkyl, lower alkyl, alkenyl, cycloalkyl, haloalkyl, acyl, hydroxy, hydroxyalkyl, heterocyclic, amino, aminoalkyl, —$NR^7R^8$, alkoxy, oxo, cyano, carboxy, carboxyalkyl, alkoxycarbonyl, heteroaryl, —$C(O)NR^7R^8$, and —$C(O)N(R^2)_2$;

$R^2$ is independently selected from the group consisting of alkyl, lower alkyl, carbocyclic, cycloalkyl, hydroxy, alkoxy, lower alkoxy, trialkylsilyloxy, cycloalkyloxy, cycloalkylalkoxy, heterocyclicoxy, aryl, heteroaryl, heterocyclic, arylalkyl, heteroarylalkyl, acyl, alkoxycarbonyl, and heterocyclicalkyl, wherein all substituents may be optionally substituted by one or more selected from the group consisting of halo, alkyl, lower alkyl, alkenyl, cycloalkyl, haloalkyl, acyl, hydroxy, hydroxyalkyl, heterocyclic, amino, aminoalkyl, —$NR^7R^8$, alkoxy, oxo, cyano, carboxy, carboxyalkyl, alkoxycarbonyl, heteroaryl, —$C(O)NR^7R^8$, —$NR^1R^2$ and —$C(O)N(R^2)_2$;

$R^1$ and $R^2$ may be taken together to form a 4- to 12-membered saturated or unsaturated heterocyclic ring which can be optionally substituted by one or more selected from the group consisting of halo, alkyl, lower alkyl, alkenyl, cycloalkyl, haloalkyl, acyl, hydroxy, hydroxyalkyl, heterocyclic, amino, aminoalkyl, —$NR^7R^8$, alkoxy, oxo, cyano, carboxy, carboxyalkyl, alkoxycarbonyl, —$C(O)NR^7R^8$, and —$C(O)N(R^2)_2$;

$R^7$ and $R^8$ are independently selected from the group consisting of alkyl, alkenyl and aryl and linked together forming a 4- to 12-membered monocyclic, bicylic, tricyclic or benzofused ring, which may be optionally substituted by one or more selected from the group consisting of halo, alkyl, lower alkyl, alkenyl, cycloalkyl, haloalkyl, acyl, hydroxy, hydroxyalkyl, heterocyclic, amino, aminoalkyl, —$NR^7R^8$, alkoxy, oxo, cyano, carboxy, carboxyalkyl, alkoxycarbonyl, —C(O)$NR^7R^8$, and —$C(O)N(R^2)_2$;

$R^3$ and $R^4$ are independently selected from hydroxy, alkoxy, lower alkoxy, —$(O(CH_2)_2)_{1-3}$—O-lower alkyl, cycloalkyloxy, cycloalkylalkoxy, haloalkoxy, aryloxy, arylalkoxy, heteroaryloxy, heteroarylalkoxy, heteroaryl lower alkoxy, heterocyclicoxy, heterocyclicalkoxy, heterocyclic lower alkoxy, —$OC(R^1)_2C(O)N(R^2)_2$, and —$OC(R^1)_2C(O)NR^7R^8$, wherein all substituents may be optionally substituted by one or more selected from the group consisting of halo, alkyl, lower alkyl, alkenyl, cycloalkyl, haloalkyl, acyl, hydroxy, hydroxyalkyl, heterocyclic, amino, aminoalkyl, —$NR^7R^8$, alkoxy, oxo, cyano, carboxy, carboxyalkyl, alkoxycarbonyl, —C(O)$NR^7R^8$, and —$C(O)N(R^2)_2$;

$R^5$ is selected from the group consisting of a carbon-nitrogen linked heteroaryl and a carbon-nitrogen linked heterocyclic, which may be optionally substituted by one or more selected from the group consisting of halo, alkyl, lower alkyl, alkenyl, cycloalkyl, haloalkyl, acyl, hydroxy, hydroxyalkyl, heterocyclic, amino, aminoalkyl, —$NR^7R^8$, alkoxy, oxo, cyano, carboxy, carboxyalkyl, alkoxycarbonyl, —$C(O)NR^7R^8$, and —$C(O)N(R^2)_2$.

20. The compound of claim 19 or its pharmaceutically acceptable salt, wherein:

$R^1$ is selected from the group consisting of hydrogen, alkyl, and lower alkyl, wherein all substituents may be optionally substituted by one or more selected from the group consisting of halo, alkyl, lower alkyl, haloalkyl, heterocyclic, —$NR^7R^8$, alkoxy, carboxy, carboxyalkyl, alkoxycarbonyl and heteroaryl;

$R^2$ is independently selected from the group consisting of alkyl, lower alkyl, alkoxy, lower alkoxy, heteroaryl, heterocyclic, heteroarylalkyl, and heterocyclicalkyl, wherein all substituents may be optionally substituted by one or more selected from the group consisting of halo, alkyl, lower alkyl, haloalkyl, heterocyclic, —$NR^7R^8$, alkoxy, carboxy, carboxyalkyl, alkoxycarbonyl and heteroaryl;

$R^1$ and $R^2$ may be taken together to form a 5- to 7-membered saturated or unsaturated heterocyclic ring which can be optionally substituted by one or more selected from the group consisting of halo, alkyl, lower alkyl, haloalkyl, heterocyclic, —$NR^7R^8$, alkoxy, carboxy, carboxyalkyl and alkoxycarbonyl;

$R^7$ and $R^8$ are independently selected from the group consisting of alkyl, alkenyl and aryl and linked together forming a 5- to 10-membered monocyclic, bicylic or benzofused ring, which may be optionally substituted by one or more selected from the group consisting of halo, alkyl, lower alkyl, haloalkyl, heterocyclic, —$NR^7R^8$, alkoxy, carboxy, carboxyalkyl and alkoxycarbonyl;

$R^3$ and $R^4$ are independently selected from hydroxy, alkoxy, lower alkoxy, —$(O(CH_2)_2)_{1-3}$—O-lower alkyl, haloalkoxy, heteroaryloxy, heteroarylalkoxy, heteroaryl lower alkoxy, heterocyclicoxy, heterocyclicalkoxy, heterocyclic lower alkoxy, —$OC(R^1)_2C(O)N(R^2)_2$, and —$OC(R^1)_2C(O)NR^7R^8$, wherein all substituents may be optionally substituted by one or more selected from the group consisting of halo, alkyl, lower alkyl, hydroxy, hydroxyalkyl, heterocyclic, —$NR^7R^8$, alkoxy, —$C(O)NR^7R^8$, and —$C(O)N(R^2)_2$;

$R^5$ is selected from the group consisting of a carbon-nitrogen linked heteroaryl and a carbon-nitrogen linked heterocyclic, which may be optionally substituted by one or more selected from the group consisting of halo, alkyl, lower alkyl, haloalkyl, heterocyclic, —$NR^7R^8$ and alkoxy.

21. The compound of claim 19 or its pharmaceutically acceptable salt, wherein:

$R^1$ is selected from the group consisting of hydrogen and lower alkyl;

$R^2$ is independently selected from the group consisting of lower alkyl, lower alkoxy, heteroaryl, heterocyclic, heteroarylalkyl, and heterocyclicalkyl, wherein all substituents may be optionally substituted by one or more selected from the group consisting of halo, lower alkyl, haloalkyl, heterocyclic, heteroaryl, —$NR^7R^8$ and carboxy;

$R^1$ and $R^2$ may be taken together to form a 5- to 6-membered heterocyclic saturated ring which can be optionally substituted by one or more selected from the group consisting of halo, lower alkyl and carboxy;

$R^7$ and $R^8$ are independently selected from the group consisting of alkyl and alkenyl, and linked together forming a 5- to 7-membered monocyclic ring, which may be optionally substituted by one or more selected from the group consisting of halo, lower alkyl, haloalkyl, heterocyclic and carboxy;

$R^3$ and $R^4$ are independently selected from hydroxy, lower alkoxy, —$(O(CH_2)_2)_{1-3}$—O-lower alkyl, heteroaryl lower alkoxy, heterocyclicoxy, heterocyclicalkoxy, heterocyclic lower alkoxy, —$OC(R^1)_2C(O)N(R^2)_2$, and —$OC(R^1)_2C(O)NR^7R^8$, wherein all substituents may be optionally substituted by one or more selected from the group consisting of hydroxy, hydroxyalkyl, heterocyclic, —$NR^7R^8$, —$C(O)NR^7R^8$, and —$C(O)N(R^2)_2$;

$R^5$ is selected from the group consisting of a carbon-nitrogen linked heteroaryl and a carbon-nitrogen linked heterocyclic, which may be optionally substituted by one or more lower alkyl.

22. The compound of claim 19 or its pharmaceutically acceptable salt, wherein:

$R^1$ is hydrogen;

$R^2$ is independently selected from the group consisting of lower alkyl, heteroaryl, heteroarylalkyl, and heterocyclicalkyl, wherein all substituents may be optionally substituted by one or more selected from the group consisting of halo, heterocyclic, heteroaryl, and lower alkyl;

$R^1$ and $R^2$ may be taken together to form a 5- to 6-membered heterocyclic saturated ring;

$R^7$ and $R^8$ are independently alkyl and linked together forming a 5- to 7-membered saturated monocyclic ring;

$R^3$ and $R^4$ are independently selected from hydroxy, lower alkoxy and heterocyclic lower alkoxy;

$R^5$ is selected from the group consisting of a carbon-nitrogen linked heterocyclic, which may be optionally substituted by one or more lower alkyl.

23. The compound of claim 19 or its pharmaceutically acceptable salt, wherein:

$R^1$ is hydrogen;

$R^2$ is independently selected from the group consisting of lower alkyl, heteroaryl, heteroarylalkyl, and heterocyclicalkyl, wherein all substituents may be optionally substituted by one or more selected from the group consisting of halo, heterocyclic, heteroaryl, and lower alkyl;

$R^3$ and $R^4$ are independently selected from lower alkoxy and heterocyclic lower alkoxy;

$R^5$ is a carbon-nitrogen linked heterocyclic.

24. The compound of claim 19 or its pharmaceutically acceptable salt, wherein the compound is selected from the group consisting of:

4-[3E-(2,4-Dimethoxy-5-pyrrolidin-1-yl-phenyl)-acryloyl]-N-pyridin-2-yl-benzenesulfonamide;

4-[3E-(2,4-Dimethoxy-5-pyrrolidin-1-ylphenyl)acryloyl]-N-pyridin-2-ylmethylbenzenesulfonamide;

4-[3E-(2,4-Dimethoxy-5-pyrrolidin-1-ylphenyl)acryloyl]-N-(3-imidazol-1-ylpropyl)benzenesulfonamide;

4-[3E-(2,4-Dimethoxy-5-pyrrolidin-1-ylphenyl)acryloyl]-N-[3-(4-methyl-piperazin-1-yl)propyl]benzenesulfonamide; and {4-[3E-(2,4-Dimethoxy-5-pyrrolidin-1-ylphenyl)acryloyl]benzenesulfonylamino}acetic acid.

25. A pharmaceutical composition comprising a therapeutically effective amount of a compound of claim 1, 2, 3, 4, 5, 6, 7, 8, 9, 10, 11, 12, 13, 14, 15, 16, 17, 18, 19, 20, 21, 22, 23 or 24, together with one or more pharmaceutically acceptable carrier.

26. A method for the treatment or prophylaxis of an inflammatory disorder, comprising administering an effective amount of a compound of claim 1, 2, 3, 4, 5, 6, 7, 8, 9, 10, 11, 12, 13, 14, 15, 16, 17, 18, 19, 20, 21, 22, 23 or 24.

27. The method of claim 26, wherein the disorder is arthritis.

28. The method of claim 26, wherein the disorder is rheumatoid arthritis.

29. The method of claim 26, wherein the disorder is asthma.

30. The method of claim 26, wherein the treatment is disease modifying for the treatment of rheumatoid arthritis.

31. The method of claim 26, wherein the disorder is allergic rhinitis.

32. The method of claim 26, wherein the disorder is chronic obstructive pulmonary disease.

33. The method of claim 26, wherein the disorder is atherosclerosis.

34. The method of claim 26, wherein the disorder is restinosis.

35. A method for inhibiting the expression of VCAM-1, comprising administering an effective amount of a compound of claim 1, 2, 3, 4, 5, 6, 7, 8, 9, 10, 11, 12, 13, 14, 15, 16, 17, 18, 19, 20, 21, 22, 23 or 24.

36. A compound having the formula

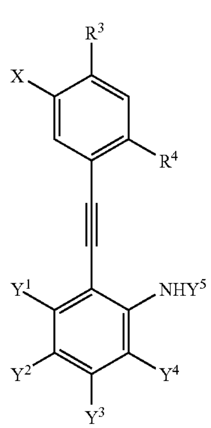

and

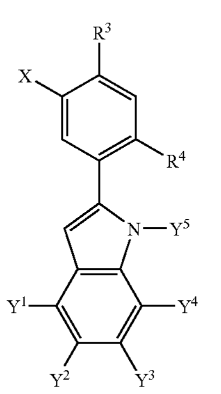

wherein

X is —C(O)H or —$CH_2OH$;

$R^3$ and $R^4$ are independently selected from the group consisting of hydroxy, alkoxy, lower alkoxy, —$(O(CH_2)_2)_{1-3}$—O-lower alkyl, cycloalkyloxy, cycloalkylalkoxy, haloalkoxy, aryloxy, arylalkoxy, heteroaryloxy, heteroarylalkoxy, heteroaryl lower alkoxy, heterocyclicoxy, heterocyclicalkoxy, heterocyclic lower alkoxy, —$OC(R^9)_2C(O)N(R^9)_2$, and —$OC(R^9)_2C(O)NR^7R^8$, wherein all substituents may be optionally substituted by one or more selected from the group consisting of halo, alkyl, lower alkyl, alkenyl, cycloalkyl, haloalkyl, acyl, hydroxy, hydroxyalkyl, heterocyclic, amino, aminoalkyl, —$NR^7R^8$, alkoxy, oxo, cyano, carboxy, carboxyalkyl, alkoxycarbonyl, —$C(O)NR^7R^8$, and —$C(O)N(R^9)_2$;

$Y^1$, $Y^2$, $Y^3$, and $Y^4$ are independently selected from the group consisting of hydrogen, hydroxyl, halo, alkyl, lower alkyl, alkenyl, cycloalkyl, haloalkyl, acyl, hydroxy, hydroxyalkyl, heterocyclic, amino, aminoalkyl, —$NR^7R^8$, alkoxy, oxo, cyano, carboxy, carboxyalkyl, alkoxycarbonyl, heteroaryl, —$C(O)NR^7R^8$, and —$C(O)N(R^9)_2$, wherein all substituents, when possible may be optionally substituted by one or more selected from the group consisting of hydroxyl, halo, alkyl, lower alkyl, alkenyl, cycloalkyl, haloalkyl, acyl, hydroxy, hydroxyalkyl, heterocyclic, amino, aminoalkyl, —$NR^7R^8$, alkoxy, oxo, cyano, carboxy, carboxyalkyl, alkoxycarbonyl, heteroaryl, —$C(O)NR^7R^8$, and —$C(O)N(R^2)^2$.

$Y^5$ is selected from the group consisting of hydrogen, alkyl, lower alkyl, acyl, and alkoxycarbonyl wherein all substituents, when possible may be optionally substituted by one or more selected from the group consisting of hydroxyl, halo, alkyl, lower alkyl, alkenyl, cycloalkyl, haloalkyl, acyl, hydroxy, hydroxyalkyl, heterocyclic, amino, aminoalkyl, —$NR^7R^8$, alkoxy, oxo, cyano, carboxy, carboxyalkyl, alkoxycarbonyl, heteroaryl, —$C(O)NR^7R^8$, and —$C(O)N(R^9)_2$;

$R^9$ is independently selected from the group consisting of alkyl, lower alkyl, carbocyclic, cycloalkyl, hydroxy, alkoxy, lower alkoxy, trialkylsilyloxy, cycloalkyloxy, cycloalkylalkoxy, heterocyclicoxy, aryl, heteroaryl, heterocyclic, arylalkyl, heteroarylalkyl, acyl, alkoxycarbonyl, and heterocyclicalkyl, wherein all substituents may be optionally substituted by one or more selected from the group consisting of halo, alkyl, lower alkyl, alkenyl, cycloalkyl, haloalkyl, acyl, hydroxy, hydroxyalkyl, heterocyclic, amino, aminoalkyl, —$NR^7R^8$, —$NHR^9$, —$N(R^9)_2$, alkoxy, oxo, cyano, carboxy, carboxyalkyl, alkoxycarbonyl, heteroaryl, —$C(O)NR^7R^8$, —$NR^9R^9$ and —$C(O)N(R^9)_2$;

$R^7$ and $R^8$ are independently selected from the group consisting of alkyl, alkenyl and aryl and linked together forming a 4- to 12-membered monocyclic, bicylic, tricyclic or benzofused ring, which may be optionally substituted by one or more selected from the group consisting of halo, alkyl, lower alkyl, alkenyl, cycloalkyl, haloalkyl, acyl, hydroxy, hydroxyalkyl, heterocyclic, amino, aminoalkyl, —$NR^7R^8$, alkoxy, oxo, cyano, carboxy, carboxyalkyl, alkoxycarbonyl, —$C(O)NR^7R^8$, and —$C(O)N(R^9)_2$.

37. The compound of claim 36 wherein the compound is selected from

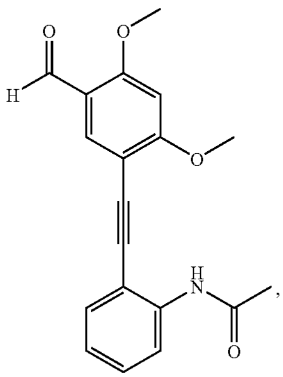
or
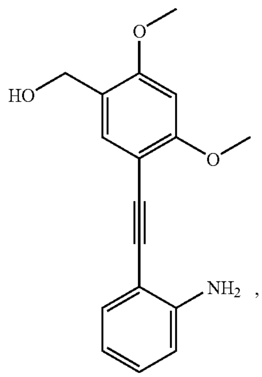
-continued
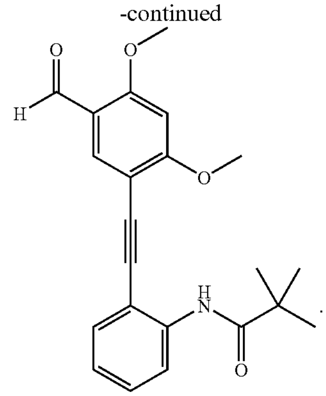
* * * * *